(12) United States Patent
Shelton, IV et al.

(10) Patent No.: US 10,639,037 B2
(45) Date of Patent: May 5, 2020

(54) SURGICAL INSTRUMENT WITH AXIALLY MOVABLE CLOSURE MEMBER

(71) Applicant: Ethicon LLC, Guaynabo, PR (US)

(72) Inventors: Frederick E. Shelton, IV, Hillsboro, OH (US); Jason L. Harris, Lebanon, OH (US); Chester O. Baxter, III, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 236 days.

(21) Appl. No.: 15/635,631

(22) Filed: Jun. 28, 2017

(65) Prior Publication Data

US 2019/0000464 A1 Jan. 3, 2019

(51) Int. Cl.
*A61B 17/072* (2006.01)
*A61B 34/30* (2016.01)
(Continued)

(52) U.S. Cl.
CPC ........ *A61B 17/07207* (2013.01); *A61B 34/30* (2016.02); *A61B 2017/00017* (2013.01);
(Continued)

(58) Field of Classification Search
CPC ...... A61B 17/07207; A61B 2017/0046; A61B 2017/07271; A61B 2017/00017; A61B 2017/00398; A61B 2017/00367; A61B 2017/00464; A61B 2017/07214; A61B 2017/07257; A61B 2017/07278; A61B 2017/07285; A61B 2017/2927; A61B 2017/2929; A61B 2017/2933;
(Continued)

(56) References Cited

U.S. PATENT DOCUMENTS 66,052 A 6/1867 Smith
662,587 A 11/1900 Blake
(Continued)

FOREIGN PATENT DOCUMENTS

AU 2011218702 B2 6/2013
AU 2012200178 B2 7/2013
(Continued)

OTHER PUBLICATIONS

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
(Continued)

*Primary Examiner* — Hemant Desai
*Assistant Examiner* — Jacob A Smith

(57) ABSTRACT

A surgical instrument that includes a first jaw and a second jaw that is coupled to the first jaw for selective pivotal travel relative thereto between a fully open position and a fully closed position. A closure member is configured to apply closure motions to the second jaw as the closure member is axially movable in a distal direction from a starting position corresponding to the fully open position of the second jaw to an ending position corresponding to the fully closed position of the second jaw. The closure member is configured to move distally from the starting position through an initial predetermined axial closure distance before applying the closure motion to the second jaw.

21 Claims, 59 Drawing Sheets

(51) Int. Cl.
　　　*A61B 17/00*　　　(2006.01)
　　　*A61B 17/29*　　　(2006.01)
　　　*A61B 90/00*　　　(2016.01)

(52) U.S. Cl.
　　　CPC .............. *A61B 2017/00022* (2013.01); *A61B 2017/0046* (2013.01); *A61B 2017/00398* (2013.01); *A61B 2017/00464* (2013.01); *A61B 2017/00473* (2013.01); *A61B 2017/00477* (2013.01); *A61B 2017/00734* (2013.01); *A61B 2017/00862* (2013.01); *A61B 2017/07214* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2017/2925* (2013.01); *A61B 2017/2927* (2013.01); *A61B 2017/2929* (2013.01); *A61B 2017/2933* (2013.01); *A61B 2017/2934* (2013.01); *A61B 2017/2936* (2013.01); *A61B 2017/2939* (2013.01); *A61B 2017/2946* (2013.01); *A61B 2017/2947* (2013.01); *A61B 2090/0814* (2016.02)

(58) Field of Classification Search
　　　CPC .... A61B 2017/2939; A61B 2017/2947; A61B 2090/0811
　　　USPC ........................................................ 227/179.1
　　　See application file for complete search history.

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 951,393 A | 3/1910 | Hahn |
| 1,188,721 A | 6/1916 | Bittner |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,037,727 A | 4/1936 | La Chapelle |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,882 A | 12/1940 | Peck |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Lee |
| 2,441,096 A | 5/1948 | Happe |
| 2,448,741 A | 9/1948 | Scott et al. |
| 2,450,527 A | 10/1948 | Smith |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,742,955 A | 4/1956 | Dominguez |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,957,353 A | 10/1960 | Lewis |
| 2,959,974 A | 11/1960 | Emrick |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,608,549 A | 9/1971 | Merrill |
| 3,618,842 A | 11/1971 | Bryan |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,666 A | 5/1972 | Foster et al. |
| 3,662,939 A | 5/1972 | Bryan |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,883,624 A | 5/1975 | McKenzie et al. |
| 3,885,491 A | 5/1975 | Curtis |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,981,051 A | 9/1976 | Brumlik |
| 4,025,216 A | 5/1977 | Hives |
| 4,027,746 A | 6/1977 | Kine |

(56) References Cited

U.S. PATENT DOCUMENTS

| | | |
|---|---|---|
| 4,034,143 A | 7/1977 | Sweet |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,154,122 A | 5/1979 | Severin |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,423,456 A | 12/1983 | Zaidenweber |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,478,220 A | 10/1984 | Di Giovanni et al. |
| 4,480,641 A | 11/1984 | Failla et al. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,981 A | 9/1986 | Rothfuss et al. |

(56) References Cited

U.S. PATENT DOCUMENTS

| | | |
|---|---|---|
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,914 A | 10/1986 | Ueda |
| 4,619,262 A | 10/1986 | Taylor |
| 4,619,391 A | 10/1986 | Sharkany et al. |
| D287,278 S | 12/1986 | Spreckelmeier |
| 4,628,459 A | 12/1986 | Shinohara et al. |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,724,840 A | 2/1988 | McVay et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| D298,967 S | 12/1988 | Hunt |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,951,860 A | 8/1990 | Peters et al. |
| 4,951,861 A | 8/1990 | Schulze et al. |
| 4,955,959 A | 9/1990 | Tompkins et al. |
| 4,957,212 A | 9/1990 | Duck et al. |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,973,274 A | 11/1990 | Hirukawa |
| 4,973,302 A | 11/1990 | Armour et al. |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |

(56) References Cited

U.S. PATENT DOCUMENTS

| | | |
|---|---|---|
| 4,996,975 A | 3/1991 | Nakamura |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,035,040 A | 7/1991 | Kerrigan et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | De Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,292,053 A | 3/1994 | Bilotti et al. |
| 5,293,024 A | 3/1994 | Sugahara et al. |

(56) References Cited

U.S. PATENT DOCUMENTS

| | | |
|---|---|---|
| 5,297,714 A | 3/1994 | Kramer |
| 5,304,204 A | 4/1994 | Bregen |
| D347,474 S | 5/1994 | Olson |
| 5,307,976 A | 5/1994 | Olson et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |

(56) References Cited

U.S. PATENT DOCUMENTS

| | | |
|---|---|---|
| 5,443,197 A | 8/1995 | Malis et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |

(56) References Cited

U.S. PATENT DOCUMENTS

| | | |
|---|---|---|
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| D381,077 S | 7/1997 | Hunt |
| 5,643,291 A | 7/1997 | Pier et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |

(56) References Cited

U.S. PATENT DOCUMENTS

| | | |
|---|---|---|
| 5,715,604 A | 2/1998 | Lanzoni |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,303 A | 6/1998 | Knodel et al. |
| 5,769,748 A | 6/1998 | Eyerly et al. |
| 5,769,791 A | 6/1998 | Benaron et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |

(56) References Cited

U.S. PATENT DOCUMENTS

| | | |
|---|---|---|
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,667 A | 3/2000 | Manna et al. |
| 6,037,724 A | 3/2000 | Buss et al. |
| 6,037,927 A | 3/2000 | Rosenberg |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |

(56) References Cited

U.S. PATENT DOCUMENTS

| | | |
|---|---|---|
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,904 B1 | 3/2001 | Ouchi |
| 6,209,414 B1 | 4/2001 | Uneme |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,270,508 B1 | 8/2001 | Klieman et al. |
| 6,270,916 B1 | 8/2001 | Sink et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |

(56) References Cited

U.S. PATENT DOCUMENTS

| | | |
|---|---|---|
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,458,077 B1 | 10/2002 | Boebel et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,527,782 B2 | 3/2003 | Hogg et al. |
| 6,527,785 B2 | 3/2003 | Sancoff et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| D473,239 S | 4/2003 | Cockerill |
| 6,539,816 B2 | 4/2003 | Kogiso et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,594,552 B1 | 7/2003 | Nowlin et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,166 B1 | 9/2003 | Wenstrom, Jr. et al. |
| 6,625,517 B1 | 9/2003 | Bogdanov et al. |

(56) References Cited

U.S. PATENT DOCUMENTS

| | | |
|---|---|---|
| 6,626,834 B2 | 9/2003 | Dunne et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,109 B2 | 4/2004 | Solingen |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban |
| 6,770,027 B2 | 8/2004 | Banik et al. |
| 6,770,070 B1 | 8/2004 | Balbierz |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,841,967 B2 | 1/2005 | Kim et al. |
| 6,843,403 B2 | 1/2005 | Whitman |

(56) References Cited

U.S. PATENT DOCUMENTS

| | | |
|---|---|---|
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |

(56) References Cited

U.S. PATENT DOCUMENTS

| | | | |
|---|---|---|---|
| 7,048,687 | B1 | 5/2006 | Reuss et al. |
| 7,048,745 | B2 | 5/2006 | Tierney et al. |
| 7,052,454 | B2 | 5/2006 | Taylor |
| 7,052,494 | B2 | 5/2006 | Goble et al. |
| 7,052,499 | B2 | 5/2006 | Steger et al. |
| 7,055,730 | B2 | 6/2006 | Ehrenfels et al. |
| 7,055,731 | B2 | 6/2006 | Shelton, IV et al. |
| 7,056,284 | B2 | 6/2006 | Martone et al. |
| 7,056,330 | B2 | 6/2006 | Gayton |
| 7,059,331 | B2 | 6/2006 | Adams et al. |
| 7,059,508 | B2 | 6/2006 | Shelton, IV et al. |
| 7,063,671 | B2 | 6/2006 | Couvillon, Jr. |
| 7,063,712 | B2 | 6/2006 | Vargas et al. |
| 7,064,509 | B1 | 6/2006 | Fu et al. |
| 7,066,879 | B2 | 6/2006 | Fowler et al. |
| 7,066,944 | B2 | 6/2006 | Laufer et al. |
| 7,067,038 | B2 | 6/2006 | Trokhan et al. |
| 7,070,083 | B2 | 7/2006 | Jankowski |
| 7,070,559 | B2 | 7/2006 | Adams et al. |
| 7,070,597 | B2 | 7/2006 | Truckai et al. |
| 7,071,287 | B2 | 7/2006 | Rhine et al. |
| 7,075,770 | B1 | 7/2006 | Smith |
| 7,077,856 | B2 | 7/2006 | Whitman |
| 7,080,769 | B2 | 7/2006 | Vresh et al. |
| 7,081,114 | B2 | 7/2006 | Rashidi |
| 7,083,073 | B2 | 8/2006 | Yoshie et al. |
| 7,083,075 | B2 | 8/2006 | Swayze et al. |
| 7,083,571 | B2 | 8/2006 | Wang et al. |
| 7,083,615 | B2 | 8/2006 | Peterson et al. |
| 7,083,619 | B2 | 8/2006 | Truckai et al. |
| 7,083,620 | B2 | 8/2006 | Jahns et al. |
| 7,083,626 | B2 | 8/2006 | Hart et al. |
| 7,086,267 | B2 | 8/2006 | Dworak et al. |
| 7,087,049 | B2 | 8/2006 | Nowlin et al. |
| 7,087,054 | B2 | 8/2006 | Truckai et al. |
| 7,087,071 | B2 | 8/2006 | Nicholas et al. |
| 7,090,637 | B2 | 8/2006 | Danitz et al. |
| 7,090,673 | B2 | 8/2006 | Dycus et al. |
| 7,090,683 | B2 | 8/2006 | Brock et al. |
| 7,090,684 | B2 | 8/2006 | McGuckin, Jr. et al. |
| 7,091,412 | B2 | 8/2006 | Wang et al. |
| 7,093,492 | B2 | 8/2006 | Treiber et al. |
| 7,094,202 | B2 | 8/2006 | Nobis et al. |
| 7,094,247 | B2 | 8/2006 | Monassevitch et al. |
| 7,094,916 | B2 | 8/2006 | DeLuca et al. |
| 7,096,972 | B2 | 8/2006 | Orozco, Jr. |
| 7,097,089 | B2 | 8/2006 | Marczyk |
| 7,097,644 | B2 | 8/2006 | Long |
| 7,097,650 | B2 | 8/2006 | Weller et al. |
| 7,098,794 | B2 | 8/2006 | Lindsay et al. |
| 7,100,949 | B2 | 9/2006 | Williams et al. |
| 7,101,187 | B1 | 9/2006 | Deconinck et al. |
| 7,101,371 | B2 | 9/2006 | Dycus et al. |
| 7,101,394 | B2 | 9/2006 | Hamm et al. |
| 7,104,741 | B2 | 9/2006 | Krohn |
| 7,108,695 | B2 | 9/2006 | Witt et al. |
| 7,108,701 | B2 | 9/2006 | Evens et al. |
| 7,108,709 | B2 | 9/2006 | Cummins |
| 7,111,768 | B2 | 9/2006 | Cummins et al. |
| 7,111,769 | B2 | 9/2006 | Wales et al. |
| 7,112,214 | B2 | 9/2006 | Peterson et al. |
| RE39,358 | E | 10/2006 | Goble |
| 7,114,642 | B2 | 10/2006 | Whitman |
| 7,116,100 | B1 | 10/2006 | Mock et al. |
| 7,118,020 | B2 | 10/2006 | Lee et al. |
| 7,118,528 | B1 | 10/2006 | Piskun |
| 7,118,563 | B2 | 10/2006 | Weckwerth et al. |
| 7,118,582 | B1 | 10/2006 | Wang et al. |
| 7,119,534 | B2 | 10/2006 | Butzmann |
| 7,121,446 | B2 | 10/2006 | Arad et al. |
| 7,121,773 | B2 | 10/2006 | Mikiya et al. |
| 7,122,028 | B2 | 10/2006 | Looper et al. |
| 7,125,403 | B2 | 10/2006 | Julian et al. |
| 7,125,409 | B2 | 10/2006 | Truckai et al. |
| 7,126,303 | B2 | 10/2006 | Farritor et al. |
| 7,126,879 | B2 | 10/2006 | Snyder |
| 7,128,253 | B2 | 10/2006 | Mastri et al. |
| 7,128,254 | B2 | 10/2006 | Shelton, IV et al. |
| 7,128,748 | B2 | 10/2006 | Mooradian et al. |
| 7,131,445 | B2 | 11/2006 | Amoah |
| 7,133,601 | B2 | 11/2006 | Phillips et al. |
| 7,134,587 | B2 | 11/2006 | Schwemberger et al. |
| 7,135,027 | B2 | 11/2006 | Delmotte |
| 7,137,980 | B2 | 11/2006 | Buysse et al. |
| 7,137,981 | B2 | 11/2006 | Long |
| 7,139,016 | B2 | 11/2006 | Squilla et al. |
| 7,140,527 | B2 | 11/2006 | Ehrenfels et al. |
| 7,140,528 | B2 | 11/2006 | Shelton, IV |
| 7,141,055 | B2 | 11/2006 | Abrams et al. |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,146,191 | B2 | 12/2006 | Kerner et al. |
| 7,147,138 | B2 | 12/2006 | Shelton, IV |
| 7,147,139 | B2 | 12/2006 | Schwemberger et al. |
| 7,147,140 | B2 | 12/2006 | Wukusick et al. |
| 7,147,637 | B2 | 12/2006 | Goble |
| 7,147,648 | B2 | 12/2006 | Lin |
| 7,147,650 | B2 | 12/2006 | Lee |
| 7,150,748 | B2 | 12/2006 | Ebbutt et al. |
| 7,153,300 | B2 | 12/2006 | Goble |
| 7,155,316 | B2 | 12/2006 | Sutherland et al. |
| 7,156,863 | B2 | 1/2007 | Sonnenschein et al. |
| 7,159,750 | B2 | 1/2007 | Racenet et al. |
| 7,160,296 | B2 | 1/2007 | Pearson et al. |
| 7,160,299 | B2 | 1/2007 | Baily |
| 7,161,036 | B2 | 1/2007 | Oikawa et al. |
| 7,161,580 | B2 | 1/2007 | Bailey et al. |
| 7,162,758 | B2 | 1/2007 | Skinner |
| 7,163,563 | B2 | 1/2007 | Schwartz et al. |
| 7,166,133 | B2 | 1/2007 | Evans et al. |
| 7,168,604 | B2 | 1/2007 | Milliman et al. |
| 7,170,910 | B2 | 1/2007 | Chen et al. |
| 7,171,279 | B2 | 1/2007 | Buckingham et al. |
| 7,172,104 | B2 | 2/2007 | Scirica et al. |
| 7,172,593 | B2 | 2/2007 | Trieu et al. |
| 7,172,615 | B2 | 2/2007 | Morriss et al. |
| 7,174,636 | B2 | 2/2007 | Lowe |
| 7,177,533 | B2 | 2/2007 | McFarlin et al. |
| 7,179,223 | B2 | 2/2007 | Motoki et al. |
| 7,179,267 | B2 | 2/2007 | Nolan et al. |
| 7,182,239 | B1 | 2/2007 | Myers |
| 7,182,763 | B2 | 2/2007 | Nardella |
| 7,183,737 | B2 | 2/2007 | Kitagawa |
| 7,187,960 | B2 | 3/2007 | Abreu |
| 7,188,758 | B2 | 3/2007 | Viola et al. |
| 7,189,207 | B2 | 3/2007 | Viola |
| 7,190,147 | B2 | 3/2007 | Gileff et al. |
| 7,195,627 | B2 | 3/2007 | Amoah et al. |
| 7,196,911 | B2 | 3/2007 | Takano et al. |
| D541,418 | S | 4/2007 | Schechter et al. |
| 7,199,537 | B2 | 4/2007 | Okamura et al. |
| 7,202,576 | B1 | 4/2007 | Dechene et al. |
| 7,202,653 | B2 | 4/2007 | Pai |
| 7,204,404 | B2 | 4/2007 | Nguyen et al. |
| 7,204,835 | B2 | 4/2007 | Latterell et al. |
| 7,207,233 | B2 | 4/2007 | Wadge |
| 7,207,471 | B2 | 4/2007 | Heinrich et al. |
| 7,207,472 | B2 | 4/2007 | Wukusick et al. |
| 7,207,556 | B2 | 4/2007 | Saitoh et al. |
| 7,208,005 | B2 | 4/2007 | Frecker et al. |
| 7,210,609 | B2 | 5/2007 | Leiboff et al. |
| 7,211,081 | B2 | 5/2007 | Goble |
| 7,211,084 | B2 | 5/2007 | Goble et al. |
| 7,211,092 | B2 | 5/2007 | Hughett |
| 7,211,979 | B2 | 5/2007 | Khatib et al. |
| 7,213,736 | B2 | 5/2007 | Wales et al. |
| 7,214,224 | B2 | 5/2007 | Goble |
| 7,215,517 | B2 | 5/2007 | Takamatsu |
| 7,217,285 | B2 | 5/2007 | Vargas et al. |
| 7,220,260 | B2 | 5/2007 | Fleming et al. |
| 7,220,272 | B2 | 5/2007 | Weadock |
| 7,225,959 | B2 | 6/2007 | Patton et al. |

(56) References Cited

U.S. PATENT DOCUMENTS

| | | |
|---|---|---|
| 7,225,963 B2 | 6/2007 | Scirica |
| 7,225,964 B2 | 6/2007 | Mastri et al. |
| 7,226,450 B2 | 6/2007 | Athanasiou et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,045 B2 | 2/2008 | Clermonts |
| 7,336,048 B2 | 2/2008 | Lohr |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,555 B2 | 3/2008 | Ootawara et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,377,918 B2 | 5/2008 | Amoah |
| 7,377,928 B2 | 5/2008 | Zubik et al. |
| RE40,388 E | 6/2008 | Gines |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |

(56) References Cited

U.S. PATENT DOCUMENTS

| | | |
|---|---|---|
| 7,427,607 B2 | 9/2008 | Suzuki |
| D578,644 S | 10/2008 | Shumer et al. |
| 7,430,772 B2 | 10/2008 | Van Es |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,448,525 B2 | 11/2008 | Shelton, IV et al. |
| 7,450,010 B1 | 11/2008 | Gravelle et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barley et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |
| 7,543,730 B1 | 6/2009 | Marczyk |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,578,825 B2 | 8/2009 | Huebner |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| D605,201 S | 12/2009 | Lorenz et al. |
| 7,624,902 B2 | 12/2009 | Marczyk et al. |
| 7,624,903 B2 | 12/2009 | Green et al. |
| 7,625,370 B2 | 12/2009 | Hart et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,457 B2 | 1/2010 | Stefanchik et al. |
| 7,648,519 B2 | 1/2010 | Lee et al. |
| 7,650,185 B2 | 1/2010 | Maile et al. |

(56) References Cited

U.S. PATENT DOCUMENTS

| | | |
|---|---|---|
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,712,182 B2 | 5/2010 | Zeiler et al. |
| 7,713,190 B2 | 5/2010 | Brock et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,762,462 B2 | 7/2010 | Gelbman |
| 7,762,998 B2 | 7/2010 | Birk et al. |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |

(56) References Cited

U.S. PATENT DOCUMENTS

| | | |
|---|---|---|
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,085 B2 | 12/2010 | Silverman et al. |
| 7,846,149 B2 | 12/2010 | Jankowski |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |

(56) References Cited

U.S. PATENT DOCUMENTS

| | | |
|---|---|---|
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,563 B2 | 7/2011 | Summerer |
| 7,979,137 B2 | 7/2011 | Tracey et al. |
| 7,980,443 B2 | 7/2011 | Scheib et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,118,206 B2 | 2/2012 | Zand et al. |
| 8,118,207 B2 | 2/2012 | Racenet et al. |
| 8,120,301 B2 | 2/2012 | Goldberg et al. |

(56) References Cited

U.S. PATENT DOCUMENTS

| | | |
|---|---|---|
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,236,010 B2 | 8/2012 | Ortiz et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,262,560 B2 | 9/2012 | Whitman |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |

(56) References Cited

U.S. PATENT DOCUMENTS

| | | |
|---|---|---|
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,287,487 B2 | 10/2012 | Estes |
| 8,287,522 B2 | 10/2012 | Moses et al. |
| 8,287,561 B2 | 10/2012 | Nunez et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,801 B2 | 10/2012 | Dejima et al. |
| 8,292,888 B2 | 10/2012 | Whitman |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,343,150 B2 | 1/2013 | Artale |
| 8,347,978 B2 | 1/2013 | Forster et al. |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| D676,866 S | 2/2013 | Chaudhri |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,719 B2 | 2/2013 | Markey et al. |
| 8,366,787 B2 | 2/2013 | Brown et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,382,773 B2 | 2/2013 | Whitfield et al. |
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,851 B2 | 3/2013 | Byun |
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,222 B2 | 4/2013 | Whitfield et al. |
| 8,409,223 B2 | 4/2013 | Sorrentino et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |

(56) References Cited

U.S. PATENT DOCUMENTS

| | | |
|---|---|---|
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |
| D686,240 S | 7/2013 | Lin |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,487,199 B2 | 7/2013 | Palmer et al. |
| 8,490,851 B2 | 7/2013 | Blier et al. |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,518,024 B2 | 8/2013 | Williams et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,427 B2 | 12/2013 | Viola |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |

(56) References Cited

U.S. PATENT DOCUMENTS

| | | | |
|---|---|---|---|
| 8,632,462 B2 | 1/2014 | Yoo et al. | |
| 8,632,525 B2 | 1/2014 | Kerr et al. | |
| 8,632,535 B2 | 1/2014 | Shelton, IV et al. | |
| 8,632,563 B2 | 1/2014 | Nagase et al. | |
| 8,636,187 B2 | 1/2014 | Hueil et al. | |
| 8,636,190 B2 | 1/2014 | Zemlok et al. | |
| 8,636,191 B2 | 1/2014 | Meagher | |
| 8,636,193 B2 | 1/2014 | Whitman et al. | |
| 8,636,736 B2 | 1/2014 | Yates et al. | |
| 8,636,766 B2 | 1/2014 | Milliman et al. | |
| 8,639,936 B2 | 1/2014 | Hu et al. | |
| 8,640,788 B2 | 2/2014 | Dachs, II et al. | |
| 8,646,674 B2 | 2/2014 | Schulte et al. | |
| 8,647,258 B2 | 2/2014 | Aranyi et al. | |
| 8,652,120 B2 | 2/2014 | Giordano et al. | |
| 8,652,151 B2 | 2/2014 | Lehman et al. | |
| 8,657,174 B2 | 2/2014 | Yates et al. | |
| 8,657,175 B2 | 2/2014 | Sonnenschein et al. | |
| 8,657,176 B2 | 2/2014 | Shelton, IV et al. | |
| 8,657,177 B2 | 2/2014 | Scirica et al. | |
| 8,657,178 B2 | 2/2014 | Hueil et al. | |
| 8,657,482 B2 | 2/2014 | Malackowski et al. | |
| 8,657,808 B2 | 2/2014 | McPherson et al. | |
| 8,657,814 B2 | 2/2014 | Werneth et al. | |
| 8,657,821 B2 | 2/2014 | Palermo | |
| 8,662,370 B2 | 3/2014 | Takei | |
| 8,663,106 B2 | 3/2014 | Stivoric et al. | |
| 8,663,192 B2 | 3/2014 | Hester et al. | |
| 8,663,245 B2 | 3/2014 | Francischelli et al. | |
| 8,663,262 B2 | 3/2014 | Smith et al. | |
| 8,663,270 B2 | 3/2014 | Donnigan et al. | |
| 8,664,792 B2 | 3/2014 | Rebsdorf | |
| 8,668,129 B2 | 3/2014 | Olson | |
| 8,668,130 B2 | 3/2014 | Hess et al. | |
| 8,672,206 B2 | 3/2014 | Aranyi et al. | |
| 8,672,207 B2 | 3/2014 | Shelton, IV et al. | |
| 8,672,208 B2 | 3/2014 | Hess et al. | |
| 8,672,922 B2 | 3/2014 | Loh et al. | |
| 8,672,935 B2 | 3/2014 | Okada et al. | |
| 8,672,951 B2 | 3/2014 | Smith et al. | |
| 8,673,210 B2 | 3/2014 | Deshays | |
| 8,675,820 B2 | 3/2014 | Baic et al. | |
| 8,678,263 B2 | 3/2014 | Viola | |
| 8,679,093 B2 | 3/2014 | Farra | |
| 8,679,098 B2 | 3/2014 | Hart | |
| 8,679,137 B2 | 3/2014 | Bauman et al. | |
| 8,679,154 B2 | 3/2014 | Smith et al. | |
| 8,679,156 B2 | 3/2014 | Smith et al. | |
| 8,679,454 B2 | 3/2014 | Guire et al. | |
| 8,684,248 B2 | 4/2014 | Milliman | |
| 8,684,249 B2 | 4/2014 | Racenet et al. | |
| 8,684,250 B2 | 4/2014 | Bettuchi et al. | |
| 8,684,253 B2 | 4/2014 | Giordano et al. | |
| 8,684,962 B2 | 4/2014 | Kirschenman et al. | |
| 8,685,004 B2 | 4/2014 | Zemlock et al. | |
| 8,685,020 B2 | 4/2014 | Weizman et al. | |
| 8,690,893 B2 | 4/2014 | Deitch et al. | |
| 8,695,866 B2 | 4/2014 | Leimbach et al. | |
| 8,696,665 B2 | 4/2014 | Hunt et al. | |
| 8,701,958 B2 | 4/2014 | Shelton, IV et al. | |
| 8,701,959 B2 | 4/2014 | Shah | |
| 8,708,210 B2 | 4/2014 | Zemlok et al. | |
| 8,708,211 B2 | 4/2014 | Zemlok et al. | |
| 8,708,213 B2 * | 4/2014 | Shelton, IV | A61B 17/068 227/180.1 |
| 8,714,352 B2 | 5/2014 | Farascioni et al. | |
| 8,714,429 B2 | 5/2014 | Demmy | |
| 8,714,430 B2 | 5/2014 | Natarajan et al. | |
| 8,715,256 B2 | 5/2014 | Greener | |
| 8,715,302 B2 | 5/2014 | Ibrahim et al. | |
| 8,720,766 B2 | 5/2014 | Hess et al. | |
| 8,721,630 B2 | 5/2014 | Ortiz et al. | |
| 8,721,666 B2 | 5/2014 | Schroeder et al. | |
| 8,727,197 B2 | 5/2014 | Hess et al. | |
| 8,727,199 B2 | 5/2014 | Wenchell | |
| 8,727,200 B2 | 5/2014 | Roy | |
| 8,727,961 B2 | 5/2014 | Ziv | |
| 8,728,099 B2 | 5/2014 | Cohn et al. | |
| 8,728,119 B2 | 5/2014 | Cummins | |
| 8,733,470 B2 | 5/2014 | Matthias et al. | |
| 8,733,612 B2 | 5/2014 | Ma | |
| 8,733,613 B2 | 5/2014 | Huitema et al. | |
| 8,733,614 B2 | 5/2014 | Ross et al. | |
| 8,734,336 B2 | 5/2014 | Bonadio et al. | |
| 8,734,359 B2 | 5/2014 | Ibanez et al. | |
| 8,734,478 B2 | 5/2014 | Widenhouse et al. | |
| 8,739,033 B2 | 5/2014 | Rosenberg | |
| 8,739,417 B2 | 6/2014 | Tokunaga et al. | |
| 8,740,034 B2 | 6/2014 | Morgan et al. | |
| 8,740,037 B2 | 6/2014 | Shelton, IV et al. | |
| 8,740,038 B2 | 6/2014 | Shelton, IV et al. | |
| 8,740,987 B2 | 6/2014 | Geremakis et al. | |
| 8,746,529 B2 | 6/2014 | Shelton, IV et al. | |
| 8,746,530 B2 | 6/2014 | Giordano et al. | |
| 8,746,533 B2 | 6/2014 | Whitman et al. | |
| 8,746,535 B2 | 6/2014 | Shelton, IV et al. | |
| 8,747,238 B2 | 6/2014 | Shelton, IV et al. | |
| 8,747,441 B2 | 6/2014 | Konieczynski et al. | |
| 8,752,264 B2 | 6/2014 | Ackley et al. | |
| 8,752,699 B2 | 6/2014 | Morgan et al. | |
| 8,752,747 B2 | 6/2014 | Shelton, IV et al. | |
| 8,752,748 B2 | 6/2014 | Whitman et al. | |
| 8,752,749 B2 | 6/2014 | Moore et al. | |
| 8,753,664 B2 | 6/2014 | Dao et al. | |
| 8,757,287 B2 | 6/2014 | Mak et al. | |
| 8,757,465 B2 | 6/2014 | Woodard, Jr. et al. | |
| 8,758,235 B2 | 6/2014 | Jaworek | |
| 8,758,366 B2 | 6/2014 | McLean et al. | |
| 8,758,391 B2 | 6/2014 | Swayze et al. | |
| 8,758,438 B2 | 6/2014 | Boyce et al. | |
| 8,763,875 B2 | 7/2014 | Morgan et al. | |
| 8,763,877 B2 | 7/2014 | Schall et al. | |
| 8,763,879 B2 | 7/2014 | Shelton, IV et al. | |
| 8,764,732 B2 | 7/2014 | Hartwell | |
| 8,770,458 B2 | 7/2014 | Scirica | |
| 8,770,459 B2 | 7/2014 | Racenet et al. | |
| 8,770,460 B2 | 7/2014 | Belzer | |
| 8,771,169 B2 | 7/2014 | Whitman et al. | |
| 8,771,260 B2 | 7/2014 | Conlon et al. | |
| 8,777,004 B2 | 7/2014 | Shelton, IV et al. | |
| 8,777,082 B2 | 7/2014 | Scirica | |
| 8,777,083 B2 | 7/2014 | Racenet et al. | |
| 8,777,898 B2 | 7/2014 | Suon et al. | |
| 8,783,541 B2 | 7/2014 | Shelton, IV et al. | |
| 8,783,542 B2 | 7/2014 | Riestenberg et al. | |
| 8,783,543 B2 | 7/2014 | Shelton, IV et al. | |
| 8,784,304 B2 | 7/2014 | Mikkaichi et al. | |
| 8,784,404 B2 | 7/2014 | Doyle et al. | |
| 8,784,415 B2 | 7/2014 | Malackowski et al. | |
| 8,789,737 B2 | 7/2014 | Hodgkinson et al. | |
| 8,789,739 B2 | 7/2014 | Swensgard | |
| 8,789,740 B2 | 7/2014 | Baxter, III et al. | |
| 8,789,741 B2 | 7/2014 | Baxter, III et al. | |
| 8,790,658 B2 | 7/2014 | Cigarini et al. | |
| 8,790,684 B2 | 7/2014 | Dave et al. | |
| D711,905 S | 8/2014 | Morrison et al. | |
| 8,794,496 B2 | 8/2014 | Scirica | |
| 8,794,497 B2 | 8/2014 | Zingman | |
| 8,795,276 B2 | 8/2014 | Dietz et al. | |
| 8,795,308 B2 | 8/2014 | Valin | |
| 8,795,324 B2 | 8/2014 | Kawai et al. | |
| 8,800,681 B2 | 8/2014 | Rousson et al. | |
| 8,800,837 B2 | 8/2014 | Zemlok | |
| 8,800,838 B2 | 8/2014 | Shelton, IV | |
| 8,800,839 B2 | 8/2014 | Beetel | |
| 8,800,840 B2 | 8/2014 | Jankowski | |
| 8,800,841 B2 | 8/2014 | Ellerhorst et al. | |
| 8,801,710 B2 | 8/2014 | Ullrich et al. | |
| 8,801,734 B2 | 8/2014 | Shelton, IV et al. | |
| 8,801,735 B2 | 8/2014 | Shelton, IV et al. | |
| 8,801,752 B2 | 8/2014 | Fortier et al. | |
| 8,801,801 B2 | 8/2014 | Datta et al. | |
| 8,806,973 B2 | 8/2014 | Ross et al. | |
| 8,807,414 B2 | 8/2014 | Ross et al. | |

(56) References Cited

U.S. PATENT DOCUMENTS

| | | |
|---|---|---|
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,498 B2 | 9/2014 | Byrum et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,851,215 B2 | 10/2014 | Goto |
| 8,851,354 B2 | 10/2014 | Swensgard et al. |
| 8,852,174 B2 | 10/2014 | Burbank |
| 8,852,185 B2 | 10/2014 | Twomey |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,986,302 B2 | 3/2015 | Aldridge et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,002,518 B2 | 4/2015 | Manzo et al. |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,011,439 B2 | 4/2015 | Shalaby et al. |
| 9,011,471 B2 | 4/2015 | Timm et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |

(56) References Cited

U.S. PATENT DOCUMENTS

| | | |
|---|---|---|
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,043,027 B2 | 5/2015 | Durant et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,241 B2 | 6/2015 | Barner et al. |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,101,475 B2 | 8/2015 | Wei et al. |
| 9,107,663 B2 | 8/2015 | Swensgard |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,769 B2 | 10/2015 | Stoddard et al. |
| 9,161,803 B2 | 10/2015 | Yates et al. |
| 9,161,807 B2 | 10/2015 | Garrison |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,508 B2 | 12/2015 | Dannaher |
| 9,220,559 B2 | 12/2015 | Worrell et al. |
| 9,220,570 B2 | 12/2015 | Kim et al. |

(56) References Cited

U.S. PATENT DOCUMENTS

| | | |
|---|---|---|
| D746,854 S | 1/2016 | Shardlow et al. |
| 9,226,750 B2 | 1/2016 | Weir et al. |
| 9,226,751 B2 | 1/2016 | Shelton, IV et al. |
| 9,226,761 B2 | 1/2016 | Burbank |
| 9,226,767 B2 | 1/2016 | Stulen et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,244,524 B2 | 1/2016 | Inoue et al. |
| D749,623 S | 2/2016 | Gray et al. |
| D750,122 S | 2/2016 | Shardlow et al. |
| D750,129 S | 2/2016 | Kwon |
| 9,254,131 B2 | 2/2016 | Soltz et al. |
| 9,259,274 B2 | 2/2016 | Prisco |
| 9,261,172 B2 | 2/2016 | Solomon et al. |
| 9,265,500 B2 | 2/2016 | Sorrentino et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,784 B2 | 3/2016 | Eggert et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,339,226 B2 | 5/2016 | van der Walt et al. |
| 9,345,477 B2 | 5/2016 | Anim et al. |
| 9,345,480 B2 | 5/2016 | Hessler et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| D758,433 S | 6/2016 | Lee et al. |
| D759,063 S | 6/2016 | Chen |
| 9,358,003 B2 | 6/2016 | Hall et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,364 B2 | 6/2016 | Smith et al. |
| 9,375,206 B2 | 6/2016 | Vidal et al. |
| 9,375,232 B2 | 6/2016 | Hunt et al. |
| 9,375,255 B2 | 6/2016 | Houser et al. |
| 9,381,058 B2 | 7/2016 | Houser et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,398,911 B2 | 7/2016 | Auld |
| D763,277 S | 8/2016 | Ahmed et al. |
| 9,402,604 B2 | 8/2016 | Williams et al. |
| 9,402,626 B2 | 8/2016 | Ortiz et al. |
| 9,402,627 B2 | 8/2016 | Stevenson et al. |
| 9,408,604 B2 | 8/2016 | Shelton, IV et al. |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |

(56) References Cited

U.S. PATENT DOCUMENTS

| | | |
|---|---|---|
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,427,223 B2 | 8/2016 | Park et al. |
| 9,427,231 B2 | 8/2016 | Racenet et al. |
| D767,624 S | 9/2016 | Lee et al. |
| 9,433,411 B2 | 9/2016 | Racenet et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,451,958 B2 | 9/2016 | Shelton, IV et al. |
| D768,152 S | 10/2016 | Gutierrez et al. |
| 9,461,340 B2 | 10/2016 | Li et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| D770,476 S | 11/2016 | Jitkoff et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,189 B2 | 11/2016 | Williams et al. |
| 9,492,192 B2 | 11/2016 | To et al. |
| 9,498,213 B2 | 11/2016 | Marczyk et al. |
| 9,498,219 B2 | 11/2016 | Moore et al. |
| 9,504,483 B2 | 11/2016 | Houser et al. |
| 9,504,521 B2 | 11/2016 | Deutmeyer et al. |
| D775,336 S | 12/2016 | Shelton, IV et al. |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,521,996 B2 | 12/2016 | Armstrong |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| D776,683 S | 1/2017 | Gobinski et al. |
| D777,773 S | 1/2017 | Shi |
| 9,532,783 B2 | 1/2017 | Swayze et al. |
| 9,539,726 B2 | 1/2017 | Simaan et al. |
| 9,545,258 B2 | 1/2017 | Smith et al. |
| 9,549,732 B2 | 1/2017 | Yates et al. |
| 9,549,735 B2 | 1/2017 | Shelton, IV et al. |
| 9,554,794 B2 | 1/2017 | Baber et al. |
| 9,554,796 B2 | 1/2017 | Kostrzewski |
| 9,554,812 B2 | 1/2017 | Inkpen et al. |
| 9,559,624 B2 | 1/2017 | Philipp |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,566,062 B2 | 2/2017 | Boudreaux |
| 9,566,065 B2 | 2/2017 | Knodel |
| 9,566,067 B2 | 2/2017 | Milliman et al. |
| 9,572,574 B2 | 2/2017 | Shelton, IV et al. |
| 9,572,577 B2 | 2/2017 | Lloyd et al. |
| 9,572,592 B2 | 2/2017 | Price et al. |
| 9,574,644 B2 | 2/2017 | Parihar |
| D780,803 S | 3/2017 | Gill et al. |
| D781,879 S | 3/2017 | Butcher et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,080 B2 | 4/2017 | Whitfield et al. |
| 9,614,258 B2 | 4/2017 | Takahashi et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,628 B2 | 4/2017 | Aranyi |
| 9,629,629 B2 | 4/2017 | Leimbach et al. |
| 9,629,652 B2 | 4/2017 | Mumaw et al. |
| 9,629,814 B2 | 4/2017 | Widenhouse et al. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,111 B2 | 5/2017 | Wenchell |
| 9,636,850 B2 | 5/2017 | Stopek (nee Prommersberger) et al. |
| 9,641,122 B2 | 5/2017 | Romanowich et al. |
| 9,642,620 B2 | 5/2017 | Baxter, III et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,624 B2 | 5/2017 | Shelton, IV et al. |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,675,344 B2 | 6/2017 | Combrowski et al. |
| 9,675,351 B2 | 6/2017 | Hodgkinson et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |

(56) References Cited

U.S. PATENT DOCUMENTS

| | | |
|---|---|---|
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,321 B2 | 7/2017 | Shelton, IV et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,005 B2 | 7/2017 | Strobl et al. |
| 9,707,026 B2 | 7/2017 | Malackowski et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,713,474 B2 | 7/2017 | Lorenz |
| 9,717,497 B2 | 8/2017 | Zerkle et al. |
| 9,717,498 B2 | 8/2017 | Aranyi et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,635 B2 | 10/2017 | Takei |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,561 B2 | 11/2017 | Forsell |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,236 B2 | 12/2017 | Shelton, IV et al. |
| 9,833,238 B2 | 12/2017 | Baxter, III et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,855,662 B2 | 1/2018 | Ruiz Morales et al. |
| 9,861,261 B2 | 1/2018 | Shahinian |

(56) References Cited

U.S. PATENT DOCUMENTS

| | | |
|---|---|---|
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,877,721 B2 | 1/2018 | Schellin et al. |
| 9,877,723 B2 | 1/2018 | Hall et al. |
| 9,883,843 B2 | 2/2018 | Garlow |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,553 B2 | 3/2018 | Cole et al. |
| 9,907,620 B2 | 3/2018 | Shelton, IV et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,924,942 B2 | 3/2018 | Swayze et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,118 B2 | 4/2018 | Shelton, IV et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,955,965 B2 | 5/2018 | Chen et al. |
| 9,955,966 B2 | 5/2018 | Zergiebel |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,541 B2 | 5/2018 | Calderoni |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,769 B2 | 5/2018 | Trees et al. |
| D819,680 S | 6/2018 | Nguyen |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,095 B2 | 6/2018 | Chowaniec et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,022,125 B2 | 7/2018 | (Prommersberger) Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| D831,209 S | 10/2018 | Huitema et al. |
| 10,085,624 B2 | 10/2018 | Isoda et al. |
| 10,085,728 B2 | 10/2018 | Jogasaki et al. |
| 10,085,748 B2 | 10/2018 | Morgan et al. |
| 10,085,749 B2 | 10/2018 | Cappola et al. |
| 10,085,751 B2 | 10/2018 | Overmyer et al. |
| 10,085,806 B2 | 10/2018 | Hagn et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,642 B2 | 10/2018 | Baxter, III et al. |
| 10,099,303 B2 | 10/2018 | Yoshida et al. |

(56) References Cited

U.S. PATENT DOCUMENTS

| | | |
|---|---|---|
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,111,679 B2 | 10/2018 | Baber et al. |
| 10,111,702 B2 | 10/2018 | Kostrzewski |
| 10,117,649 B2 | 11/2018 | Baxter, III et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,143,474 B2 | 12/2018 | Bucciaglia et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,154,841 B2 | 12/2018 | Weaner et al. |
| 10,159,482 B2 | 12/2018 | Swayze et al. |
| 10,159,483 B2 | 12/2018 | Beckman et al. |
| 10,163,589 B2 | 12/2018 | Zergiebel et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,616 B2 | 1/2019 | Murray et al. |
| 10,172,617 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,188,385 B2 | 1/2019 | Kerr et al. |
| 10,188,393 B2 | 1/2019 | Smith et al. |
| 10,188,394 B2 | 1/2019 | Shelton, IV et al. |
| D839,900 S | 2/2019 | Gan |
| 10,194,904 B2 | 2/2019 | Viola et al. |
| 10,194,910 B2 | 2/2019 | Shelton, IV et al. |
| 10,194,913 B2 | 2/2019 | Nalagatla et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,262 B2 | 2/2019 | Shelton, IV et al. |
| 10,219,832 B2 | 3/2019 | Bagwell et al. |
| 10,220,522 B2 | 3/2019 | Rockrohr |
| 10,226,249 B2 | 3/2019 | Jaworek et al. |
| 10,226,250 B2 | 3/2019 | Beckman et al. |
| 10,231,634 B2 | 3/2019 | Zand et al. |
| 10,231,653 B2 | 3/2019 | Bohm et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,058 B2 | 4/2019 | Omori et al. |
| 10,251,648 B2 | 4/2019 | Harris et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,074 B2 | 4/2019 | Shelton, IV et al. |
| 10,265,090 B2 | 4/2019 | Ingmanson et al. |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| 10,278,697 B2 | 5/2019 | Shelton, IV et al. |
| 10,278,702 B2 | 5/2019 | Shelton, IV et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,705 B2 | 5/2019 | Shelton, IV et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,577 B2 | 6/2019 | Laurent et al. |
| 10,314,582 B2 | 6/2019 | Shelton, IV et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,764 B2 | 6/2019 | Harris et al. |
| 10,327,765 B2 | 6/2019 | Timm et al. |

(56) References Cited

U.S. PATENT DOCUMENTS

| | | |
|---|---|---|
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,342,533 B2 | 7/2019 | Shelton, IV et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0087048 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0158593 A1 | 10/2002 | Henderson et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0212444 A1* | 11/2003 | Truckai et al. ............... 607/115 |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0085180 A1 | 5/2004 | Juang |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0124855 A1 | 6/2005 | Jaffe et al. |
| 2005/0125897 A1 | 6/2005 | Wyslucha et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |

(56) References Cited

U.S. PATENT DOCUMENTS

| | | |
|---|---|---|
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2006/0008787 A1 | 1/2006 | Hayman et al. |
| 2006/0015009 A1 | 1/2006 | Jaffe et al. |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0176031 A1 | 8/2006 | Forman et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0235368 A1 | 10/2006 | Oz |
| 2006/0244460 A1 | 11/2006 | Weaver |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0106113 A1 | 5/2007 | Ravo |
| 2007/0106317 A1 | 5/2007 | Shelton et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1* | 8/2007 | Shelton, IV ...... A61B 17/07207 227/176.1 |
| 2007/0175951 A1* | 8/2007 | Shelton, IV ...... A61B 17/07207 227/176.1 |
| 2007/0175955 A1 | 8/2007 | Shelton et al. |
| 2007/0179477 A1 | 8/2007 | Danger |
| 2007/0185545 A1 | 8/2007 | Duke |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0262592 A1 | 11/2007 | Hwang et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0042861 A1 | 2/2008 | Dacquay et al. |
| 2008/0051833 A1 | 2/2008 | Gramuglia et al. |

(56) References Cited

U.S. PATENT DOCUMENTS

| | | |
|---|---|---|
| 2008/0064921 A1 | 3/2008 | Larkin et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0234709 A1 | 9/2008 | Houser |
| 2008/0242939 A1 | 10/2008 | Johnston |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 * | 12/2008 | Shelton, IV ..... A61B 17/07207 227/180.1 |
| 2008/0297287 A1 | 12/2008 | Shachar et al. |
| 2008/0308602 A1 | 12/2008 | Timm et al. |
| 2008/0308603 A1 | 12/2008 | Shelton et al. |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0092651 A1 | 4/2009 | Shah et al. |
| 2009/0099579 A1 | 4/2009 | Nentwick et al. |
| 2009/0099876 A1 | 4/2009 | Whitman |
| 2009/0119011 A1 | 5/2009 | Kondo et al. |
| 2009/0131819 A1 | 5/2009 | Ritchie et al. |
| 2009/0132400 A1 | 5/2009 | Conway |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0221993 A1 | 9/2009 | Sohi et al. |
| 2009/0234273 A1 | 9/2009 | Intoccia et al. |
| 2009/0242610 A1 | 10/2009 | Shelton, IV et al. |
| 2009/0247368 A1 | 10/2009 | Chiang |
| 2009/0247901 A1 | 10/2009 | Zimmer |
| 2009/0248041 A1 | 10/2009 | Williams et al. |
| 2009/0253959 A1 | 10/2009 | Yoshie et al. |
| 2009/0255974 A1 | 10/2009 | Viola |
| 2009/0262078 A1 | 10/2009 | Pizzi |
| 2009/0270895 A1 | 10/2009 | Churchill et al. |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2010/0005035 A1 | 1/2010 | Carpenter et al. |
| 2010/0012703 A1 | 1/2010 | Calabrese et al. |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0036370 A1 | 2/2010 | Mirel et al. |
| 2010/0057118 A1 | 3/2010 | Dietz et al. |
| 2010/0065604 A1 | 3/2010 | Weng |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094340 A1 | 4/2010 | Stopek et al. |
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0179022 A1 | 7/2010 | Shirokoshi |
| 2010/0180711 A1 | 7/2010 | Kilibarda et al. |
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0241137 A1 | 9/2010 | Doyle et al. |
| 2010/0249497 A1 | 9/2010 | Peine et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1 | 11/2010 | Castro et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |

(56) References Cited

U.S. PATENT DOCUMENTS

| | | |
|---|---|---|
| 2011/0025311 A1 | 2/2011 | Chauvin et al. |
| 2011/0034910 A1 | 2/2011 | Ross et al. |
| 2011/0036891 A1 | 2/2011 | Zemlok et al. |
| 2011/0046667 A1 | 2/2011 | Culligan et al. |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0095064 A1 | 4/2011 | Taylor et al. |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0121049 A1 | 5/2011 | Malinouskas et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0230713 A1 | 9/2011 | Kleemann et al. |
| 2011/0238044 A1 | 9/2011 | Main et al. |
| 2011/0241597 A1 | 10/2011 | Zhu et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078139 A1 | 3/2012 | Aldridge et al. |
| 2012/0078244 A1 | 3/2012 | Worrell et al. |
| 2012/0080332 A1* | 4/2012 | Shelton, IV ............ A61B 90/92 206/339 |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0171539 A1 | 7/2012 | Rejman et al. |
| 2012/0175398 A1 | 7/2012 | Sandborn et al. |
| 2012/0197272 A1 | 8/2012 | Oray et al. |
| 2012/0211542 A1 | 8/2012 | Racenet |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2012/0303002 A1 | 11/2012 | Chowaniec et al. |
| 2013/0006227 A1 | 1/2013 | Takashino |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0105552 A1 | 5/2013 | Weir et al. |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153636 A1 | 6/2013 | Shelton, IV et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0172878 A1 | 7/2013 | Smith |
| 2013/0175317 A1 | 7/2013 | Yates et al. |
| 2013/0214025 A1 | 8/2013 | Zemlok et al. |
| 2013/0233906 A1 | 9/2013 | Hess et al. |
| 2013/0238021 A1 | 9/2013 | Gross et al. |
| 2013/0245704 A1 | 9/2013 | Koltz et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256379 A1 | 10/2013 | Schmid et al. |
| 2013/0256380 A1 | 10/2013 | Schmid et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0317753 A1 | 11/2013 | Kamen et al. |
| 2013/0324982 A1 | 12/2013 | Smith et al. |
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001235 A1* | 1/2014 | Shelton, IV ............ A61B 34/37 227/176.1 |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0012289 A1 | 1/2014 | Snow et al. |
| 2014/0012299 A1 | 1/2014 | Stoddard et al. |
| 2014/0014705 A1 | 1/2014 | Baxter, III |
| 2014/0018832 A1 | 1/2014 | Shelton, IV |
| 2014/0039549 A1 | 2/2014 | Belsky et al. |
| 2014/0048580 A1 | 2/2014 | Merchant et al. |
| 2014/0081176 A1 | 3/2014 | Hassan |
| 2014/0094681 A1 | 4/2014 | Valentine et al. |
| 2014/0100558 A1 | 4/2014 | Schmitz et al. |
| 2014/0107640 A1 | 4/2014 | Yates et al. |

(56) References Cited

U.S. PATENT DOCUMENTS

| | | |
|---|---|---|
| 2014/0110456 A1 | 4/2014 | Taylor |
| 2014/0115229 A1 | 4/2014 | Kothamasu et al. |
| 2014/0131418 A1 | 5/2014 | Kostrzewski |
| 2014/0151433 A1 | 6/2014 | Shelton, IV et al. |
| 2014/0158747 A1 | 6/2014 | Measamer et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0188159 A1 | 7/2014 | Steege |
| 2014/0207124 A1 | 7/2014 | Aldridge et al. |
| 2014/0207125 A1 | 7/2014 | Applegate et al. |
| 2014/0209658 A1 | 7/2014 | Skalla et al. |
| 2014/0224857 A1 | 8/2014 | Schmid |
| 2014/0228867 A1 | 8/2014 | Thomas et al. |
| 2014/0230595 A1 | 8/2014 | Butt et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0249573 A1 | 9/2014 | Arav |
| 2014/0263541 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291378 A1 | 10/2014 | Shelton, IV et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0309666 A1 | 10/2014 | Shelton, IV et al. |
| 2014/0330161 A1 | 11/2014 | Swayze et al. |
| 2014/0330579 A1 | 11/2014 | Cashman et al. |
| 2014/0367445 A1 | 12/2014 | Ingmanson et al. |
| 2014/0374130 A1 | 12/2014 | Nakamura et al. |
| 2014/0378950 A1 | 12/2014 | Chiu |
| 2015/0002089 A1 | 1/2015 | Rejman et al. |
| 2015/0008248 A1 | 1/2015 | Giordano et al. |
| 2015/0053737 A1 | 2/2015 | Leimbach et al. |
| 2015/0053742 A1 | 2/2015 | Shelton, IV et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083781 A1 | 3/2015 | Giordano et al. |
| 2015/0083782 A1 | 3/2015 | Scheib et al. |
| 2015/0088547 A1 | 3/2015 | Balram et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0108199 A1 | 4/2015 | Shelton, IV et al. |
| 2015/0122870 A1 | 5/2015 | Zemlok et al. |
| 2015/0134077 A1 | 5/2015 | Shelton, IV et al. |
| 2015/0136831 A1* | 5/2015 | Baxter, III ......... A61B 17/0644 227/176.1 |
| 2015/0148830 A1 | 5/2015 | Stulen et al. |
| 2015/0150554 A1 | 6/2015 | Soltz |
| 2015/0150620 A1 | 6/2015 | Miyamoto et al. |
| 2015/0173749 A1 | 6/2015 | Shelton, IV et al. |
| 2015/0173756 A1 | 6/2015 | Baxter, III et al. |
| 2015/0173760 A1* | 6/2015 | Shelton, IV ....... A61B 17/0644 227/177.1 |
| 2015/0173789 A1 | 6/2015 | Baxter, III et al. |
| 2015/0182220 A1 | 7/2015 | Yates et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196348 A1 | 7/2015 | Yates et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0222212 A1 | 8/2015 | Iwata |
| 2015/0223868 A1 | 8/2015 | Brandt et al. |
| 2015/0231409 A1 | 8/2015 | Racenet et al. |
| 2015/0238118 A1 | 8/2015 | Legassey et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272604 A1 | 10/2015 | Chowaniec et al. |
| 2015/0282809 A1* | 10/2015 | Shelton, IV ......... A61B 17/068 227/176.1 |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297229 A1 | 10/2015 | Schellin et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0302539 A1 | 10/2015 | Mazar et al. |
| 2015/0303417 A1 | 10/2015 | Koeder et al. |
| 2015/0313594 A1 | 11/2015 | Shelton, IV et al. |
| 2015/0324317 A1 | 11/2015 | Collins et al. |
| 2015/0327864 A1 | 11/2015 | Hodgkinson et al. |
| 2015/0336249 A1 | 11/2015 | Iwata et al. |
| 2015/0351762 A1 | 12/2015 | Vendely et al. |
| 2015/0352699 A1 | 12/2015 | Sakai et al. |
| 2015/0366585 A1 | 12/2015 | Lemay et al. |
| 2015/0372265 A1 | 12/2015 | Morisaku et al. |
| 2015/0374361 A1 | 12/2015 | Gettinger et al. |
| 2015/0374369 A1 | 12/2015 | Yates et al. |
| 2015/0374371 A1 | 12/2015 | Richard et al. |
| 2015/0374372 A1 | 12/2015 | Zergiebel et al. |
| 2015/0374375 A1 | 12/2015 | Shelton, IV et al. |
| 2015/0374378 A1 | 12/2015 | Giordano et al. |
| 2016/0000430 A1 | 1/2016 | Ming et al. |
| 2016/0000431 A1 | 1/2016 | Giordano et al. |
| 2016/0000437 A1 | 1/2016 | Giordano et al. |
| 2016/0000438 A1 | 1/2016 | Swayze et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0023342 A1 | 1/2016 | Koenig et al. |
| 2016/0030042 A1 | 2/2016 | Heinrich et al. |
| 2016/0051257 A1 | 2/2016 | Shelton, IV et al. |
| 2016/0058439 A1* | 3/2016 | Shelton, IV ..... A61B 17/07207 227/176.1 |
| 2016/0058443 A1 | 3/2016 | Yates et al. |
| 2016/0066913 A1 | 3/2016 | Swayze et al. |
| 2016/0069449 A1 | 3/2016 | Kanai et al. |
| 2016/0074040 A1 | 3/2016 | Widenhouse et al. |
| 2016/0074103 A1 | 3/2016 | Sartor |
| 2016/0082161 A1 | 3/2016 | Zilberman et al. |
| 2016/0089137 A1 | 3/2016 | Hess et al. |
| 2016/0089146 A1 | 3/2016 | Harris et al. |
| 2016/0089149 A1 | 3/2016 | Harris et al. |
| 2016/0089198 A1 | 3/2016 | Arya et al. |
| 2016/0095585 A1 | 4/2016 | Zergiebel et al. |

(56) References Cited

U.S. PATENT DOCUMENTS

| | | |
|---|---|---|
| 2016/0106424 A1* | 4/2016 | Yates .................... H02J 7/0044 227/175.1 |
| 2016/0106425 A1* | 4/2016 | Yates .................... H02J 7/0047 320/113 |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0120594 A1* | 5/2016 | Privitera ............ A61B 18/1445 606/41 |
| 2016/0166248 A1 | 6/2016 | Deville et al. |
| 2016/0166256 A1 | 6/2016 | Baxter, III et al. |
| 2016/0166308 A1 | 6/2016 | Manwaring et al. |
| 2016/0174974 A1 | 6/2016 | Schmid et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192977 A1 | 7/2016 | Manwaring et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199089 A1 | 7/2016 | Hess et al. |
| 2016/0199956 A1 | 7/2016 | Shelton, IV et al. |
| 2016/0206310 A1 | 7/2016 | Shelton, IV |
| 2016/0206314 A1 | 7/2016 | Scheib et al. |
| 2016/0220248 A1 | 8/2016 | Timm et al. |
| 2016/0220266 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235409 A1 | 8/2016 | Shelton, IV et al. |
| 2016/0235467 A1 | 8/2016 | Godara et al. |
| 2016/0235494 A1 | 8/2016 | Shelton, IV et al. |
| 2016/0242777 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249910 A1 | 9/2016 | Shelton, IV et al. |
| 2016/0249922 A1 | 9/2016 | Morgan et al. |
| 2016/0256071 A1 | 9/2016 | Shelton, IV et al. |
| 2016/0256154 A1 | 9/2016 | Shelton, IV et al. |
| 2016/0256159 A1 | 9/2016 | Pinjala et al. |
| 2016/0256160 A1 | 9/2016 | Shelton, IV et al. |
| 2016/0256185 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0270780 A1 | 9/2016 | Hall et al. |
| 2016/0278765 A1 | 9/2016 | Shelton, IV et al. |
| 2016/0287249 A1 | 10/2016 | Alexander, III et al. |
| 2016/0287250 A1 | 10/2016 | Shelton, IV et al. |
| 2016/0287253 A1 | 10/2016 | Shelton, IV et al. |
| 2016/0287279 A1 | 10/2016 | Bovay et al. |
| 2016/0310143 A1 | 10/2016 | Bettuchi |
| 2016/0331375 A1 | 11/2016 | Shelton, IV et al. |
| 2016/0345976 A1 | 12/2016 | Gonzalez et al. |
| 2016/0346034 A1 | 12/2016 | Arya et al. |
| 2016/0354085 A1 | 12/2016 | Shelton, IV et al. |
| 2016/0367122 A1 | 12/2016 | Ichimura et al. |
| 2016/0367246 A1 | 12/2016 | Baxter, III et al. |
| 2016/0367255 A1 | 12/2016 | Wise et al. |
| 2016/0374672 A1 | 12/2016 | Bear et al. |
| 2016/0374675 A1 | 12/2016 | Shelton, IV et al. |
| 2017/0000485 A1 | 1/2017 | Shelton, IV et al. |
| 2017/0007236 A1 | 1/2017 | Shelton, IV et al. |
| 2017/0007237 A1 | 1/2017 | Yates et al. |
| 2017/0007238 A1 | 1/2017 | Yates et al. |
| 2017/0007239 A1 | 1/2017 | Shelton, IV |
| 2017/0007241 A1 | 1/2017 | Shelton, IV et al. |
| 2017/0007243 A1 | 1/2017 | Shelton, IV et al. |
| 2017/0007244 A1 | 1/2017 | Shelton, IV et al. |
| 2017/0007245 A1 | 1/2017 | Shelton, IV et al. |
| 2017/0007246 A1 | 1/2017 | Shelton, IV et al. |
| 2017/0007247 A1 | 1/2017 | Shelton, IV et al. |
| 2017/0007248 A1 | 1/2017 | Shelton, IV et al. |
| 2017/0007249 A1 | 1/2017 | Shelton, IV et al. |
| 2017/0007250 A1 | 1/2017 | Shelton, IV et al. |
| 2017/0007251 A1 | 1/2017 | Yates et al. |
| 2017/0007347 A1 | 1/2017 | Jaworek et al. |
| 2017/0014125 A1 | 1/2017 | Shelton, IV et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0049444 A1 | 2/2017 | Schellin et al. |
| 2017/0049447 A1 | 2/2017 | Barton et al. |
| 2017/0049448 A1 | 2/2017 | Widenhouse et al. |
| 2017/0055986 A1 | 3/2017 | Harris et al. |
| 2017/0055991 A1 | 3/2017 | Kang |
| 2017/0055998 A1 | 3/2017 | Baxter, III et al. |
| 2017/0055999 A1 | 3/2017 | Baxter, III et al. |
| 2017/0056000 A1 | 3/2017 | Nalagatla et al. |
| 2017/0056002 A1 | 3/2017 | Nalagatla et al. |
| 2017/0056005 A1 | 3/2017 | Shelton, IV et al. |
| 2017/0056006 A1 | 3/2017 | Shelton, IV et al. |
| 2017/0056007 A1 | 3/2017 | Eckert et al. |
| 2017/0056014 A1 | 3/2017 | Harris et al. |
| 2017/0079642 A1 | 3/2017 | Overmyer et al. |
| 2017/0079643 A1 | 3/2017 | Yates et al. |
| 2017/0086827 A1 | 3/2017 | Vendely et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086832 A1 | 3/2017 | Harris et al. |
| 2017/0086836 A1 | 3/2017 | Harris et al. |
| 2017/0086837 A1 | 3/2017 | Vendely et al. |
| 2017/0086838 A1 | 3/2017 | Harris et al. |
| 2017/0086842 A1 | 3/2017 | Shelton, IV et al. |
| 2017/0086843 A1 | 3/2017 | Vendely et al. |
| 2017/0086844 A1 | 3/2017 | Vendely et al. |
| 2017/0095250 A1 | 4/2017 | Kostrzewski et al. |
| 2017/0119386 A1 | 5/2017 | Scheib et al. |
| 2017/0119387 A1 | 5/2017 | Dalessandro et al. |
| 2017/0119390 A1 | 5/2017 | Schellin et al. |
| 2017/0119392 A1 | 5/2017 | Shelton, IV et al. |
| 2017/0119397 A1 | 5/2017 | Harris et al. |
| 2017/0135695 A1 | 5/2017 | Shelton, IV et al. |
| 2017/0135697 A1 | 5/2017 | Mozdzierz et al. |
| 2017/0150983 A1 | 6/2017 | Ingmanson et al. |
| 2017/0172382 A1 | 6/2017 | Nir et al. |
| 2017/0172550 A1 | 6/2017 | Mukherjee et al. |
| 2017/0172662 A1 | 6/2017 | Panescu et al. |
| 2017/0172672 A1 | 6/2017 | Bailey et al. |
| 2017/0182211 A1 | 6/2017 | Raxworthy et al. |
| 2017/0189019 A1 | 7/2017 | Harris et al. |
| 2017/0196558 A1 | 7/2017 | Morgan et al. |
| 2017/0196561 A1 | 7/2017 | Shelton, IV et al. |
| 2017/0196562 A1 | 7/2017 | Shelton, IV et al. |
| 2017/0196637 A1 | 7/2017 | Shelton, IV et al. |
| 2017/0196649 A1 | 7/2017 | Yates et al. |
| 2017/0202596 A1 | 7/2017 | Shelton, IV et al. |
| 2017/0209145 A1 | 7/2017 | Swayze et al. |
| 2017/0209146 A1 | 7/2017 | Yates et al. |
| 2017/0209226 A1 | 7/2017 | Overmyer et al. |
| 2017/0215881 A1 | 8/2017 | Shelton, IV et al. |
| 2017/0215943 A1 | 8/2017 | Allen, IV |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224334 A1 | 8/2017 | Worthington et al. |
| 2017/0224335 A1 | 8/2017 | Weaner et al. |
| 2017/0224339 A1 | 8/2017 | Huang et al. |
| 2017/0224342 A1 | 8/2017 | Worthington et al. |
| 2017/0224343 A1 | 8/2017 | Baxter, III et al. |
| 2017/0231626 A1 | 8/2017 | Shelton, IV et al. |
| 2017/0231627 A1 | 8/2017 | Shelton, IV et al. |
| 2017/0231628 A1 | 8/2017 | Shelton, IV et al. |
| 2017/0238928 A1 | 8/2017 | Morgan et al. |
| 2017/0238929 A1 | 8/2017 | Yates et al. |
| 2017/0245952 A1 | 8/2017 | Shelton, IV et al. |
| 2017/0249431 A1 | 8/2017 | Shelton, IV et al. |
| 2017/0258469 A1 | 9/2017 | Shelton, IV et al. |

(56) References Cited

U.S. PATENT DOCUMENTS

| | | |
|---|---|---|
| 2017/0265856 A1 | 9/2017 | Shelton, IV et al. |
| 2017/0281155 A1 | 10/2017 | Shelton, IV et al. |
| 2017/0281161 A1 | 10/2017 | Shelton, IV et al. |
| 2017/0281162 A1 | 10/2017 | Shelton, IV et al. |
| 2017/0281164 A1 | 10/2017 | Harris et al. |
| 2017/0281166 A1 | 10/2017 | Morgan et al. |
| 2017/0281167 A1 | 10/2017 | Shelton, IV et al. |
| 2017/0281168 A1 | 10/2017 | Shelton, IV et al. |
| 2017/0281169 A1 | 10/2017 | Harris et al. |
| 2017/0281171 A1 | 10/2017 | Shelton, IV et al. |
| 2017/0281172 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281177 A1 | 10/2017 | Harris et al. |
| 2017/0281179 A1 | 10/2017 | Shelton, IV et al. |
| 2017/0281180 A1 | 10/2017 | Morgan et al. |
| 2017/0281183 A1 | 10/2017 | Miller et al. |
| 2017/0281184 A1 | 10/2017 | Shelton, IV et al. |
| 2017/0281185 A1 | 10/2017 | Miller et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290584 A1 | 10/2017 | Jasemian et al. |
| 2017/0290585 A1 | 10/2017 | Shelton, IV et al. |
| 2017/0296169 A1 | 10/2017 | Yates et al. |
| 2017/0296170 A1 | 10/2017 | Shelton, IV et al. |
| 2017/0296171 A1 | 10/2017 | Shelton, IV et al. |
| 2017/0296172 A1 | 10/2017 | Harris et al. |
| 2017/0296173 A1 | 10/2017 | Shelton, IV et al. |
| 2017/0296177 A1 | 10/2017 | Harris et al. |
| 2017/0296178 A1 | 10/2017 | Miller et al. |
| 2017/0296179 A1 | 10/2017 | Shelton, IV et al. |
| 2017/0296180 A1 | 10/2017 | Harris et al. |
| 2017/0296183 A1 | 10/2017 | Shelton, IV et al. |
| 2017/0296185 A1 | 10/2017 | Swensgard et al. |
| 2017/0296189 A1 | 10/2017 | Vendely et al. |
| 2017/0296190 A1 | 10/2017 | Aronhalt et al. |
| 2017/0296191 A1 | 10/2017 | Shelton, IV et al. |
| 2017/0296213 A1 | 10/2017 | Swensgard et al. |
| 2017/0311944 A1 | 11/2017 | Morgan et al. |
| 2017/0311949 A1 | 11/2017 | Shelton, IV |
| 2017/0311950 A1 | 11/2017 | Shelton, IV et al. |
| 2017/0312041 A1 | 11/2017 | Giordano et al. |
| 2017/0312042 A1 | 11/2017 | Giordano et al. |
| 2017/0319201 A1 | 11/2017 | Morgan et al. |
| 2017/0319207 A1 | 11/2017 | Shelton, IV et al. |
| 2017/0319209 A1 | 11/2017 | Morgan et al. |
| 2017/0325813 A1 | 11/2017 | Aranyi et al. |
| 2017/0333034 A1 | 11/2017 | Morgan et al. |
| 2017/0333035 A1 | 11/2017 | Morgan et al. |
| 2017/0333070 A1 | 11/2017 | Laurent et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0354415 A1 | 12/2017 | Casasanta, Jr. et al. |
| 2017/0360441 A1 | 12/2017 | Sgroi |
| 2017/0360442 A1 | 12/2017 | Shelton, IV et al. |
| 2017/0367695 A1 | 12/2017 | Shelton, IV et al. |
| 2017/0367696 A1 | 12/2017 | Shelton, IV et al. |
| 2017/0367697 A1 | 12/2017 | Shelton, IV et al. |
| 2017/0367698 A1 | 12/2017 | Shelton, IV et al. |
| 2017/0367699 A1 | 12/2017 | Shelton, IV et al. |
| 2017/0367700 A1 | 12/2017 | Leimbach et al. |
| 2017/0367991 A1 | 12/2017 | Widenhouse et al. |
| 2018/0000483 A1 | 1/2018 | Leimbach et al. |
| 2018/0000545 A1 | 1/2018 | Giordano et al. |
| 2018/0008270 A1 | 1/2018 | Moore et al. |
| 2018/0008271 A1 | 1/2018 | Moore et al. |
| 2018/0008356 A1 | 1/2018 | Giordano et al. |
| 2018/0008357 A1 | 1/2018 | Giordano et al. |
| 2018/0028184 A1 | 2/2018 | Shelton, IV et al. |
| 2018/0028185 A1 | 2/2018 | Shelton, IV et al. |
| 2018/0042611 A1 | 2/2018 | Swayze et al. |
| 2018/0049824 A1 | 2/2018 | Harris et al. |
| 2018/0049883 A1 | 2/2018 | Moskowitz et al. |
| 2018/0055513 A1 | 3/2018 | Shelton, IV et al. |
| 2018/0055524 A1 | 3/2018 | Shelton, IV et al. |
| 2018/0055525 A1 | 3/2018 | Shelton, IV et al. |
| 2018/0055526 A1 | 3/2018 | Shelton, IV et al. |
| 2018/0064437 A1 | 3/2018 | Yates et al. |
| 2018/0064440 A1 | 3/2018 | Shelton, IV et al. |
| 2018/0064441 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070939 A1 | 3/2018 | Giordano et al. |
| 2018/0070942 A1 | 3/2018 | Shelton, IV et al. |
| 2018/0078248 A1 | 3/2018 | Swayze et al. |
| 2018/0085116 A1 | 3/2018 | Yates et al. |
| 2018/0085117 A1 | 3/2018 | Shelton, IV et al. |
| 2018/0103952 A1 | 4/2018 | Aronhalt et al. |
| 2018/0103953 A1 | 4/2018 | Shelton, IV et al. |
| 2018/0103955 A1 | 4/2018 | Shelton, IV et al. |
| 2018/0110516 A1 | 4/2018 | Baxter et al. |
| 2018/0110518 A1 | 4/2018 | Overmyer et al. |
| 2018/0110519 A1 | 4/2018 | Lytle, IV et al. |
| 2018/0110520 A1 | 4/2018 | Shelton, IV et al. |
| 2018/0110521 A1 | 4/2018 | Shelton, IV et al. |
| 2018/0110522 A1 | 4/2018 | Shelton, IV et al. |
| 2018/0110523 A1 | 4/2018 | Shelton, IV |
| 2018/0110574 A1 | 4/2018 | Shelton, IV et al. |
| 2018/0110575 A1 | 4/2018 | Shelton, IV et al. |
| 2018/0114591 A1 | 4/2018 | Pribanic et al. |
| 2018/0116658 A1 | 5/2018 | Aronhalt, IV et al. |
| 2018/0116662 A1 | 5/2018 | Shelton, IV et al. |
| 2018/0116665 A1 | 5/2018 | Hall et al. |
| 2018/0125481 A1 | 5/2018 | Yates et al. |
| 2018/0125487 A1 | 5/2018 | Beardsley |
| 2018/0125488 A1 | 5/2018 | Morgan et al. |
| 2018/0125489 A1 | 5/2018 | Leimbach et al. |
| 2018/0125590 A1 | 5/2018 | Giordano et al. |
| 2018/0126504 A1 | 5/2018 | Shelton, IV et al. |
| 2018/0132845 A1 | 5/2018 | Schmid et al. |
| 2018/0132850 A1 | 5/2018 | Leimbach et al. |
| 2018/0132851 A1 | 5/2018 | Hall et al. |
| 2018/0132952 A1 | 5/2018 | Spivey et al. |
| 2018/0133856 A1 | 5/2018 | Shelton, IV et al. |
| 2018/0140299 A1 | 5/2018 | Weaner et al. |
| 2018/0140368 A1 | 5/2018 | Shelton, IV et al. |
| 2018/0146960 A1 | 5/2018 | Shelton, IV et al. |
| 2018/0153542 A1 | 6/2018 | Shelton, IV et al. |
| 2018/0161034 A1 | 6/2018 | Scheib et al. |
| 2018/0168575 A1 | 6/2018 | Simms et al. |
| 2018/0168576 A1 | 6/2018 | Hunter et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |
| 2018/0168581 A1 | 6/2018 | Hunter et al. |
| 2018/0168582 A1 | 6/2018 | Swayze et al. |
| 2018/0168583 A1 | 6/2018 | Hunter et al. |
| 2018/0168584 A1 | 6/2018 | Harris et al. |
| 2018/0168585 A1 | 6/2018 | Shelton, IV et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168595 A1 | 6/2018 | Overmyer et al. |
| 2018/0168596 A1 | 6/2018 | Beckman et al. |
| 2018/0168597 A1 | 6/2018 | Fanelli et al. |
| 2018/0168598 A1 | 6/2018 | Shelton, IV et al. |
| 2018/0168599 A1 | 6/2018 | Bakos et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |

(56) References Cited

U.S. PATENT DOCUMENTS

| | | |
|---|---|---|
| 2018/0168610 A1 | 6/2018 | Shelton, IV et al. |
| 2018/0168611 A1 | 6/2018 | Shelton, IV et al. |
| 2018/0168612 A1 | 6/2018 | Shelton, IV et al. |
| 2018/0168613 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168616 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168620 A1 | 6/2018 | Huang et al. |
| 2018/0168621 A1 | 6/2018 | Shelton, IV et al. |
| 2018/0168622 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168634 A1 | 6/2018 | Harris et al. |
| 2018/0168635 A1 | 6/2018 | Shelton, IV et al. |
| 2018/0168636 A1 | 6/2018 | Shelton, IV et al. |
| 2018/0168637 A1 | 6/2018 | Harris et al. |
| 2018/0168638 A1 | 6/2018 | Harris et al. |
| 2018/0168639 A1 | 6/2018 | Shelton, IV et al. |
| 2018/0168640 A1 | 6/2018 | Shelton, IV et al. |
| 2018/0168641 A1 | 6/2018 | Harris et al. |
| 2018/0168642 A1 | 6/2018 | Shelton, IV et al. |
| 2018/0168643 A1 | 6/2018 | Shelton, IV et al. |
| 2018/0168644 A1 | 6/2018 | Shelton, IV et al. |
| 2018/0168645 A1 | 6/2018 | Shelton, IV et al. |
| 2018/0168646 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0199940 A1 | 7/2018 | Zergiebel et al. |
| 2018/0206843 A1 | 7/2018 | Yates et al. |
| 2018/0206906 A1 | 7/2018 | Moua et al. |
| 2018/0214147 A1 | 8/2018 | Merchant et al. |
| 2018/0221046 A1 | 8/2018 | Demmy et al. |
| 2018/0221050 A1 | 8/2018 | Kostrzewski et al. |
| 2018/0228490 A1 | 8/2018 | Richard et al. |
| 2018/0250001 A1 | 9/2018 | Aronhalt et al. |
| 2018/0256184 A1 | 9/2018 | Shelton, IV et al. |
| 2018/0271520 A1 | 9/2018 | Shelton, IV et al. |
| 2018/0273597 A1 | 9/2018 | Stimson |
| 2018/0280020 A1 | 10/2018 | Hess et al. |
| 2018/0280021 A1 | 10/2018 | Timm et al. |
| 2018/0280023 A1 | 10/2018 | Timm et al. |
| 2018/0286274 A1 | 10/2018 | Kamiguchi et al. |
| 2018/0289369 A1 | 10/2018 | Shelton, IV et al. |
| 2018/0296211 A1 | 10/2018 | Timm et al. |
| 2018/0296215 A1 | 10/2018 | Baxter, III et al. |
| 2018/0296216 A1 | 10/2018 | Shelton, IV et al. |
| 2018/0296217 A1 | 10/2018 | Moore et al. |
| 2018/0303481 A1 | 10/2018 | Shelton, IV et al. |
| 2018/0303482 A1 | 10/2018 | Shelton, IV et al. |
| 2018/0310931 A1 | 11/2018 | Hall et al. |
| 2018/0311002 A1 | 11/2018 | Giordano et al. |
| 2018/0317907 A1 | 11/2018 | Kostrzewski |
| 2018/0317916 A1 | 11/2018 | Wixey |
| 2018/0317917 A1 | 11/2018 | Huang et al. |
| 2018/0317918 A1 | 11/2018 | Shelton, IV |
| 2018/0317919 A1 | 11/2018 | Shelton, IV et al. |
| 2018/0333155 A1 | 11/2018 | Hall et al. |
| 2018/0333169 A1 | 11/2018 | Leimbach et al. |
| 2018/0344319 A1 | 12/2018 | Shelton, IV et al. |
| 2018/0353170 A1 | 12/2018 | Overmyer et al. |
| 2018/0353176 A1 | 12/2018 | Shelton, IV et al. |
| 2018/0353177 A1 | 12/2018 | Shelton, IV et al. |
| 2018/0353178 A1 | 12/2018 | Shelton, IV et al. |
| 2018/0353179 A1 | 12/2018 | Shelton, IV et al. |
| 2018/0360443 A1 | 12/2018 | Shelton, IV et al. |
| 2018/0360444 A1 | 12/2018 | Harris et al. |
| 2018/0360445 A1 | 12/2018 | Shelton, IV et al. |
| 2018/0360446 A1 | 12/2018 | Shelton, IV et al. |
| 2018/0360447 A1 | 12/2018 | Shelton, IV et al. |
| 2018/0360448 A1 | 12/2018 | Harris et al. |
| 2018/0360449 A1 | 12/2018 | Shelton, IV et al. |
| 2018/0360450 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360455 A1 | 12/2018 | Shelton, IV et al. |
| 2018/0360456 A1 | 12/2018 | Shelton, IV et al. |
| 2018/0360469 A1 | 12/2018 | Shelton, IV et al. |
| 2018/0360471 A1 | 12/2018 | Parfett et al. |
| 2018/0360472 A1 | 12/2018 | Harris et al. |
| 2018/0360473 A1 | 12/2018 | Shelton, IV et al. |
| 2018/0360549 A1 | 12/2018 | Hares et al. |
| 2018/0368822 A1 | 12/2018 | Shelton, IV et al. |
| 2018/0368833 A1 | 12/2018 | Shelton, IV et al. |
| 2018/0368837 A1 | 12/2018 | Morgan et al. |
| 2018/0368838 A1 | 12/2018 | Shelton, IV et al. |
| 2018/0368839 A1 | 12/2018 | Shelton, IV et al. |
| 2018/0368840 A1 | 12/2018 | Shelton, IV et al. |
| 2018/0368841 A1 | 12/2018 | Shelton, IV et al. |
| 2018/0368842 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0368845 A1 | 12/2018 | Bakos et al. |
| 2018/0368846 A1 | 12/2018 | Shelton, IV et al. |
| 2018/0368847 A1 | 12/2018 | Shelton, IV et al. |
| 2019/0000446 A1 | 1/2019 | Shelton, IV et al. |
| 2019/0000447 A1 | 1/2019 | Shelton, IV et al. |
| 2019/0000448 A1 | 1/2019 | Shelton, IV et al. |
| 2019/0000450 A1 | 1/2019 | Shelton, IV et al. |
| 2019/0000454 A1 | 1/2019 | Swayze et al. |
| 2019/0000456 A1 | 1/2019 | Shelton, IV et al. |
| 2019/0000457 A1 | 1/2019 | Shelton, IV et al. |
| 2019/0000458 A1 | 1/2019 | Shelton, IV et al. |
| 2019/0000459 A1 | 1/2019 | Shelton, IV et al. |
| 2019/0000460 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000463 A1 | 1/2019 | Shelton, IV et al. |
| 2019/0000465 A1 | 1/2019 | Shelton, IV et al. |
| 2019/0000466 A1 | 1/2019 | Shelton, IV et al. |
| 2019/0000467 A1 | 1/2019 | Shelton, IV et al. |
| 2019/0000469 A1 | 1/2019 | Shelton, IV et al. |
| 2019/0000470 A1 | 1/2019 | Yates et al. |
| 2019/0000471 A1 | 1/2019 | Shelton, IV et al. |
| 2019/0000472 A1 | 1/2019 | Shelton, IV et al. |
| 2019/0000473 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000478 A1 | 1/2019 | Messerly et al. |
| 2019/0000479 A1 | 1/2019 | Harris et al. |
| 2019/0000525 A1 | 1/2019 | Messerly et al. |
| 2019/0000528 A1 | 1/2019 | Yates et al. |
| 2019/0000530 A1 | 1/2019 | Yates et al. |
| 2019/0000534 A1 | 1/2019 | Messerly et al. |
| 2019/0000565 A1 | 1/2019 | Shelton, IV et al. |
| 2019/0008509 A1 | 1/2019 | Shelton, IV et al. |
| 2019/0008511 A1 | 1/2019 | Kerr et al. |
| 2019/0015096 A1 | 1/2019 | Shelton, IV et al. |
| 2019/0015102 A1 | 1/2019 | Baber et al. |
| 2019/0015165 A1 | 1/2019 | Giordano et al. |
| 2019/0029675 A1 | 1/2019 | Yates et al. |
| 2019/0029676 A1 | 1/2019 | Yates et al. |
| 2019/0029677 A1 | 1/2019 | Yates et al. |
| 2019/0029678 A1 | 1/2019 | Shelton, IV et al. |
| 2019/0029681 A1 | 1/2019 | Swayze et al. |
| 2019/0029682 A1 | 1/2019 | Huitema et al. |
| 2019/0029701 A1 | 1/2019 | Shelton, IV et al. |
| 2019/0033955 A1 | 1/2019 | Leimbach et al. |

(56) References Cited

U.S. PATENT DOCUMENTS

| | | |
|---|---|---|
| 2019/0038279 A1 | 2/2019 | Shelton, IV et al. |
| 2019/0038281 A1 | 2/2019 | Shelton, IV et al. |
| 2019/0038282 A1 | 2/2019 | Shelton, IV et al. |
| 2019/0038283 A1 | 2/2019 | Shelton, IV et al. |
| 2019/0038371 A1 | 2/2019 | Wixey et al. |
| 2019/0046187 A1 | 2/2019 | Yates et al. |
| 2019/0059886 A1 | 2/2019 | Shelton, IV et al. |
| 2019/0090870 A1 | 3/2019 | Shelton, IV et al. |
| 2019/0090871 A1 | 3/2019 | Shelton, IV et al. |
| 2019/0099177 A1 | 4/2019 | Yates et al. |
| 2019/0099178 A1 | 4/2019 | Leimbach et al. |
| 2019/0099179 A1 | 4/2019 | Leimbach et al. |
| 2019/0099180 A1 | 4/2019 | Leimbach et al. |
| 2019/0099181 A1 | 4/2019 | Shelton, IV et al. |
| 2019/0099182 A1 | 4/2019 | Bakos et al. |
| 2019/0099183 A1 | 4/2019 | Leimbach et al. |
| 2019/0099184 A1 | 4/2019 | Setser et al. |
| 2019/0099224 A1 | 4/2019 | Leimbach et al. |
| 2019/0099229 A1 | 4/2019 | Spivey et al. |
| 2019/0102930 A1 | 4/2019 | Leimbach et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105038 A1 | 4/2019 | Schmid et al. |
| 2019/0105039 A1 | 4/2019 | Morgan et al. |
| 2019/0105043 A1 | 4/2019 | Jaworek et al. |
| 2019/0105044 A1 | 4/2019 | Shelton, IV et al. |
| 2019/0105049 A1 | 4/2019 | Moore et al. |
| 2019/0110791 A1 | 4/2019 | Shelton, IV et al. |
| 2019/0110792 A1 | 4/2019 | Shelton, IV et al. |
| 2019/0110793 A1 | 4/2019 | Parihar et al. |
| 2019/0117216 A1 | 4/2019 | Overmyer et al. |
| 2019/0117217 A1 | 4/2019 | Overmyer et al. |
| 2019/0117222 A1 | 4/2019 | Shelton, IV et al. |
| 2019/0117224 A1 | 4/2019 | Setser et al. |
| 2019/0117225 A1 | 4/2019 | Moore et al. |
| 2019/0125343 A1 | 5/2019 | Wise et al. |
| 2019/0125344 A1 | 5/2019 | DiNardo et al. |
| 2019/0125345 A1 | 5/2019 | Baber et al. |
| 2019/0125365 A1 | 5/2019 | Parfett et al. |
| 2019/0125380 A1 | 5/2019 | Hunter et al. |
| 2019/0125475 A1 | 5/2019 | Wise et al. |
| 2019/0133585 A1 | 5/2019 | Smith et al. |
| 2019/0142421 A1 | 5/2019 | Shelton, IV |
| 2019/0183490 A1 | 6/2019 | Shelton, IV et al. |
| 2019/0183491 A1 | 6/2019 | Shelton, IV et al. |
| 2019/0183492 A1 | 6/2019 | Shelton, IV et al. |
| 2019/0183493 A1 | 6/2019 | Shelton, IV et al. |
| 2019/0183494 A1 | 6/2019 | Shelton, IV et al. |
| 2019/0183495 A1 | 6/2019 | Shelton, IV et al. |
| 2019/0183496 A1 | 6/2019 | Shelton, IV et al. |
| 2019/0183497 A1 | 6/2019 | Shelton, IV et al. |
| 2019/0183498 A1 | 6/2019 | Shelton, IV et al. |
| 2019/0183499 A1 | 6/2019 | Shelton, IV et al. |
| 2019/0183500 A1 | 6/2019 | Shelton, IV et al. |
| 2019/0183501 A1 | 6/2019 | Shelton, IV et al. |
| 2019/0183502 A1 | 6/2019 | Shelton, IV et al. |
| 2019/0183503 A1 | 6/2019 | Shelton, IV et al. |
| 2019/0183504 A1 | 6/2019 | Shelton, IV et al. |
| 2019/0183505 A1 | 6/2019 | Vendely et al. |
| 2019/0183592 A1 | 6/2019 | Shelton, IV et al. |
| 2019/0183594 A1 | 6/2019 | Shelton, IV et al. |
| 2019/0183597 A1 | 6/2019 | Shelton, IV et al. |
| 2019/0192137 A1 | 6/2019 | Shelton, IV et al. |
| 2019/0192138 A1 | 6/2019 | Shelton, IV et al. |
| 2019/0192141 A1 | 6/2019 | Shelton, IV et al. |
| 2019/0192144 A1 | 6/2019 | Parfett et al. |
| 2019/0192145 A1 | 6/2019 | Shelton, IV et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192149 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0192152 A1 | 6/2019 | Morgan et al. |
| 2019/0192153 A1 | 6/2019 | Shelton, IV et al. |
| 2019/0192154 A1 | 6/2019 | Shelton, IV et al. |
| 2019/0192155 A1 | 6/2019 | Shelton, IV et al. |
| 2019/0192227 A1 | 6/2019 | Shelton, IV et al. |
| 2019/0192235 A1 | 6/2019 | Harris et al. |
| 2019/0192236 A1 | 6/2019 | Shelton, IV et al. |

FOREIGN PATENT DOCUMENTS

| | | |
|---|---|---|
| CA | 1015829 A | 8/1977 |
| CA | 1125615 A | 6/1982 |
| CA | 2520413 A1 | 3/2007 |
| CA | 2725181 A1 | 11/2007 |
| CA | 2664874 A1 | 11/2009 |
| CA | 2940510 A1 | 8/2015 |
| CN | 1163558 A | 10/1997 |
| CN | 2488482 Y | 5/2002 |
| CN | 1634601 A | 7/2005 |
| CN | 2716900 Y | 8/2005 |
| CN | 2738962 Y | 11/2005 |
| CN | 2868212 Y | 2/2007 |
| CN | 200942099 Y | 9/2007 |
| CN | 200991269 Y | 12/2007 |
| CN | 201001747 Y | 1/2008 |
| CN | 101143105 A | 3/2008 |
| CN | 201029899 Y | 3/2008 |
| CN | 101522120 A | 9/2009 |
| CN | 101669833 A | 3/2010 |
| CN | 101721236 A | 6/2010 |
| CN | 101828940 A | 9/2010 |
| CN | 101873834 A | 10/2010 |
| CN | 201719298 U | 1/2011 |
| CN | 102038532 A | 5/2011 |
| CN | 201879759 U | 6/2011 |
| CN | 201949071 U | 8/2011 |
| CN | 101779977 B | 12/2011 |
| CN | 101912284 B | 7/2012 |
| CN | 202313537 U | 7/2012 |
| CN | 202397539 U | 8/2012 |
| CN | 202426586 U | 9/2012 |
| CN | 202489990 U | 10/2012 |
| CN | 102835977 A | 12/2012 |
| CN | 203564285 U | 4/2014 |
| CN | 203564287 U | 4/2014 |
| CN | 203597997 U | 5/2014 |
| CN | 103829983 A | 6/2014 |
| CN | 103908313 A | 7/2014 |
| CN | 203736251 U | 7/2014 |
| CN | 103981635 A | 8/2014 |
| CN | 203815517 U | 9/2014 |
| CN | 102783741 B | 10/2014 |
| CN | 102973300 B | 10/2014 |
| CN | 104337556 A | 2/2015 |
| CN | 204158441 U | 2/2015 |
| CN | 102469995 B | 3/2015 |
| CN | 204636451 U | 9/2015 |
| CN | 103860225 B | 3/2016 |
| CN | 103750872 B | 5/2016 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19534043 A1 | 3/1997 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 202004012389 U1 | 9/2004 |
| DE | 10314072 A1 | 10/2004 |
| DE | 102004014011 A1 | 10/2005 |
| DE | 102004063606 A1 | 7/2006 |
| DE | 202007003114 U1 | 6/2007 |
| DE | 102010013150 A1 | 9/2011 |
| EP | 0000756 A1 | 2/1979 |
| EP | 0122046 A1 | 10/1984 |
| EP | 0129442 B1 | 11/1987 |
| EP | 0255631 A1 | 2/1988 |

(56) References Cited

FOREIGN PATENT DOCUMENTS

| | | |
|---|---|---|
| EP | 0169044 B1 | 6/1991 |
| EP | 0541950 A1 | 5/1993 |
| EP | 0548998 A1 | 6/1993 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 0726632 B1 | 10/2000 |
| EP | 1053719 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1234587 A1 | 8/2002 |
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 2116196 A2 | 11/2009 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2606812 A1 | 6/2013 |
| EP | 2649948 A1 | 10/2013 |
| EP | 2649949 A1 | 10/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2842500 A1 | 3/2015 |
| EP | 2853220 A1 | 4/2015 |
| EP | 2298220 B1 | 6/2016 |
| EP | 2510891 B1 | 6/2016 |
| EP | 2364651 B1 | 11/2016 |
| EP | 2747235 B1 | 11/2016 |
| EP | 2789299 B1 | 5/2017 |
| EP | 3363378 A1 | 8/2018 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S56112235 A | 9/1981 |
| JP | S62170011 U | 10/1987 |
| JP | S63270040 A | 11/1988 |
| JP | H0129503 B2 | 6/1989 |
| JP | H0378514 U | 8/1991 |
| JP | H0385009 U | 8/1991 |
| JP | H04215747 A | 8/1992 |
| JP | H04131860 U | 12/1992 |
| JP | H0584252 A | 4/1993 |
| JP | H05123325 A | 5/1993 |
| JP | H 05226945 A | 9/1993 |
| JP | H0630945 A | 2/1994 |
| JP | H06237937 A | 8/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H09-323068 A | 12/1997 |
| JP | H10118090 A | 5/1998 |
| JP | H10-200699 A | 7/1998 |
| JP | H 10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001087272 A | 4/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013576 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |

(56) References Cited

FOREIGN PATENT DOCUMENTS

| | | |
|---|---|---|
| JP | 2005187954 A | 7/2005 |
| JP | 2005328882 A | 12/2005 |
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006346445 A | 12/2006 |
| JP | 2008-220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | 2010069307 A | 4/2010 |
| JP | 2010069310 A | 4/2010 |
| JP | 2010098844 A | 4/2010 |
| JP | 2011072574 A | 4/2011 |
| JP | 4722849 B2 | 7/2011 |
| JP | 2011524199 A | 9/2011 |
| JP | 5154710 B1 | 2/2013 |
| JP | 2014121599 A | 7/2014 |
| JP | 2016-512057 A | 4/2016 |
| KR | 20100110134 A | 10/2010 |
| KR | 20110003229 A | 1/2011 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2069981 C1 | 12/1996 |
| RU | 2098025 C1 | 12/1997 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006/073581 A2 | 7/2006 |
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-2007137304 A2 | 11/2007 |
| WO | WO-2007142625 A2 | 12/2007 |
| WO | WO-2008021969 A2 | 2/2008 |
| WO | WO-2008/061566 A1 | 5/2008 |
| WO | WO-2008089404 A2 | 7/2008 |
| WO | WO-2009005969 A1 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A2 | 1/2012 |
| WO | WO-2012/013577 A1 | 2/2012 |
| WO | WO-2012044606 A2 | 4/2012 |
| WO | WO-2012166503 A1 | 12/2012 |
| WO | WO-2013151888 A1 | 10/2013 |
| WO | WO-2014004209 A2 | 1/2014 |
| WO | WO-2014/113438 A1 | 7/2014 |
| WO | WO-2015/032797 A1 | 3/2015 |
| WO | WO-2015138760 A1 | 9/2015 |
| WO | WO-2015187107 A1 | 12/2015 |

OTHER PUBLICATIONS

Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications:

(56) References Cited

OTHER PUBLICATIONS

Polymers, Surfaes, Dendrimers, Nanoparticles, and Hydrogels, Edited by Ravin Narain, 2011, pp. 337-345.
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
Disclosed Anonymously, "Motor-Driven Surgical Stapler Improvements," Research Disclosure Database No. 526041, Published: Feb. 2008.
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Solorio et al., "Gelatin Microspheres Crosslinked with Genipin for Local Delivery of Growth Factors," J. Tissue Eng. Regen. Med. (2010), 4(7): pp. 514-523.
Pitt et al., "Attachment of Hyaluronan to Metallic Surfaces," J. Biomed. Mater. Res. 68A: pp. 95-106, 2004.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
"Indian Standard: Automotive Vehicles—Brakes and Braking Systems (IS 11852-1:2001)", Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Covidien Brochure "iDrive™ Ultra Powered Stapling System," (6 pages).
Allegro MicroSystems, LLC, Automotive Full Bridge Mosfet Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.

Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
"Biomedical Coatings," Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mousercom/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mousercom/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al, Comparison of the effects of Mg—6Zn and Ti—3Al—2.5V alloys on TGF-$\beta$/TNF-$\alpha$/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.

(56) References Cited

OTHER PUBLICATIONS

Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.

Youtube.com; video by Fibran (retrieved from URL https://www.youtube.com/watch?v=vN2Qjt51gFQ); (Year: 2018).

"Foot and Ankle: Core Knowledge in Orthopaedics"; by DiGiovanni MD, Elsevier; (p. 27, left column, heading "Materials for Soft Orthoses", 7th bullet point); (Year: 2007).

Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.

Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.

Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).

Slow Safety Sign, shutterstock.com [online], published on or before May 19, 2017, [retrieved on May 31, 2019], retrieved from the https://www.shutterstock.com/image-victor/slow-safety-sign-twodimensional-turtle-symbolizing- . . . see PDF in file for full URL] (Year: 2017).

Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).

Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).

Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).

"Tutorial overview of inductively coupled RFID Systems," UPM, May 2003, pp. 1-7, UPM Rafsec,<http://cdn.mobiusconsulting.com/papers/rfidsystems.pdf>.

Schroeter, John, "*Demystifying UHF Gen 2 RFID, HF RFID*," Online Article, Jun. 2, 2008, pp. 1-3, <https://www.edn.com/design/industrial-control/4019123/Demystifying-UHF-Gen-2-RFID-HF-RFID>.

Adeeb, et al., "An Inductive Link-Based Wireless Power Transfer System for Biomedical Applications," *Research Article*, Nov. 14, 2011, pp. 1-12, vol. 2012, Article ID 879294, Hindawi Publishing Corporation.

\* cited by examiner

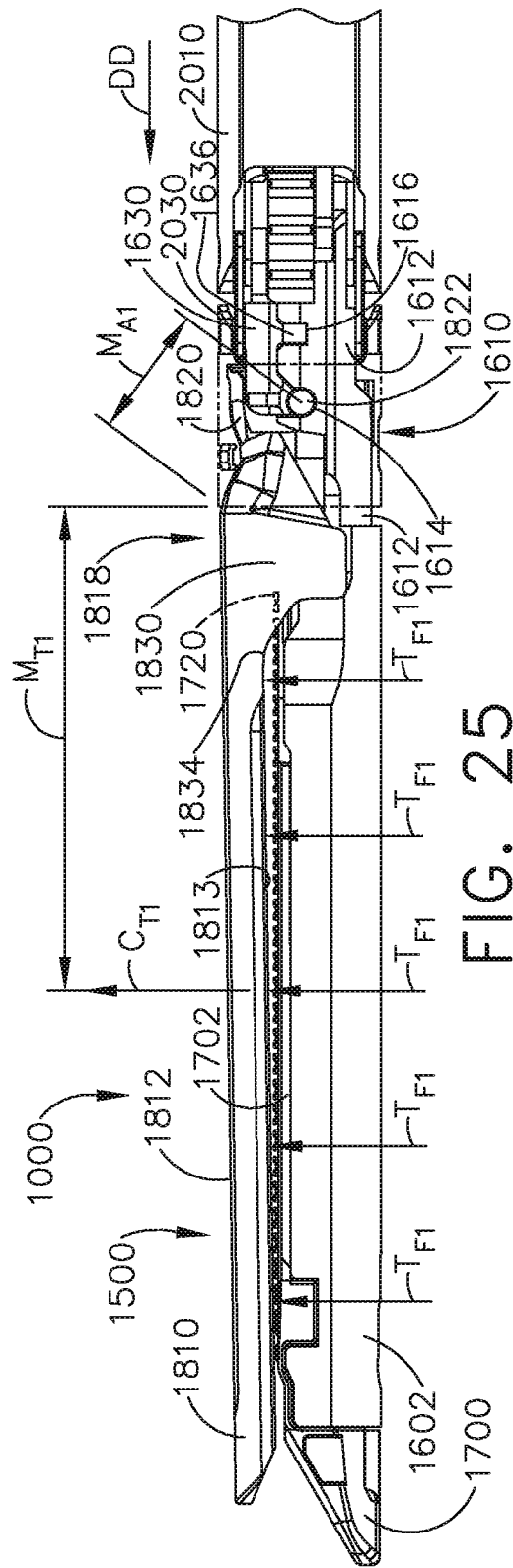
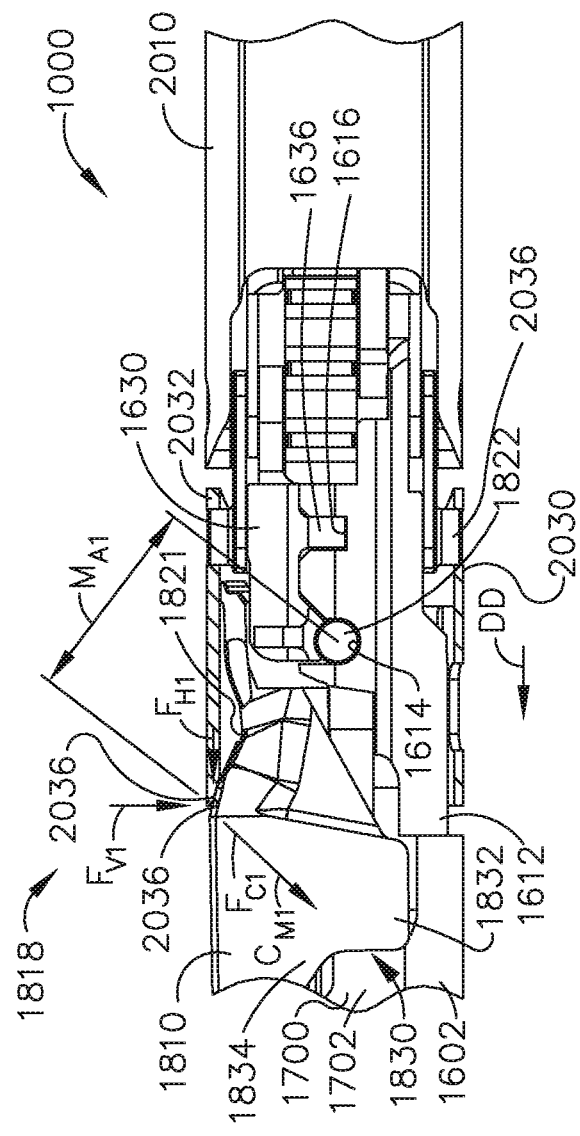

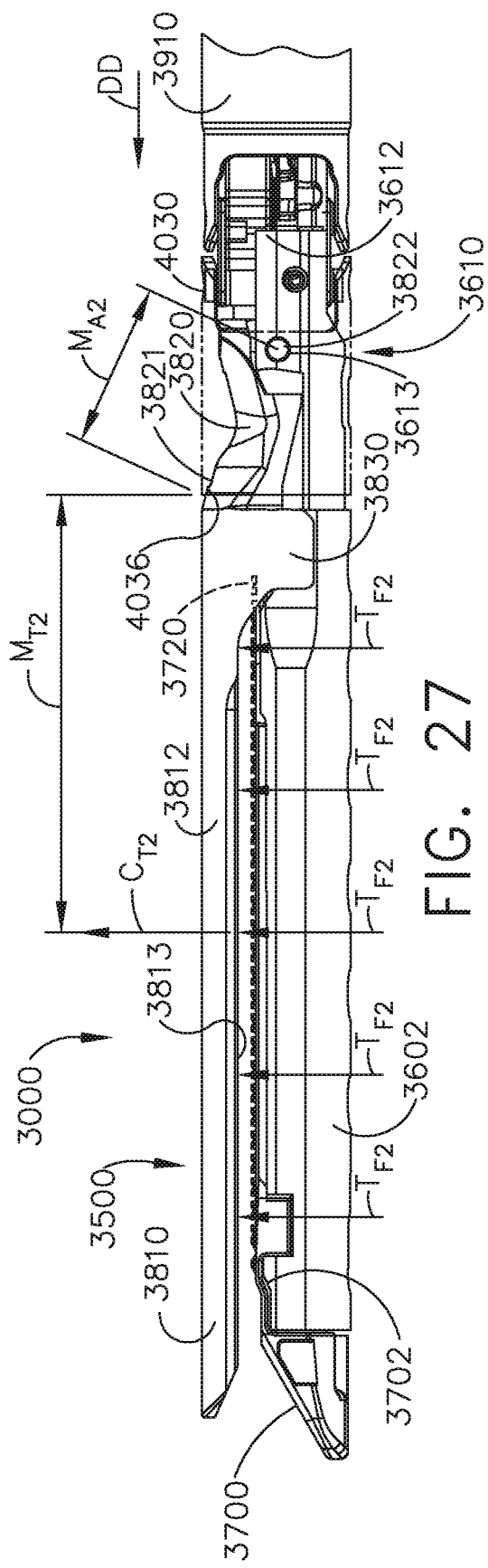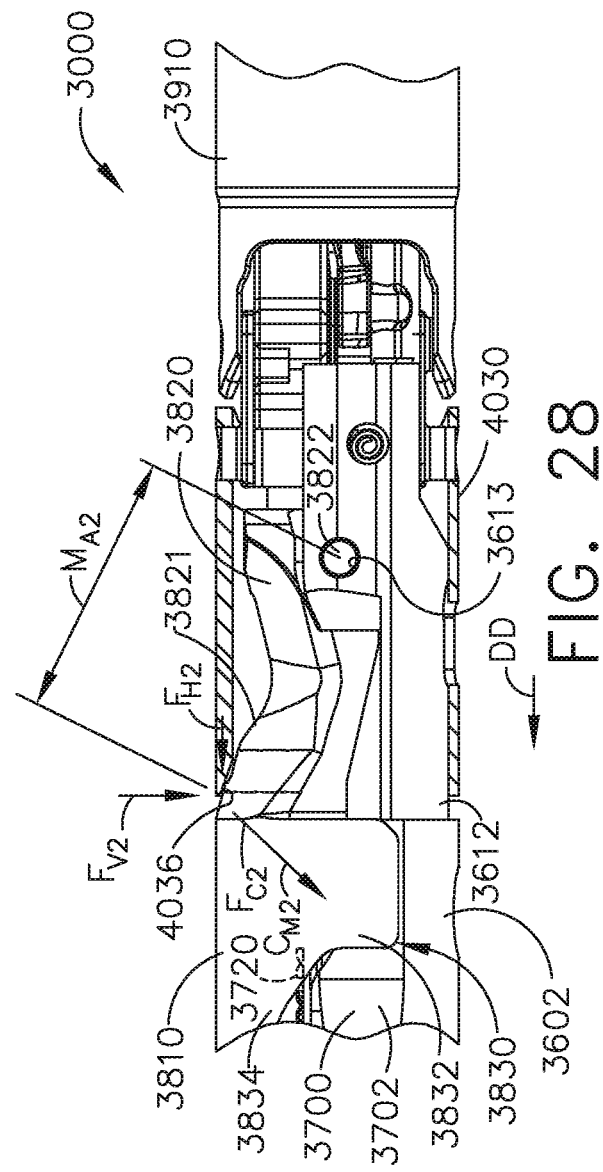

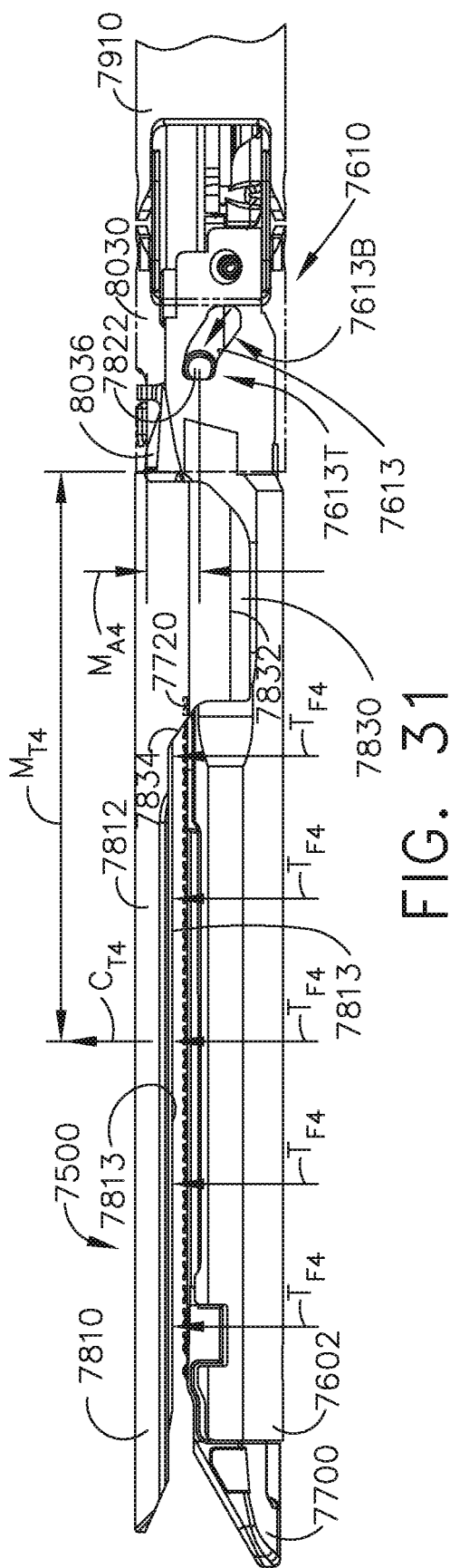
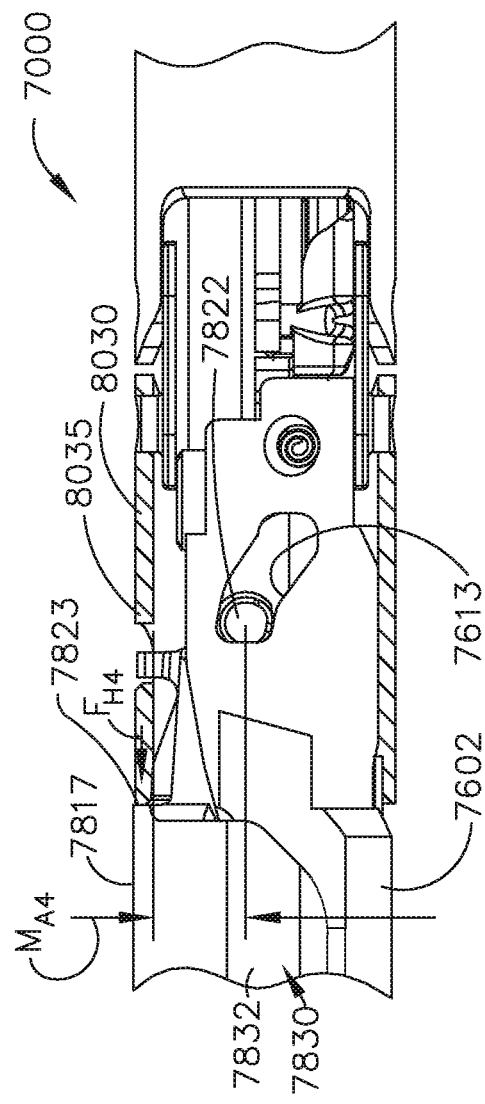
FIG. 31
FIG. 32

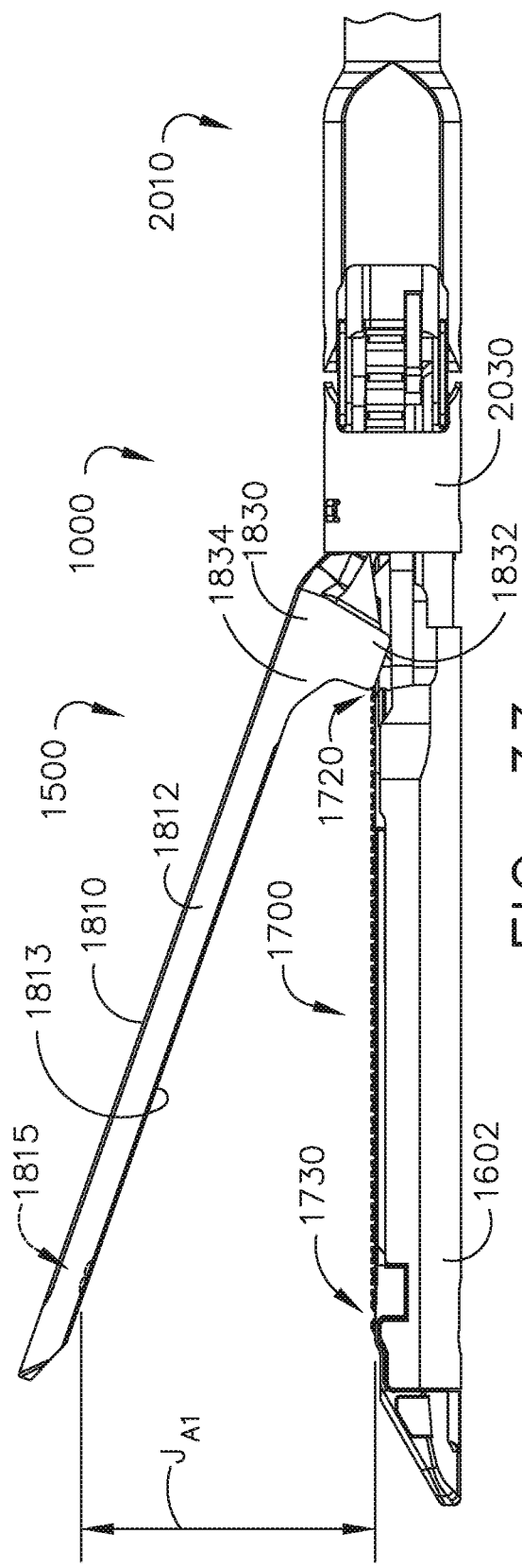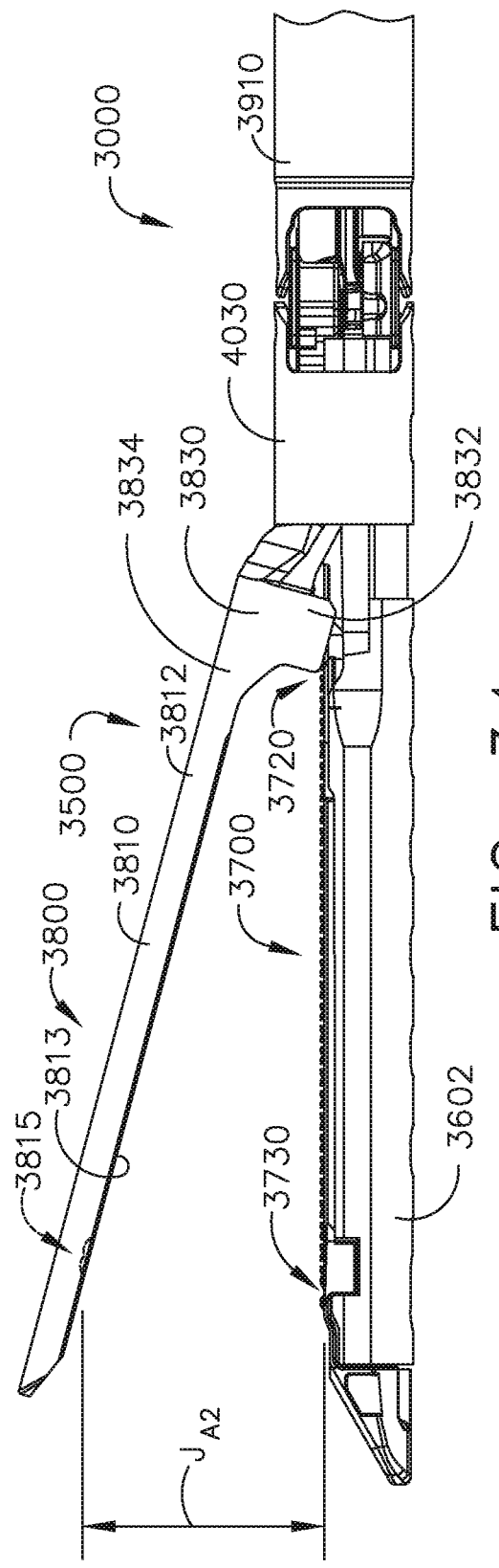

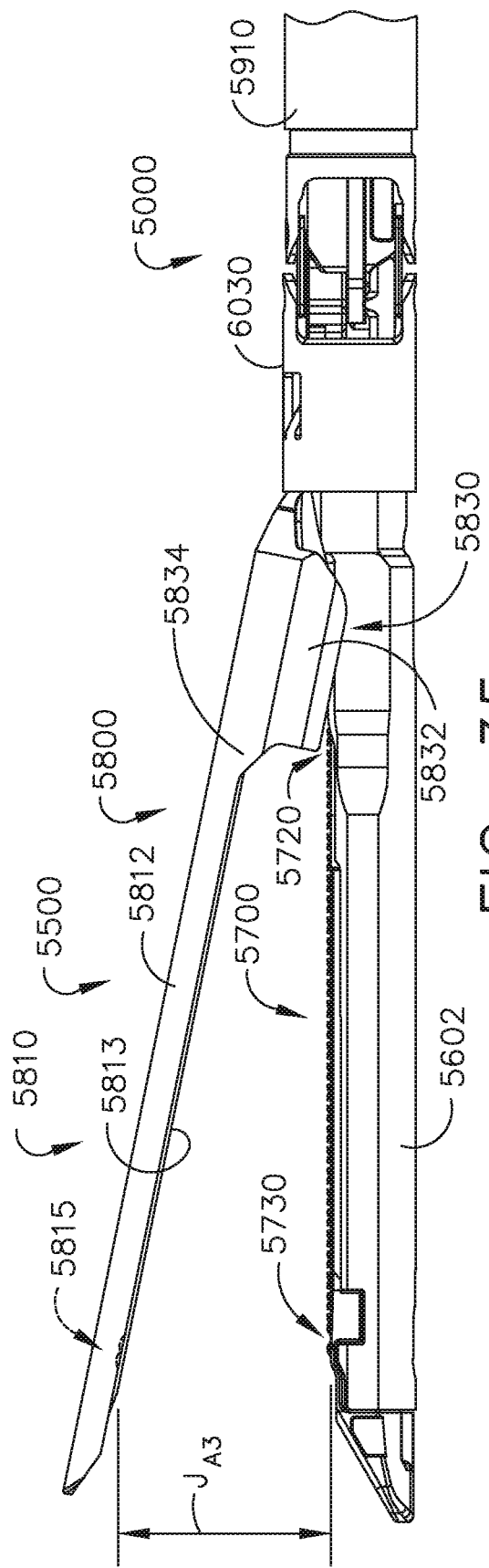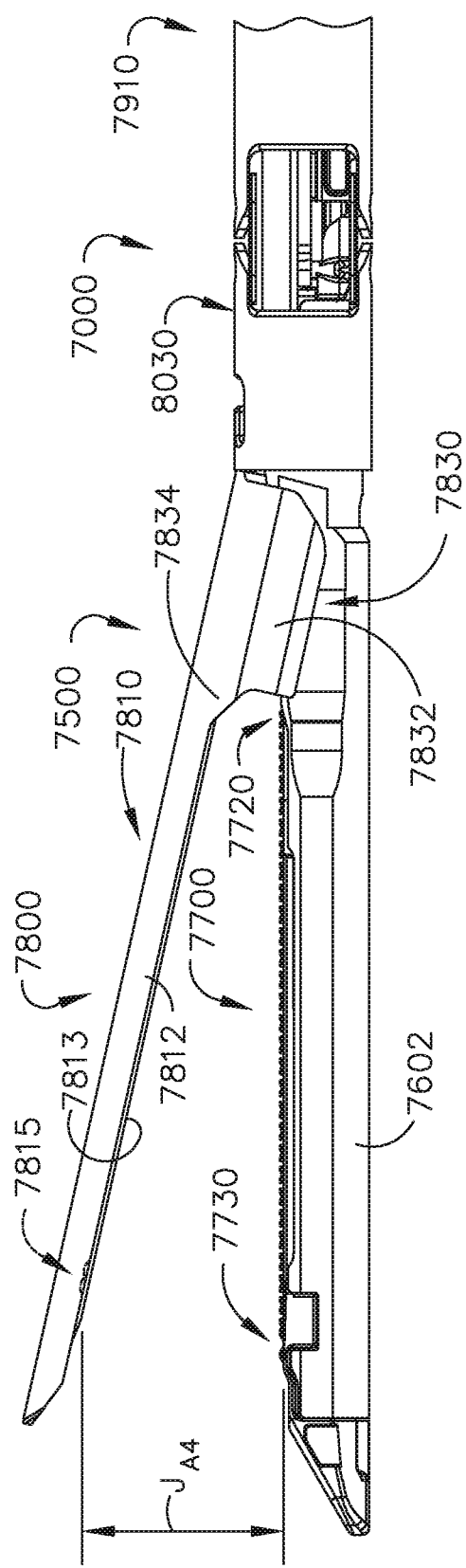

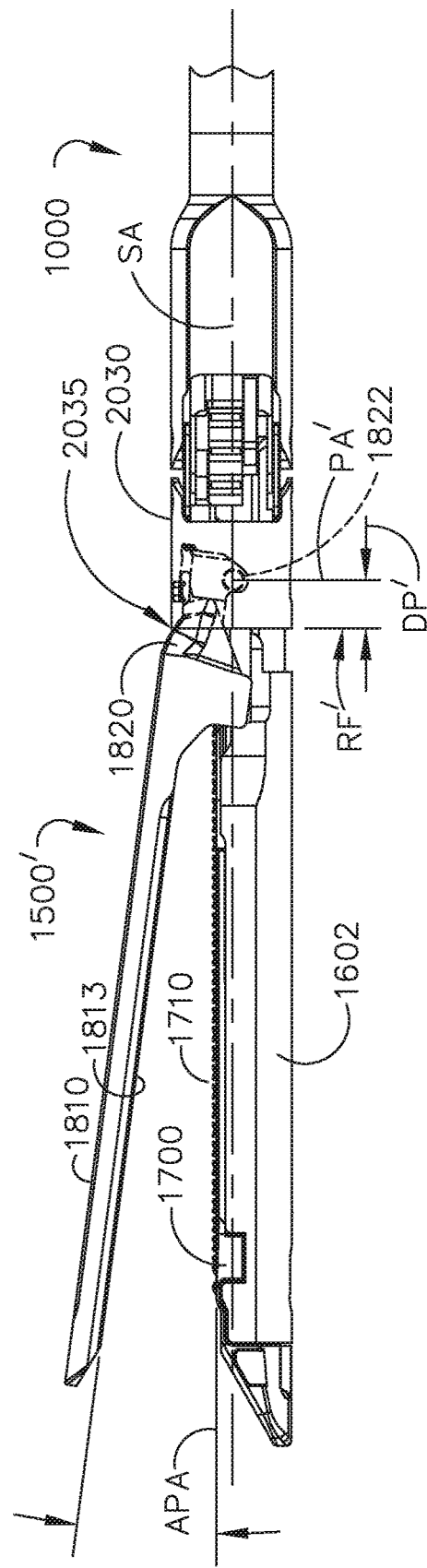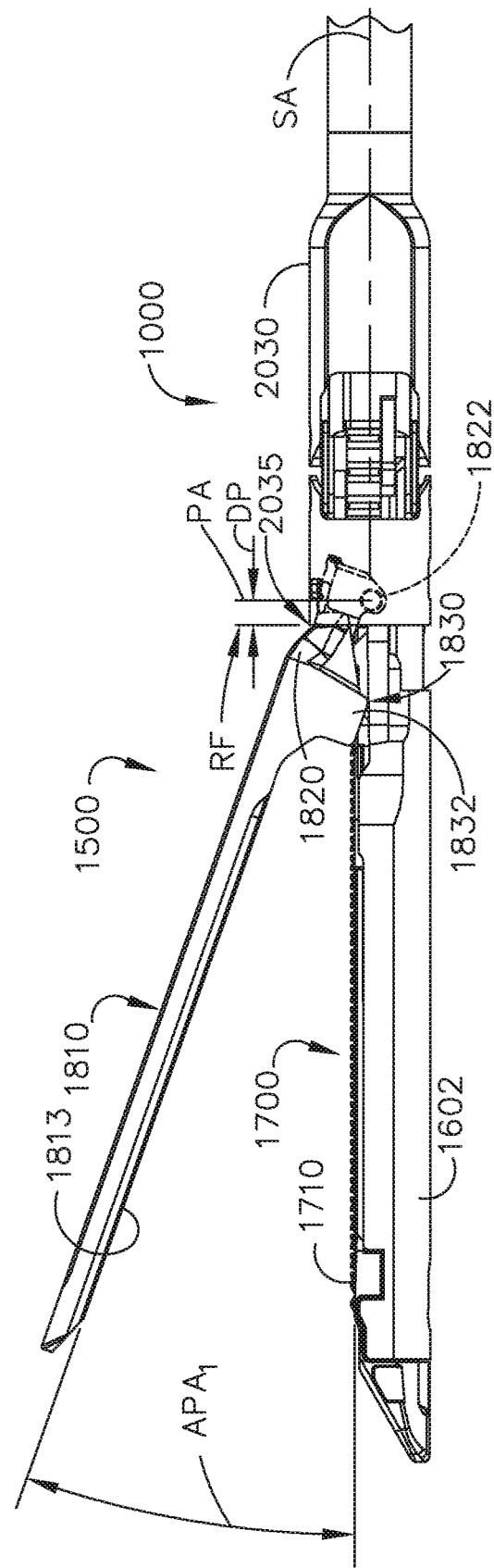

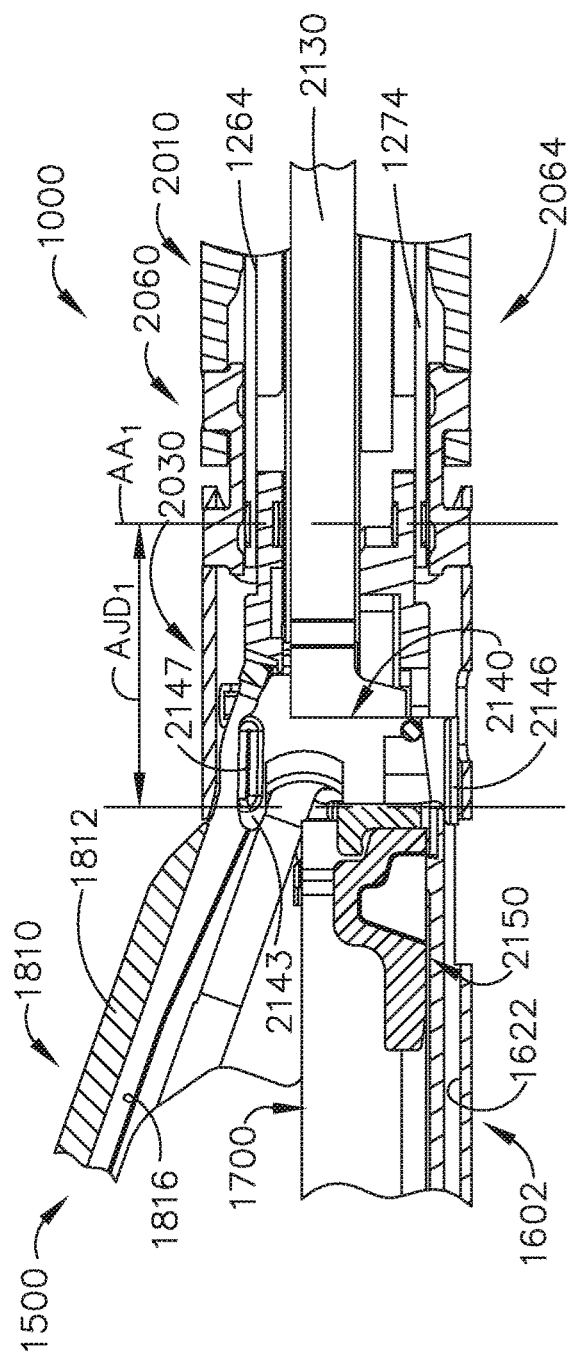
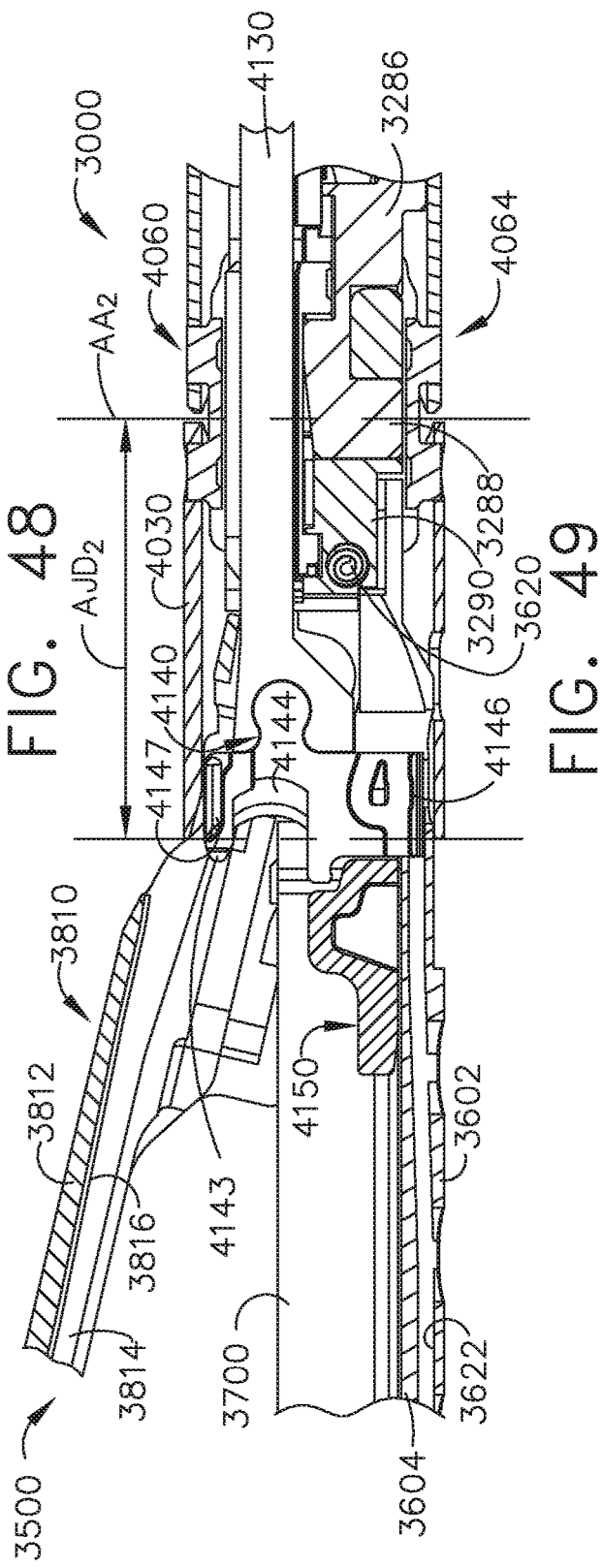
FIG. 48
FIG. 49

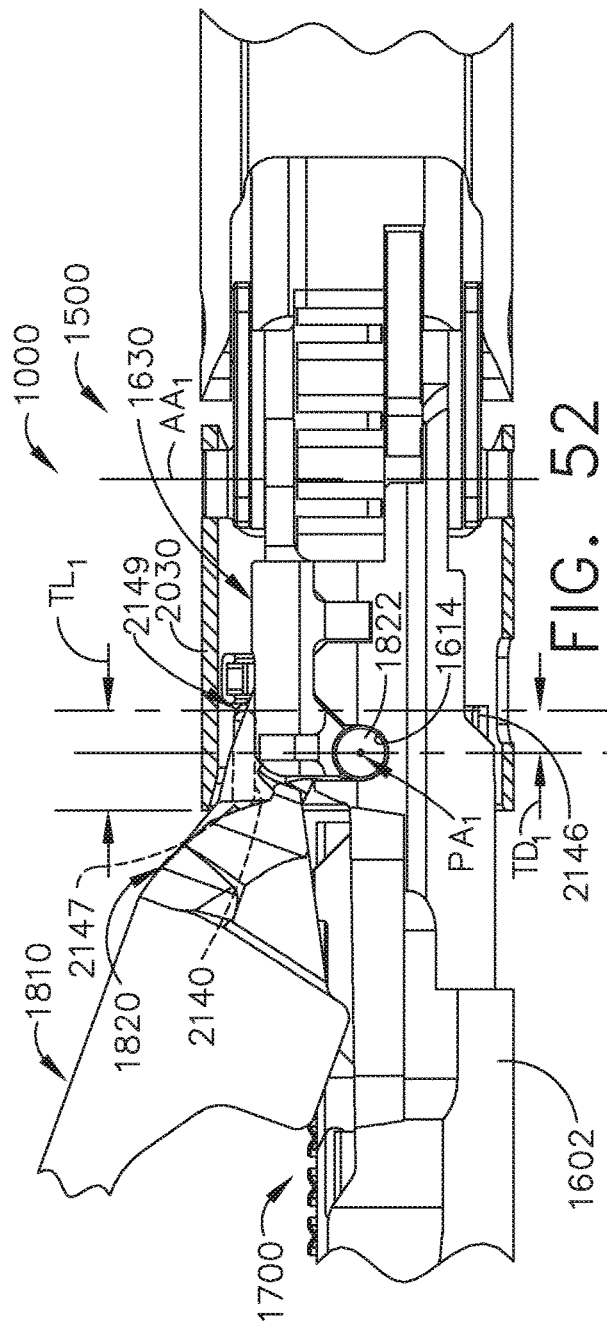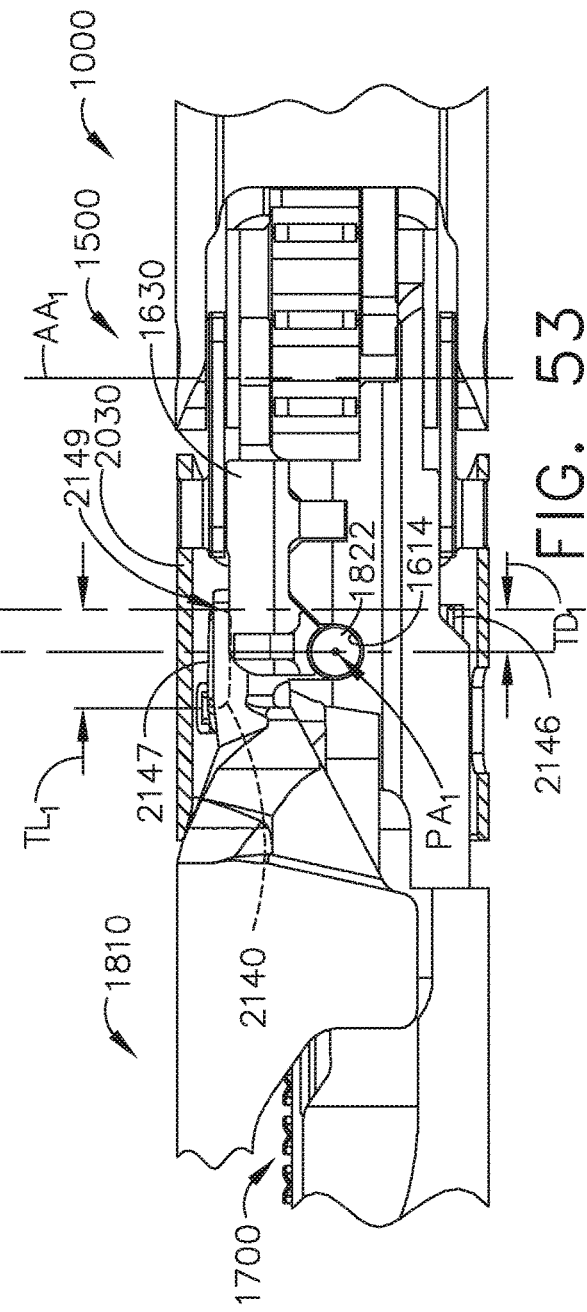

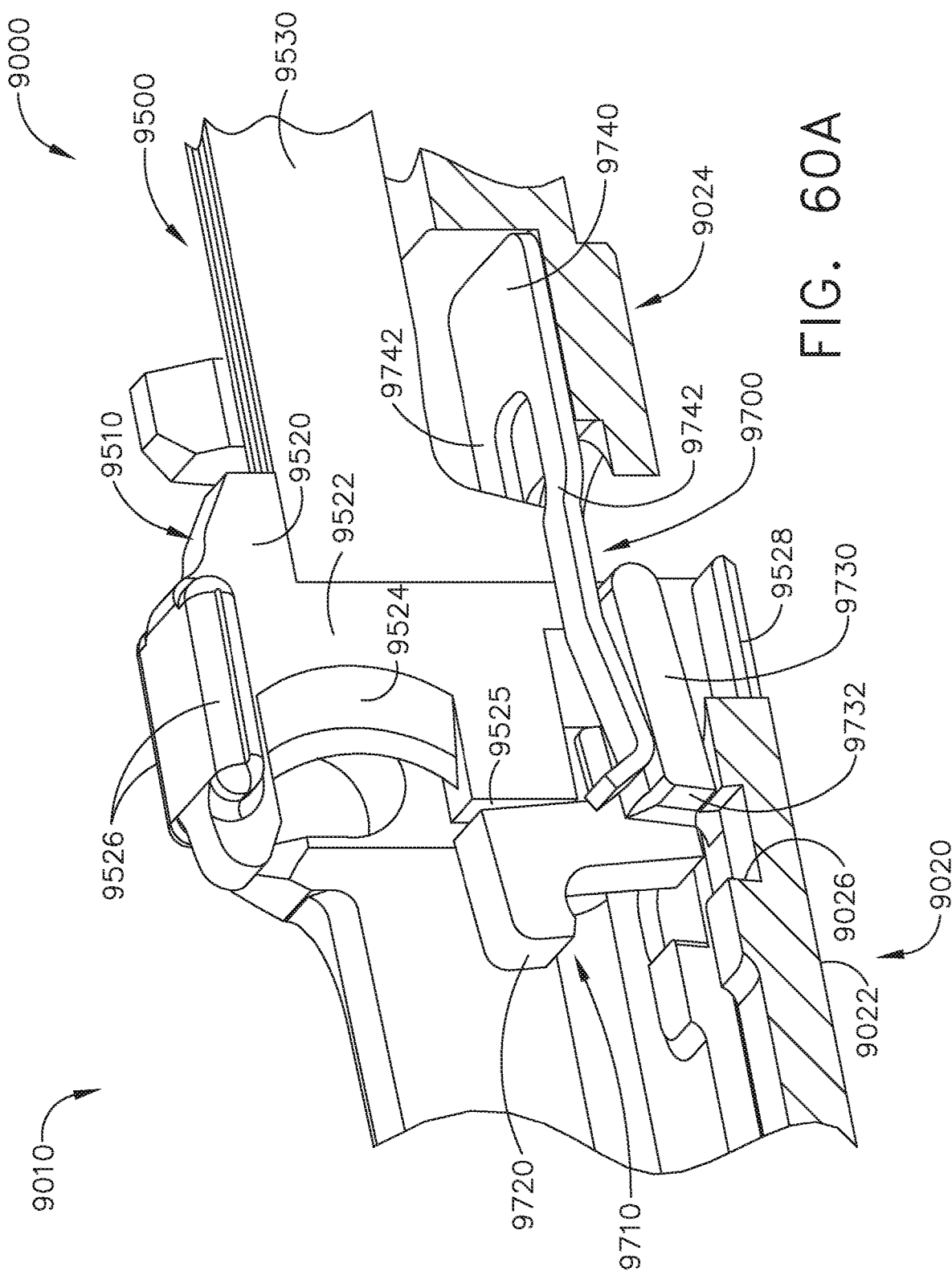

SURGICAL INSTRUMENT WITH AXIALLY MOVABLE CLOSURE MEMBER

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 25 is a side elevational view of a distal portion of the interchangeable surgical tool assembly of FIG. 3 with the anvil thereof in a fully closed position;

FIG. 26 is an enlarged side elevational view of the anvil mounting portion and elongate channel of the interchangeable surgical tool assembly of FIG. 25;

FIG. 27 is a side elevational view of a distal portion of the interchangeable surgical tool assembly of FIG. 16 with the anvil thereof in a fully closed position;

FIG. 28 is an enlarged side elevational view of the anvil mounting portion and elongate channel of the interchangeable surgical tool assembly of FIG. 27;

FIG. 31 is a side elevational view of a distal portion of the interchangeable surgical tool assembly of FIG. 22 with the anvil thereof in a fully closed position;

FIG. 32 is an enlarged side elevational view of the anvil mounting portion and elongate channel of the interchangeable surgical tool assembly of FIG. 31;

FIG. 33 is a side elevational view of a distal portion of the interchangeable surgical tool assembly of FIG. 3 with the anvil thereof in a fully open position;

FIG. 34 is a side elevational view of a distal portion of the interchangeable surgical tool assembly of FIG. 16 with the anvil thereof in a fully open position;

FIG. 35 is a side elevational view of a distal portion of the interchangeable surgical tool assembly of FIG. 19 with the anvil thereof in a fully open position;

FIG. 36 is a side elevational view of a distal portion of the interchangeable surgical tool assembly of FIG. 22 with the anvil thereof in a fully open position;

FIG. 38 is a side elevational view of a distal portion of another interchangeable surgical tool assembly with the anvil thereof in an open position;

FIG. 39 is a side elevational view of a distal portion of the interchangeable surgical tool assembly of FIG. 3 with the anvil thereof in a fully open position;

FIG. 48 is a partial cross-sectional view of the anvil mounting portion and elongate channel of the interchangeable surgical tool assembly of FIG. 3 with the anvil in a fully open position;

FIG. 49 is a partial cross-sectional view of the anvil mounting portion and elongate channel of the interchangeable surgical tool assembly of FIG. 16 with the anvil in a fully open position;

FIG. 52 is another partial cross-sectional view of a portion of the interchangeable surgical tool assembly of FIG. 3 with the anvil of the surgical end effector thereof in a fully open position;

FIG. 53 is another partial cross-sectional view of a portion of the interchangeable surgical tool assembly of FIG. 52 with the anvil in a fully closed position;

FIG. 60A is a perspective view of a portion of a firing member assembly of surgical stapling instrument that includes a first firing member element and a second firing member element that is movable relative to the first firing member element between a locked and an unlocked position;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
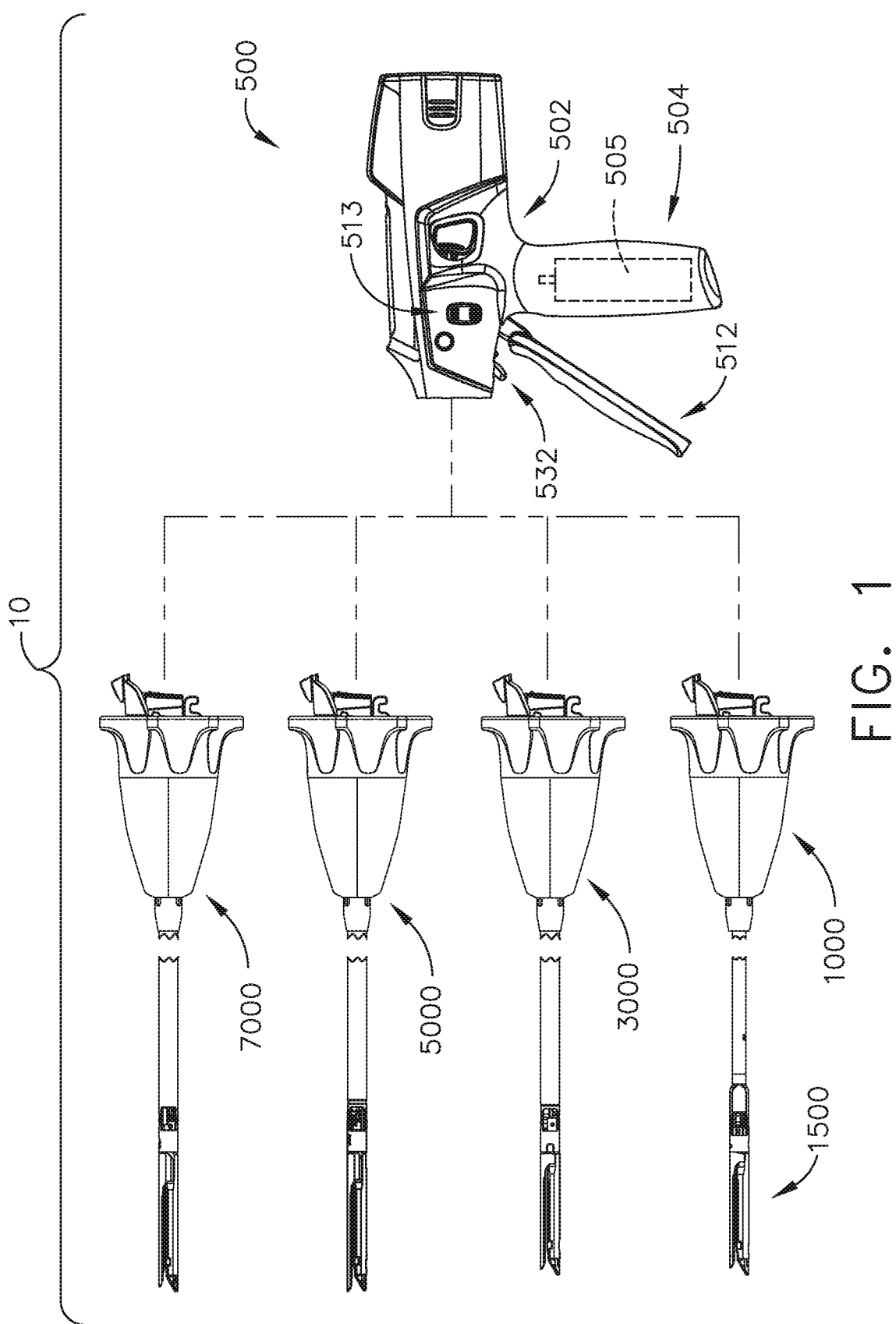
FIG. 1 is a side elevational view of a surgical system comprising a handle assembly and multiple interchangeable surgical tool assemblies that may be used therewith.

Applicant of the present application owns the following U.S. Patent Applications that were filed on Jun. 28, 2017 and which are each herein incorporated by reference in their respective entireties:

U.S. patent application Ser. No. 15/635,693, entitled SURGICAL INSTRUMENT COMPRISING AN OFFSET ARTICULATION JOINT;

U.S. patent application Ser. No. 15/635,729, entitled SURGICAL INSTRUMENT COMPRISING AN ARTICULATION SYSTEM RATIO;

U.S. patent application Ser. No. 15/635,785, entitled SURGICAL INSTRUMENT COMPRISING AN ARTICULATION SYSTEM RATIO;

U.S. patent application Ser. No. 15/635,808, entitled SURGICAL INSTRUMENT COMPRISING FIRING MEMBER SUPPORTS;

U.S. patent application Ser. No. 15/635,837, entitled SURGICAL INSTRUMENT COMPRISING AN ARTICULATION SYSTEM LOCKABLE TO A FRAME;

U.S. patent application Ser. No. 15/635,941, entitled SURGICAL INSTRUMENT COMPRISING AN ARTICULATION SYSTEM LOCKABLE BY A CLOSURE SYSTEM;

U.S. patent application Ser. No. 15/636,029, entitled SURGICAL INSTRUMENT COMPRISING A SHAFT INCLUDING A HOUSING ARRANGEMENT;

U.S. patent application Ser. No. 15/635,958, entitled SURGICAL INSTRUMENT COMPRISING SELECTIVELY ACTUATABLE ROTATABLE COUPLERS;

U.S. patent application Ser. No. 15/635,981, entitled SURGICAL STAPLING INSTRUMENTS COMPRISING SHORTENED STAPLE CARTRIDGE NOSES;

U.S. patent application Ser. No. 15/636,009, entitled SURGICAL INSTRUMENT COMPRISING A SHAFT INCLUDING A CLOSURE TUBE PROFILE;

U.S. patent application Ser. No. 15/635,663, entitled METHOD FOR ARTICULATING A SURGICAL INSTRUMENT;

U.S. patent application Ser. No. 15/635,530, entitled SURGICAL INSTRUMENTS WITH ARTICULATABLE END EFFECTOR WITH AXIALLY SHORTENED ARTICULATION JOINT CONFIGURATIONS;

U.S. patent application Ser. No. 15/635,549, entitled SURGICAL INSTRUMENTS WITH OPEN AND CLOSABLE JAWS AND AXIALLY MOVABLE FIRING MEMBER THAT IS INITIALLY PARKED IN CLOSE PROXIMITY TO THE JAWS PRIOR TO FIRING;

U.S. patent application Ser. No. 15/635,559, entitled SURGICAL INSTRUMENTS WITH JAWS CONSTRAINED TO PIVOT ABOUT AN AXIS UPON CONTACT WITH A CLOSURE MEMBER THAT IS PARKED IN CLOSE PROXIMITY TO THE PIVOT AXIS;

U.S. patent application Ser. No. 15/635,578, entitled SURGICAL END EFFECTORS WITH IMPROVED JAW APERTURE ARRANGEMENTS;

U.S. patent application Ser. No. 15/635,594, entitled SURGICAL CUTTING AND FASTENING DEVICES WITH PIVOTABLE ANVIL WITH A TISSUE LOCATING ARRANGEMENT IN CLOSE PROXIMITY TO AN ANVIL PIVOT AXIS;

U.S. patent application Ser. No. 15/635,612, entitled JAW RETAINER ARRANGEMENT FOR RETAINING A PIVOTABLE SURGICAL INSTRUMENT JAW IN PIVOTABLE RETAINING ENGAGEMENT WITH A SECOND SURGICAL INSTRUMENT JAW;

U.S. patent application Ser. No. 15/635,621, entitled SURGICAL INSTRUMENT WITH POSITIVE JAW OPENING FEATURES;

U.S. patent application Ser. No. 15/635,521, entitled SURGICAL INSTRUMENT LOCKOUT ARRANGEMENT;

U.S. Design patent application Ser. No. 29/609,087, entitled STAPLE FORMING ANVIL;

U.S. Design patent application Ser. No. 29/609,083, entitled SURGICAL INSTRUMENT SHAFT; and U.S. Design patent application Ser. No. 29/609,093, entitled SURGICAL FASTENER CARTRIDGE.

Applicant of the present application owns the following U.S. Patent Applications that were filed on Jun. 27, 2017 and which are each herein incorporated by reference in their respective entireties:

U.S. patent application Ser. No. 15/634,024, entitled SURGICAL ANVIL MANUFACTURING METHODS;

U.S. patent application Ser. No. 15/634,035, entitled SURGICAL ANVIL ARRANGEMENTS;

U.S. patent application Ser. No. 15/634,046, entitled SURGICAL ANVIL ARRANGEMENTS;

U.S. patent application Ser. No. 15/634,054, entitled SURGICAL ANVIL ARRANGEMENTS;

U.S. patent application Ser. No. 15/634,068, entitled SURGICAL FIRING MEMBER ARRANGEMENTS;

U.S. patent application Ser. No. 15/634,076, entitled STAPLE FORMING POCKET ARRANGEMENTS;

U.S. patent application Ser. No. 15/634,090, entitled STAPLE FORMING POCKET ARRANGEMENTS;

U.S. patent application Ser. No. 15/634,099, entitled SURGICAL END EFFECTORS AND ANVILS; and U.S. patent application Ser. No. 15/634,117, entitled ARTICULATION SYSTEMS FOR SURGICAL INSTRUMENTS.

Applicant of the present application owns the following U.S. Patent Applications that were filed on Dec. 21, 2016 and which are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF;

U.S. patent application Ser. No. 15/386,230, entitled ARTICULATABLE SURGICAL STAPLING INSTRUMENTS;

U.S. patent application Ser. No. 15/386,221, entitled LOCKOUT ARRANGEMENTS FOR SURGICAL END EFFECTORS;

U.S. patent application Ser. No. 15/386,209, entitled SURGICAL END EFFECTORS AND FIRING MEMBERS THEREOF;

U.S. patent application Ser. No. 15/386,198, entitled LOCKOUT ARRANGEMENTS FOR SURGICAL END EFFECTORS AND REPLACEABLE TOOL ASSEMBLIES;

U.S. patent application Ser. No. 15/386,240, entitled SURGICAL END EFFECTORS AND ADAPTABLE FIRING MEMBERS THEREFOR;

U.S. patent application Ser. No. 15/385,939, entitled STAPLE CARTRIDGES AND ARRANGEMENTS OF STAPLES AND STAPLE CAVITIES THEREIN;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS;

U.S. patent application Ser. No. 15/385,943, entitled SURGICAL STAPLING INSTRUMENTS AND STAPLE-FORMING ANVILS;

U.S. patent application Ser. No. 15/385,950, entitled SURGICAL TOOL ASSEMBLIES WITH CLOSURE STROKE REDUCTION FEATURES;

U.S. patent application Ser. No. 15/385,945, entitled STAPLE CARTRIDGES AND ARRANGEMENTS OF STAPLES AND STAPLE CAVITIES THEREIN;

U.S. patent application Ser. No. 15/385,946, entitled SURGICAL STAPLING INSTRUMENTS AND STAPLE-FORMING ANVILS;

U.S. patent application Ser. No. 15/385,951, entitled SURGICAL INSTRUMENTS WITH JAW OPENING FEATURES FOR INCREASING A JAW OPENING DISTANCE;

U.S. patent application Ser. No. 15/385,953, entitled METHODS OF STAPLING TISSUE;

U.S. patent application Ser. No. 15/385,954, entitled FIRING MEMBERS WITH NON-PARALLEL JAW ENGAGEMENT FEATURES FOR SURGICAL END EFFECTORS;

U.S. patent application Ser. No. 15/385,955, entitled SURGICAL END EFFECTORS WITH EXPANDABLE TISSUE STOP ARRANGEMENTS;

U.S. patent application Ser. No. 15/385,948, entitled SURGICAL STAPLING INSTRUMENTS AND STAPLE-FORMING ANVILS;

U.S. patent application Ser. No. 15/385,956, entitled SURGICAL INSTRUMENTS WITH POSITIVE JAW OPENING FEATURES;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT;

U.S. patent application Ser. No. 15/385,947, entitled STAPLE CARTRIDGES AND ARRANGEMENTS OF STAPLES AND STAPLE CAVITIES THEREIN;

U.S. patent application Ser. No. 15/385,896, entitled METHOD FOR RESETTING A FUSE OF A SURGICAL INSTRUMENT SHAFT;

U.S. patent application Ser. No. 15/385,898, entitled STAPLE FORMING POCKET ARRANGEMENT TO ACCOMMODATE DIFFERENT TYPES OF STAPLES;

U.S. patent application Ser. No. 15/385,899, entitled SURGICAL INSTRUMENT COMPRISING IMPROVED JAW CONTROL;

U.S. patent application Ser. No. 15/385,901, entitled STAPLE CARTRIDGE AND STAPLE CARTRIDGE CHANNEL COMPRISING WINDOWS DEFINED THEREIN;

U.S. patent application Ser. No. 15/385,902, entitled SURGICAL INSTRUMENT COMPRISING A CUTTING MEMBER;

U.S. patent application Ser. No. 15/385,904, entitled STAPLE FIRING MEMBER COMPRISING A MISSING CARTRIDGE AND/OR SPENT CARTRIDGE LOCKOUT;

U.S. patent application Ser. No. 15/385,905, entitled FIRING ASSEMBLY COMPRISING A LOCKOUT;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT;

U.S. patent application Ser. No. 15/385,908, entitled FIRING ASSEMBLY COMPRISING A FUSE;

U.S. patent application Ser. No. 15/385,909, entitled FIRING ASSEMBLY COMPRISING A MULTIPLE FAILED-STATE FUSE;

U.S. patent application Ser. No. 15/385,920, entitled STAPLE FORMING POCKET ARRANGEMENTS;

U.S. patent application Ser. No. 15/385,913, entitled ANVIL ARRANGEMENTS FOR SURGICAL STAPLE/FASTENERS;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT;

U.S. patent application Ser. No. 15/385,893, entitled BILATERALLY ASYMMETRIC STAPLE FORMING POCKET PAIRS;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS;

U.S. patent application Ser. No. 15/385,911, entitled SURGICAL STAPLE/FASTENERS WITH INDEPENDENTLY ACTUATABLE CLOSING AND FIRING SYSTEMS;

U.S. patent application Ser. No. 15/385,927, entitled SURGICAL STAPLING INSTRUMENTS WITH SMART STAPLE CARTRIDGES;

U.S. patent application Ser. No. 15/385,917, entitled STAPLE CARTRIDGE COMPRISING STAPLES WITH DIFFERENT CLAMPING BREADTHS;

U.S. patent application Ser. No. 15/385,900, entitled STAPLE FORMING POCKET ARRANGEMENTS COMPRISING PRIMARY SIDEWALLS AND POCKET SIDEWALLS;

U.S. patent application Ser. No. 15/385,931, entitled NO-CARTRIDGE AND SPENT CARTRIDGE LOCKOUT ARRANGEMENTS FOR SURGICAL STAPLE/FASTENERS;

U.S. patent application Ser. No. 15/385,915, entitled FIRING MEMBER PIN ANGLE;

U.S. patent application Ser. No. 15/385,897, entitled STAPLE FORMING POCKET ARRANGEMENTS COMPRISING ZONED FORMING SURFACE GROOVES;

U.S. patent application Ser. No. 15/385,922, entitled SURGICAL INSTRUMENT WITH MULTIPLE FAILURE RESPONSE MODES;

U.S. patent application Ser. No. 15/385,924, entitled SURGICAL INSTRUMENT WITH PRIMARY AND SAFETY PROCESSORS;

U.S. patent application Ser. No. 15/385,912, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS;

U.S. patent application Ser. No. 15/385,910, entitled ANVIL HAVING A KNIFE SLOT WIDTH;

U.S. patent application Ser. No. 15/385,906, entitled FIRING MEMBER PIN CONFIGURATIONS;

U.S. patent application Ser. No. 15/386,188, entitled STEPPED STAPLE CARTRIDGE WITH ASYMMETRICAL STAPLES;

U.S. patent application Ser. No. 15/386,192, entitled STEPPED STAPLE CARTRIDGE WITH TISSUE RETENTION AND GAP SETTING FEATURES;

U.S. patent application Ser. No. 15/386,206, entitled STAPLE CARTRIDGE WITH DEFORMABLE DRIVER RETENTION FEATURES;

U.S. patent application Ser. No. 15/386,226, entitled DURABILITY FEATURES FOR END EFFECTORS AND FIRING ASSEMBLIES OF SURGICAL STAPLING INSTRUMENTS;

U.S. patent application Ser. No. 15/386,222, entitled SURGICAL STAPLING INSTRUMENTS HAVING END EFFECTORS WITH POSITIVE OPENING FEATURES;

U.S. patent application Ser. No. 15/386,236, entitled CONNECTION PORTIONS FOR DEPOSABLE LOADING UNITS FOR SURGICAL STAPLING INSTRUMENTS;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM;

U.S. patent application Ser. No. 15/385,890, entitled SHAFT ASSEMBLY COMPRISING SEPARATELY ACTUATABLE AND RETRACTABLE SYSTEMS;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM;

U.S. patent application Ser. No. 15/385,894, entitled SHAFT ASSEMBLY COMPRISING A LOCKOUT;

U.S. patent application Ser. No. 15/385,895, entitled SHAFT ASSEMBLY COMPRISING FIRST AND SECOND ARTICULATION LOCKOUTS;

U.S. patent application Ser. No. 15/385,916, entitled SURGICAL STAPLING SYSTEMS;

U.S. patent application Ser. No. 15/385,918, entitled SURGICAL STAPLING SYSTEMS;

U.S. patent application Ser. No. 15/385,919, entitled SURGICAL STAPLING SYSTEMS;

U.S. patent application Ser. No. 15/385,921, entitled SURGICAL STAPLE/FASTENER CARTRIDGE WITH MOVABLE CAMMING MEMBER CONFIGURED TO DISENGAGE FIRING MEMBER LOCKOUT FEATURES;

U.S. patent application Ser. No. 15/385,923, entitled SURGICAL STAPLING SYSTEMS;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS;

U.S. patent application Ser. No. 15/385,932, entitled ARTICULATABLE SURGICAL END EFFECTOR WITH ASYMMETRIC SHAFT ARRANGEMENT;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION; and U.S. patent application Ser. No. 15/385,936, entitled ARTICULATABLE SURGICAL INSTRUMENTS WITH ARTICULATION STROKE AMPLIFICATION FEATURES.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES;

U.S. patent application Ser. No. 15/191,807, entitled STAPLING SYSTEM FOR USE WITH WIRE STAPLES AND STAMPED STAPLES;

U.S. patent application Ser. No. 15/191,834, entitled STAMPED STAPLES AND STAPLE CARTRIDGES USING THE SAME;

U.S. patent application Ser. No. 15/191,788, entitled STAPLE CARTRIDGE COMPRISING OVER-DRIVEN STAPLES; and U.S. patent application Ser. No. 15/191,818, entitled STAPLE CARTRIDGE COMPRISING OFFSET LONGITUDINAL STAPLE ROWS.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER;

U.S. Design patent application Ser. No. 29/569,227, entitled SURGICAL FASTENER;

U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM;

U.S. patent application Ser. No. 15/089,321, entitled MODULAR SURGICAL STAPLING SYSTEM COMPRISING A DISPLAY;

U.S. patent application Ser. No. 15/089,326, entitled SURGICAL STAPLING SYSTEM COMPRISING A DISPLAY INCLUDING A RE-ORIENTABLE DISPLAY FIELD;

U.S. patent application Ser. No. 15/089,263, entitled SURGICAL INSTRUMENT HANDLE ASSEMBLY WITH RECONFIGURABLE GRIP PORTION;

U.S. patent application Ser. No. 15/089,262, entitled ROTARY POWERED SURGICAL INSTRUMENT WITH MANUALLY ACTUATABLE BAILOUT SYSTEM;

U.S. patent application Ser. No. 15/089,277, entitled SURGICAL CUTTING AND STAPLING END EFFECTOR WITH ANVIL CONCENTRIC DRIVE MEMBER;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS;

U.S. patent application Ser. No. 15/089,258, entitled SURGICAL STAPLING SYSTEM COMPRISING A SHIFTABLE TRANSMISSION;

U.S. patent application Ser. No. 15/089,278, entitled SURGICAL STAPLING SYSTEM CONFIGURED TO PROVIDE SELECTIVE CUTTING OF TISSUE;

U.S. patent application Ser. No. 15/089,284, entitled SURGICAL STAPLING SYSTEM COMPRISING A CONTOURABLE SHAFT;

U.S. patent application Ser. No. 15/089,295, entitled SURGICAL STAPLING SYSTEM COMPRISING A TISSUE COMPRESSION LOCKOUT;

U.S. patent application Ser. No. 15/089,300, entitled SURGICAL STAPLING SYSTEM COMPRISING AN UNCLAMPING LOCKOUT;

U.S. patent application Ser. No. 15/089,196, entitled SURGICAL STAPLING SYSTEM COMPRISING A JAW CLOSURE LOCKOUT;

U.S. patent application Ser. No. 15/089,203, entitled SURGICAL STAPLING SYSTEM COMPRISING A JAW ATTACHMENT LOCKOUT;

U.S. patent application Ser. No. 15/089,210, entitled SURGICAL STAPLING SYSTEM COMPRISING A SPENT CARTRIDGE LOCKOUT;

U.S. patent application Ser. No. 15/089,324, entitled SURGICAL INSTRUMENT COMPRISING A SHIFTING MECHANISM;

U.S. patent application Ser. No. 15/089,335, entitled SURGICAL STAPLING INSTRUMENT COMPRISING MULTIPLE LOCKOUTS;

U.S. patent application Ser. No. 15/089,339, entitled SURGICAL STAPLING INSTRUMENT;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS;

U.S. patent application Ser. No. 15/089,304, entitled SURGICAL STAPLING SYSTEM COMPRISING A GROOVED FORMING POCKET;

U.S. patent application Ser. No. 15/089,331, entitled ANVIL MODIFICATION MEMBERS FOR SURGICAL STAPLE/FASTENERS;

U.S. patent application Ser. No. 15/089,336, entitled STAPLE CARTRIDGES WITH ATRAUMATIC FEATURES;

U.S. patent application Ser. No. 15/089,312, entitled CIRCULAR STAPLING SYSTEM COMPRISING AN INCISABLE TISSUE SUPPORT;

U.S. patent application Ser. No. 15/089,309, entitled CIRCULAR STAPLING SYSTEM COMPRISING ROTARY FIRING SYSTEM; and U.S. patent application Ser. No. 15/089,349, entitled CIRCULAR STAPLING SYSTEM COMPRISING LOAD CONTROL.

Applicant of the present application also owns the U.S. Patent applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS;

U.S. patent application Ser. No. 14/984,525, entitled MECHANISMS FOR COMPENSATING FOR DRIVETRAIN FAILURE IN POWERED SURGICAL INSTRUMENTS; and U.S. patent application Ser. No. 14/984,552, entitled SURGICAL INSTRUMENTS WITH SEPARABLE MOTORS AND MOTOR CONTROL CIRCUITS.

Applicant of the present application also owns the U.S. Patent Applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR;

U.S. patent application Ser. No. 15/019,228, entitled SURGICAL INSTRUMENTS WITH MULTIPLE LINK ARTICULATION ARRANGEMENTS;

U.S. patent application Ser. No. 15/019,196, entitled SURGICAL INSTRUMENT ARTICULATION MECHANISM WITH SLOTTED SECONDARY CONSTRAINT;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY;

U.S. patent application Ser. No. 15/019,215, entitled SURGICAL INSTRUMENTS WITH NON-SYMMETRICAL ARTICULATION ARRANGEMENTS;

U.S. patent application Ser. No. 15/019,227, entitled ARTICULATABLE SURGICAL INSTRUMENTS WITH SINGLE ARTICULATION LINK ARRANGEMENTS;

U.S. patent application Ser. No. 15/019,235, entitled SURGICAL INSTRUMENTS WITH TENSIONING ARRANGEMENTS FOR CABLE DRIVEN ARTICULATION SYSTEMS;

U.S. patent application Ser. No. 15/019,230, entitled ARTICULATABLE SURGICAL INSTRUMENTS WITH OFF-AXIS FIRING BEAM ARRANGEMENTS; and U.S. patent application Ser. No. 15/019,245, entitled SURGICAL INSTRUMENTS WITH CLOSURE STROKE REDUCTION ARRANGEMENTS.

Applicant of the present application also owns the U.S. Patent Applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS;

U.S. patent application Ser. No. 15/043,259, entitled MECHANISMS FOR COMPENSATING FOR DRIVETRAIN FAILURE IN POWERED SURGICAL INSTRUMENTS;

U.S. patent application Ser. No. 15/043,275, entitled MECHANISMS FOR COMPENSATING FOR DRIVETRAIN FAILURE IN POWERED SURGICAL INSTRUMENTS; and U.S. patent application Ser. No. 15/043,289, entitled MECHANISMS FOR COMPENSATING FOR DRIVETRAIN FAILURE IN POWERED SURGICAL INSTRUMENTS.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Patent Application Publication No. 2016/0367256;

U.S. patent application Ser. No. 14/742,941, entitled SURGICAL END EFFECTORS WITH DUAL CAM ACTUATED JAW CLOSING FEATURES, now U.S. Patent Application Publication No. 2016/0367248;

U.S. patent application Ser. No. 14/742,914, entitled MOVABLE FIRING BEAM SUPPORT ARRANGEMENTS FOR ARTICULATABLE SURGICAL INSTRUMENTS, now U.S. Patent Application Publication No. 2016/0367255;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Patent Application Publication No. 2016/0367254;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Patent Application Publication No. 2016/0367246; and U.S. patent application Ser. No. 14/742,876, entitled PUSH/PULL ARTICULATION DRIVE SYSTEMS FOR ARTICULATABLE SURGICAL INSTRUMENTS, now U.S. Patent Application Publication No. 2016/0367245.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Patent Application Publication No. 2016/0256184;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Patent Application Publication No. 2016/0256153;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Patent Application Publication No. 2016/0256187;

U.S. patent application Ser. No. 14/640,817, entitled INTERACTIVE FEEDBACK SYSTEM FOR POWERED SURGICAL INSTRUMENTS, now U.S. Patent Application Publication No. 2016/0256186;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Patent Application Publication No. 2016/0256155;

U.S. patent application Ser. No. 14/640,837, entitled SMART SENSORS WITH LOCAL SIGNAL PROCESSING, now U.S. Patent Application Publication No. 2016/0256163;

U.S. patent application Ser. No. 14/640,765, entitled SYSTEM FOR DETECTING THE MIS-INSERTION OF A STAPLE CARTRIDGE INTO A SURGICAL STAPLE/FASTENER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Patent Application Publication No. 2016/0256162; and U.S. patent application Ser. No. 14/640,780, entitled SURGICAL INSTRUMENT COMPRISING A LOCKABLE BATTERY HOUSING, now U.S. Patent Application Publication No. 2016/0256161.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Patent Application Publication No. 2016/0249919;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Patent Application Publication No. 2016/0249915;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Patent Application Publication No. 2016/0249918;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Patent Application Publication No. 2016/0249908;

U.S. patent application Ser. No. 14/633,548, entitled POWER ADAPTER FOR A SURGICAL INSTRUMENT, now U.S. Patent Application Publication No. 2016/0249909;

U.S. patent application Ser. No. 14/633,526, entitled ADAPTABLE SURGICAL INSTRUMENT HANDLE, now U.S. Patent Application Publication No. 2016/0249945;

U.S. patent application Ser. No. 14/633,541, entitled MODULAR STAPLING ASSEMBLY, now U.S. Patent Application Publication No. 2016/0249927; and U.S. patent application Ser. No. 14/633,562, entitled SURGICAL APPARATUS CONFIGURED TO TRACK AN END-OF-LIFE PARAMETER, now U.S. Patent Application Publication No. 2016/0249917.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Patent Application Publication No. 2016/0174977;

U.S. patent application Ser. No. 14/574,483, entitled SURGICAL INSTRUMENT ASSEMBLY COMPRISING LOCKABLE SYSTEMS, now U.S. Patent Application Publication No. 2016/0174969;

U.S. patent application Ser. No. 14/575,139, entitled DRIVE ARRANGEMENTS FOR ARTICULATABLE SURGICAL INSTRUMENTS, now U.S. Patent Application Publication No. 2016/0174978;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Patent Application Publication No. 2016/0174976;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Patent Application Publication No. 2016/0174972;

U.S. patent application Ser. No. 14/575,143, entitled SURGICAL INSTRUMENTS WITH IMPROVED CLOSURE ARRANGEMENTS, now U.S. Patent Application Publication No. 2016/0174983;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Patent Application Publication No. 2016/0174975;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Patent Application Publication No. 2016/0174973;

U.S. patent application Ser. No. 14/574,493, entitled SURGICAL INSTRUMENT ASSEMBLY COMPRISING A FLEXIBLE ARTICULATION SYSTEM, now U.S. Patent Application Publication No. 2016/0174970; and U.S. patent application Ser. No. 14/574,500, entitled SURGICAL INSTRUMENT ASSEMBLY COMPRISING A LOCKABLE ARTICULATION SYSTEM, now U.S. Patent Application Publication No. 2016/0174971.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWREEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Patent Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Patent Application Publication No. 2015/0272579;

U.S. patent application Ser. No. 14/226,093, entitled FEEDBACK ALGORITHMS FOR MANUAL BAIL-OUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Patent Application Publication No. 2015/0272578;

U.S. patent application Ser. No. 14/226,097, entitled SURGICAL INSTRUMENT COMPRISING INTER- ACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Patent Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION, now U.S. Patent Application Publication No. 2015/0280424;

U.S. patent application Ser. No. 14/226,111, entitled SURGICAL STAPLING INSTRUMENT SYSTEM, now U.S. Patent Application Publication No. 2015/0272583; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION, now U.S. Patent Application Publication No. 2016/0066914;

U.S. patent application Ser. No. 14/478,908, entitled MONITORING DEVICE DEGRADATION BASED ON COMPONENT EVALUATION, now U.S. Patent Application Publication No. 2016/0066910;

U.S. patent application Ser. No. 14/478,895, entitled MULTIPLE SENSORS WITH ONE SENSOR AFFECTING A SECOND SENSOR'S OUTPUT OR INTERPRETATION, now U.S. Patent Application Publication No. 2016/0066909;

U.S. patent application Ser. No. 14/479,110, entitled POLARITY OF HALL MAGNET TO DETECT MIS-LOADED CARTRIDGE, now U.S. Patent Application Publication No. 2016/0066915;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Patent Application Publication No. 2016/0066916; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLE/FASTENER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLE/FASTENER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 depicts a motor-driven surgical system 10 that may be used to perform a variety of different surgical procedures. As can be seen in that Figure, one example of the surgical system 10 includes four interchangeable surgical tool assemblies 1000, 3000, 5000 and 7000 that are each adapted for interchangeable use with a handle assembly 500. Each interchangeable surgical tool assembly 1000, 3000, 5000 and 7000 may be designed for use in connection with the performance of one or more specific surgical procedures. In another surgical system embodiment, one or more of the interchangeable surgical tool assemblies 1000, 3000, 5000 and 7000 may also be effectively employed with a tool drive assembly of a robotically controlled or automated surgical system. For example, the surgical tool assemblies disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety.

Figure 2:
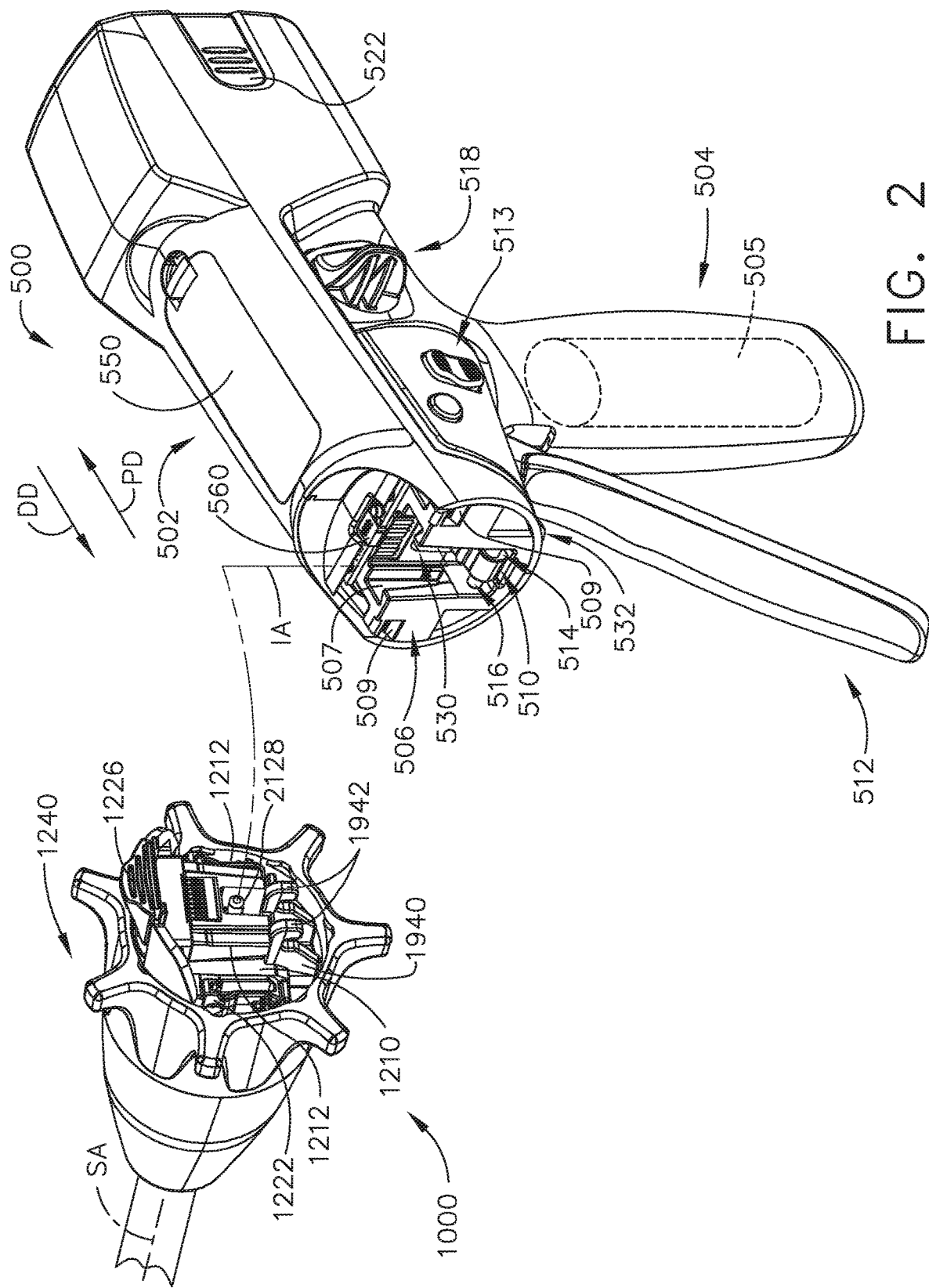
FIG. 2 is an exploded assembly view of portions of the handle assembly and one of the interchangeable surgical tool assemblies depicted in FIG. 1.

FIG. 2 illustrates attachment of an interchangeable surgical tool assembly 1000 to the handle assembly 500. It will be understood that any of the other interchangeable tool assemblies 3000, 5000, and 7000 may be coupled to the handle assembly 500 in a similar manner. The attachment arrangement and process depicted in FIG. 2 may also be employed in connection with attachment of any of the interchangeable surgical tool assemblies 1000, 3000, 5000 and 7000 to a tool drive portion or tool drive housing of a robotic system. The handle assembly 500 may comprise a handle housing 502 that includes a pistol grip portion 504 that can be gripped and manipulated by the clinician. As will be briefly discussed below, the handle assembly 500 operably supports a plurality of drive systems 510, 530 that are configured to generate and apply various control motions to corresponding portions of the interchangeable surgical tool assembly 1000, 3000, 5000 and/or 7000 that is operably attached thereto.

As can be seen in FIG. 2, the handle assembly 500 may further include a handle frame 506 that operably supports the plurality of drive systems. For example, the handle frame 506 can operably support a "first" or closure drive system, generally designated as 510, which may be employed to apply closing and opening motions to the interchangeable surgical tool assembly 1000, 3000, 5000 and 7000 that is operably attached or coupled to the handle assembly 500. In at least one form, the closure drive system 510 may include an actuator in the form of a closure trigger 512 that is pivotally supported by the handle frame 506. Such arrangement enables the closure trigger 512 to be manipulated by a clinician such that when the clinician grips the pistol grip portion 504 of the handle assembly 500, the closure trigger 512 may be easily pivoted from a starting or "unactuated" position to an "actuated" position and more particularly to a fully compressed or fully actuated position. In various forms, the closure drive system 510 further includes a closure linkage assembly 514 that is pivotally coupled to the closure trigger 512 or otherwise operably interfaces therewith. As will be discussed in further detail below, in the illustrated example, the closure linkage assembly 514 includes a transverse attachment pin 516 that facilitates attachment to a corresponding drive system on the surgical tool assembly. In use, to actuate the closure drive system 510, the clinician depresses the closure trigger 512 towards the pistol grip portion 504. As described in further detail in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein, when the clinician fully depresses the closure trigger 512 to attain the full closure stroke, the closure drive system 510 is configured to lock the closure trigger 512 into the fully depressed or fully actuated position. When the clinician desires to unlock the closure trigger 512 to permit it to be biased to the unactuated position, the clinician simply activates a closure release button assembly 518 which enables the closure trigger to return to unactuated position. The closure release button assembly 518 may also be configured to interact with various sensors that communicate with a microprocessor 560 in the handle assembly 500 for tracking the position of the closure trigger 512. Further details concerning the configuration and operation of the closure release button assembly 518 may be found in U.S. Patent Application Publication No. 2015/0272575.

In at least one form, the handle assembly 500 and the handle frame 506 may operably support another drive system referred to herein as a firing drive system 530 that is configured to apply firing motions to corresponding portions of the interchangeable surgical tool assembly that is attached thereto. As was described in detail in U.S. Patent Application Publication No. 2015/0272575, the firing drive system 530 may employ an electric motor 505 that is located in the pistol grip portion 504 of the handle assembly 500. In various forms, the motor 505 may be a DC brushed driving motor having a maximum rotation of, approximately, 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries connected in series may be used as the power source 522 for the surgical system 10. In addition, the power source 522 may be replaceable and/or rechargeable.

The electric motor 505 is configured to axially drive a longitudinally movable drive member (not shown) in a distal and proximal directions depending upon the polarity of the motor. For example, when the motor is driven in one rotary direction, the longitudinally movable drive member will be axially driven in a distal direction "DD". When the motor 505 is driven in the opposite rotary direction, the longitudinally movable drive member will be axially driven in a proximal direction "PD". The handle assembly 500 can include a switch 513 which can be configured to reverse the polarity applied to the electric motor 505 by the power source 522 or otherwise control the motor 505. The handle assembly 500 can also include a sensor or sensors (not shown) that is configured to detect the position of the drive member and/or the direction in which the drive member is being moved. Actuation of the motor 505 can be controlled by a firing trigger 532 (FIG. 1) that is pivotally supported on the handle assembly 500. The firing trigger 532 may be pivoted between an unactuated position and an actuated position. The firing trigger 532 may be biased into the unactuated position by a spring or other biasing arrangement such that when the clinician releases the firing trigger 532, it may be pivoted or otherwise returned to the unactuated position by the spring or biasing arrangement. In at least one form, the firing trigger 532 can be positioned "outboard" of the closure trigger 512 as was discussed above. As discussed in U.S. Patent Application Publication No. 2015/0272575, the handle assembly 500 may be equipped with a firing trigger safety button (not shown) to prevent inadvertent actuation of the firing trigger 532. When the closure trigger 512 is in the unactuated position, the safety button is contained in the handle assembly 500 where the clinician cannot readily access it and move it between a safety position preventing actuation of the firing trigger 532 and a firing position wherein the firing trigger 532 may be fired. As the clinician depresses the closure trigger 512, the safety button and the firing trigger 532 pivot down wherein they can then be manipulated by the clinician.

In at least one form, the longitudinally movable drive member may have a rack of teeth (not shown) formed thereon for meshing engagement with a corresponding drive gear arrangement (not shown) that interfaces with the motor. Further details regarding those features may be found in U.S. Patent Application Publication No. 2015/0272575. At least one form also includes a manually-actuatable "bailout" assembly that is configured to enable the clinician to manually retract the longitudinally movable drive member should the motor 505 become disabled. The bailout assembly may include a lever or bailout handle assembly that is stored within the handle assembly 500 under a releasable door 550. See FIG. 2. The lever may be configured to be manually pivoted into ratcheting engagement with the teeth in the drive member. Thus, the clinician can manually retract the drive member by using the bailout handle assembly to ratchet the drive member in the proximal direction "PD". U.S. Pat. No. 8,608,045, entitled POWERED SURGICAL CUTTING AND STAPLING APPARATUS WITH MANUALLY RETRACTABLE FIRING SYSTEM, the entire disclosure of which is hereby incorporated by reference herein, discloses bailout arrangements and other components, arrangements and systems that may also be employed with any one of the various interchangeable surgical tool assemblies disclosed herein.

Figure 3:
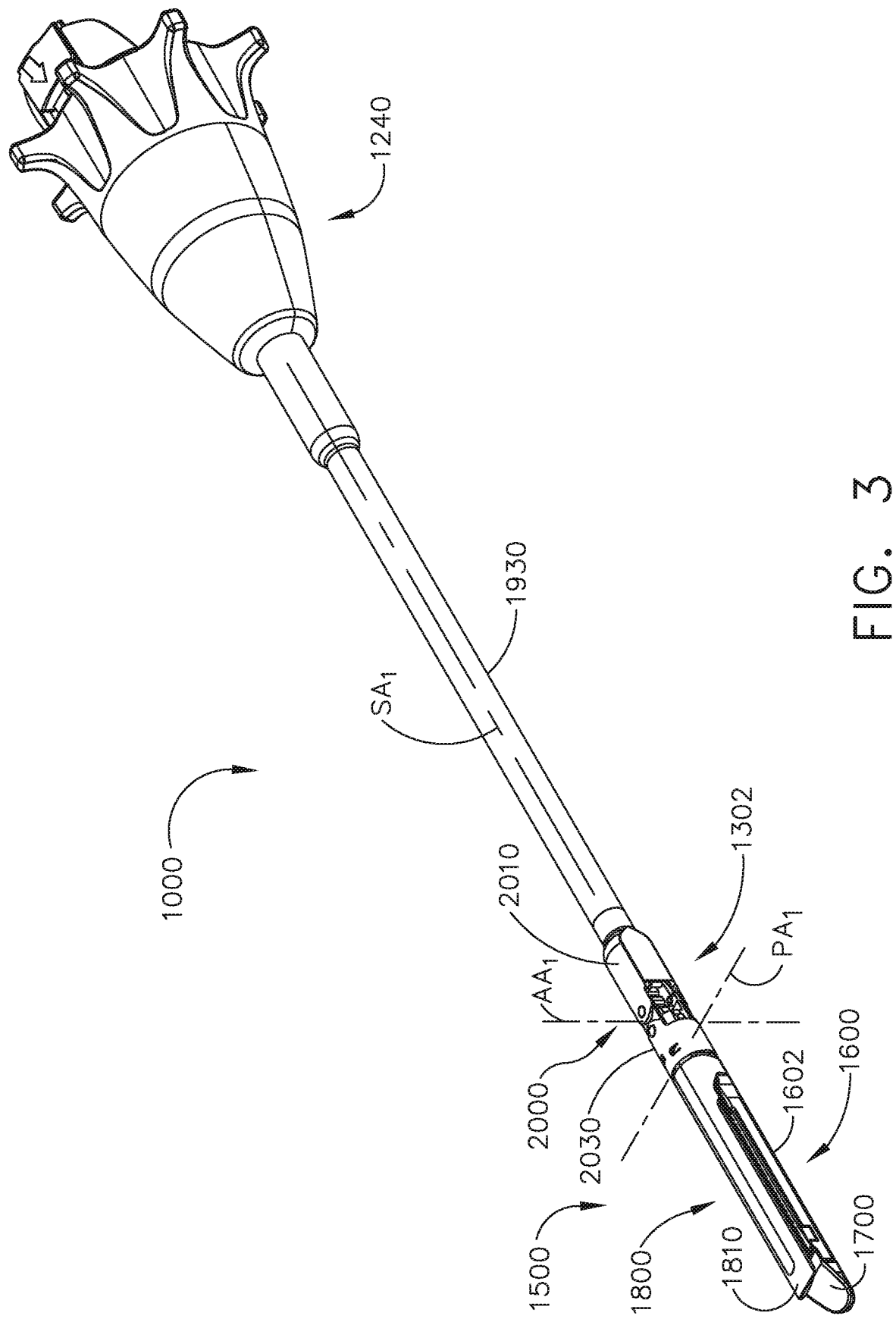
FIG. 3 is a perspective view of one of the interchangeable surgical tool assemblies depicted in FIG. 1.
Figure 4:
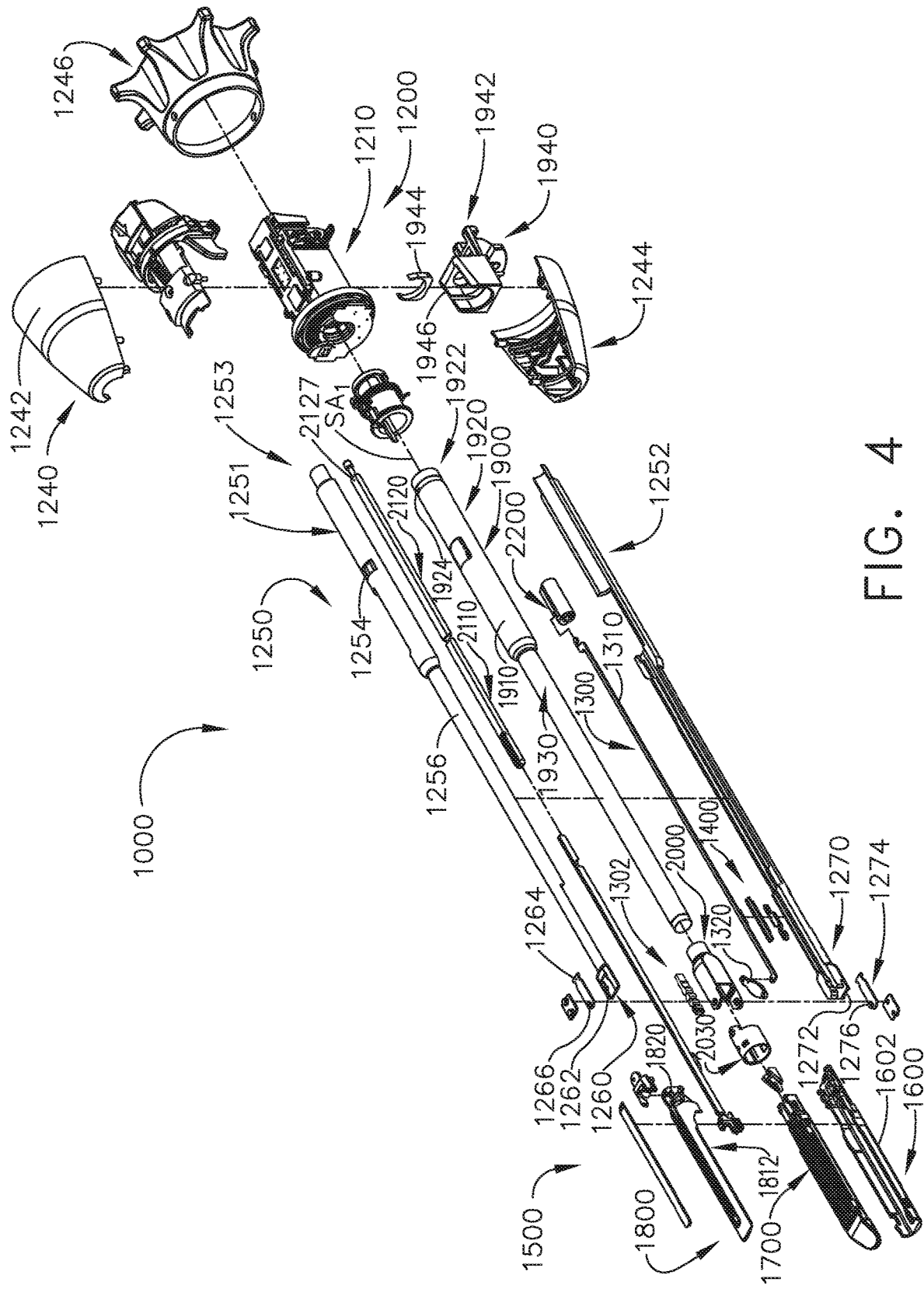
FIG. 4 is an exploded assembly view of the interchangeable surgical tool assembly of FIG. 3.

Turning now to FIGS. 3 and 4, the interchangeable surgical tool assembly 1000 includes a surgical end effector 1500 that comprises a first jaw 1600 and a second jaw 1800. In one arrangement, the first jaw comprises an elongate channel 1602 that is configured to operably support a surgical staple/fastener cartridge 1700 therein. The second jaw 1800 comprises an anvil 1810 that is pivotally supported relative to the elongate channel 1602. The interchangeable surgical tool assembly 1000 includes an articulation system 1300 that comprises an articulation joint 1302 and an articulation lock 1400 (FIGS. 4-6) which can be configured to releasably hold the surgical end effector 1500 in a desired articulated position relative to a shaft axis $SA_1$. Further details regarding the articulation system and articulation lock may be found in U.S. patent application Ser. No. 15/635,837, entitled SURGICAL INSTRUMENT COMPRISING AN ARTICULATION SYSTEM LOCKABLE TO A FRAME, now U.S. Patent Application Publication No. 2019/0000472, filed on Jun. 28, 2017 and hereby incorporated by reference herein in its entirety.

As can be further seen in FIGS. 4 and 7-9, the interchangeable surgical tool assembly 1000 includes a tool frame assembly 1200 that comprises a tool chassis 1210 that operably supports a nozzle assembly 1240 thereon. In one form, the nozzle assembly 1240 is comprised of nozzle portions 1242, 1244 as well as an actuator wheel portion 1246 that is configured to be coupled to the assembled nozzle portions 1242, 1244 by snaps, lugs, screws etc. The interchangeable surgical tool assembly 1000 includes a proximal closure assembly 1900 which is operably coupled to a distal closure assembly 2000 that is utilized to close and/or open the anvil 1810 of the surgical end effector 1500 as will be discussed in further detail below. In addition, the interchangeable surgical tool assembly 1000 includes a spine assembly 1250 that operably supports the proximal closure assembly 1900 and is coupled to the surgical end effector 1500. In various circumstances, for ease of assembly, the spine assembly 1250 may be fabricated from an upper spine segment 1251 and a lower spine segment 1252 that are interconnected together by snap features, adhesive, welding, etc. In assembled form, the spine assembly 1250 includes a proximal end 1253 that is rotatably supported in the tool chassis 1210. In one arrangement, for example, the proximal end 1253 of the spine assembly 1250 is attached to a spine bearing (not shown) that is configured to be supported within the tool chassis 1210. Such arrangement facilitates rotatable attachment of the spine assembly 1250 to the tool chassis 1210 such that the spine assembly 1250 may be selectively rotated about the shaft axis $SA_1$ relative to the tool chassis 1210. In particular, in one arrangement, for example, the proximal end 1253 of the spine assembly 1250 includes an upper lug seat 1254 (FIGS. 4, 5, 7, 8 and 10) and a lower lug seat (not shown) that are each configured to receive a corresponding nozzle lug 1245 extending inwardly from each of the nozzle portions 1242, 1244. Such arrangement facilitates rotation of the spine assembly 1250 about the shaft axis $SA_1$ by rotating the actuator wheel portion 1246 of the nozzle assembly 1240.

Figure 5:
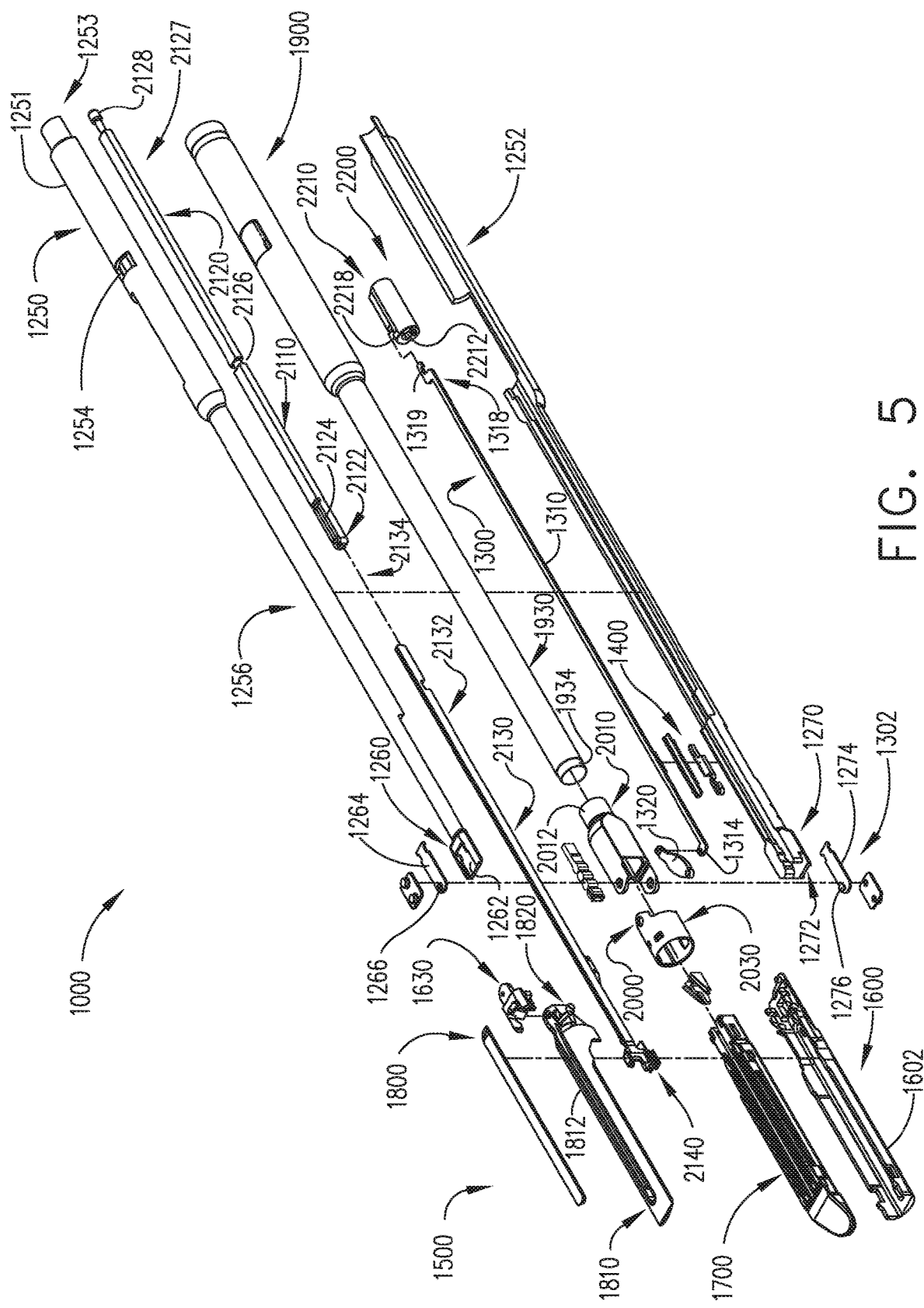
FIG. 5 is another exploded assembly view of a distal portion of the interchangeable surgical tool assembly of FIGS. 3 and 4.

As can be seen in FIGS. 4 and 5, spine assembly 1250 further includes an intermediate spine shaft segment 1256 that has a diameter that is less than the diameter of the proximal end 1253 of the spine assembly 1250. The intermediate spine shaft segment 1256 of the upper spine segment 1251 terminates in an upper lug mount feature 1260 and the intermediate spine shaft segment of the lower spine segment 1252 terminates in a lower lug mount feature 1270. As can be most particularly seen in FIG. 6, for example, the upper lug mount feature 1260 is formed with a lug slot 1262 therein that is adapted to mountingly support an upper mounting link 1264 therein. Similarly, the lower lug mount feature 1270 is formed with a lug slot 1272 therein that is adapted to mountingly support a lower mounting link 1274 therein. The upper mounting link 1264 includes a pivot socket 1266 therein that is offset from the shaft axis $SA_1$. The pivot socket 1266 is adapted to rotatably receive therein a pivot pin 1634 that is formed on a channel cap or anvil retainer 1630 that is attached to a proximal end portion 1610 of the elongate channel 1602. The lower mounting link 1274 includes lower pivot pin 1276 that adapted to be received within a pivot hole 1611 formed in the proximal end portion 1610 of the elongate channel 1602. See FIG. 6. The lower pivot pin 1276 as well as the pivot hole 1611 is offset from the shaft axis $SA_1$. The lower pivot pin 1276 is vertically aligned with the pivot socket 1266 to define an articulation axis $AA_1$ about which the surgical end effector 1500 may articulate relative to the shaft axis $SA_1$. Although the articulation axis $AA_1$ is transverse to the shaft axis $SA_1$, the articulation axis $AA_1$ is laterally offset therefrom and does not intersect the shaft axis $SA_1$.

Figure 6:
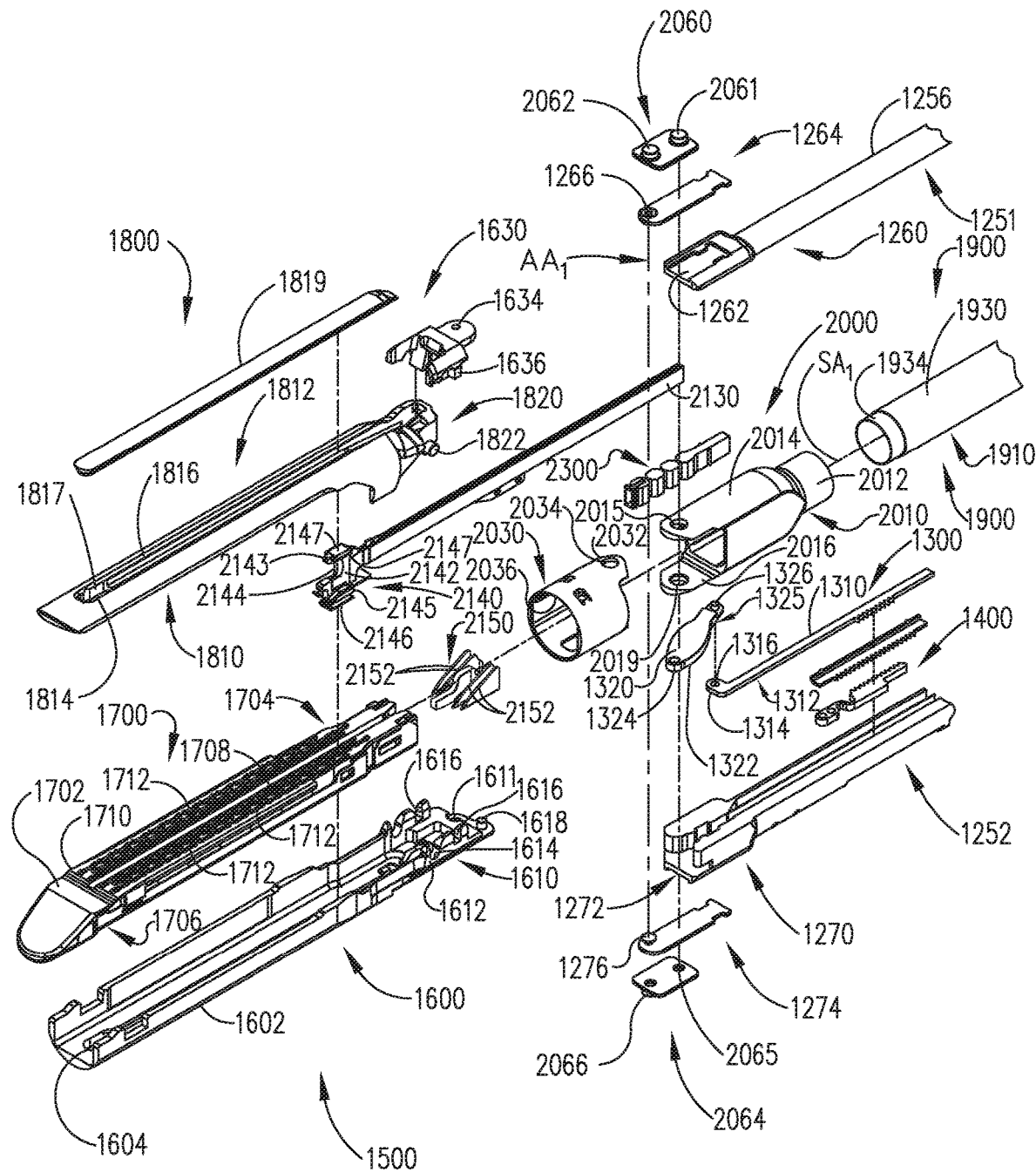
FIG. 6 is another exploded assembly view of a distal portion of the interchangeable surgical tool assembly of FIGS. 3-5.
Figure 15:
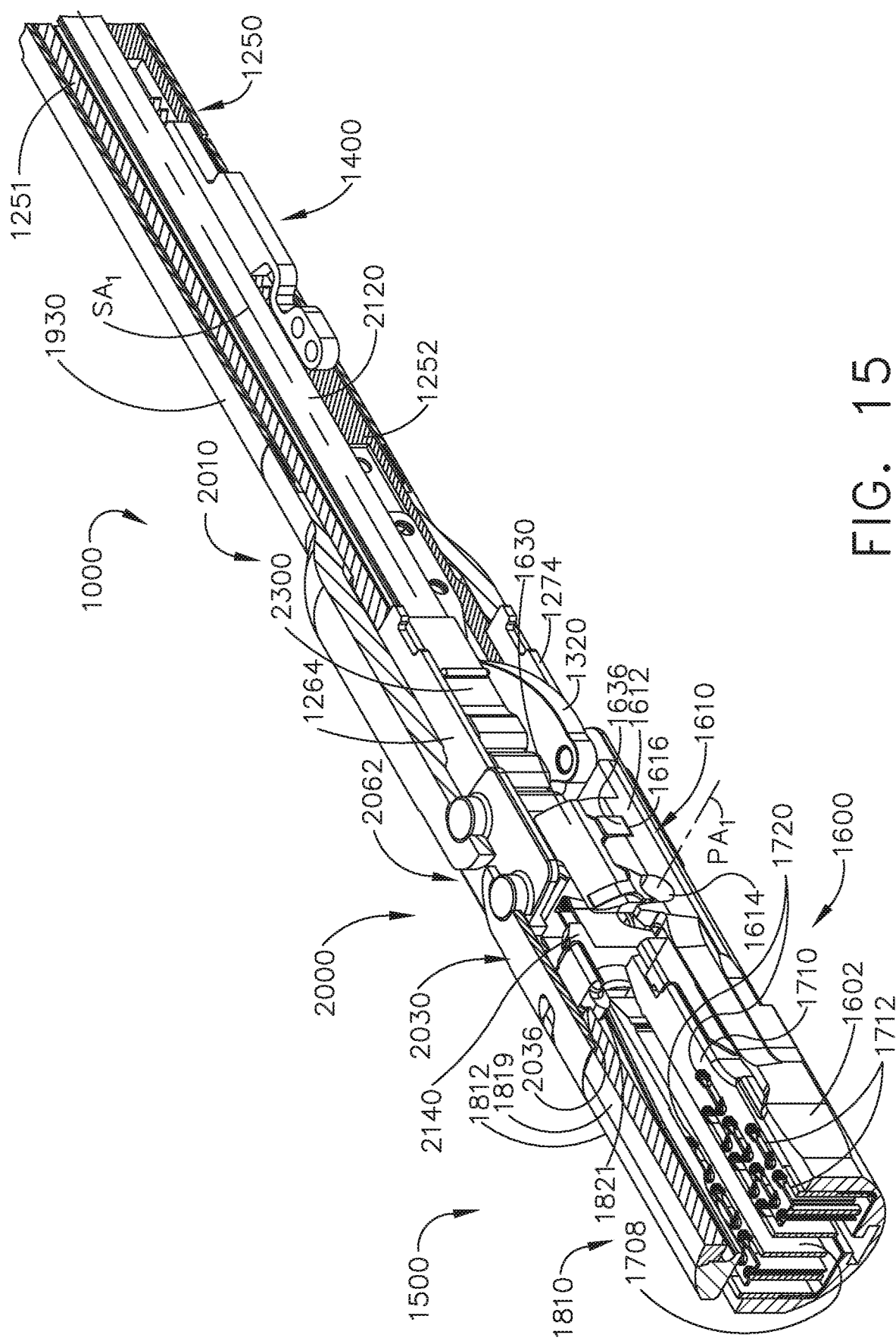
FIG. 15 is a cross-sectional perspective view of a distal portion of the interchangeable surgical tool assembly of FIGS. 3-14.

Referring now to FIGS. 6 and 15, the anvil 1810 in the illustrated example includes an anvil body 1812 that terminates in anvil mounting portion 1820. The anvil mounting portion 1820 is movably or pivotably supported on the elongate channel 1602 for selective pivotal travel relative thereto about a fixed anvil pivot axis $PA_1$ (FIG. 15) that is transverse to the shaft axis $SA_1$. In the illustrated arrangement, a pivot member or anvil trunnion 1822 extends laterally out of each lateral side of the anvil mounting portion 1820 to be received in a corresponding trunnion cradle 1614 formed in the upstanding walls 1612 of the proximal end portion 1610 of the elongate channel 1602. The anvil trunnions 1822 are pivotally retained in their corresponding trunnion cradle 1614 by the channel cap or anvil retainer 1630. The channel cap or anvil retainer 1630 includes a pair of attachment lugs 1636 that are configured to be retainingly received within corresponding lug grooves or notches 1616 formed in the upstanding walls 1612 of the proximal end portion 1610 of the elongate channel 1602.

In the illustrated example, the surgical end effector 1500 is selectively articulatable about the articulation axis $AA_1$ by the articulation system 1300. In one form, the articulation system 1300 includes proximal articulation driver 1310 that is pivotally coupled to an articulation link 1320. As can be most particularly seen in FIG. 6, an offset attachment lug 1314 is formed on a distal end 1312 of the proximal articulation driver 1310. A pivot hole 1316 is formed in the offset attachment lug 1314 and is configured to pivotally receive therein a proximal link pin 1326 formed on the proximal end 1325 of the articulation link 1320. A distal end 1322 of the articulation link 1320 includes a pivot hole 1324 that is configured to pivotally receive therein a channel pin 1618 formed on the proximal end portion 1610 of the elongate channel 1602. Thus, axial movement of proximal articulation driver 1310 will thereby apply articulation motions to the elongate channel 1602 to thereby cause the surgical end effector 1500 to articulate about the articulation axis $AA_1$ relative to the spine assembly 1250.

Figure 7:
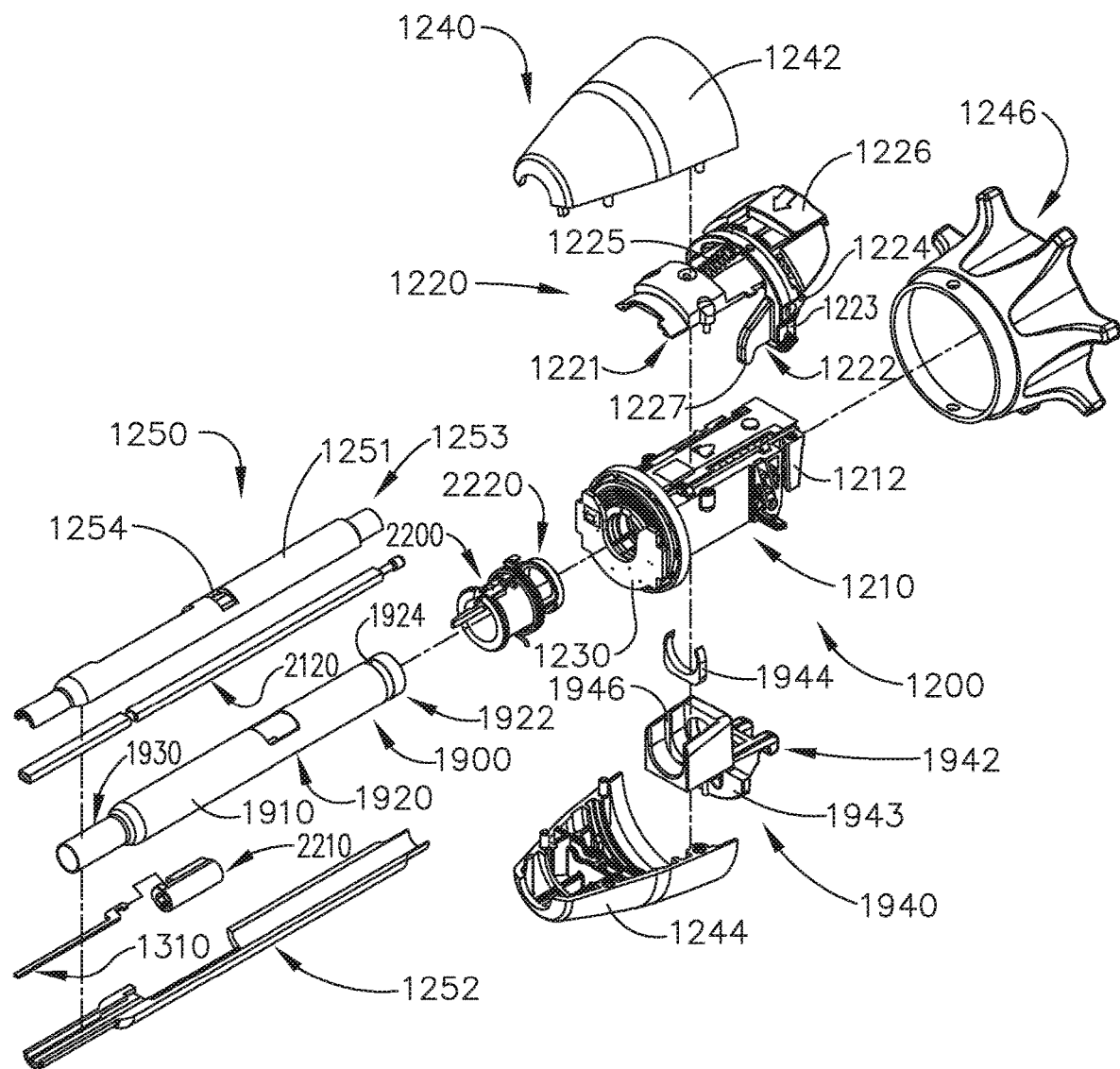
FIG. 7 is an exploded assembly view of a proximal portion of the interchangeable surgical tool assembly of FIGS. 3-6.
Figure 8:
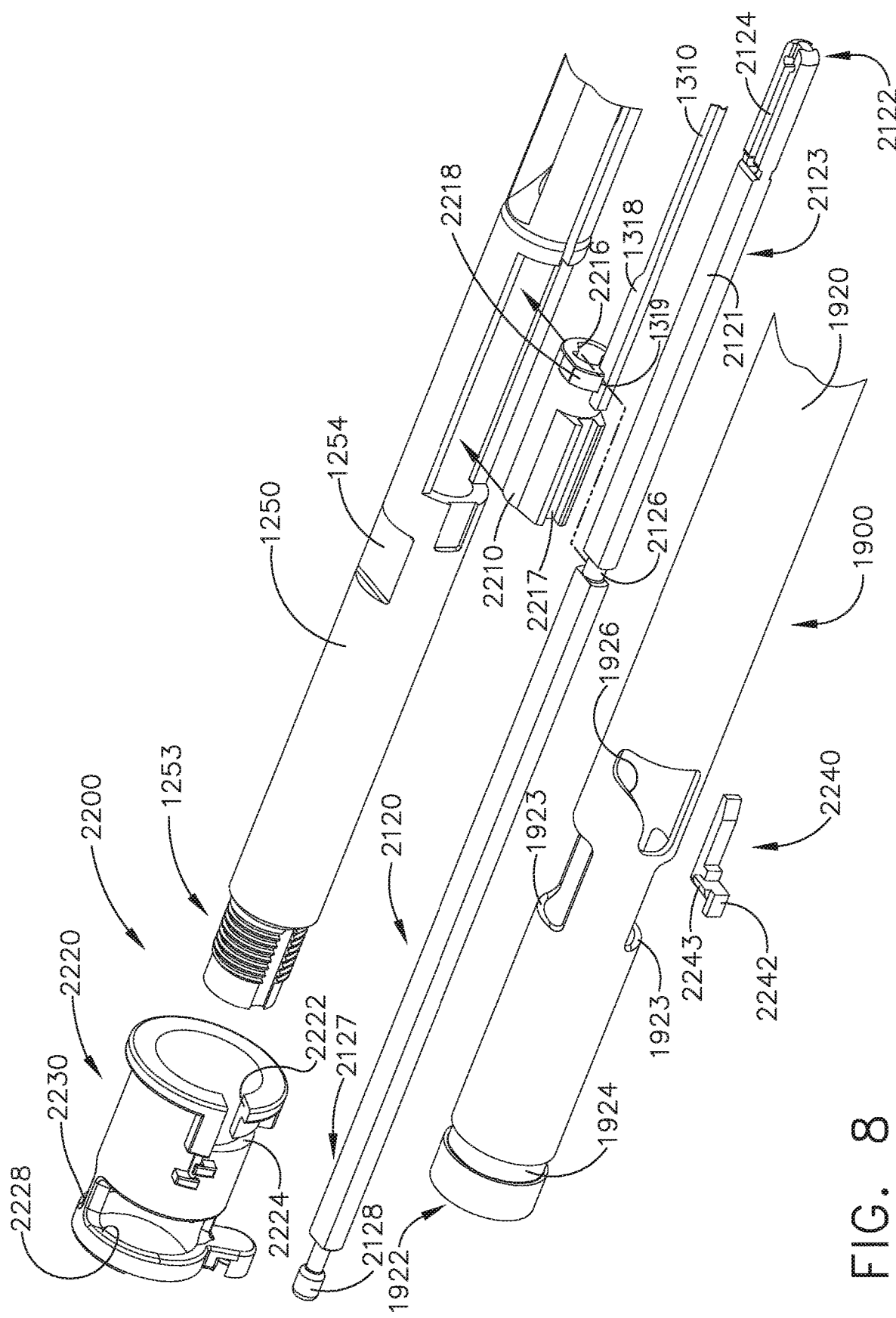
FIG. 8 is another exploded assembly view of a portion of the interchangeable surgical tool assembly of FIGS. 3-7.
Figure 9:
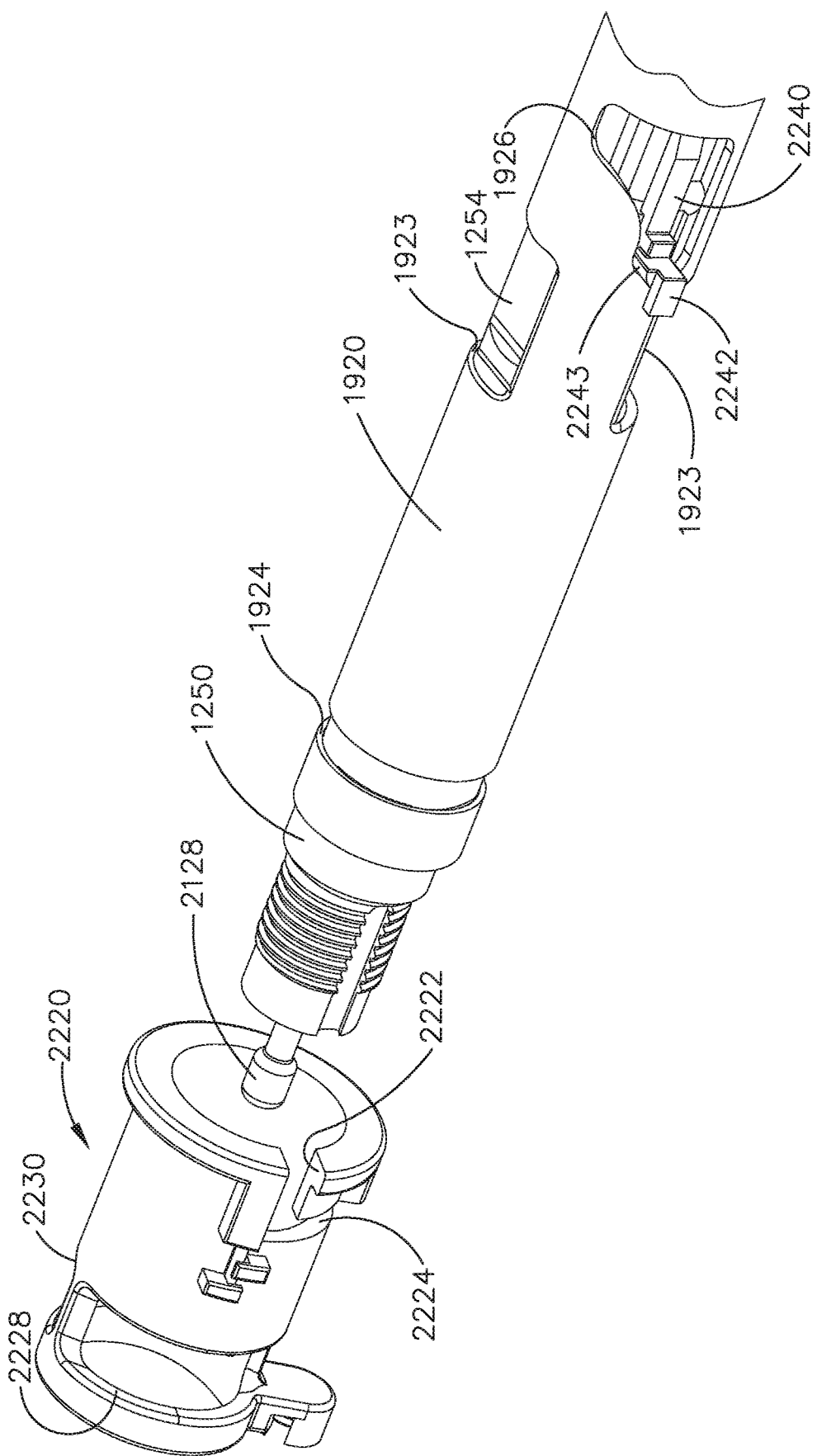
FIG. 9 is another exploded assembly view of a portion of the interchangeable surgical tool assembly of FIGS. 3-8.
Figure 10:
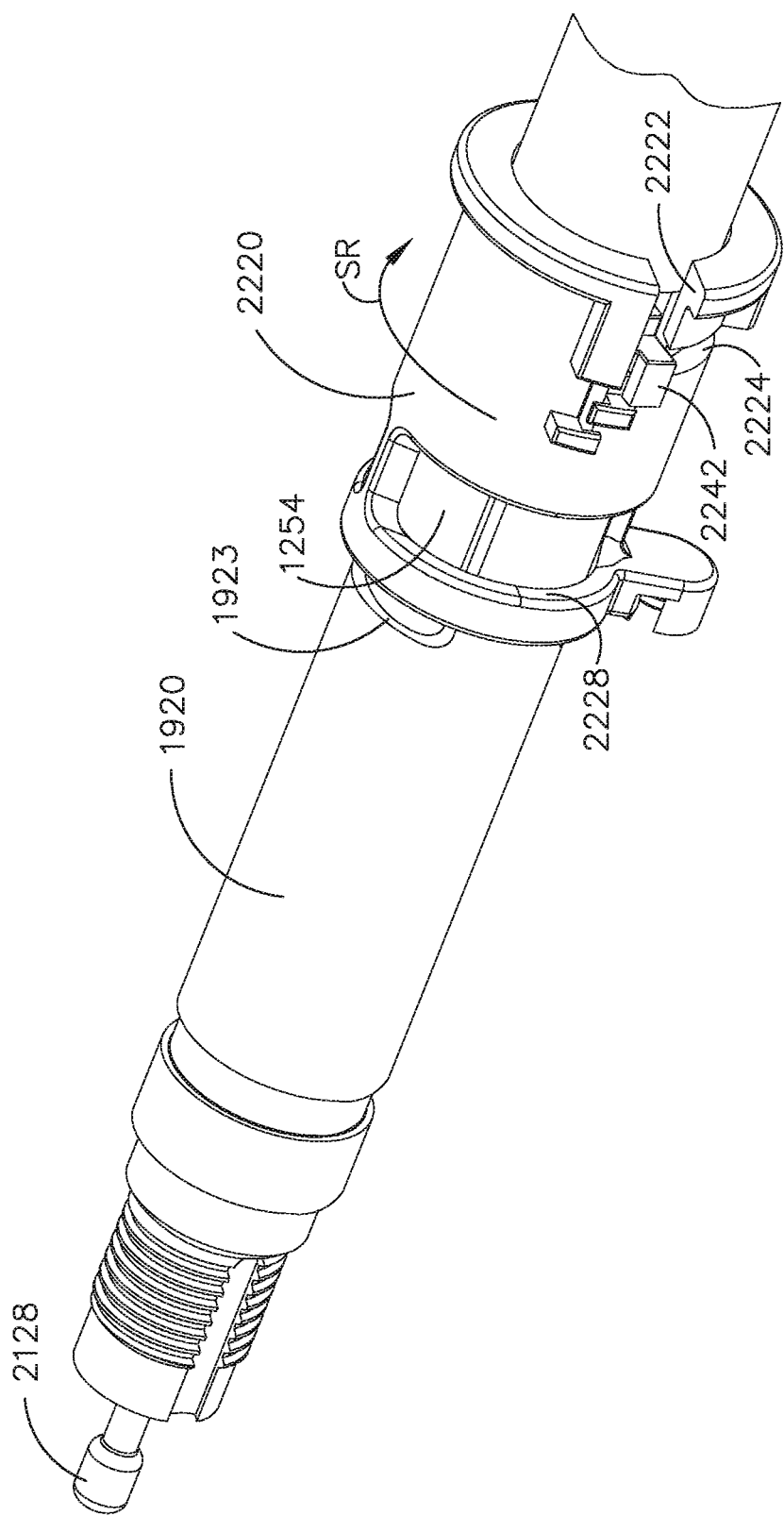
FIG. 10 is a perspective view of a proximal portion of the interchangeable surgical tool assembly of FIGS. 3-9.
Figure 11:
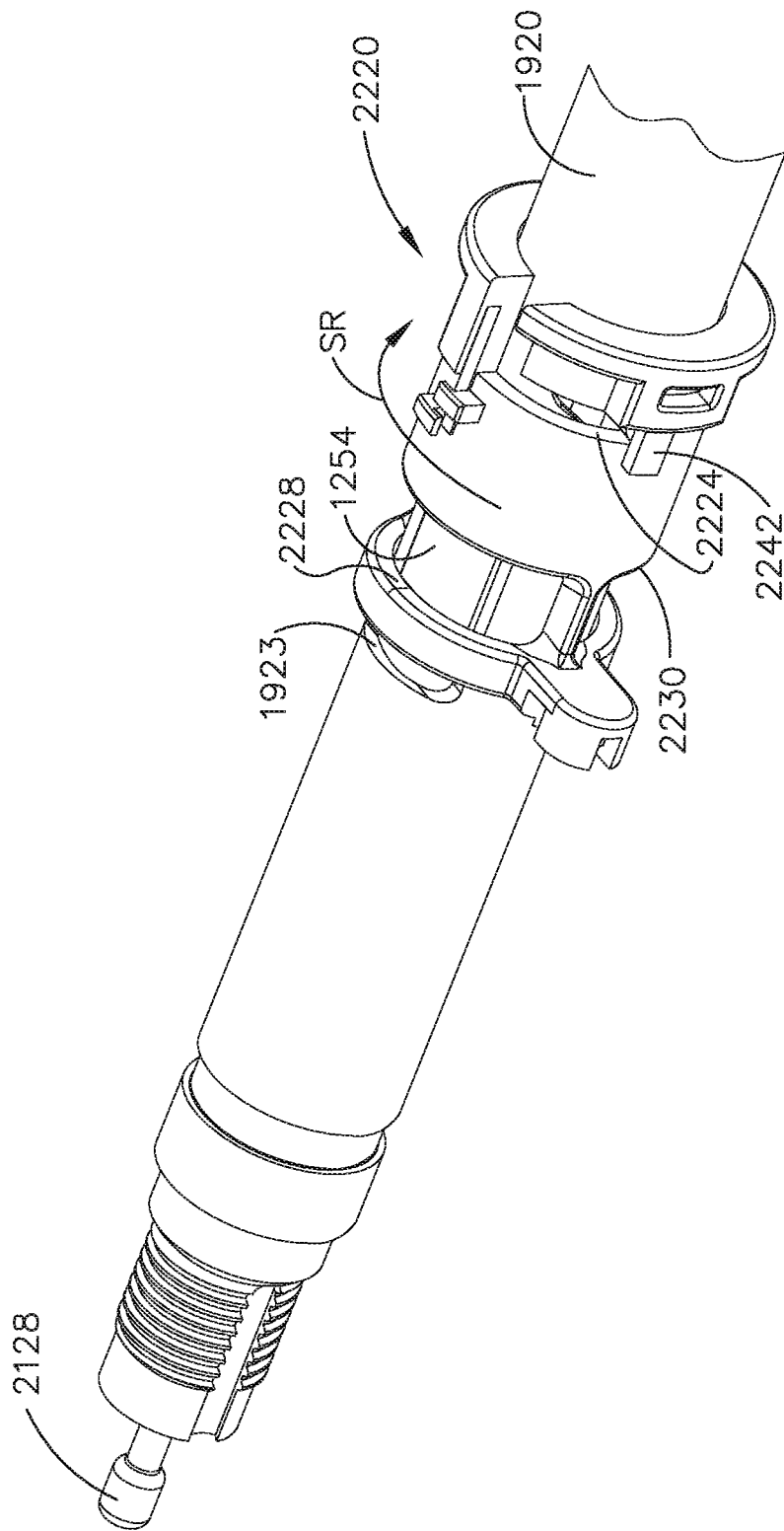
FIG. 11 is another perspective view of the proximal portion of the interchangeable surgical tool assembly of FIGS. 3-10.
Figure 12:
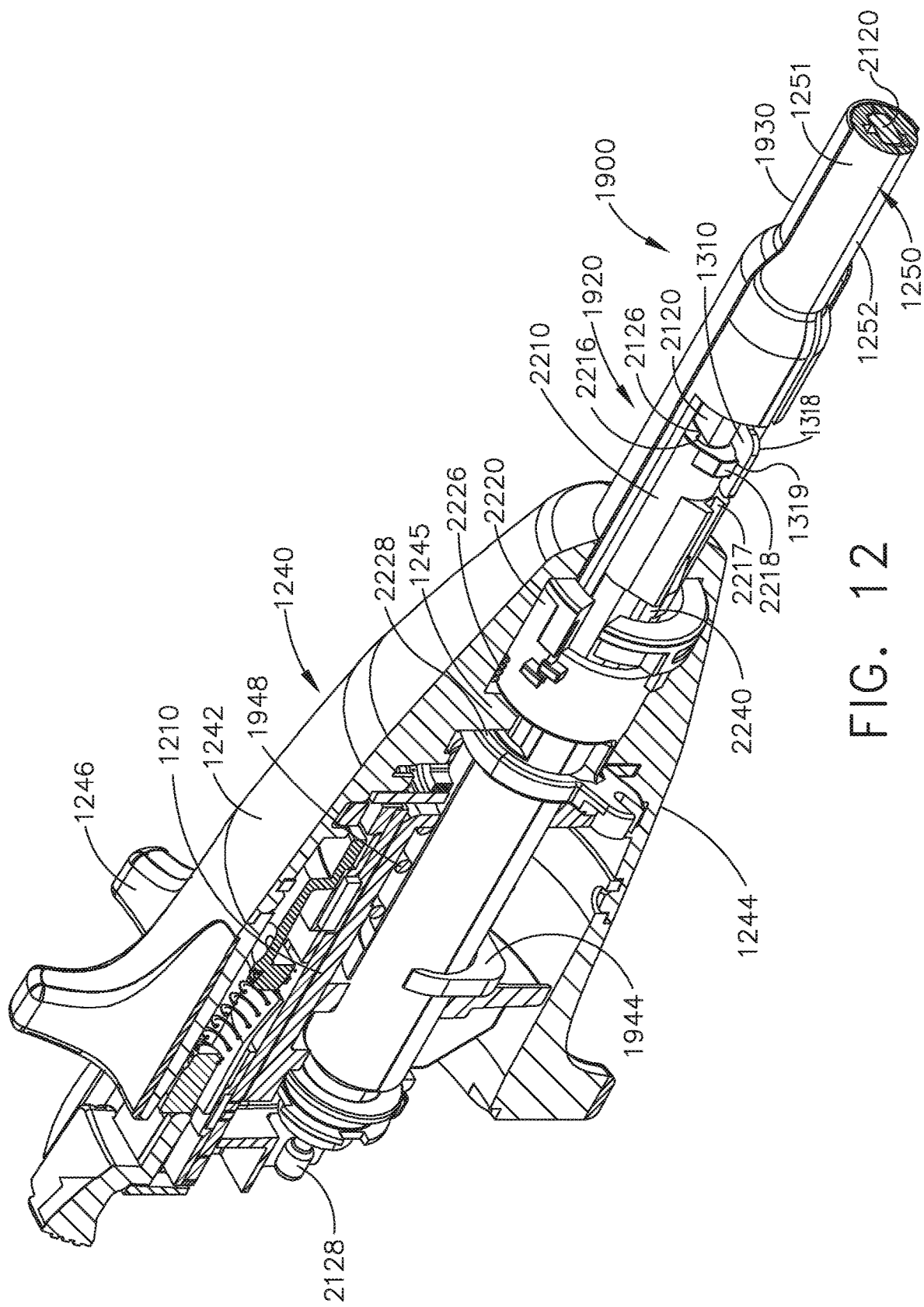
FIG. 12 is a cross-sectional perspective view of the proximal portion of the interchangeable surgical tool assembly of FIGS. 3-11.
Figure 13:
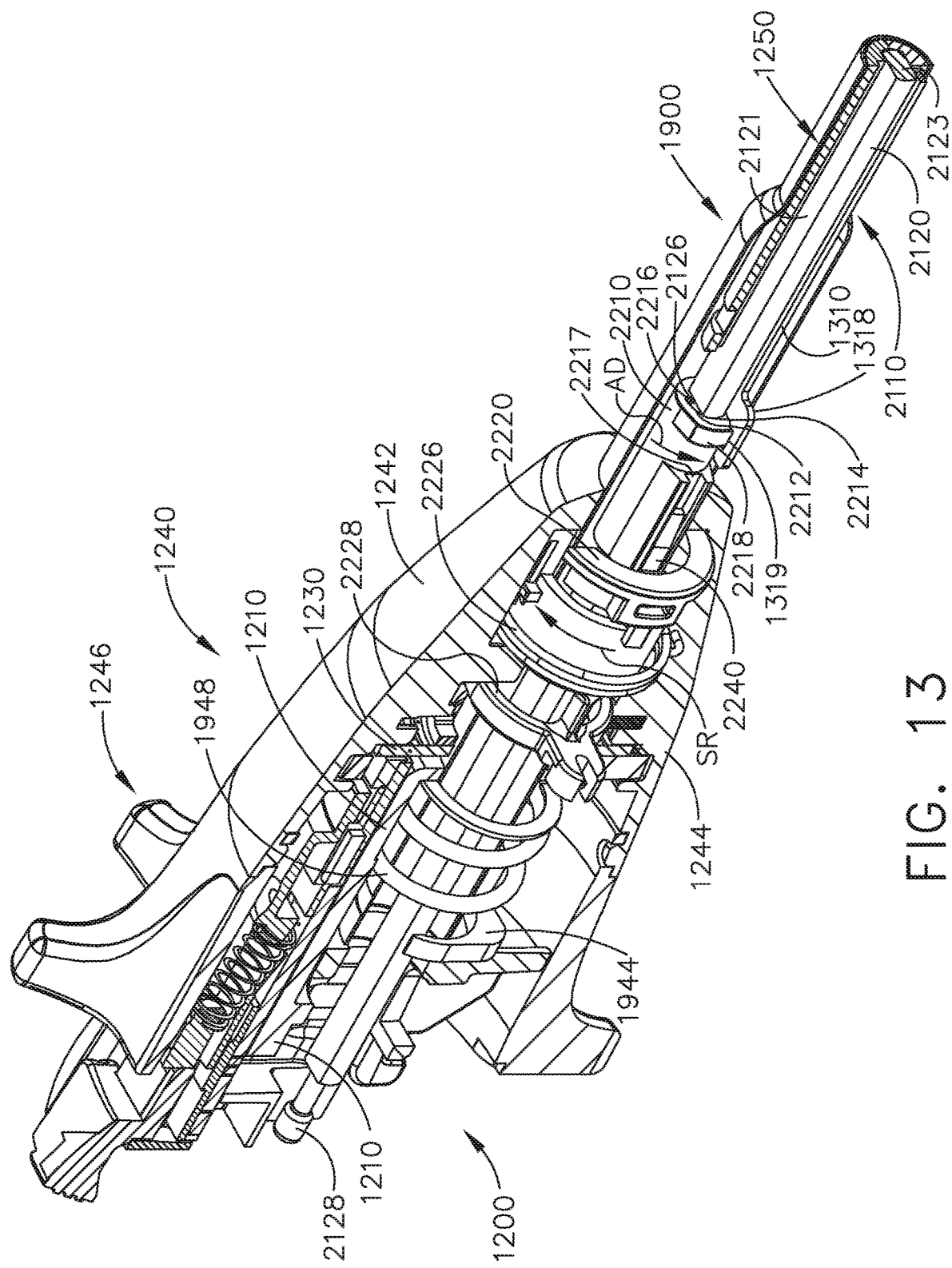
FIG. 13 is another cross-sectional perspective view of the proximal portion of the interchangeable surgical tool assembly of FIGS. 3-12.
Figure 14:
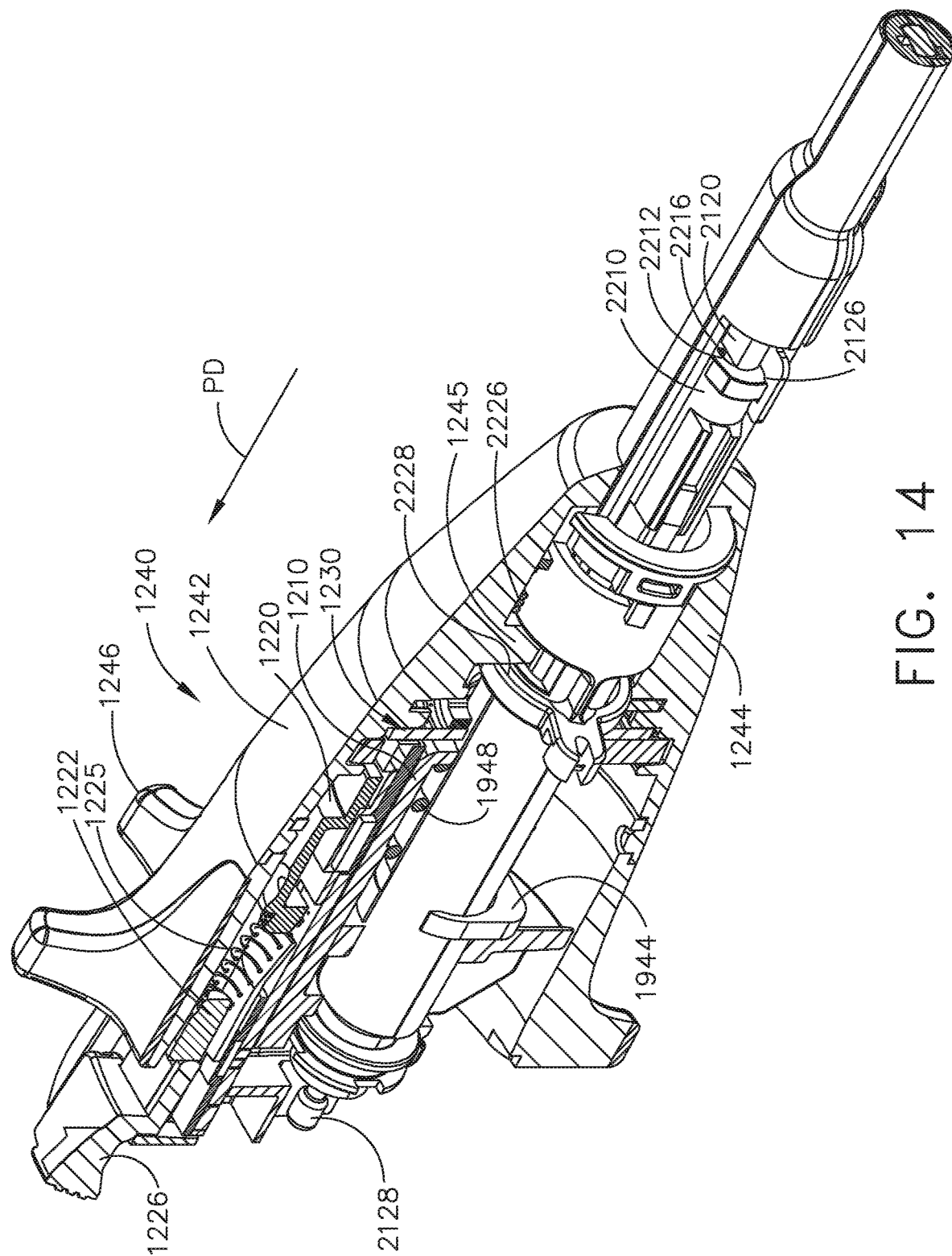
FIG. 14 is another cross-sectional perspective view of the proximal portion of the interchangeable surgical tool assembly of FIGS. 3-13.

Movement of the anvil 1810 relative to the elongate channel 1602 is effectuated by axial movement of the proximal closure assembly 1900 and the distal closure assembly 2000. Referring now to FIGS. 4 and 7, in the illustrated arrangement, the proximal closure assembly 1900 comprises a proximal closure tube 1910 that has a proximal closure tube portion 1920 and a distal portion 1930. The distal portion 1930 has a diameter that is less than the diameter of the proximal closure tube portion 1920. The proximal end 1922 of the proximal closure tube portion 1920 is rotatably supported in a closure shuttle 1940 that is slidably supported within the tool chassis 1210 such that it may be axially moved relative thereto. In one form, the closure shuttle 1940 includes a pair of proximally-protruding hooks 1942 that are configured for attachment to the attachment pin 516 that is attached to the closure linkage assembly 514 of the handle assembly 500. The proximal end 1922 of the proximal closure tube portion 1920 is coupled to the closure shuttle 1940 for relative rotation thereto. For example, a U-shaped connector 1944 is inserted into an annular slot 1924 in the proximal closure tube portion 1920 and is retained within vertical slots 1946 in the closure shuttle 1940. Such arrangement serves to attach the proximal closure assembly 1900 to the closure shuttle 1940 for axial travel therewith while enabling the proximal closure assembly 1900 to rotate relative to the closure shuttle 1940 about the shaft axis $SA_1$. A closure spring 1948 (FIGS. 12-14) extends over the proximal closure tube portion 1920 to bias the closure shuttle 1940 in the proximal direction PD which can serve to pivot the closure trigger 512 on the handle assembly 500 (FIG. 2) into the unactuated position when the interchangeable surgical tool assembly 1000 is operably coupled to the handle assembly 500.

Referring now to FIGS. 5 and 6, a distal portion 1930 of the proximal closure tube 1910 is attached to the distal closure assembly 2000. In the illustrated arrangement for example, the distal closure assembly 2000 includes an articulation connector 2010 that is coupled to a distal closure tube segment 2030. In the illustrated example, the distal closure tube segment 2030 has a diameter that is larger than the diameter of the distal portion 1930 of the proximal closure tube 1910. The articulation connector 2010 has a proximally extending end portion 2012 that is adapted to be received on a connection flange 1934 formed on the distal end of the distal portion 1930. The articulation connector 2010 may be retained on the connection flange 1934 by an appropriate fastener arrangement such as adhesive, welding, etc. The articulation connector 2010 includes upper and lower tangs 2014, 2016 protrude distally from a distal end of the articulation connector 2010 to be movably coupled to an end effector closure sleeve or distal closure tube segment 2030. The distal closure tube segment 2030 includes an upper tang 2032 and a lower tang (not shown) that protrude proximally from a proximal end thereof. An upper double pivot link 2060 includes proximal and distal pins 2061, 2062 that engage corresponding holes 2015, 2034 in the upper tangs 2014, 2032 of the articulation connector 2010 and distal closure tube segment 2030, respectively. Similarly, a lower double pivot link 2064 includes proximal and distal pins 2065, 2066 that engage corresponding holes 2019 in the lower tangs 2016 of the articulation connector 2010 and distal closure tube segment 2030, respectively. As will be discussed in further detail below, distal and proximal axial translation of the proximal closure assembly 1900 and distal closure assembly 2000 will result in the closing and opening of the anvil 1810 relative to the elongate channel 1602.

In at least one arrangement, the interchangeable surgical tool assembly 1000 further includes a firing system generally designated as 2100. In the illustrated example, the firing system 2100 includes a firing member assembly 2110 that is supported for axial travel within the spine assembly 1250. In the illustrated embodiment, the firing member assembly 2110 includes an intermediate firing shaft portion 2120 that is configured for attachment to a distal cutting portion or knife bar 2130. The firing member assembly 2110 may also be referred to herein as a "second shaft" and/or a "second shaft assembly". As can be seen in FIG. 5, the intermediate firing shaft portion 2120 may include a longitudinal slot 2124 in a distal end 2122 thereof which can be configured to receive a proximal end 2132 of the knife bar 2130. The longitudinal slot 2124 and the proximal end 2132 of the knife bar 2130 can be sized and configured to permit relative movement therebetween and can comprise a slip joint 2134. The slip joint 2134 can permit the intermediate firing shaft portion 2120 of the firing member assembly 2110 to be moved to articulate the end effector 1500 without moving, or at least substantially moving, the knife bar 2130. Once the end effector 1500 has been suitably oriented, the intermediate firing shaft portion 2120 can be advanced distally until a proximal sidewall of the longitudinal slot 2124 comes into contact with a portion of the knife bar 2130 to advance the knife bar 2130 and fire the surgical staple/fastener cartridge 1700 positioned within the elongate channel 1602. In the illustrated arrangement, a proximal end 2127 of the intermediate firing shaft portion 2120 has a firing shaft attachment lug 2128 formed thereon (FIG. 8) that is configured to be seated into an attachment cradle (not shown) that is on the distal end of the longitudinally movable drive member (not shown) of the firing drive system 530 within the handle assembly 500. Such arrangement facilitates the axial movement of the intermediate firing shaft portion 2120 upon actuation of the firing drive system 530.

Further to the above, the interchangeable tool assembly 1000 can include a shifter assembly 2200 which can be configured to selectively and releasably couple the proximal articulation driver 1310 to the firing system 2100. In one form, the shifter assembly 2200 includes a lock collar, or lock sleeve 2210, positioned around the intermediate firing shaft portion 2120 of the firing system 2100 wherein the lock sleeve 2210 can be rotated between an engaged position in which the lock sleeve 2210 couples the proximal articulation driver 1310 to the firing member assembly 2110 and a disengaged position in which the proximal articulation driver 1310 is not operably coupled to the firing member assembly 2110. When lock sleeve 2210 is in its engaged position, distal movement of the firing member assembly 2110 can move the proximal articulation driver 1310 distally and, correspondingly, proximal movement of the firing member assembly 2110 can move the proximal articulation driver 1310 proximally. When lock sleeve 2210 is in its disengaged position, movement of the firing member assembly 2110 is not transmitted to the proximal articulation driver 1310 and, as a result, the firing member assembly 2110 can move independently of the proximal articulation driver 1310. In various circumstances, the proximal articulation driver 1310 can be held in position by the articulation lock 1400 when the proximal articulation driver 1310 is not being moved in the proximal or distal directions by the firing member assembly 2110.

In the illustrated arrangement, the intermediate firing shaft portion 2120 of the firing member assembly 2110 is formed with two opposed flat sides 2121, 2123 with a drive notch 2126 formed therein. See FIG. 8. As can also be seen in FIG. 13, the lock sleeve 2210 comprises a cylindrical, or an at least substantially cylindrical, body that includes a longitudinal aperture 2212 that is configured to receive the intermediate firing shaft portion 2120 therethrough. The lock sleeve 2210 can comprise diametrically-opposed, inwardly-facing lock protrusions 2214, 2216 that, when the lock sleeve 2210 is in one position, are engagingly received within corresponding portions of the drive notch 2126 in the intermediate firing shaft portion 2120 and, when in another position, are not received within the drive notch 2126 to thereby permit relative axial motion between the lock sleeve 2210 and the intermediate firing shaft portion 2120.

Referring now to FIGS. 8 and 12-14, in the illustrated example, the lock sleeve 2210 further includes a lock member 2218 that is sized to be movably received within a notch 1319 in a proximal end 1318 of the proximal articulation driver 1310. Such arrangement permits the lock sleeve 2210 to slightly rotate into and out of engagement with the intermediate firing shaft portion 2120 while remaining in engagement with the notch 1319 in the proximal articulation driver 1310. For example, when the lock sleeve 2210 is in its engaged position, the lock protrusions 2214, 2216 are positioned within the drive notch 2126 in the intermediate firing shaft portion 2120 such that a distal pushing force and/or a proximal pulling force can be transmitted from the firing member assembly 2110 to the lock sleeve 2210. Such axial pushing or pulling motion is then transmitted from the lock sleeve 2210 to the proximal articulation driver 1310 to thereby articulate the surgical end effector 1500. In effect, the firing member assembly 2110, the lock sleeve 2210, and the proximal articulation driver 1310 will move together when the lock sleeve 2210 is in its engaged (articulation) position. On the other hand, when the lock sleeve 2210 is in its disengaged position, the lock protrusions 2214, 2216 are not received within the drive notch 2126 in the intermediate firing shaft portion 2120 and, as a result, a distal pushing force and/or a proximal pulling force may not be transmitted from the firing member assembly 2110 to the lock sleeve 2210 (and the proximal articulation driver 1310).

In the illustrated example, relative movement of the lock sleeve 2210 between its engaged and disengaged positions may be controlled by a shifter assembly 2200 that is interfaces with the proximal closure tube 1910 of the proximal closure assembly 1900. More specifically and with reference to FIGS. 8 and 9, the shifter assembly 2200 further includes a shifter key 2240 that is configured to be slidably received within a key groove 2217 formed in the outer perimeter of the lock sleeve 2210. Such arrangement enables the shifter key 2240 to move axially with respect to the lock sleeve 2210. Referring to FIGS. 8-11, the shifter key 2240 includes an actuator lug 2242 that extends through a cam slot or cam opening 1926 in the proximal closure tube portion 1920. See FIG. 9. A cam surface 2243 is also provided adjacent the actuator lug 2242 which is configured to cammingly interact with the cam opening 1926 so as to cause the shifter key 2240 to rotate in response to axial motion of the proximal closure tube portion 1920.

Also in the illustrated example, the shifter assembly 2200 further includes a switch drum 2220 that is rotatably received on a proximal end portion of the proximal closure tube portion 1920. As can be seen in FIGS. 10-14, the actuator lug 2242 extends through an axial slot segment 2222 in the switch drum 2220 and is movably received within an arcuate slot segment 2224 in the switch drum 2220. A switch drum torsion spring 2226 (FIGS. 12-14) is mounted on the switch drum 2220 and engages nozzle portion 1244 to apply a torsional bias or rotation (arrow SR in FIGS. 10 and 11) which serves to rotate the switch drum 2220 until the actuator lug 2242 reaches the end of the arcuate slot segment 2224. See FIGS. 11 and 12. When in this position, the switch drum 2220 may provide a torsional bias to the shifter key 2240 which thereby causes the lock sleeve 2210 to rotate into its engaged position with the intermediate firing shaft portion 2120. This position also corresponds to the unactuated configuration of the proximal closure assembly 1900. In one arrangement, for example, when the proximal closure assembly 1900 is in an unactuated configuration (anvil 1810 is in an open position spaced away from the surgical staple/fastener cartridge 1700) the actuator lug 2242 is located in the upper portion of the cam opening 1926 in the proximal closure tube portion 1920. When in that position, actuation of the intermediate firing shaft portion 2120 will result in the axial movement of the proximal articulation driver 1310. Once the user has articulated the surgical end effector 1500 to a desired orientation, the user may then actuate the proximal closure assembly 1900. Actuation of the proximal closure assembly 1900 will result in the distal travel of the proximal closure tube portion 1920 to ultimately apply a closing motion to the anvil 1810. This distal travel of the proximal closure tube portion 1920 will result in the cam opening 1926 cammingly interacting with the cam surface 2243 on the actuator lug 2242 to thereby cause the shifter key 2240 to rotate the lock sleeve 2210 in an actuation direction AD. Such rotation of the lock sleeve 2210 will result in the disengagement of the lock protrusions 2214, 2216 from the drive notch 2126 in the intermediate firing shaft portion 2120. When in such configuration, the firing drive system 530 may be actuated to actuate the intermediate firing shaft portion 2120 without actuating the proximal articulation driver 1310. Further details concerning the operation of the switch drum 2220 and lock sleeve 2210, as well as alternative articulation and firing drive arrangements that may be employed with the various interchangeable surgical tool assemblies described herein, may be found in U.S. patent application Ser. No. 13/803,086, now U.S. Patent Application Publication No. 2014/0263541, and U.S. patent application Ser. No. 15/019,196, the entire disclosures of which are hereby incorporated by reference herein.

Referring again to FIGS. 8-13, the switch drum 2220 can further comprise at least partially circumferential openings 2228, 2230 defined therein which can receive circumferential lugs/mounts 1245 that extend from the nozzle portions 1242, 1244 and permit relative rotation, but not translation, between the switch drum 2220 and the nozzle assembly 1240. The nozzle lugs 1245 extend through corresponding openings 1923 in the proximal closure tube portion 1920 to be seated in lug seats 1254 in the spine assembly 1250. See FIGS. 8 and 9. Such arrangement enables the user to rotate the spine assembly 1250 about the shaft axis by rotating the nozzle assembly 1240.

As also illustrated in FIGS. 7 and 12-14, the interchangeable tool assembly 1000 can comprise a slip ring assembly 1230 which can be configured to conduct electrical power to and/or from the surgical end effector 1500 and/or communicate signals to and/or from the surgical end effector 1500, back to a microprocessor 560 (FIG. 2) in the handle assembly 500 or robotic system controller, for example. Further details concerning the slip ring assembly 1230 and associated connectors may be found in U.S. patent application Ser. No. 13/803,086, now U.S. Patent Application Publication No. 2014/0263541, and U.S. patent application Ser. No. 15/019,196 which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety. As also described in further detail in the aforementioned patent applications that have been incorporated by reference herein, the interchangeable surgical tool assembly 1000 can also comprise at least one sensor that is configured to detect the position of the switch drum 2220.

Referring again to FIG. 2, the tool chassis 1210 includes at least one, and preferably two, tapered attachment portions 1212 formed thereon that are adapted to be received within corresponding dovetail slots 507 formed within the distal end portion of the handle frame 506 of the handle assembly 500. Various interchangeable surgical tool assemblies employ a latch system 1220 for removably coupling the interchangeable surgical tool assembly 1000 to the handle frame 506 of the handle assembly 500. As can be seen in FIG. 7, for example, in at least one form, the latch system 1220 includes a lock member or lock yoke 1222 that is movably coupled to the tool chassis 1210. In the illustrated embodiment, for example, the lock yoke 1222 has a U-shape with two spaced downwardly extending legs 1223. The legs 1223 each have a pivot lug (not shown) formed thereon that are adapted to be received in corresponding holes formed in the tool chassis 1210. Such arrangement facilitates pivotal attachment of the lock yoke 1222 to the tool chassis 1210. The lock yoke 1222 may include two proximally protruding lock lugs 1224 that are configured for releasable engagement with corresponding lock detents or grooves 509 in the distal end of the handle frame 506 of the handle assembly 500. See FIG. 2. In various forms, the lock yoke 1222 is biased in the proximal direction by a spring or biasing member 1225. Actuation of the lock yoke 1222 may be accomplished by a latch button 1226 that is slidably mounted on a latch actuator assembly 1221 that is mounted to the tool chassis 1210. The latch button 1226 may be biased in a proximal direction relative to the lock yoke 1222. The lock yoke 1222 may be moved to an unlocked position by biasing the latch button 1226 in the distal direction which also causes the lock yoke 1222 to pivot out of retaining engagement with the distal end of the handle frame 506. When the lock yoke 1222 is in "retaining engagement" with the distal end of the handle frame 506, the lock lugs 1224 are retainingly seated within the corresponding lock detents or grooves 509 in the distal end of the handle frame 506.

In the illustrated arrangement, the lock yoke 1222 includes at least one and preferably two lock hooks 1227 that are adapted to contact corresponding lock lug portions 1943 that are formed on the closure shuttle 1940. When the closure shuttle 1940 is in an unactuated position, the lock yoke 1222 may be pivoted in a distal direction to unlock the interchangeable surgical tool assembly 1000 from the handle assembly 500. When in that position, the lock hooks 1227 do not contact the lock lug portions 1943 on the closure shuttle 1940. However, when the closure shuttle 1940 is moved to an actuated position, the lock yoke 1222 is prevented from being pivoted to an unlocked position. Stated another way, if the clinician were to attempt to pivot the lock yoke 1222 to an unlocked position or, for example, the lock yoke 1222 was inadvertently bumped or contacted in a manner that might otherwise cause it to pivot distally, the lock hooks 1227 on the lock yoke 1222 will contact the lock lug portions 1943 on the closure shuttle 1940 and prevent movement of the lock yoke 1222 to an unlocked position.

Referring again to FIG. 6, the knife bar 2130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 2130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS which is hereby incorporated by reference in its entirety. As can also be seen in FIG. 6, a firing shaft support assembly 2300 is employed to provide lateral support to the knife bar 2130 as it flexes to accommodate articulation of the surgical end effector 1500. Further details concerning the operation of the firing shaft support assembly 2300 and alternative knife bar support arrangements may be found in U.S. patent application Ser. No. 15/019,245, entitled SURGICAL INSTRUMENTS WITH CLOSURE STROKE REDUCTION ARRANGEMENTS and U.S. patent application Ser. No. 15/019,220, entitled SURGICAL INSTRUMENT WITH ARTICULATING AND AXIALLY TRANSLATABLE END EFFECTOR, which are each hereby incorporated by reference herein in their respective entireties.

As can also be seen in FIG. 6, a firing member or knife member 2140 is attached to the distal end of the knife bar 2130. In one exemplary form, the firing member 2140 comprises a body portion 2142 that supports a knife or tissue cutting portion 2144. The body portion 2142 protrudes through an elongate slot 1604 in the elongate channel 1602 and terminates in a foot member 2146 that extends laterally on each side of the body portion 2142. As the firing member 2140 is driven distally through the surgical staple/fastener cartridge 1700, the foot member 2146 rides within a passage 1622 (FIG. 48) in the elongate channel 1602 that is located under the surgical staple/fastener cartridge 1700. In one arrangement, the body portion 2142 includes two laterally protruding central tabs 2145 that may ride above the central passage within the surgical staple/fastener cartridge 1700. See FIG. 6. The tissue cutting portion 2144 is disposed between a distally protruding top nose portion 2143. As can be further seen in FIG. 6, the firing member 2140 may further include two laterally extending top tabs, pins or anvil engagement features 2147. As the firing member 2140 is driven distally, a top portion of the body portion 2142 extends through a centrally disposed anvil slot 1814 and the anvil engagement features 2147 ride on corresponding anvil ledges 1816 formed on each side of the anvil slot 1814. In one arrangement, to facilitate assembly of the anvil 1810 and firing member 2140 arrangement, the top of the anvil body 1812 has an opening 1817 therein. Once the anvil 1810 is assembled onto the elongate channel 1602 and the firing member 2140 is installed, the opening 1817 is covered by an anvil cap 1819 that is affixed to the anvil body 1812 by welding or other suitable fastening means.

Returning to FIG. 6, the firing member 2140 is configured to operably interface with a sled assembly 2150 that is operably supported within a body 1702 of the surgical staple/fastener cartridge 1700. The sled assembly 2150 is slidably displaceable within the surgical staple/fastener cartridge body 1702 from a proximal starting position adjacent the proximal end 1704 of the cartridge body 1702 to an ending position adjacent a distal end 1706 of the cartridge body 1702. The cartridge body 1702 operably supports therein a plurality of staple drivers (not shown) that are aligned in rows on each side of a centrally disposed slot 1708. The centrally disposed slot 1708 enables the firing member 2140 to pass therethrough and cut the tissue that is clamped between the anvil 1810 and the surgical staple/fastener cartridge 1700. The drivers are associated with corresponding staple/fastener pockets 1712 that open through an upper deck surface 1710 of the cartridge body 1702. Each of the staple drivers supports one or more surgical staple/fastener or fastener (not shown) thereon. The sled assembly 2150 includes a plurality of sloped or wedge-shaped cams 2152 wherein each cam 2152 corresponds to a particular line of fasteners or drivers located on a side of the slot 1708.

Attachment of the interchangeable surgical tool assembly 1000 to the handle assembly 500 will now be described with reference to FIG. 2. To commence the coupling process, the clinician may position the tool chassis 1210 of the interchangeable surgical tool assembly 1000 above or adjacent to the distal end of the handle frame 506 such that the tapered attachment portions 1212 formed on the tool chassis 1210 are aligned with the dovetail slots 507 in the handle frame 506. The clinician may then move the surgical tool assembly 1000 along an installation axis IA that is perpendicular to the shaft axis $SA_1$ to seat the tapered attachment portions 1212 in "operable engagement" with the corresponding dovetail receiving slots 507 in the distal end of the handle frame 506. In doing so, the firing shaft attachment lug 2128 on the intermediate firing shaft portion 2120 will also be seated in the attachment cradle (not shown) in the longitudinally movable drive member (not shown) within the handle assembly 500 and the portions of attachment pin 516 on the closure link 514 will be seated in the corresponding hooks 1942 in the closure shuttle 1940. As used herein, the term "operable engagement" in the context of two components means that the two components are sufficiently engaged with each other so that upon application of an actuation motion thereto, the components may carry out their intended action, function and/or procedure.

During a typical surgical procedure, the clinician may introduce the surgical end effector 1500 into the surgical site through a trocar or other opening in the patient to access the target tissue. When doing so, the clinician typically axially aligns the surgical end effector 1500 along the shaft axis (unarticulated state). Once the surgical end effector 1500 has passed through the trocar port, for example, the clinician may need to articulate the end effector 1500 to advantageously position it adjacent the target tissue. This is prior to closing the anvil onto the target tissue, so the closure drive system 510 would remain unactuated. When in this position, actuation of the firing drive system 530 will result in the application of articulation motions to the proximal articulation driver 1310. Once the end effector has attained the desired articulated position, the firing drive system 530 is deactivated and the articulation lock 1400 may retain the surgical end effector 1500 in the articulated position. The clinician may then actuate the closure drive system 510 to close the anvil 1810 onto the target tissue. Such actuation of the closure drive system 510 may also result in the shifter assembly 2200 delinking the proximal articulation driver from the intermediate firing shaft portion 2120. Thus, once the target tissue has been captured in the surgical end effector 1500, the clinician may once again actuate the firing drive system 530 to axially advance the firing member 2140 through the surgical staple/fastener cartridge 1700 to cut the clamped tissue and fire the staples into the cut tissue. Other closure and firing drive arrangements, actuator arrangements (both handheld, manual and automated or robotic) may also be employed to control the axial movement of the closure system components, the articulation system components and/or the firing system components of the surgical tool assembly 1000 without departing from the spirit and scope of the various inventions disclosed herein.

Figure 16:
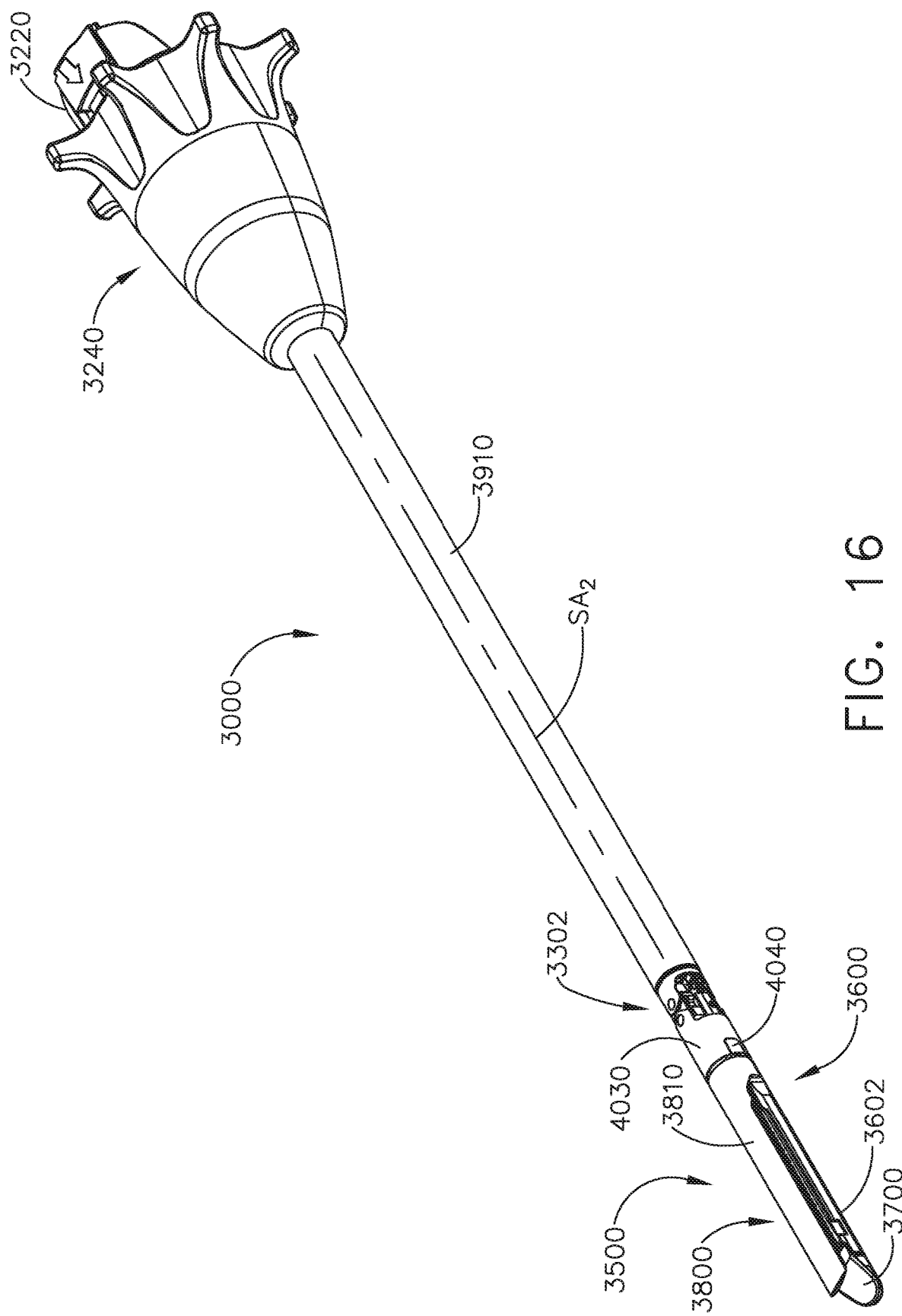
FIG. 16 is a perspective view of another one of the interchangeable surgical tool assemblies depicted in FIG. 1.
Figure 17:
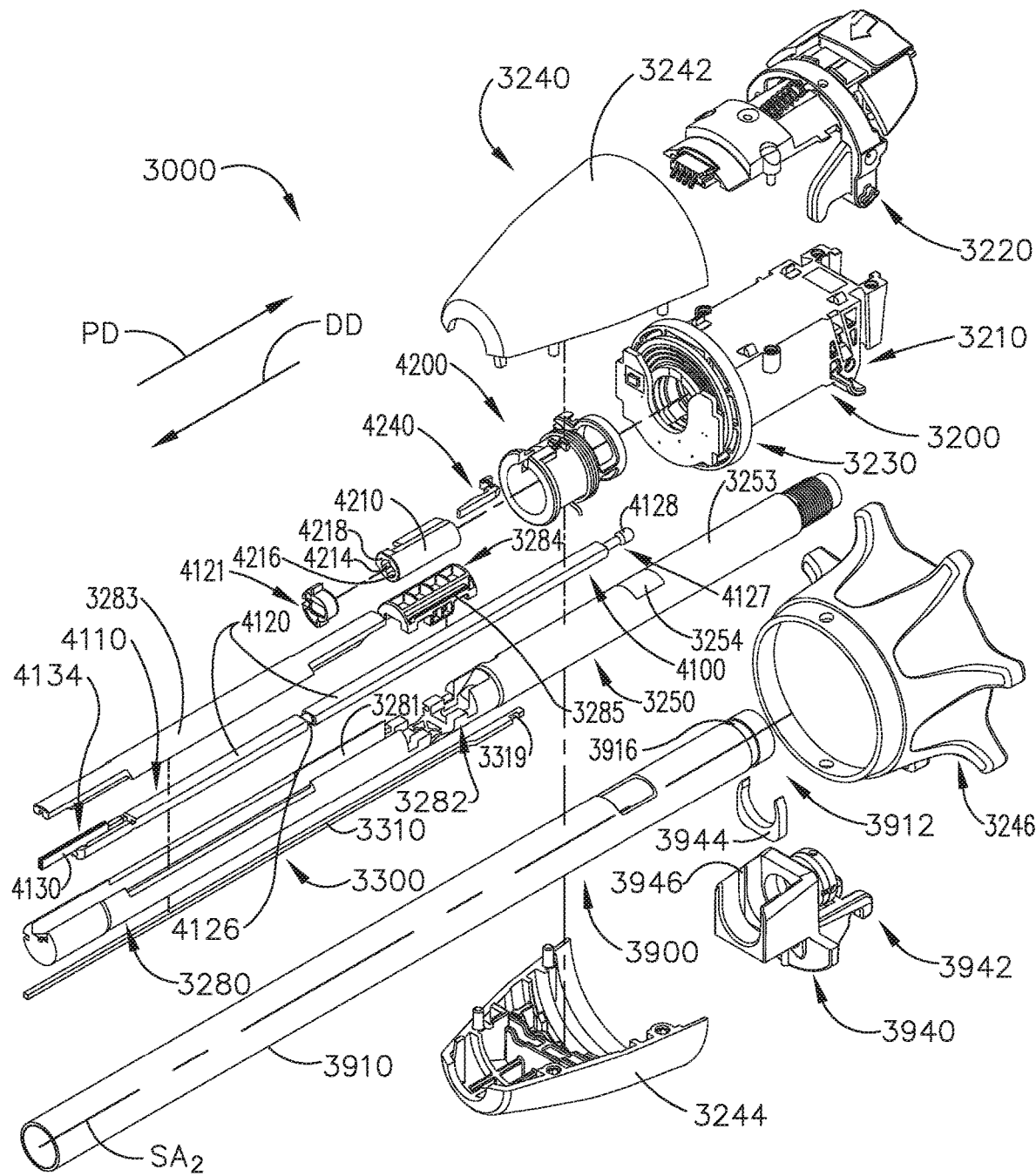
FIG. 17 is an exploded assembly view of a proximal portion of the interchangeable surgical tool assembly of FIG. 16.
Figure 18:
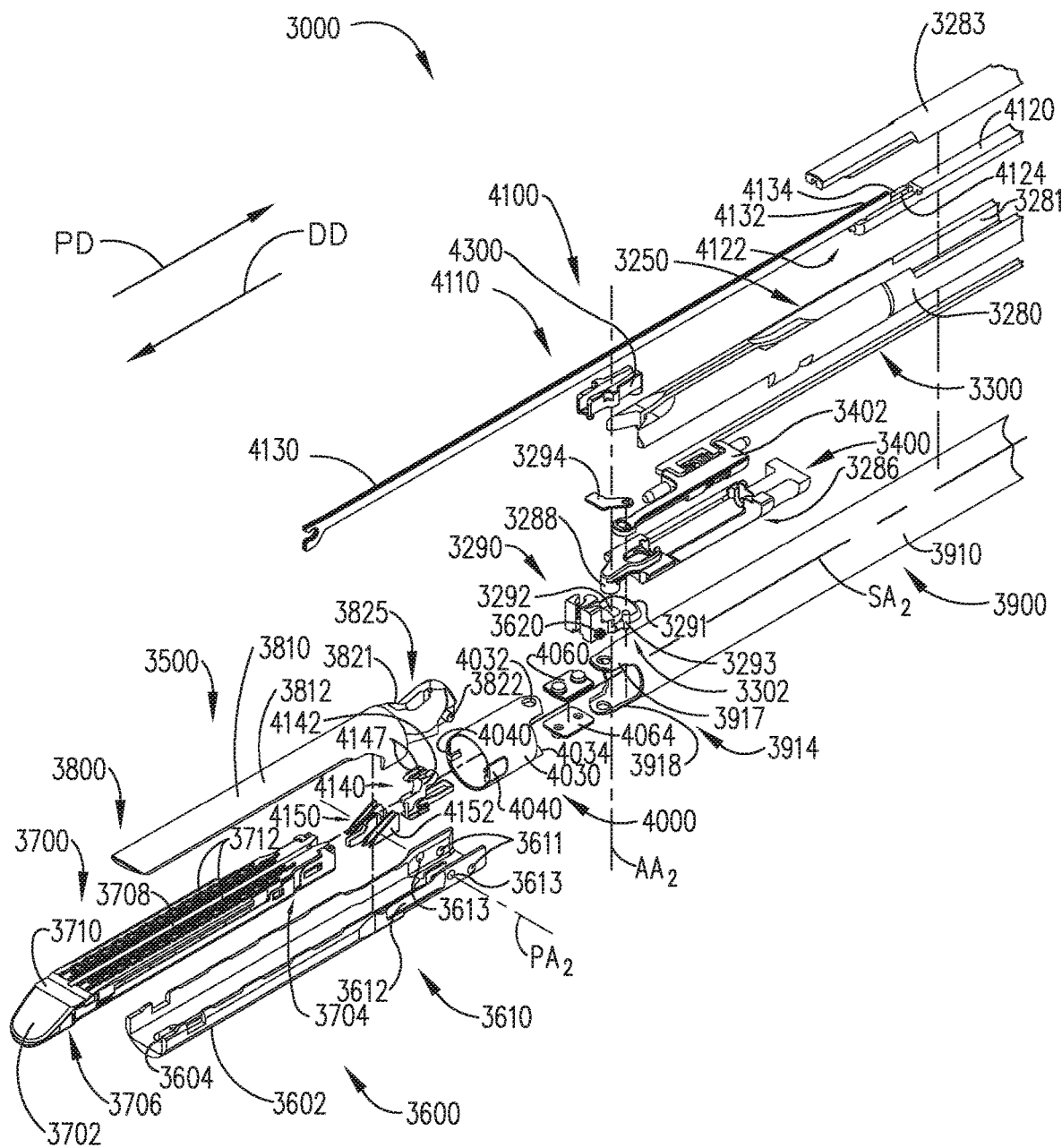
FIG. 18 is another exploded assembly view of a distal portion of the interchangeable surgical tool assembly of FIGS. 16 and 17.

Returning now to FIG. 1, the surgical system 10 illustrated in that Figure includes four interchangeable surgical tool assemblies 1000, 3000, 5000 and 7000 that may each be effectively employed with the same handle assembly 500 to perform different surgical procedures. Turning now to FIGS. 16-18, the interchangeable surgical tool assembly 3000 includes a surgical end effector 3500 that comprises a first jaw 3600 and a second jaw 3800. In one arrangement, the first jaw comprises an elongate channel 3602 that is configured to operably support a surgical staple/fastener cartridge 3700 therein. The second jaw 3800 comprises an anvil 3810 that is pivotally supported relative to the elongate channel 3602. The interchangeable surgical tool assembly 3000 includes an articulation system 3300 that comprises an articulation joint 3302 and an articulation lock 3400 which can be configured to releasably hold the surgical end effector 3500 in a desired articulated position relative to a shaft axis $SA_2$. Details regarding the construction and operation of the articulation lock 3400 as well as alternative lock configurations and operational details may be found in in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock 3400 may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, the entire disclosure of which is hereby incorporated by reference herein.

As can be seen in FIG. 17, the interchangeable surgical tool assembly 3000 includes a tool frame assembly 3200 that comprises a tool chassis 3210 that operably supports a nozzle assembly 3240 thereon. In one form, the nozzle assembly 3240 is comprised of nozzle portions 3242, 3244 as well as an actuator wheel portion 3246 that is configured to be coupled to the assembled nozzle portions 3242, 3244 by snaps, lugs, screws etc. The interchangeable surgical tool assembly 3000 includes a proximal closure assembly 3900 which is operably coupled to a distal closure assembly 4000 that is utilized to close and/or open the anvil 3810 of the surgical end effector 3500 as will be discussed in further detail below. In addition, the interchangeable surgical tool assembly 3000 includes an "elastic" spine assembly 3250 that operably supports the proximal closure assembly 3900 and is coupled to the surgical end effector 3500. One exemplary form of spine assembly 3250 is disclosed in U.S.

patent application Ser. No. 15/385,911, entitled SURGICAL STAPLE/FASTENERS WITH INDEPENDENTLY ACTUATABLE CLOSING AND FIRING SYSTEMS, the entire disclosure of which is hereby incorporated by reference herein. For example, the spine assembly 3250 may comprise an elastic spine member that has a proximal end portion 3253 and a distal end portion 3280 that is separated from the proximal end portion 3253 of the elastic spine assembly 3250 by a stretch feature 3282 formed therebetween. In addition, a stretch limiting insert 3284 is retainingly supported between the distal end portion 3280 and the proximal end portion 3253. In various arrangements, the elastic spine assembly 3250 may be fabricated from, for example, suitable polymeric material, rubber, etc. which has a modulus of elasticity designated as $ME_1$ for reference purposes. The stretch limiting insert 3284 may have a modulus of elasticity designated as $ME_2$ for reference purposes. In various circumstances, the stretch limiting insert 3284 also includes a pair of stretch limiters 3285 (only one is shown in FIG. 17). The stretch limiter 3285 may have a modulus of elasticity for reference purposes of $ME_3$. In at least one arrangement, $ME_3<ME_2<ME_1$. Further details about at least one implementation of the elastic spine assembly 3250 and stretch limiting insert 3284 may be found in U.S. patent application Ser. No. 15/385,911.

In the illustrated arrangement, the distal end portion 3280 of the spine assembly 3250 has an opening 3281 therein for ease of assembly. A spine cap 3283 may be attached thereto to cover the opening 3281 after the various components have been assembled therein. In assembled form, the proximal end portion 3253 of the spine assembly 3250 is rotatably supported in the tool chassis 3210. In one arrangement, for example, the proximal end of the proximal end portion 3253 of the spine assembly 3250 is attached to a spine bearing (not shown) that is configured to be supported within the tool chassis 3210. Such arrangement facilitates rotatable attachment of the spine assembly 3250 to the tool chassis 3210 such that the spine assembly 3250 may be selectively rotated about a shaft axis $SA_2$ relative to the tool chassis 3210. In particular, in one arrangement, for example, the proximal end portion 3253 of the spine assembly 3250 includes two diametrically opposed lug seats 3254 (only one can be seen in FIG. 17) that are each configured to receive a corresponding nozzle lug (not shown) that extend inwardly from each of the nozzle portions 3242, 3244. Such arrangement facilitates rotation of the spine assembly 3250 about the shaft axis $SA_2$ by rotating the actuator wheel portion 3246 of the nozzle assembly 3240.

Referring now to FIG. 18, the distal end portion 3280 of the elastic spine assembly 3250 is attached to a distal frame segment 3286 that operably supports the articulation lock 3400 therein. The spine assembly 3250 is configured to, one, slidably support a firing member assembly 4110 therein and, two, slidably support the proximal closure tube 3910 which extends around the spine assembly 3250. The spine assembly 3250 can also be configured to slidably support a proximal articulation driver 3310. As can be seen in FIG. 18, the distal frame segment 3286 is pivotally coupled to the elongate channel 3602 by an end effector mounting assembly 3290. In one arrangement, for example, the distal end of the distal frame segment 3286 has a pivot pin 3288 formed thereon. The pivot pin 3288 is adapted to be pivotally received within a pivot hole 3292 formed in pivot base portion 3291 of the end effector mounting assembly 3290. The end effector mounting assembly 3290 is attached to a proximal end 3610 of the elongate channel 3602 by a spring pin 3620 or other suitable member that is received within mounting holes 3611 in the proximal end portion 3610. The pivot pin 3288 defines an articulation axis $AA_2$ that is transverse to the shaft axis $SA_2$. See FIG. 18. Such arrangement facilitates pivotal travel (i.e., articulation) of the surgical end effector 3500 about the articulation axis $AA_2$ relative to the elastic spine assembly 3250. The distal frame segment 3286 is further configured to support the articulation lock 3400 therein. Various articulation lock arrangements may be employed. At least one form of articulation lock 3400 is described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT.

In the illustrated example, the surgical end effector 3500 is electively articulatable about the articulation axis $AA_2$ by the articulation system 3300. In one form, the articulation system 3300 includes the proximal articulation driver 3310 that operably interfaces with the articulation lock 3400. The articulation lock 3400 includes an articulation frame 3402 that is adapted to operably engage a drive pin 3293 on the pivot base portion 3291 of the end effector mounting assembly 3290. In addition, a cross link 3294 may be linked to the drive pin 3293 and articulation frame 3402 to assist articulation of the surgical end effector 3500. As indicated above, further details regarding the operation of the articulation lock 3400 and the articulation frame 3402 may be found in U.S. patent application Ser. No. 13/803,086, now U.S. Patent Application Publication No. 2014/0263541. Further details regarding the end effector mounting assembly and cross link 3294 may be found in U.S. patent application Ser. No. 15/019,245, filed Feb. 9, 2016, entitled SURGICAL INSTRUMENTS WITH CLOSURE STROKE REDUCTION ARRANGEMENTS, the entire disclosure of which is hereby incorporated by reference herein. As further described therein, as well as in other disclosures incorporated by reference herein, axial movement of proximal articulation driver 3310 will result in the engagement/disengagement of the articulation lock 3400 to thereby apply articulation motions to the elongate channel 3602 and thereby cause the surgical end effector 3500 to articulate about the articulation axis $AA_2$ relative to the spine assembly 3250.

The anvil 3810 in the illustrated example includes an anvil body 3812 that terminates in anvil mounting portion 3820. The anvil mounting portion 3820 is movably or pivotably supported on the elongate channel 3602 for selective pivotal travel relative thereto about a fixed anvil pivot axis $PA_2$ (FIG. 18) that is transverse to the shaft axis $SA_2$. In the illustrated arrangement, an anvil trunnion 3822 extends laterally out of each lateral side of the anvil mounting portion 3820 to be received in a corresponding trunnion pivot hole 3613 formed in the upstanding walls 3612 of the proximal end portion 3610 of the elongate channel 3602. Movement of the anvil 3810 relative to the elongate channel 3602 is effectuated by axial movement of the proximal closure assembly 3900 and the distal closure assembly 4000. In the illustrated arrangement, the proximal closure assembly 3900 comprises a proximal closure tube 3910 that has a proximal end 3912 and a distal end 3914. The proximal end 3912 is rotatably supported in a closure shuttle 3940 that is slidably supported within the tool chassis 3210 such that it may be axially moved relative thereto. In one form, the closure shuttle 3940 includes a pair of proximally-protruding hooks 3942 that are configured for attachment to the transverse attachment pin 516 that is attached to the closure linkage assembly 514 of the handle assembly 500. The proximal end 3912 is coupled to the closure shuttle 3940 for relative rotation thereto. For example, a U-shaped connector 3944 is inserted into an annular slot 3916 in the proximal end 3912 and is retained within vertical slots 3946 in the closure shuttle 3940. Such arrangement serves to attach the proximal closure assembly 3900 to the closure shuttle 3940 for axial travel therewith while enabling the proximal closure tube 3910 to rotate relative to the closure shuttle 3940 about the shaft axis $SA_2$. As was discussed above in connection with the interchangeable surgical tool assembly 1000, a closure spring (not shown) may extend over the proximal end 3912 of the proximal closure tube 3910 to bias the closure shuttle 3940 in the proximal direction PD which can serve to pivot the closure trigger 512 on the handle assembly 500 (FIG. 2) into the unactuated position when the interchangeable surgical tool assembly 3000 is operably coupled to the handle assembly 500 in the above described manner.

As can be seen in FIG. 18, the distal end 3914 of the proximal closure tube 3910 is attached to the distal closure assembly 4000. The distal end 3914 includes upper and lower tangs 3917, 3918 that are configured to be movably coupled to an end effector closure sleeve or distal closure tube segment 4030. The distal closure tube segment 4030 includes an upper tang 4032 and a lower tang 4034 that protrude proximally from a proximal end thereof. An upper double pivot link 4060 pivotally couples the upper tangs 3917 and 4032 and a lower double pivot link 4064 pivotally couples the lower tangs 3918 and 4034 together in the above-described manner. The distal advancement of the distal closure tube segment 4030 on the anvil mounting portion 3820 will result in closure or pivotal travel of the anvil 3810 towards the elongate channel 3602 about the fixed anvil pivot axis $PA_2$. In the illustrated arrangement, the distal closure tube segment 4030 also includes positive jaw or anvil opening features 4040 that are configured to coact with surfaces or ramp portions on the anvil mounting portion 3820 so as to cause the anvil 3810 to pivot from a closed position to an open position as the distal closure tube segment 4030 is moved proximally back to a starting position. Other embodiments may not employ the positive jaw opening features, but may rely on springs or other biasing arrangements to bias the anvil to the open position when the distal closure tube segment has been retracted to its proximal-most starting position. Further details regarding configurations and operation of the anvil opening features may be found in for example, U.S. patent application Ser. No. 15/385,911, entitled SURGICAL STAPLE/FASTENERS WITH INDEPENDENTLY ACTUATABLE CLOSING AND FIRING SYSTEMS.

In the illustrated arrangement, the interchangeable surgical tool assembly 3000 further includes a firing system generally designated as 4100. In various instances, the firing system 4100 includes a firing member assembly 4110 that is supported for axial travel within the spine assembly 3250. In the illustrated embodiment, the firing member assembly 4110 includes an intermediate firing shaft portion 4120 that is configured for attachment to a distal cutting portion or knife bar 4130. A support bushing arrangement 4121 may be employed to support the intermediate firing shaft portion 4120 within the spine assembly 3250. The firing member assembly 4110 may also be referred to herein as a "second shaft" and/or a "second shaft assembly". As can be seen in FIG. 18, the intermediate firing shaft portion 4120 may include a longitudinal slot 4124 in a distal end 4122 thereof which can be configured to receive a proximal end 4132 of the knife bar 4130. The longitudinal slot 4124 and the proximal end 4132 of the knife bar 4130 can be sized and configured to permit relative movement therebetween and can comprise a slip joint 4134. The slip joint 4134 can permit the intermediate firing shaft portion 4120 of the firing member assembly 4110 to be moved to articulate the end effector 3500 without moving, or at least substantially moving, the knife bar 4130 as was discussed above. In the illustrated arrangement, a proximal end 4127 of the intermediate firing shaft portion 4120 has a firing shaft attachment lug 4128 formed thereon that is configured to be seated into the attachment cradle (not shown) that is on the distal end of the longitudinally movable drive member (not shown) of the firing drive system 530 within the handle assembly 500 as was discussed above. Such arrangement facilitates the axial movement of the intermediate firing shaft portion 4120 upon actuation of the firing drive system 530. Other attachment configurations may also be employed to couple the intermediate firing shaft portion 4120 to other firing drive arrangements (e.g., manually actuated, robotic, etc.).

Further to the above, the interchangeable tool assembly 3000 can include a shifter assembly 4200 which can be configured to selectively and releasably couple the proximal articulation driver 3310 to the firing member assembly 4110 in the manner described above. In one form, the shifter assembly 4200 includes a lock collar, or lock sleeve 4210, positioned around the intermediate firing shaft portion 4120 of the firing member assembly 4110 wherein the lock sleeve 4210 can be rotated between an engaged position in which the lock sleeve 4210 couples the proximal articulation driver 3310 to the firing member assembly 4110 and a disengaged position in which the proximal articulation driver 3310 is not operably coupled to the firing member assembly 4110. As was discussed above, the intermediate firing shaft portion 4120 of the firing member assembly 4110 is formed with a drive notch 4126. The lock sleeve 4210 comprises a cylindrical, or an at least substantially cylindrical, body that includes a longitudinal aperture 4212 that is configured to receive the intermediate firing shaft portion 4120 therethrough. The lock sleeve 4210 can comprise diametrically-opposed, inwardly-facing lock protrusions 4214, 4216 that, when the lock sleeve 4210 is in one position, are engagingly received within corresponding portions of the drive notch 4126 in the intermediate firing shaft portion 4120 and, when in another position, are not received within the drive notch 4126 to thereby permit relative axial motion between the lock sleeve 4210 and the intermediate firing shaft 4120 as was discussed in further detail above. The lock sleeve 4210 further includes a lock member 4218 that is sized to be movably received within a notch 3319 in a proximal end of the proximal articulation driver 3310. When the lock sleeve 4210 is in its engaged position, the lock protrusions 4214, 4216 are positioned within the drive notch 4126 in the intermediate firing shaft portion 4120 such that a distal pushing force and/or a proximal pulling force can be transmitted from the firing member assembly 4110 to the lock sleeve 4210. Such axial pushing or pulling motion is then transmitted from the lock sleeve 4210 to the proximal articulation driver 3310 to thereby articulate the surgical end effector 3500.

As was discussed above, in the illustrated example, relative movement of the lock sleeve 4210 between its engaged and disengaged positions may be controlled by the shifter assembly 4200 that interfaces with the proximal closure tube 3910 of the proximal closure assembly 3900. The shifter assembly 4200 further includes a shifter key 4240 that is configured to be slidably received within a key groove (similar to the key groove 2217 illustrated in FIG. 8) formed in the outer perimeter of the lock sleeve 4210. Such arrangement enables the shifter key 4240 to move axially with respect to the lock sleeve 4210. Operation of the shifter assembly 4200 may be identical to the operation of the shifter assembly 2200 which was described in further detail above and which will not be repeated again for brevity. Further details, alternative arrangements and drive configurations that may be employed are disclosed in other arrangements that may be employed are disclosed in U.S. patent application Ser. No. 15/385,911, entitled SURGICAL STAPLE/FASTENERS WITH INDEPENDENTLY ACTUATABLE CLOSING AND FIRING SYSTEMS, U.S. patent application Ser. No. 13/803,086, now U.S. Patent Application Publication No. 2014/0263541, and U.S. patent application Ser. No. 15/019,196, the as well as other disclosures that have bee incorporated herein.

The interchangeable tool assembly 3000 can comprise a slip ring assembly 3230 which can be configured to conduct electrical power to and/or from the surgical end effector 3500 and/or communicate signals to and/or from the surgical end effector 3500, back to a microprocessor 560 in the handle assembly 500 or robotic system controller, for example as was discussed above. Further details concerning the slip ring assembly 3230 and associated connectors may be found in U.S. patent application Ser. No. 13/803,086, now U.S. Patent Application Publication No. 2014/0263541, and U.S. patent application Ser. No. 15/019,196 which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

The illustrated interchangeable surgical tool assembly 3000 also employs a latch system 3220 for removably coupling the interchangeable surgical tool assembly 3000 to the handle frame 506 of the handle assembly 500, for example. The latch system 3220 may be identical to the latch system 1220 described in detail above. The knife bar 4130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 4130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS which is hereby incorporated by reference in its entirety. As can also be seen in FIG. 18, a firing shaft support assembly 4300 is employed to provide lateral support to the knife bar 4130 as it flexes to accommodate articulation of the surgical end effector 3500. Further details concerning the operation of the firing shaft support assembly 4300 and alternative knife bar support arrangements may be found in U.S. patent application Ser. No. 15/019,245, entitled SURGICAL INSTRUMENTS WITH CLOSURE STROKE REDUCTION ARRANGEMENTS and U.S. patent application Ser. No. 15/019,220, entitled SURGICAL INSTRUMENT WITH ARTICULATING AND AXIALLY TRANSLATABLE END EFFECTOR, which are each hereby incorporated by reference herein in their respective entireties.

As can also be seen in FIG. 18, a firing member or knife member 4140 is attached to the distal end of the knife bar 4130. The firing member 4140 is configured to operably interface with a sled assembly 4150 that is operably supported within the body 3702 of the surgical staple/fastener cartridge 3700. The sled assembly 4150 is slidably displaceable within the surgical staple/fastener cartridge body 3702 from a proximal starting position adjacent the proximal end 3704 of the cartridge body 3702 to an ending position adjacent a distal end 3706 of the cartridge body 3702. The cartridge body 3702 operably supports therein a plurality of staple drivers (not shown) that are aligned in rows on each side of a centrally disposed slot 3708. The centrally disposed slot 3708 enables the firing member 4140 to pass therethrough and cut the tissue that is clamped between the anvil 3810 and the staple cartridge 3700. The drivers are associated with corresponding staple pockets 3712 that open through the deck surface 3710 of the cartridge body 3702. Each of the staple drivers supports one or more surgical staple/fastener or fastener (not shown) thereon. The sled assembly 4150 includes a plurality of sloped or wedge-shaped cams 4152 wherein each cam 4152 corresponds to a particular line of fasteners or drivers located on a side of the slot 3708.

In one exemplary form, the firing member 4140 comprises a body portion 4142 that supports a knife or tissue cutting portion 4144. See FIG. 49. The body portion 4142 protrudes through an elongate slot 3604 in the elongate channel 3602 and terminates in a foot member 4146 that extends laterally on each side of the body portion 4142. As the firing member 4140 is driven distally through the surgical staple/fastener cartridge 3700, the foot member 4146 rides within a passage 3622 in the elongate channel 3602 that is located under the surgical staple/fastener cartridge 3700. The tissue cutting portion 4144 is disposed between a distally protruding top nose portion 4143. As can be further seen in FIG. 18, the firing member 4140 may further include two laterally extending top tabs, pins or anvil engagement features 4147. As the firing member 4140 is driven distally, a top portion of the body portion 4142 extends through a centrally disposed anvil slot 3814 and the anvil engagement features 4147 ride on corresponding ledges 3816 formed on each side of the anvil slot 3814. Further details concerning the firing member 4140, sled assembly 4150 and their various alternatives as well as examples of their operation will be discussed in further detail below and may also be found in U.S. patent application Ser. No. 15/385,911, entitled SURGICAL STAPLE/FASTENERS WITH INDEPENDENTLY ACTUATABLE CLOSING AND FIRING SYSTEMS. The interchangeable surgical tool assembly 3000 may be to the handle assembly 500 in the manner as described above with respect to the interchangeable surgical tool assembly 1000.

Figure 19:
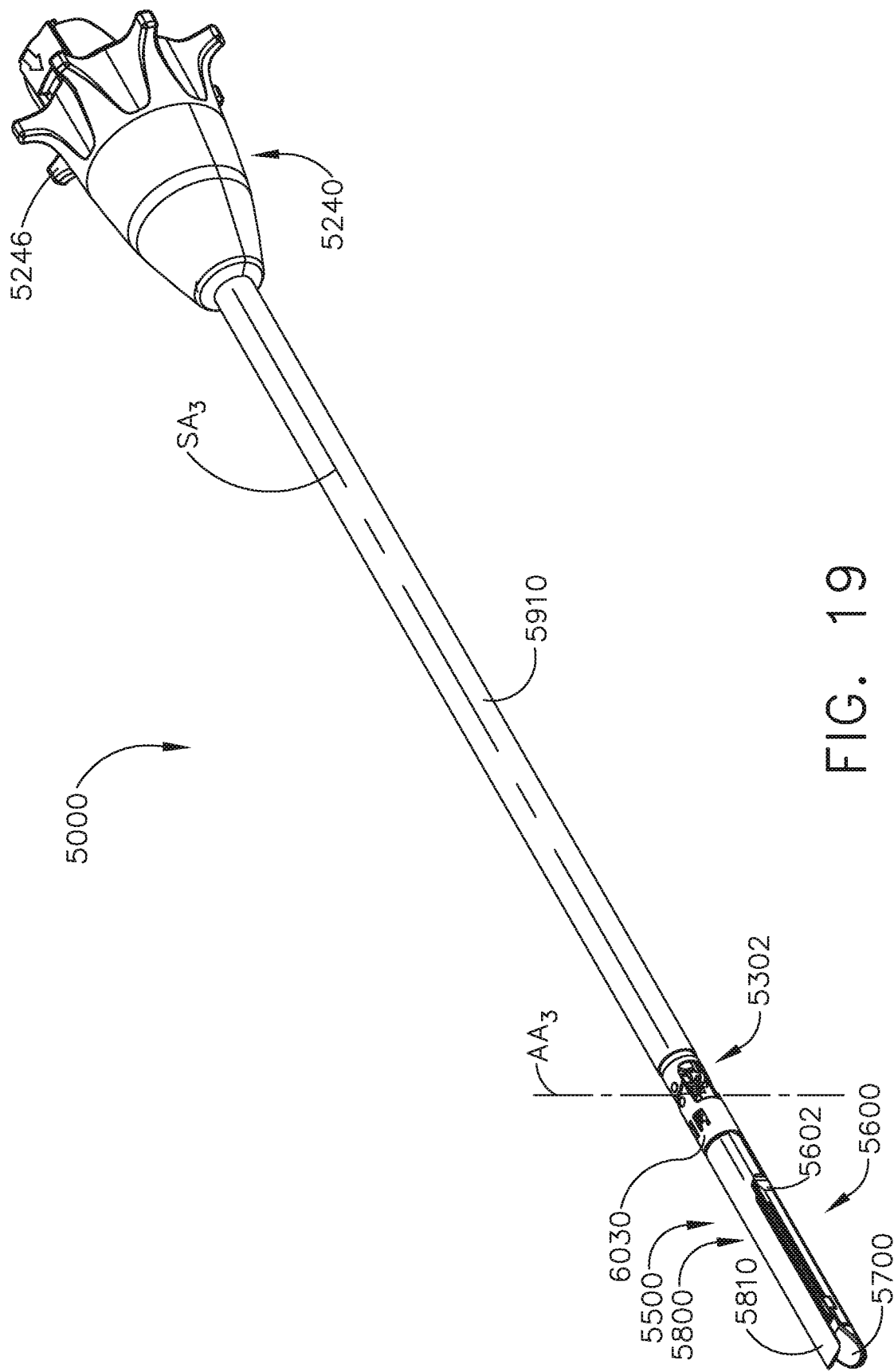
FIG. 19 is a perspective view of another one of the interchangeable surgical tool assemblies depicted in FIG. 1.
Figure 20:
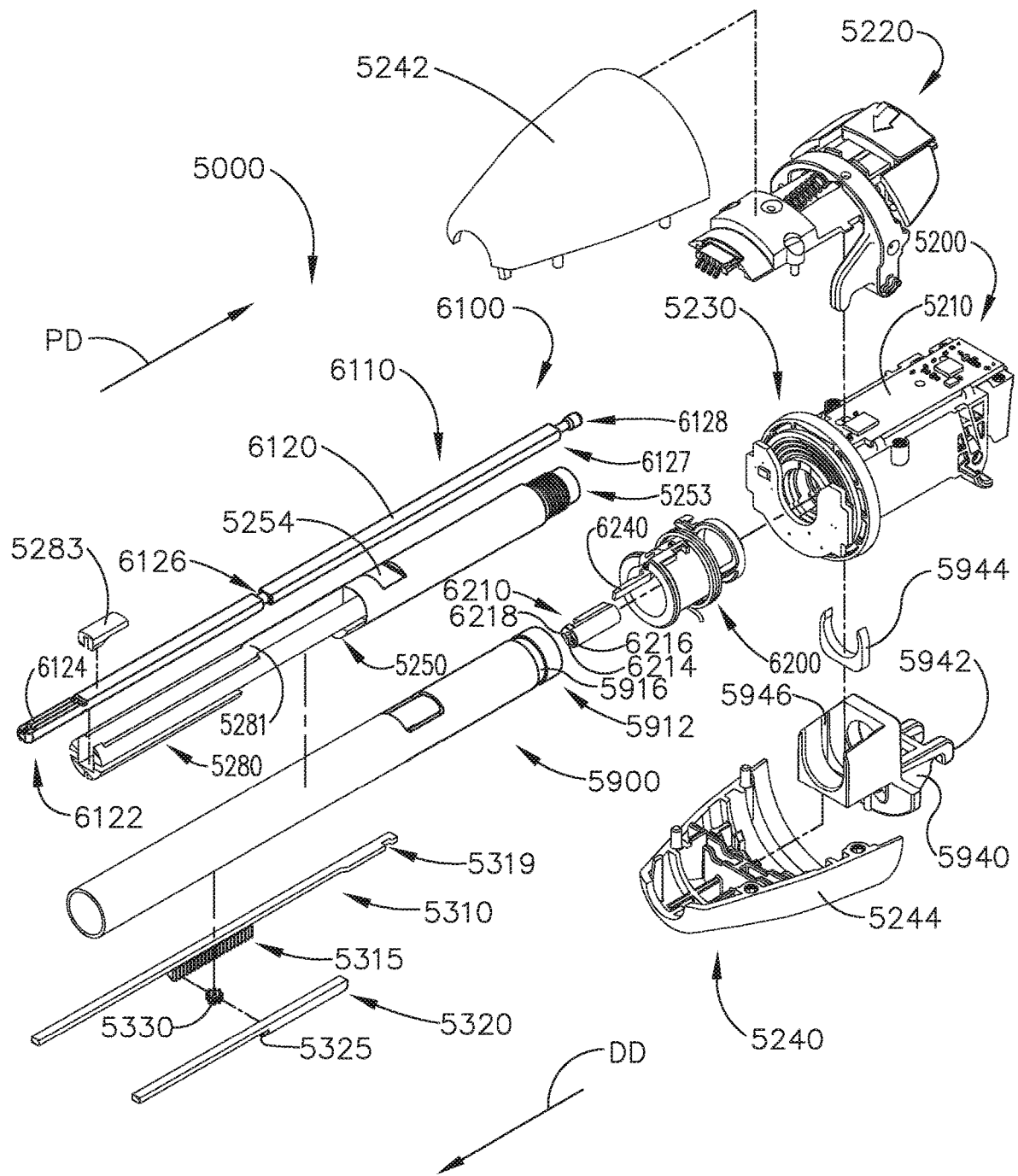
FIG. 20 is an exploded assembly view of a proximal portion of the interchangeable surgical tool assembly of FIG. 19.
Figure 21:
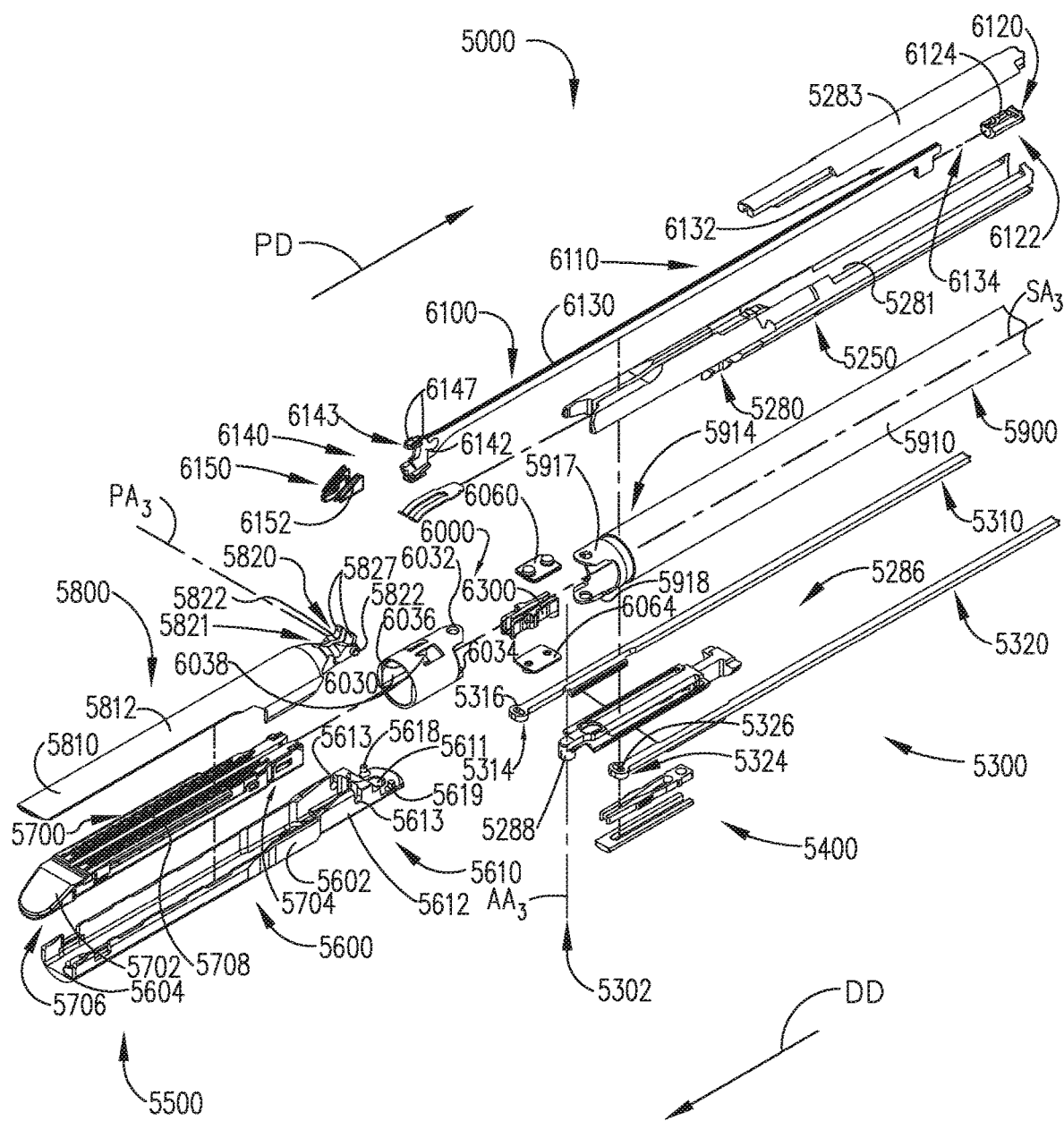
FIG. 21 is another exploded assembly view of a distal portion of the interchangeable surgical tool assembly of FIGS. 19 and 20.

Returning again to FIG. 1, as was discussed above, the surgical system 10 illustrated in that Figure includes four interchangeable surgical tool assemblies 1000, 3000, 5000 and 7000 that may each be effectively employed with the same handle assembly 500 to perform different surgical procedures. Turning now to FIGS. 19-21, the interchangeable surgical tool assembly 5000 includes a surgical end effector 5500 that comprises a first jaw 5600 and a second jaw 5800. In one arrangement, the first jaw comprises an elongate channel 5602 that is configured to operably support a surgical staple/fastener cartridge 5700 therein. The second jaw 5800 comprises an anvil 5810 that is movably supported relative to the elongate channel 5602. The interchangeable surgical tool assembly 5000 includes an articulation system 5300 that comprises an articulation joint 5302 and an articulation lock 5400 which can be configured to releasably hold the surgical end effector 5500 in a desired articulated position relative to a shaft axis $SA_3$. Details regarding the construction and operation of the articulation lock 5400 as well as alternative lock configurations and operational details may be found in in U.S. patent application Ser. No. 15/385,894, entitled SHAFT ASSEMBLY COMPRISING A LOCK OUT, the entire disclosure of which is hereby incorporated by reference herein. Alternative articulation lock arrangements may also be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541 and U.S. patent application Ser. No. 15/019,196, filed Feb. 9, 2016, entitled SURGICAL INSTRUMENT ARTICULATION MECHANISM WITH SLOTTED SECONDARY CONSTRAINT, the entire disclosures of each such reference being hereby incorporated by reference herein.

As can be seen in FIG. 20, the interchangeable surgical tool assembly 5000 includes a tool frame assembly 5200 that comprises a tool chassis 5210 that operably supports a nozzle assembly 5240 thereon. In one form, the nozzle assembly 5240 is comprised of nozzle portions 5242, 5244 as well as an actuator wheel portion 5246 that is configured to be coupled to the assembled nozzle portions 5242, 5244 by snaps, lugs, screws etc. The interchangeable surgical tool assembly 5000 includes a proximal closure assembly 5900 which is operably coupled to a distal closure assembly 6000 that is utilized to close and/or open the anvil 5810 of the surgical end effector 5500 as will be discussed in further detail below. In addition, the interchangeable surgical tool assembly 5000 includes a spine assembly 5250 that operably supports the proximal closure assembly 5900 and is coupled to the surgical end effector 5500. In the illustrated arrangement, the spine assembly 5250 includes a distal end portion 5280 that has an opening 5281 therein for ease of assembly. A spine cap 5283 may be attached thereto to cover the opening 5281 after the various components have been assembled therein. In assembled form, a proximal end portion 5253 of the spine assembly 5250 is rotatably supported in the tool chassis 5210. In one arrangement, for example, the proximal end of the proximal end portion 5253 of the spine assembly 5250 is attached to a spine bearing (not shown) that is configured to be supported within the tool chassis 5210. Such arrangement facilitates rotatable attachment of the spine assembly 5250 to the tool chassis 5210 such that the spine assembly 5250 may be selectively rotated about the shaft axis $SA_3$ relative to the tool chassis 5210. In particular, in one arrangement, for example, the proximal end portion 5253 of the spine assembly 5250 includes two diametrically opposed lug seats 5254 (only one can be seen in FIG. 20) that are each configured to receive a corresponding nozzle lug (not shown) that extend inwardly from each of the nozzle portions 5242, 5244. Such arrangement facilitates rotation of the spine assembly 5250 about the shaft axis $SA_3$ by rotating the actuator wheel portion 5246 of the nozzle assembly 5240.

Referring now to FIG. 21, the distal end portion 5280 of the spine assembly 5250 is attached to a distal frame segment 5286 that operably supports the articulation lock 5400 therein. The spine assembly 5250 is configured to, one, slidably support a firing member assembly 6110 therein and, two, slidably support a proximal closure tube 5910 which extends around the spine assembly 5250. The spine assembly 5250 can also be configured to slidably support a first articulation driver 5310 and a second articulation driver 5320. As can be seen in FIG. 21, the distal frame segment 5286 is pivotally coupled to a proximal end 5610 of the elongate channel 5602. In one arrangement, for example, the distal end of the distal frame segment 5286 has a pivot pin 5288 formed thereon. The pivot pin 5288 is adapted to be pivotally received within a pivot hole 5611 formed in the proximal end portion 5610 of the elongate channel 5602. The pivot pin 5288 defines an articulation axis $AA_3$ that is transverse to the shaft axis $SA_3$. See FIG. 21. Such arrangement facilitates pivotal travel (i.e., articulation) of the surgical end effector 5500 about the articulation axis $AA_3$ relative to the spine assembly 5250. The distal frame segment 5286 is further configured to support the articulation lock 5400 therein.

In the illustrated arrangement, a distal end 5314 of the first articulation driver 5310 is formed with a loop 5316 that is adapted to receive a first articulation pin 5618 therein that is formed on the proximal end portion 5610 of the elongate channel 5602. Similarly, a distal end 5324 of the second articulation driver 5320 has a loop 5326 that is adapted to receive a second articulation pin 5619 therein that is formed on the proximal end portion 5610 of the elongate channel 5602. In one arrangement, for example, the first articulation driver 5310 further comprises a proximal rack of teeth 5315 that is in meshing engagement with an idler gear 5330 rotatably supported in the spine assembly 5250. Similarly the second articulation driver 5320 further comprises a proximal rack of teeth 5325 that is in meshing engagement with the idler gear 5330. Thus, in such arrangement, movement of the first articulation driver 5310 in the distal direction DD will result in movement of the second articulation driver 5320 in the proximal direction PD. Movement of the first articulation driver 5310 in the proximal direction PD will result in the movement of the second articulation driver 5320 in the distal direction DD. Thus, such movement of the first and second articulation drivers 5310, 5320 will provide simultaneously pushing and pulling motions to the surgical end effector 5500 to articulate the surgical end effector about the articulation axis $AA_3$.

The anvil 5810 in the illustrated example includes an anvil body 5812 that terminates in anvil mounting portion 5820. The anvil mounting portion 5820 is movably supported on the elongate channel 5602 for selective pivotal and vertical travel relative thereto. In the illustrated arrangement, an anvil trunnion 5822 extends laterally out of each lateral side of the anvil mounting portion 5820 to be received in a corresponding "open-ended" vertical cradle 5613 formed in upstanding walls 5612 of the proximal end portion 5610 of the elongate channel 5602. Movement of the anvil 5810 relative to the elongate channel 5602 is effectuated by axial movement of the proximal closure assembly 5900 and the distal closure assembly 6000. In the illustrated arrangement, the proximal closure assembly 5900 comprises the proximal closure tube 5910 that has a proximal end 5912 and a distal end 5914. The proximal end 5912 is rotatably supported in a closure shuttle 5940 that is slidably supported within the tool chassis 5210 such that it may be axially moved relative thereto. In one form, the closure shuttle 5940 includes a pair of proximally-protruding hooks 5942 that are configured for attachment to the transverse attachment pin 516 that is attached to the closure linkage assembly 514 of the handle assembly 500. The proximal end 5912 of the proximal closure tube 5910 is coupled to the closure shuttle 5940 for relative rotation thereto. For example, a U-shaped connector 5944 is inserted into an annular slot 5916 in the proximal end 5912 and is retained within vertical slots 5946 in the closure shuttle 5940. Such arrangement serves to attach the proximal closure assembly 5900 to the closure shuttle 5940 for axial travel therewith while enabling the proximal closure tube 5910 to rotate relative to the closure shuttle 5940 about the shaft axis $SA_3$. As was discussed above in connection with the interchangeable surgical tool assembly 1000, a closure spring (not shown) may extend over the proximal end 5912 of the proximal closure tube 5910 to bias the closure shuttle 5940 in the proximal direction PD which can serve to pivot the closure trigger 512 on the handle assembly 500 (FIG. 2) into the unactuated position when the interchangeable surgical tool assembly 5000 is operably coupled to the handle assembly 500 in the above described manner.

As can be seen in FIG. 21, the distal end 5914 of the proximal closure tube 5910 is attached to the distal closure assembly 6000. The distal end 5914 includes upper and lower tangs 5917, 7918 that are configured to be movably coupled to an end effector closure sleeve or distal closure tube segment 6030. The distal closure tube segment 6030 includes an upper tang 6032 and a lower tang 6034 that protrude proximally from a proximal end thereof. An upper double pivot link 6060 pivotally couples the upper tangs 5917 and 6032 and a lower double pivot link 6064 pivotally couples the lower tangs 5918 and 6034 together in the above-described manner. The distal closure tube segment 6030 includes an internal cam surface 6036 that is configured to cammingly engage an anvil cam surface 5821 on the anvil mounting portion 5820. The distal advancement of the distal closure tube segment 6030 on the anvil mounting portion 5820 will result in closure or pivotal travel of the anvil 5810 towards the elongate channel 5602. In the illustrated arrangement, upstanding anvil tabs 5827 are formed on the anvil mounting portion 5820 and are configured to be contacted by two positive jaw opening tabs 6038 that extend inwardly within the distal closure tube segment 6030. Each positive jaw opening tab 6038 is configured to engage a corresponding one of the anvil tabs 5827 to pivot the anvil 5810 to an open position when the distal closure tube segment 6030 is axially moved in the proximal direction PD.

In the illustrated arrangement, the interchangeable surgical tool assembly 5000 further includes a firing system generally designated as 6100. In various instances, the firing system 6100 includes the firing member assembly 6110 that is supported for axial travel within the spine assembly 5250. In the illustrated embodiment, the firing member assembly 6110 includes an intermediate firing shaft portion 6120 that is configured for attachment to a distal cutting portion or knife bar 6130. The firing member assembly 6110 may also be referred to herein as a "second shaft" and/or a "second shaft assembly". As can be seen in FIG. 21, the intermediate firing shaft portion 6120 may include a longitudinal slot 6124 in a distal end 6122 thereof which can be configured to receive a proximal end 6132 of the knife bar 6130. The longitudinal slot 6124 and the proximal end 6132 of the knife bar 6130 can be sized and configured to permit relative movement therebetween and can comprise a slip joint 6134. The slip joint 6134 can permit the intermediate firing shaft portion 6120 of the firing member assembly 6110 to be moved to articulate the end effector 5500 without moving, or at least substantially moving, the knife bar 6130 as was discussed above. In the illustrated arrangement, a proximal end 6127 of the intermediate firing shaft portion 6120 has a firing shaft attachment lug 6128 formed thereon that is configured to be seated into an attachment cradle (not shown) that is on the distal end of the longitudinally movable drive member (not shown) of the firing drive system 530 within the handle assembly 500 as was discussed above. Such arrangement facilitates the axial movement of the intermediate firing shaft portion 6120 upon actuation of the firing drive system 530. Other attachment configurations may also be employed to couple the intermediate firing shaft portion to other firing drive arrangements (e.g., manually actuated, robotic, etc.).

Further to the above, the interchangeable tool assembly 5000 can include a shifter assembly 6200 which can be configured to selectively and releasably couple the first articulation driver 5310 to the firing member assembly 6110 in the manner described above. In one form, the shifter assembly 6200 includes a lock collar, or lock sleeve 6210, positioned around the intermediate firing shaft portion 6120 of the firing member assembly 6110 wherein the lock sleeve 6210 can be rotated between an engaged position in which the lock sleeve 6210 couples the first articulation driver 5310 to the firing member assembly 6110 and a disengaged position in which the first articulation driver 5310 is not operably coupled to the firing member assembly 6110. As was discussed above, the intermediate firing shaft portion 6120 of the firing member assembly 6110 is formed with a drive notch 6126. The lock sleeve 6210 comprises a cylindrical, or an at least substantially cylindrical, body that includes a longitudinal aperture that is configured to receive the intermediate firing shaft portion 6120 therethrough. The lock sleeve 6210 can comprise diametrically-opposed, inwardly-facing lock protrusions 6214, 6216 that, when the lock sleeve 6210 is in one position, are engagingly received within corresponding portions of the drive notch 6126 in the intermediate firing shaft portion 6120 and, when in another position, are not received within the drive notch 6126 to thereby permit relative axial motion between the lock sleeve 6210 and the intermediate firing shaft 6120 as was discussed in further detail above. The lock sleeve 6210 further includes a lock member 6218 that is sized to be movably received within a notch 5319 in a proximal end of the first articulation driver 5310. When the lock sleeve 6210 is in its engaged position, the lock protrusions 6214, 6216 are positioned within the drive notch 6126 in the intermediate firing shaft portion 6120 such that a distal pushing force and/or a proximal pulling force can be transmitted from the firing member assembly 6110 to the lock sleeve 6210. Such axial pushing or pulling motion is then transmitted from the lock sleeve 6210 to the first articulation driver 5310. Axial movement of the first articulation driver 5310 results in the axial movement of the second articulation driver 5320 in an opposite direction to thereby articulate the surgical end effector 5500.

As was discussed above, in the illustrated example, relative movement of the lock sleeve 6210 between its engaged and disengaged positions may be controlled by the shifter assembly 6200 that interfaces with the proximal closure tube 5910 of the proximal closure assembly 5900. The shifter assembly 6200 further includes a shifter key 6240 that is configured to be slidably received within a key groove (similar to the key groove 2217 illustrated in FIG. 8) formed in the outer perimeter of the lock sleeve 6210. Such arrangement enables the shifter key 6240 to move axially with respect to the lock sleeve 6210. Operation of the shifter assembly 6200 may be identical to the operation of the shifter assembly 2200 which was described in further detail above and which will not be repeated again for brevity. Further details, alternative arrangements and drive configurations that may be employed are disclosed in Other arrangements that may be employed are disclosed in U.S. patent application Ser. No. 15/385,911, entitled SURGICAL STAPLE/FASTENERS WITH INDEPENDENTLY ACTUATABLE CLOSING AND FIRING SYSTEMS, U.S. patent application Ser. No. 13/803,086, now U.S. Patent Application Publication No. 2014/0263541, and U.S. patent application Ser. No. 15/019,196, the as well as other disclosures that have been incorporated herein.

The interchangeable tool assembly 5000 can comprise a slip ring assembly 5230 which can be configured to conduct electrical power to and/or from the surgical end effector 5500 and/or communicate signals to and/or from the surgical end effector 5500, back to a microprocessor 560 in the handle assembly 500 or robotic system controller, for example as was discussed above. Further details concerning the slip ring assembly 5230 and associated connectors may be found in U.S. patent application Ser. No. 13/803,086, now U.S. Patent Application Publication No. 2014/0263541, and U.S. patent application Ser. No. 15/019,196 which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

The illustrated interchangeable surgical tool assembly 5000 also employs a latch system 5220 for removably coupling the interchangeable surgical tool assembly 5000 to the handle frame 506 of the handle assembly 500, for example. The latch system 5220 may be identical to the latch system 1220 described in detail above. The knife bar 6130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 6130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS which is hereby incorporated by reference in its entirety. As can also be seen in FIG. 21, a firing shaft support assembly 6300 is employed to provide lateral support to the knife bar 6130 as it flexes to accommodate articulation of the surgical end effector 5500. Further details concerning the operation of the firing shaft support assembly 6300 and alternative knife bar support arrangements may be found in U.S. patent application Ser. No. 15/019,245, entitled SURGICAL INSTRUMENTS WITH CLOSURE STROKE REDUCTION ARRANGEMENTS and U.S. patent application Ser. No. 15/019,220, entitled SURGICAL INSTRUMENT WITH ARTICULATING AND AXIALLY TRANSLATABLE END EFFECTOR, which are each hereby incorporated by reference herein in their respective entireties.

Figure 50:
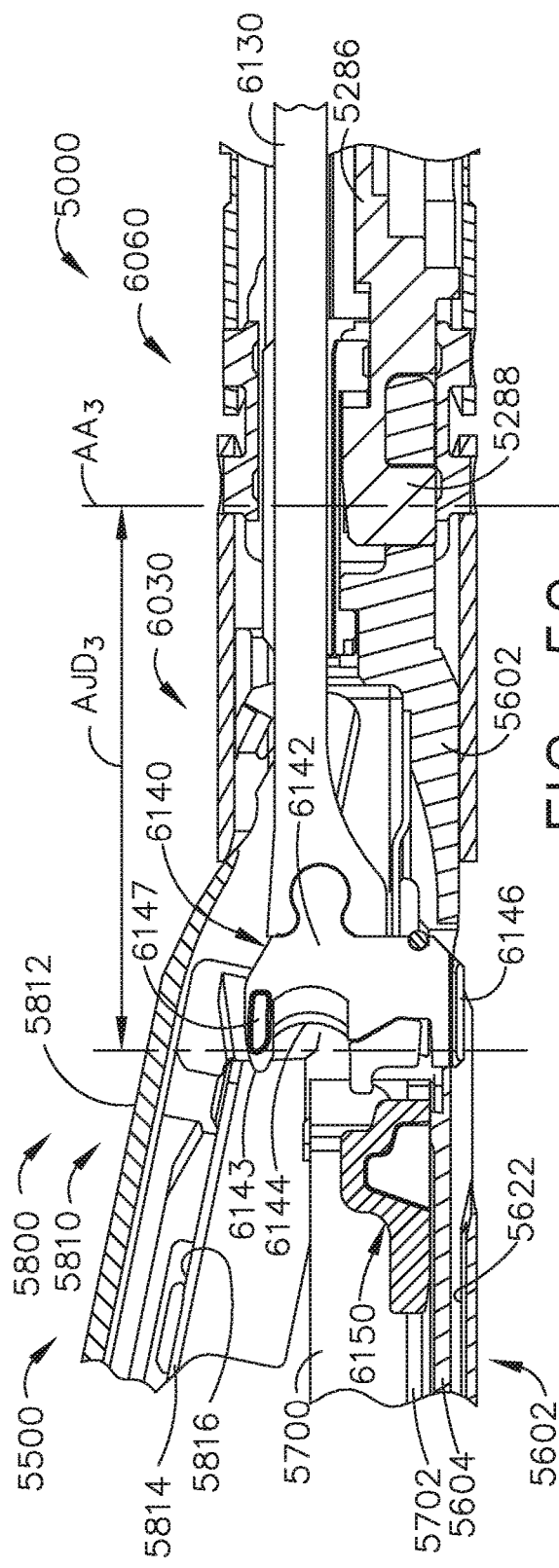
FIG. 50 is a partial cross-sectional view of the anvil mounting portion and elongate channel of the interchangeable surgical tool assembly of FIG. 19 with the anvil in a fully open position.

As can also be seen in FIGS. 21 and 50, a firing member or knife member 6140 is attached to the distal end of the knife bar 6130. The firing member 6140 is configured to operably interface with a sled assembly 6150 that is operably supported within the body 5702 of the surgical staple/fastener cartridge 5700. The sled assembly 6150 is slidably displaceable within the surgical staple/fastener cartridge body 5702 from a proximal starting position adjacent a proximal end 5704 of the cartridge body 5702 to an ending position adjacent a distal end 5706 of the cartridge body 5702. The cartridge body 5702 operably supports therein a plurality of staple drivers (not shown) that are aligned in rows on each side of a centrally disposed slot 5708. The centrally disposed slot 5708 enables the firing member 6140 to pass therethrough and cut the tissue that is clamped between the anvil 5810 and the staple cartridge 5700. The drivers are associated with corresponding staple pockets that open through the upper deck surface of the cartridge body 5702. Each of the staple drivers supports one or more surgical staple/fastener or fastener (not shown) thereon. The sled assembly includes a plurality of sloped or wedge-shaped cams 6152 wherein each cam corresponds to a particular line of fasteners or drivers located on a side of the slot 5708.

In one exemplary form, the firing member 6140 comprises a body portion 6142 that supports a knife or tissue cutting portion 6144. See FIG. 50. The body portion 6142 protrudes through an elongate slot 5604 in the elongate channel 5602 and terminates in a foot member 6146 that extends laterally on each side of the body portion 6142. As the firing member 6140 is driven distally through the surgical staple/fastener cartridge 5700, the foot member 6146 rides within a passage 5622 in the elongate channel 5602 that is located under the surgical staple/fastener cartridge 5700. The tissue cutting portion 6144 is disposed between a distally protruding top nose portion 6143. As can be further seen in FIGS. 21 and 50, the firing member 6140 may further include two laterally extending top tabs, pins or anvil engagement features 6147. As the firing member 6140 is driven distally, a top portion of the body portion 6142 extends through a centrally disposed anvil slot 5814 and the anvil engagement features 6147 ride on corresponding ledges 5816 formed on each side of the anvil slot 5814. Further details concerning the firing member 6140, sled assembly 6150, and their various alternatives as well as examples of their operation will be discussed in further detail below and may also be found in U.S. patent application Ser. No. 15/385,911, entitled SURGICAL STAPLE/FASTENERS WITH INDEPENDENTLY ACTUATABLE CLOSING AND FIRING SYSTEMS. The interchangeable surgical tool assembly 5000 may be operably coupled to the handle assembly 500 in the manner as described above with respect to the interchangeable surgical tool assembly 1000.

Figure 22:
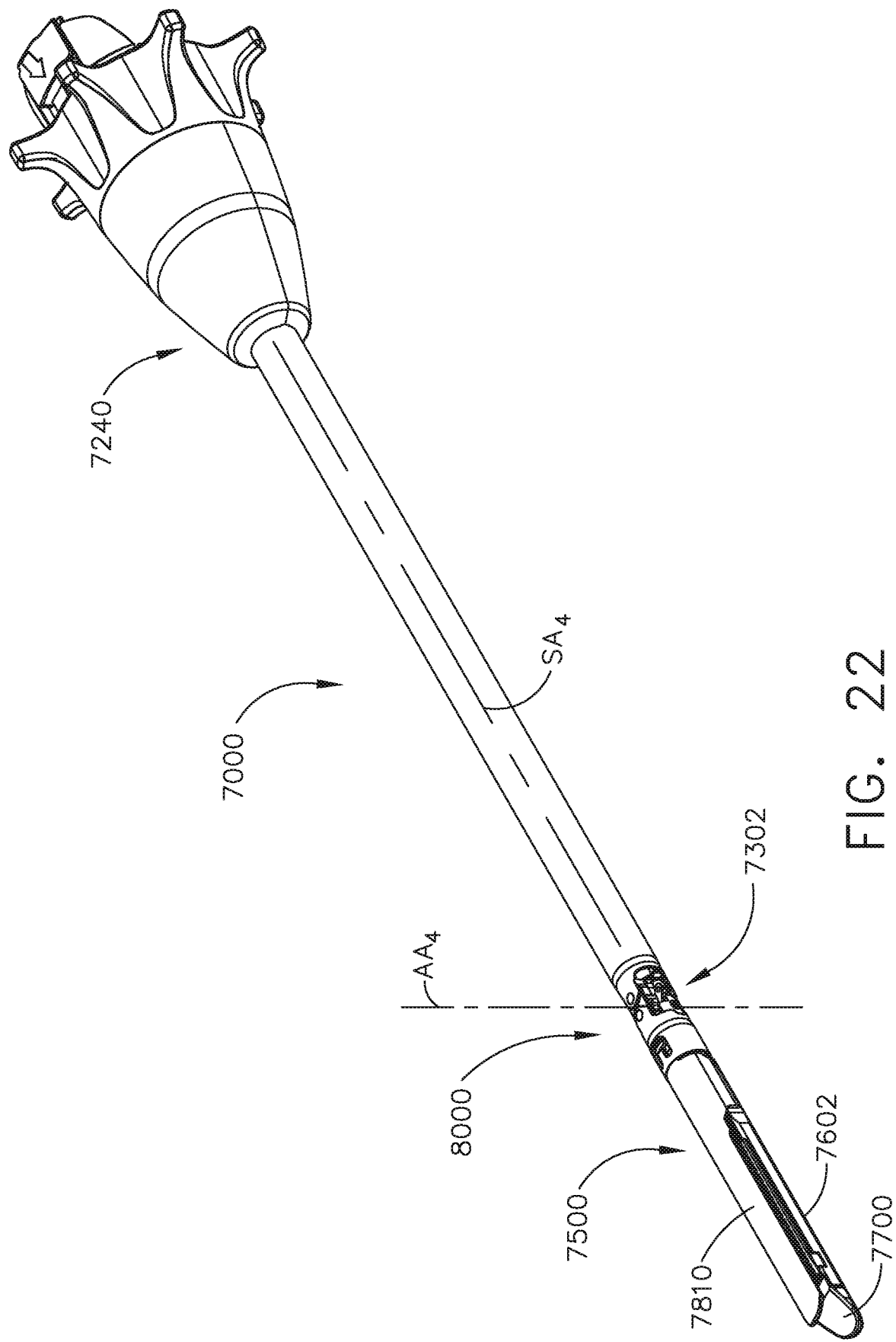
FIG. 22 is a perspective view of another one of the interchangeable surgical tool assemblies depicted in FIG. 1.
Figure 23:
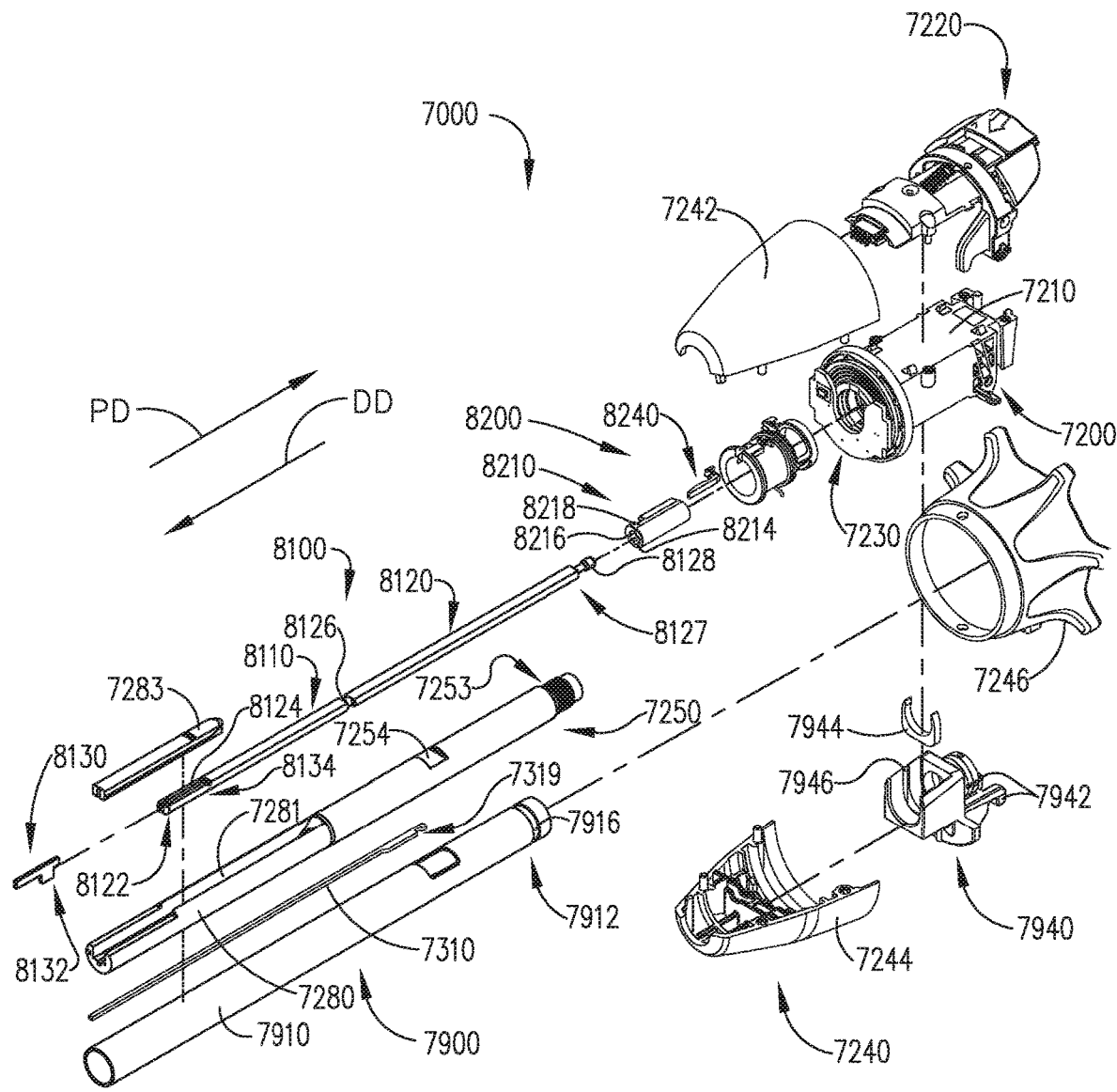
FIG. 23 is an exploded assembly view of a proximal portion of the interchangeable surgical tool assembly of FIG. 22.
Figure 24:
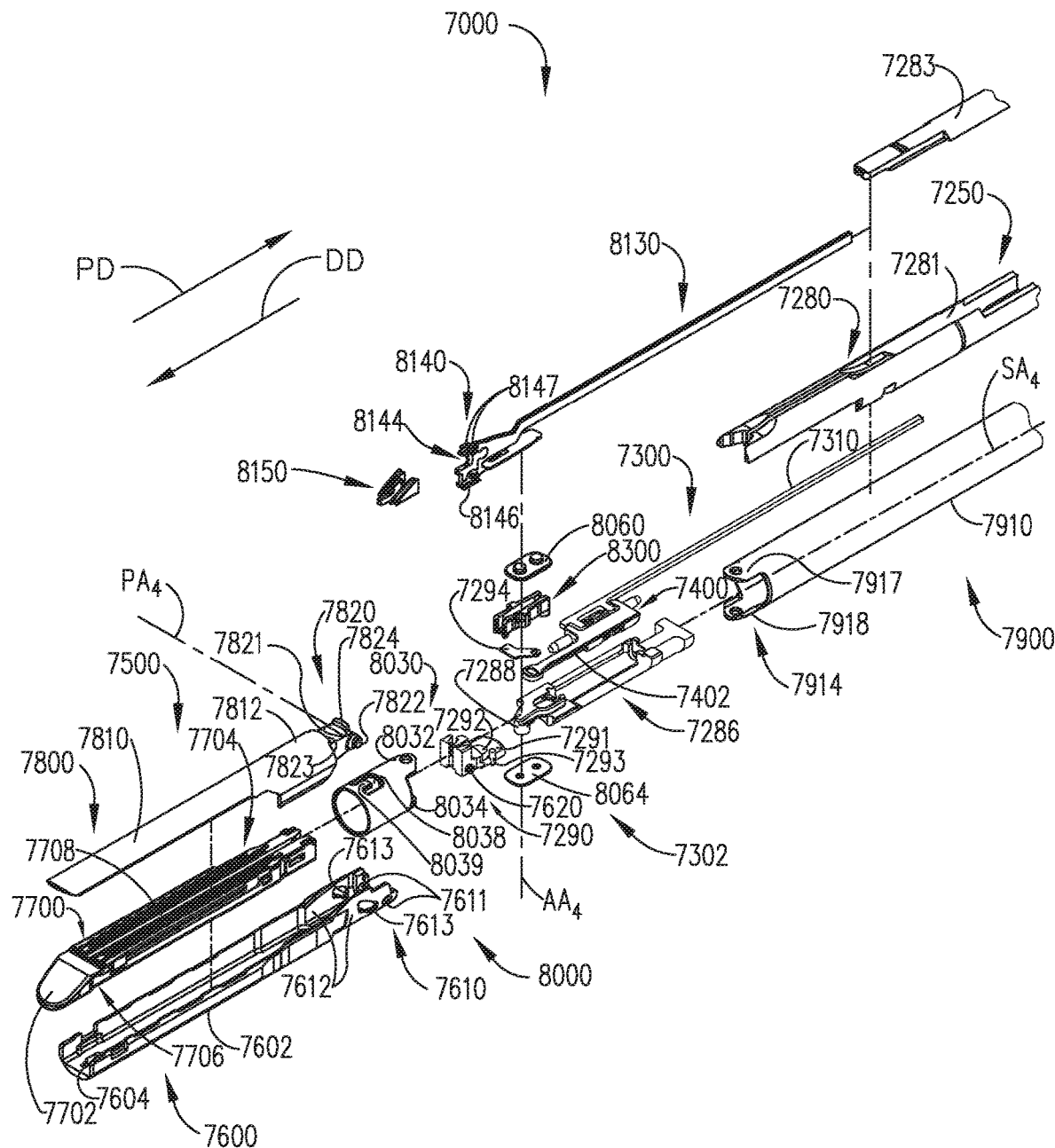
FIG. 24 is another exploded assembly view of a distal portion of the interchangeable surgical tool assembly of FIGS. 22 and 23.

Returning again to FIG. 1, as was discussed above, the surgical system 10 illustrated in that Figure includes four interchangeable surgical tool assemblies 1000, 3000, 5000 and 7000 that may each be effectively employed with the same handle assembly 500 to perform different surgical procedures. Turning now to FIGS. 22-24, the interchangeable surgical tool assembly 7000 includes a surgical end effector 7500 that comprises a first jaw 7600 and a second jaw 7800. In one arrangement, the first jaw comprises an elongate channel 7602 that is configured to operably support a surgical staple/fastener cartridge 7700 therein. The second jaw 7800 comprises an anvil 7810 that is movably supported relative to the elongate channel 7602. The interchangeable surgical tool assembly 7000 includes an articulation system 7300 that comprises an articulation joint 7302 and an articulation lock 7400 which can be configured to releasably hold the surgical end effector 7500 in a desired articulated position relative to a shaft axis $SA_4$. Details regarding the construction and operation of the articulation lock 7400 as well as alternative lock configurations and operational details may be found in in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock 7400 and/or alternative articulation lock arrangements may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, the entire disclosure of which is hereby incorporated by reference herein.

As can be seen in FIG. 24, the interchangeable surgical tool assembly 7000 includes a tool frame assembly 7200 that comprises a tool chassis 7210 that operably supports a nozzle assembly 7240 thereon. In one form, the nozzle assembly 7240 is comprised of nozzle portions 7242, 7244 as well as an actuator wheel portion 7246 that is configured to be coupled to the assembled nozzle portions 7242, 7244 by snaps, lugs, screws etc. The interchangeable surgical tool assembly 7000 includes a proximal closure assembly 7900 which is operably coupled to a distal closure assembly 8000 that is utilized to close and/or open the anvil 7810 of the surgical end effector 7500 as will be discussed in further detail below. In addition, the interchangeable surgical tool assembly 7000 includes a spine assembly 7250 that operably supports the proximal closure assembly 7900 and is coupled to the surgical end effector 3500. In the illustrated arrangement, the spine assembly 7250 includes a distal end portion 7280 that has an opening 7281 therein for ease of assembly. A spine cap 7283 may be attached thereto to cover the opening 7281 after the various components have been assembled therein. In assembled form, a proximal end portion 7253 of the spine assembly 7250 is rotatably supported in the tool chassis 7210. In one arrangement, for example, the proximal end of the proximal end portion 7253 of the spine assembly 7250 is attached to a spine bearing (not shown) that is configured to be supported within the tool chassis 7210. Such arrangement facilitates rotatable attachment of the spine assembly 7250 to the tool chassis 7210 such that the spine assembly 7250 may be selectively rotated about the shaft axis $SA_4$ relative to the tool chassis 7210. In particular, in one arrangement, for example, the proximal end portion 7253 of the spine assembly 7250 includes two diametrically opposed lug seats 7254 (only one can be seen in FIG. 23) that are each configured to receive a corresponding nozzle lug (not shown) that extend inwardly from each of the nozzle portions 7242, 7244. Such arrangement facilitates rotation of the spine assembly 7250 about the shaft axis $SA_4$ by rotating the actuator wheel portion 7246 of the nozzle assembly 7240.

Referring now to FIG. 24, the distal end portion 7280 of the spine assembly 7250 is attached to a distal frame segment 7286 that operably supports the articulation lock 7400 therein. The spine assembly 7250 is configured to, one, slidably support a firing member assembly 8110 therein and, two, slidably support a proximal closure tube 7910 which extends around the spine assembly 7250. The spine assembly 7250 can also be configured to slidably support a proximal articulation driver 7310 as can be seen in FIG. 24. The distal frame segment 7286 is pivotally coupled to the elongate channel 7602 by an end effector mounting assembly 7290. In one arrangement, for example, the distal end of the distal frame segment 7286 has a pivot pin 7288 formed thereon. The pivot pin 7288 is adapted to be pivotally received within a pivot hole 7292 formed in pivot base portion 7291 of the end effector mounting assembly 7290. The end effector mounting assembly 7290 is attached to a proximal end portion 7610 of the elongate channel 7602 by a spring pin 7620 or other suitable member that is received within mounting holes 7611 in the proximal end portion 7610. The pivot pin 7288 defines an articulation axis $AA_4$ that is transverse to the shaft axis $SA_4$. See FIG. 24. Such arrangement facilitates pivotal travel (i.e., articulation) of the surgical end effector 7500 about the articulation axis $AA_4$ relative to the spine assembly 7250. The distal frame segment 7286 is further configured to support the articulation lock 7400 therein. Various articulation lock arrangements may be employed. At least one form of articulation lock 7400 is described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT.

In the illustrated example, the surgical end effector 7500 is electively articulatable about the articulation axis $AA_4$ by the articulation system 7300. In one form, the articulation system 7300 includes the proximal articulation driver 7310 that operably interfaces with the articulation lock 7400. The articulation lock 7400 includes an articulation frame 7402 that is adapted to operably engage a drive pin 7293 on the pivot base portion 7291 of the end effector mounting assembly 7290. In addition, a cross link 7294 may be linked to the drive pin 7293 and articulation frame 7402 to assist articulation of the surgical end effector 7500. As indicated above, further details regarding the operation of the articulation lock 7400 and the articulation frame 7402 may be found in U.S. patent application Ser. No. 13/803,086, now U.S. Patent Application Publication No. 2014/0263541. Further details regarding the end effector mounting assembly and cross link 7294 may be found in U.S. patent application Ser. No. 15/019,245, filed Feb. 9, 2016, entitled SURGICAL INSTRUMENTS WITH CLOSURE STROKE REDUCTION ARRANGEMENTS, the entire disclosure of which is hereby incorporated by reference herein. As further described therein, as well as in other disclosures incorporated by reference herein, axial movement of proximal articulation driver 7310 will result in the engagement/disengagement of the articulation lock 7400 to thereby apply articulation motions to the elongate channel 7602 and thereby cause the surgical end effector 7500 to articulate about the articulation axis $AA_4$ relative to the spine assembly 7250.

The anvil 7810 in the illustrated example includes an anvil body 7812 that terminates in anvil mounting portion 7820. The anvil mounting portion 7820 is movably supported on the elongate channel 7602 for selective pivotal and axial travel relative thereto. In the illustrated arrangement, an anvil trunnion 7822 extends laterally out of each lateral side of the anvil mounting portion 7820 to be received in a corresponding "kidney-shaped" opening 7613 formed in upstanding walls 7612 of the proximal end portion 7610 of the elongate channel 7602. Movement of the anvil 7810 relative to the elongate channel 7602 is effectuated by axial movement of the proximal closure assembly 7900 and the distal closure assembly 8000. In the illustrated arrangement, the proximal closure assembly 7900 comprises the proximal closure tube 7910 that has a proximal end 7912 and a distal end 7914. The proximal end 7912 is rotatably supported in a closure shuttle 7940 that is slidably supported within the tool chassis 7210 such that it may be axially moved relative thereto. In one form, the closure shuttle 7940 includes a pair of proximally-protruding hooks 7942 that are configured for attachment to the transverse attachment pin 516 that is attached to the closure linkage assembly 514 of the handle assembly 500. The proximal end 7912 of the proximal closure tube 7910 is coupled to the closure shuttle 7940 for relative rotation thereto. For example, a U-shaped connector 7944 is inserted into an annular slot 7916 in the proximal end 7912 of the proximal closure tube 7910 and is retained within vertical slots 7946 in the closure shuttle 7940. Such arrangement serves to attach the proximal closure assembly 7900 to the closure shuttle 7940 for axial travel therewith while enabling the proximal closure tube 7910 to rotate relative to the closure shuttle 7940 about the shaft axis $SA_4$. As was discussed above in connection with the interchangeable surgical tool assembly 1000, a closure spring (not shown) may extend over the proximal end 7912 of the proximal closure tube 7910 to bias the closure shuttle 7940 in the proximal direction PD which can serve to pivot the closure trigger 512 on the handle assembly 500 (FIG. 2) into the unactuated position when the interchangeable surgical tool assembly 7000 is operably coupled to the handle assembly 500 in the above described manner.

As can be seen in FIG. 24, the distal end 7914 of the proximal closure tube 3910 is attached to the distal closure assembly 8000. The distal end 7914 includes upper and lower tangs 7917, 7918 that are configured to be movably coupled to an end effector closure sleeve or distal closure tube segment 8030. The distal closure tube segment 8030 includes an upper tang 8032 and a lower tang 8034 that protrude proximally from a proximal end thereof. An upper double pivot link 8060 pivotally couples the upper tangs 7917 and 8032 and a lower double pivot link 8064 pivotally couples the lower tangs 7918 and 8034 together in the above-described manner. The distal advancement of the distal closure tube segment 8030 on the anvil mounting portion 7820 will result in closure or pivotal travel of the anvil 7810 towards the elongate channel 7602. In the illustrated arrangement, an upstanding anvil tab 7824 is formed on the anvil mounting portion 7820 and extends into a horseshoe-shaped opening 8038. Opening 8038 defines an opening tab 8039 configured to operably interface with the anvil tab 7824 as the distal closure tube is retracted in the distal direction. Such interaction between the opening tab 8039 and the anvil tab 7824 applies an opening motion to the anvil 7810 to thereby cause the anvil 7810 to move to an open position.

In the illustrated arrangement, the interchangeable surgical tool assembly 7000 further includes a firing system generally designated as 8100. In various instances, the firing system 8100 includes the firing member assembly 8110 that is supported for axial travel within the spine assembly 7250. In the illustrated embodiment, the firing member assembly 8110 includes an intermediate firing shaft portion 8120 that is configured for attachment to a distal cutting portion or knife bar 8130. The firing member assembly 8110 may also be referred to herein as a "second shaft" and/or a "second shaft assembly". As can be seen in FIG. 24, the intermediate firing shaft portion 8120 may include a longitudinal slot 8124 in a distal end 8122 thereof which can be configured to receive a proximal end 8132 of the knife bar 8130. The longitudinal slot 8124 and the proximal end 8132 of the knife bar 8130 can be sized and configured to permit relative movement therebetween and can comprise a slip joint 8134. The slip joint 8134 can permit the intermediate firing shaft portion 8120 of the firing member assembly 8110 to be moved to articulate the end effector 7500 without moving, or at least substantially moving, the knife bar 8130 as was discussed above. In the illustrated arrangement, a proximal end 8127 of the intermediate firing shaft portion 8120 has a firing shaft attachment lug 8128 formed thereon that is configured to be seated into an attachment cradle (not shown) that is on the distal end of the longitudinally movable drive member (not shown) of the firing drive system 530 within the handle assembly 500 as was discussed above. Such arrangement facilitates the axial movement of the intermediate firing shaft portion 8120 upon actuation of the firing drive system 530. Other attachment configurations may also be employed to couple the intermediate firing shaft portion to other firing drive arrangements (e.g., manually actuated, robotic, etc.).

Further to the above, the interchangeable tool assembly 7000 can include a shifter assembly 8200 which can be configured to selectively and releasably couple the proximal articulation driver 7310 to the firing member assembly 8110 in the manner described above. In one form, the shifter assembly 8200 includes a lock collar, or lock sleeve 8210, positioned around the intermediate firing shaft portion 8120 of the firing member assembly 8110 wherein the lock sleeve 8210 can be rotated between an engaged position in which the lock sleeve 8210 couples the proximal articulation driver 7310 to the firing member assembly 8110 and a disengaged position in which the proximal articulation driver 7310 is not operably coupled to the firing member assembly 8110. As was discussed above, the intermediate firing shaft portion 8120 of the firing member assembly 8110 is formed with a drive notch 8126. The lock sleeve 8210 comprises a cylindrical, or an at least substantially cylindrical, body that includes a longitudinal aperture that is configured to receive the intermediate firing shaft portion 8120 therethrough. The lock sleeve 8210 can comprise diametrically-opposed, inwardly-facing lock protrusions 8214, 8216 that, when the lock sleeve 8210 is in one position, are engagingly received within corresponding portions of the drive notch 8126 in the intermediate firing shaft portion 8120 and, when in another position, are not received within the drive notch 8126 to thereby permit relative axial motion between the lock sleeve 8210 and the intermediate firing shaft 8120 as was discussed in further detail above. The lock sleeve 8210 further includes a lock member 8218 that is sized to be movably received within a notch 7319 in a proximal end of the proximal articulation driver 7310. When the lock sleeve 8210 is in its engaged position, the lock protrusions 8214, 8216 are positioned within the drive notch 7126 in the intermediate firing shaft portion 8120 such that a distal pushing force and/or a proximal pulling force can be transmitted from the firing member assembly 8110 to the lock sleeve 8210. Such axial pushing or pulling motion is then transmitted from the lock sleeve 8210 to the proximal articulation driver 7310 to thereby articulate the surgical end effector 7500.

As was discussed above, in the illustrated example, relative movement of the lock sleeve 8210 between its engaged and disengaged positions may be controlled by the shifter assembly 8200 that interfaces with the proximal closure tube 7910 of the proximal closure assembly 7900. The shifter assembly 8200 further includes a shifter key 8240 that is configured to be slidably received within a key groove (similar to the key groove 2217 illustrated in FIG. 8) formed in the outer perimeter of the lock sleeve 8210. Such arrangement enables the shifter key 8240 to move axially with respect to the lock sleeve 8210. Operation of the shifter assembly 8200 may be identical to the operation of the shifter assembly 2200 which was described in further detail above and which will not be repeated again for brevity. Further details, alternative arrangements and drive configurations that may be employed are disclosed in Other arrangements that may be employed are disclosed in U.S. patent application Ser. No. 15/385,911, entitled SURGICAL STAPLE/FASTENERS WITH INDEPENDENTLY ACTUATABLE CLOSING AND FIRING SYSTEMS, U.S. patent application Ser. No. 13/803,086, now U.S. Patent Application Publication No. 2014/0263541, and U.S. patent application Ser. No. 15/019,196, the as well as other disclosures that have been incorporated herein.

The interchangeable tool assembly 7000 can comprise a slip ring assembly 7230 which can be configured to conduct electrical power to and/or from the surgical end effector 7500 and/or communicate signals to and/or from the surgical end effector 7500, back to a microprocessor 560 in the handle assembly 500 or robotic system controller, for example as was discussed above. Further details concerning the slip ring assembly 7230 and associated connectors may be found in U.S. patent application Ser. No. 13/803,086, now U.S. Patent Application Publication No. 2014/0263541, and U.S. patent application Ser. No. 15/019,196 which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

The illustrated interchangeable surgical tool assembly 7000 also employs a latch system 7220 for removably coupling the interchangeable surgical tool assembly 7000 to the handle frame 506 of the handle assembly 500, for example. The latch system 7220 may be identical to the latch system 1220 described in detail above. The knife bar 8130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 8130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS which is hereby incorporated by reference in its entirety. As can also be seen in FIG. 24, a firing shaft support assembly 8300 is employed to provide lateral support to the knife bar 8130 as it flexes to accommodate articulation of the surgical end effector 7500. Further details concerning the operation of the firing shaft support assembly 8300 and alternative knife bar support arrangements may be found in U.S. patent application Ser. No. 15/019,245, entitled SURGICAL INSTRUMENTS WITH CLOSURE STROKE REDUCTION ARRANGEMENTS and U.S. patent application Ser. No. 15/019,220, entitled SURGICAL INSTRUMENT WITH ARTICULATING AND AXIALLY TRANSLATABLE END EFFECTOR, which are each hereby incorporated by reference herein in their respective entireties.

As can also be seen in FIG. 24, a firing member or knife member 8140 is attached to the distal end of the knife bar 8130. The firing member 8140 is configured to operably interface with a sled assembly 8150 that is operably supported within the body 7702 of the surgical staple/fastener cartridge 7700. See FIG. 51. The sled assembly 8150 is slidably displaceable within the surgical staple/fastener cartridge body 7702 from a proximal starting position adjacent a proximal end 7704 of the cartridge body 7702 to an ending position adjacent a distal end 7706 of the cartridge body 7702. The cartridge body 7702 operably supports therein a plurality of staple drivers (not shown) that are aligned in rows on each side of a centrally disposed slot 7708. The centrally disposed slot 7708 enables the firing member 8140 to pass therethrough and cut the tissue that is clamped between the anvil 7810 and the staple cartridge 7700. The drivers are associated with corresponding staple pockets that open through the upper deck surface of the cartridge body 7702. Each of the staple drivers supports one or more surgical staple/fastener or fastener (not shown) thereon. The sled assembly includes a plurality of sloped or wedge-shaped cams wherein each cam corresponds to a particular line of fasteners or drivers located on a side of the slot 7708.

In one exemplary form, the firing member 8140 comprises a body portion 8142 that supports a knife or tissue cutting portion 8144. See FIG. 51. The body portion 8142 protrudes through an elongate slot 7604 in the elongate channel 7602 and terminates in a foot member 8146 that extends laterally on each side of the body portion 8142. As the firing member 8140 is driven distally through the surgical staple/fastener cartridge 7700, the foot member 8146 rides within a passage 7622 in the elongate channel 7602 that is below the staple cartridge 7700. The tissue cutting portion 8144 is disposed between a distally protruding top nose portion 8143. As can be further seen in FIG. 24, the firing member 8140 may further include two laterally extending top tabs, pins or anvil engagement features 8147. As the firing member 8140 is driven distally, a top portion of the body portion 8142 extends through a centrally disposed anvil slot 7814 and the anvil engagement features 8147 ride on corresponding ledges 7816 formed on each side of the anvil slot 7814. Further details concerning the firing member 8140, sled assembly 8150, and their various alternatives as well as examples of their operation will be discussed in further detail below and may also be found in U.S. patent application Ser. No. 15/385,911, entitled SURGICAL STAPLE/FASTENERS WITH INDEPENDENTLY ACTUATABLE CLOSING AND FIRING SYSTEMS. The interchangeable surgical tool assembly 7000 may be operably coupled to the handle assembly 500 in the manner as described above with respect to the interchangeable surgical tool assembly 1000.

As can be appreciated from the foregoing descriptions, the interchangeable surgical tool assemblies described herein may be actuated by the same handle assembly, robotic system or other automated actuation system. All of the above described interchangeable surgical tool assemblies comprise surgical cutting and fastening instruments that have somewhat similar closure and firing components. However, the closure and firing systems and components of each of these tool assemblies have differences that may seem somewhat subtle at first blush, but, as will be further discussed below, such differences can result in significant improvements in the material composition, design, construction, manufacture and use of such tools. As will become apparent as the present Detailed Description proceeds, the interchangeable surgical tool assembly 1000 contains subtle design differences when compared to the other interchangeable surgical tool assemblies 3000, 5000, 7000 described herein that can result in significant improvements in the overall functionality, reliability, and cost of the tool assembly. Moreover, we have discovered that, in some cases, a synergistic effect exists between certain component arrangements employed by the tool assembly 1000 which can further enhance the overall efficiency and functionality of the tool assembly 1000. In order to better understand these differences and improvements, certain components and systems of each of the tool assemblies 1000, 3000, 5000, 7000 will now be further described and compared to each other below.

For example, each of the interchangeable surgical tool assemblies 1000, 3000, 5000, 7000 must be able to apply a sufficient amount of closure force to cause the jaws to sufficiently clamp the target tissue so as to permit the firing member to properly treat the clamped tissue upon actuation of the firing drive system. For example, in the illustrated assemblies, the respective closure system components must be able to clamp the anvil and surgical staple/fastener cartridge onto the target tissue to enable the firing member to properly sever the clamped tissue and eject lines of staples or fasteners on each side of the tissue cut line. Depending upon the thickness and composition of the target tissue, significant closure forces and firing forces are often required. Thus, the closure and firing drive systems in the handle assembly housing, robotic housing, etc. must be able to generate such forces of sufficient magnitude (through the use of a motor or manually generated motion, for example) to sufficiently close the jaws and fire the firing member through the clamped tissue. Such procedures further require that the components within the interchangeable shaft assemblies to be sufficiently robust to accommodate the magnitudes of the forces being transmitted therethrough. In the past, the magnitudes of such forces often dictated that the closure system components, as well as the firing system components, be fabricated from metal or other suitable materials with relatively large cross-sectional thicknesses and of substantial reinforced configurations.

The tissue loads encountered during the clamping process typically create a large "moment" about the anvil pivot axis PA. The closure system components must be designed to counteract such moment. In various circumstances, for example, a moment about the anvil pivot axis PA in the opposite direction is needed. To maximize the efficiency of the system (e.g., minimize the magnitude of the force applied), the largest practical moment arm is desired. However, as will be further discussed below, there are trade-offs with other design variables when seeking to establish a large counter moment. For example, there is a balance between the distance from the articulation joint to the first staple and the length of the moment arm for a closure system where the firing and closing systems are separate and distinct. The larger the moment arm of the closure system, the more efficiently it handles clamp loads and tissue compression. However, the distance between the articulation joint and the first staple may have a large impact on the access of the surgical end effector as it is positioned into tight spaces within a laparoscopic environment.

FIGS. 25-32 illustrate exemplary moment arms for each of the surgical end effectors 1500, 3500, 5500, 7500. Turning first to FIG. 25, as was described above, the anvil trunnions 1822 extend laterally out of each lateral side of the anvil mounting portion 1820 to be received in a corresponding trunnion cradle 1614 formed in the upstanding walls 1612 of the proximal end portion 1610 of the elongate channel 1602. The anvil trunnions 1822 are pivotally retained in their corresponding trunnion cradle 1614 by the channel cap or anvil retainer 1630. The channel cap 1630 includes a pair of attachment lugs 1636 that are configured to be retainingly received within corresponding lug grooves or notches 1616 formed in the upstanding walls 1612 of the proximal end portion 1610 of the elongate channel 1602. Such arrangement constrains the anvil 1810 to only pivot about the pivot axis $PA_1$ (see FIG. 3). Under such arrangement, the anvil mounting portion 1820 does not move axially or vertically. As the distal closure tube segment 2030 is advanced in the distal direction DD under a horizontal closure force $F_{H1}$ (FIG. 26), the interaction between an internal cam surface 2036 on the distal closure tube segment 2030 and an anvil cam surface 1821 on the anvil mounting portion 1820 results in the application of a closure force $F_{C1}$ to the anvil cam surface 1821. The closure force $F_{C1}$ comprises the resultant force of the horizontal closure force $F_{H1}$ and a vertical closure force $F_{V1}$ and is essentially "normal to" or perpendicular to the cam surface 1821 on the anvil mounting portion 1820. See FIG. 26. $M_{A1}$ represents a closure moment arm from the anvil pivot axis $PA_1$ (coincident with the center of anvil trunnions 1822) to the point of contact between the internal cam surface 2036 on the distal closure tube segment 2030 and the anvil cam surface 1821 on the anvil mounting portion 1820 when the anvil 1810 has been pivoted to the fully closed position. In one example, the closure moment arm $M_{A1}$ may be approximately 0.415 inches, for example. $M_{A1} \times F_{C1} =$ a closure moment $C_{M1}$ that is applied to the anvil mounting portion 1820.

To ensure that the each side of the tissue cut line is fastened with staples or fasteners extending from the proximal end to the distal end of the tissue cutline, a proximal end portion 1818 of the anvil body 1812 is formed with two tissue stop formations or tissue locating features 1830 that extend downwardly from each lateral side of the anvil body 1812 (only one tissue stop formation 1830 may be seen in FIGS. 25 and 26). When the anvil 1810 is opened to receive the target tissue between the underside of the anvil and the cartridge deck surface, the downwardly extending tissue stop 1830 serve to prevent the target tissue from extending proximally past the proximal most staples/fasteners in the surgical staple/fastener cartridge 1700. If the tissue were to extend proximally beyond the proximal most staples/fasteners, that portion of tissue may be severed by the firing member during the firing process and may not be fastened which may lead to catastrophic results. The downwardly extending tissue stops 1830 may prevent this from happening. In the embodiment depicted in FIG. 26, for example, the proximal-most staple/fastener pockets 1720 are shown in phantom lines relative to the tissue stops 1830. As can be seen in that Figure, the tissue stop 1830 has a downwardly extending portion 1832 and a chamfered portion 1834. The target tissue is contacted by the portions 1832, 1834 to prevent the target tissue from extending proximally beyond the proximal most staples/fasteners that are supported in the proximal most staple/fastener pockets 1720 in the staple/fastener cartridge body 1702.

Returning again to FIG. 25, as the anvil 1810 is pivoted closed onto the target tissue (not shown) that is positioned between the underside or tissue contacting surface 1813 of the anvil body 1812, the tissue applies tissue forces $T_{F1}$ to the underside 1813 of the anvil body 1812 which cause the anvil 1810 to experience a tissue counter moment $C_{T1}$ that must be overcome by the closure moment $C_{M1}$ established by the closure system components. The example depicted in FIG. 25 illustrates equally distributed tissue forces $T_{F1}$ on the anvil 1810 and a tissue moment arm $M_{T1}$ established by the clamped tissue (the clamped tissue is not shown in FIG. 25 for clarity purposes). As can be seen in that Figure, in that example, the tissue moment arm $M_{T1}$ is considerably longer than the closure moment arm $M_{A1}$ (i.e., $M_{T1} > M_{A1}$).

Turning next to FIGS. 27 and 28, as was described above, the anvil trunnions 3822 of the anvil 3810 of the interchangeable surgical tool assembly 3000 extend laterally out of each lateral side of the anvil mounting portion 3820 to be received in corresponding trunnion holes 3613 formed in the upstanding walls 3612 of the proximal end portion 3610 of the elongate channel 3602. Such arrangement constrains the anvil 3810 to only pivot about the anvil pivot axis $PA_2$ (see FIG. 18). Under such arrangement, the anvil mounting portion 3820 does not move axially or vertically. As the distal closure tube segment 4030 is advanced in the distal direction DD under a horizontal closure force $F_{H2}$ (FIG. 28), the interaction between an internal cam surface 4036 on the distal closure tube segment 4030 and an anvil cam surface 3821 on the anvil mounting portion 3820 results in the application of a closure force $F_{C2}$ to the anvil cam surface 3821. The closure force $F_{C2}$ comprises the resultant force of the horizontal closure force $F_{H2}$ and a vertical closure force $F_{V2}$ and is essentially "normal to" or perpendicular to the anvil cam surface 3821 on the anvil mounting portion 3820. See FIG. 28. $M_{A2}$ represents the closure moment arm from the anvil pivot axis $PA_2$ (center of anvil trunnions 3822) to the point of contact between the internal cam surface 4036 on the distal closure tube 4030 and the anvil cam surface 3821 on the anvil mounting portion 3820 when the anvil 3810 has been pivoted to the fully closed position. In one example, closure moment arm $M_{A2}$ may be approximately 0.539 inches, for example. $M_{A2} \times F_{C2}$ = a closure moment $C_{M2}$ that is applied to the anvil mounting portion 3820.

In the example depicted in FIGS. 27 and 28, the anvil body 3812 is formed with two tissue stop formations or tissue locating features 3830 that extend downwardly from each lateral side of the anvil body 3812 (only one tissue stop formation 3830 may be seen in FIGS. 27 and 28). When the anvil 3810 is opened to receive the target tissue between the underside of the anvil and the cartridge deck surface, the downwardly extending tissue stop formations 3830 serve to prevent the target tissue from extending proximally past the proximal most staples/fasteners in the surgical staple/fastener/fastener cartridge 3700. In the embodiment depicted in FIG. 28, for example, the proximal-most staple pockets 3720 are shown in phantom lines relative to the tissue stop formations 3830. As can be seen in that Figure, the tissue stop formation 3830 has a downwardly extending portion 3832 and a chamfered portion 3834. The target tissue is contacted by the portions 3832, 3834 to prevent the target tissue from extending proximally beyond the proximal most staples/fasteners that are supported in the proximal-most staple/fastener pockets 3720 in the staple/fastener cartridge body 3702.

Returning again to FIG. 27, as the anvil 3810 is pivoted closed onto the target tissue (not shown) that is positioned between the underside or tissue contacting surface 3813 of the anvil body 3812, the tissue applies tissue forces $T_{F2}$ to the underside 3813 of the anvil body 3812 which cause the anvil 3810 to experience a tissue counter moment $C_{T2}$ that must be overcome by the closure moment $C_{M2}$ established by the closure system components. The example depicted FIG. 27 illustrates equally distributed tissue forces $T_{F2}$ on the anvil 3810 and a tissue moment arm $M_{T2}$ established by the clamped tissue (the clamped tissue is not shown in FIG. 27 for clarity purposes). As can be seen in that Figure, in that example, the tissue moment arm $M_{T2}$ is considerably longer than the closure moment arm $M_{A2}$ (i.e., $M_{T2} > M_{A2}$).

Figure 29:
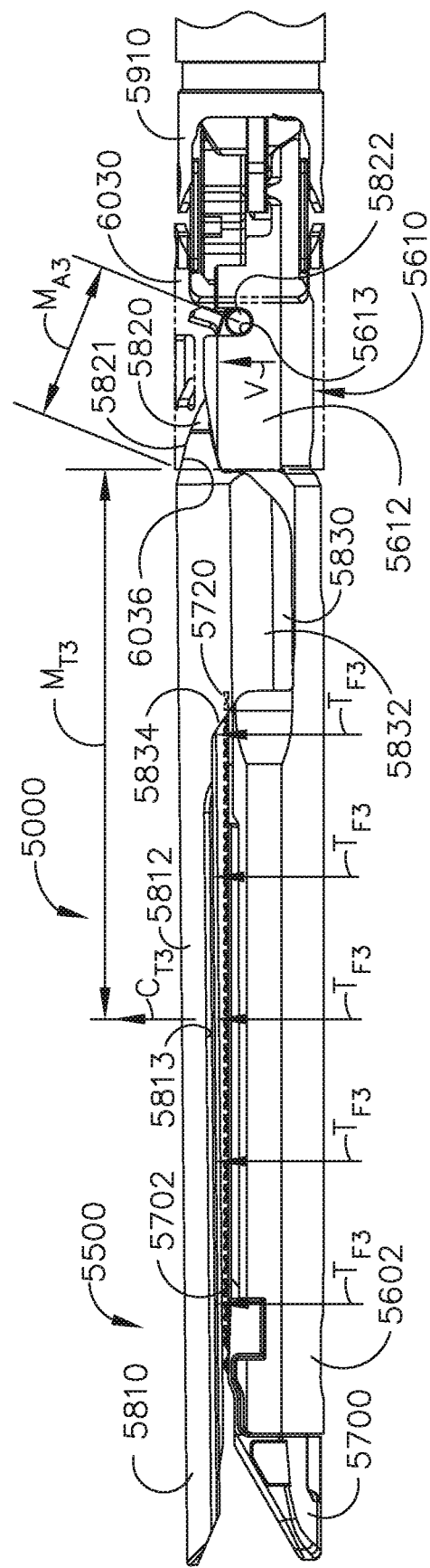
FIG. 29 is a side elevational view of a distal portion of the interchangeable surgical tool assembly of FIG. 19 with the anvil thereof in a fully closed position.
Figure 30:
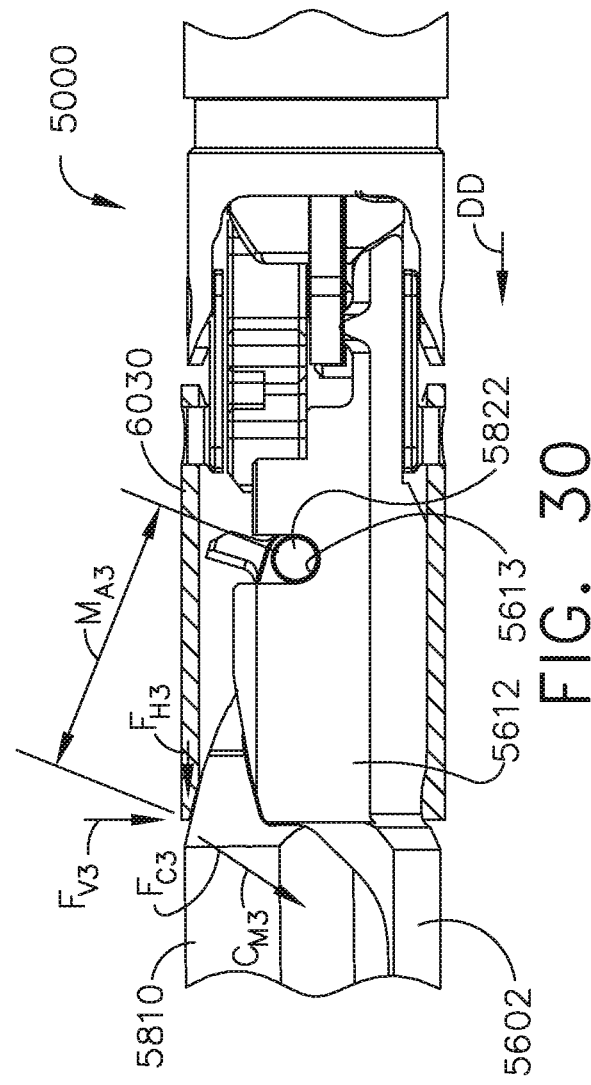
FIG. 30 is an enlarged side elevational view of the anvil mounting portion and elongate channel of the interchangeable surgical tool assembly of FIG. 29.

Turning next to FIGS. 29 and 30, as was described above, the anvil trunnions 5822 of the anvil 5810 of the interchangeable surgical tool assembly 5000 extend laterally out of each lateral side of the anvil mounting portion 5820 to be received in the corresponding "open-ended" vertical cradle 5613 formed in the upstanding walls 5612 of the proximal end portion 5610 of the elongate channel 5602. In this arrangement, the anvil trunnions 5822 are free to pivot within their respective cradles 5613 as the distal closure tube segment 6030 cammingly contacts the anvil cam surface 5821 on the anvil mounting portion 5820. Under such arrangement, the anvil 5810 does not move axially, but the anvil trunnions 5822 are free to move vertically (arrow V) within their respective cradles 5613. As the distal closure tube segment 6030 is advanced in the distal direction DD under the horizontal closure force $F_{H3}$ (FIG. 30), the interaction between an internal cam surface 6036 on the distal closure tube segment 6030 and the anvil cam surface 5821 on the anvil mounting portion 5820 results in the application of a closure force $F_{C3}$ to the anvil cam surface 5821. The closure force $F_{C3}$ comprises the resultant force of the horizontal closure force $F_{H3}$ and a vertical closure force $F_{V3}$ and is essentially "normal to" or perpendicular to the anvil cam surface 5821 on the anvil mounting portion 5820. See FIG. 30. $M_{A3}$ represents the closure moment arm from the anvil pivot axis $PA_3$ (coincident with the center of anvil trunnions 5822) to the point of contact between the internal cam surface 6036 on the distal closure tube 6030 and the anvil cam surface 5821 on the anvil mounting portion 5820 when the anvil 5810 has been pivoted to the closed position. In one example, closure moment arm $M_{A3}$ may be approximately 0.502 inches, for example. $M_{A3} \times F_{C3}$ = a closure moment $C_{M3}$ that is applied to the anvil mounting portion 5820.

In the example depicted in FIGS. 29 and 30, the anvil body 5812 is formed with two tissue stop formations or tissue locator features 5830 that extend downwardly from each lateral side of the anvil body 5812 (only one tissue stop formation 5830 may be seen in FIGS. 29 and 30). When the anvil 5810 is opened to receive the target tissue between the underside of the anvil and the cartridge deck surface, the downwardly extending tissue stop formations 5830 serve to prevent the target tissue from extending proximally past the proximal most staples/fasteners in the surgical staple/fastener cartridge 5700. In the embodiment depicted in FIG. 29, for example, the proximal-most staple/fastener pockets 5720 are shown in phantom lines relative to the tissue stop formations 5830. As can be seen in that Figure, the tissue stop formation 5830 has a downwardly extending portion 5832 and a chamfered portion 5834. The target tissue is contacted by the portions 5832, 5834 to prevent the target tissue from extending proximally beyond the proximal most staples/fasteners that are supported in the proximal-most staple/fastener pockets 5720 in the staple/fastener cartridge body 5702.

Returning again to FIG. 29, as the anvil 5810 is pivoted closed onto the target tissue (not shown) that is positioned between the underside 5813 of the anvil body 5812, the tissue applies tissue forces $T_{F3}$ to the underside or tissue contacting surface 5813 of the anvil body 5812 which cause the anvil 5810 to experience a tissue counter moment $C_{T3}$ that must be overcome by the closure moment $C_{M3}$ established by the closure system components. The example depicted in FIG. 29 illustrates equally distributed tissue forces $T_{F3}$ on the anvil 5810 and a tissue moment arm $M_{T3}$ established by the clamped tissue (the clamped tissue is not shown in FIG. 29 for clarity purposes). As can be seen in that Figure, in that example, the tissue moment arm $M_{T3}$ is considerably longer than the closure moment arm $M_{A3}$ (i.e., $M_{T3}>M_{A3}$).

Turning now to FIGS. 31 and 32, as was described above, the anvil trunnions 7822 of the anvil 7810 of the interchangeable surgical tool assembly 7000 extend laterally out of each lateral side of the anvil mounting portion 7820 to be received in the corresponding "kidney-shaped" opening 7613 formed in the upstanding walls 7612 of the proximal end portion 7610 of the elongate channel 7602. When the anvil 7810 is in a "fully" open position, the anvil trunnions 7822 may generally be located in the bottom portion 7613B of the kidney slot 7613. The anvil 7810 can be moved to a closed position by distally advancing the distal closure tube segment 8030 in the distal direction DD so that the internal cam surface 8036 on the distal end 8035 of the distal closure tube segment 8030 rides up an anvil cam surface 7821 that is formed on the anvil mounting portion 7820 of the anvil 7810. As the internal cam surface 8036 on the distal end 8035 of the distal closure tube segment 8030 is distally advanced along the anvil cam surface 7821 on the anvil mounting portion 7820 under the horizontal closure force $F_{H4}$ (FIG. 32), the distal closure tube segment 8030 causes the body portion 7812 of the anvil 7810 to pivot and move axially relative to the surgical staple/fastener cartridge 7700 as the anvil trunnions 7822 move upwardly and distally in the kidney slots 7613. When the distal closure tube segment 8030 reaches the end of its closure stroke, the distal end 8035 of the distal closure tube segment 8030 abuts/contacts an abrupt anvil ledge 7823 and serves to position the anvil 7810 so that the forming pockets (not shown) in the underside or tissue contacting surface 7813 of the body portion 7812 are properly aligned with the staples/fasteners in the staple/fastener cartridge 7700. The anvil ledge 7823 is defined between the anvil cam surface 7821 on the anvil mounting portion 7820 and the anvil body portion 7812. Stated another way, in this arrangement, the anvil cam surface 7821 does not extend to an outermost surface 7817 of the anvil body 7812. When in that position, the anvil trunnions 7822 are located at top portions 7613T of the kidney slots 7613. $M_{A4}$ represents the moment arm from the anvil pivot axis $PA_4$ (coincident with the center of the anvil trunnions 7822) when the trunnions 7822 are located in the top portions 7613T of the kidney slots 7613 as shown. In one example, the moment arm $M_{A4}$ may be approximately 0.184 inches, for example. $M_{A4} \times F_{H4} =$ a closure moment $C_{M4}$ that is applied to the anvil mounting portion 7820.

In the example depicted in FIGS. 31 and 32, the anvil body 7812 is formed with two tissue stop formations or tissue locator formations 7830 that extend downwardly from each lateral side of the anvil body 7812 (only one tissue stop formation 7830 may be seen in FIGS. 31 and 32). When the anvil 7810 is opened to receive the target tissue between the underside of the anvil and the cartridge deck surface, the downwardly extending tissue stop formations 7830 serve to prevent the target tissue from extending proximally past the proximal most staples/fasteners in the surgical staple/fastener cartridge 7700. In the embodiment depicted in FIG. 31, for example, the proximal most staple/fastener pockets 7720 are shown in phantom lines relative to the tissue stop formations 7830. As can be seen in that Figure, the tissue stop formation 7830 has a downwardly extending portion 7832 and a chamfered portion 7834. The target tissue is contacted by the portions 7832, 7834 to prevent the target tissue from extending proximally beyond the proximal most staples/fasteners that are supported in the proximal most staple/fastener pockets 7720 in the staple/fastener cartridge body 7702.

Returning again to FIG. 31, as the anvil 7810 is pivoted closed onto the target tissue (not shown) that is positioned between the underside or tissue contacting surface 7813 of the anvil body portion 7812, the tissue applies tissue forces $T_{F4}$ to the underside 7813 of the anvil body 7812 which cause the anvil 7810 to experience a tissue counter moment $C_{T4}$ that must be overcome by a closure moment $C_{M4}$ established by the closure system components. The example depicted FIG. 31 illustrates equally distributed tissue forces $T_{F4}$ on the anvil 7810 and a tissue moment arm $M_{T4}$ established by the clamped tissue (the clamped tissue is not shown in FIG. 31 for clarity purposes). As can be seen in that Figure, in that example, the tissue moment arm $M_{T4}$ is considerably longer than the closure moment arm $M_{A4}$ (i.e., $M_{T4}>M_{A4}$).

The illustrated exemplary interchangeable surgical tool assemblies 1000, 3000, 5000, 7000 comprise surgical stapling devices that employ "separate and distinct" closure and firing systems. That is, the closure system employed to close the jaws is separately actuatable from the firing system used to drive the firing member through the surgical staple/fastener cartridge to cut and fasten tissue. These separate and distinct closure and firing systems may be distinguishable from those surgical stapling instruments wherein actuation of the firing system to advance the firing member is required to move the jaws from an open position to a closed position. As will be discussed in further detail below, however, the firing members of some of the interchangeable surgical tool assemblies disclosed herein may also apply additional closure motions to the anvil as the firing member is fired (i.e., distally advanced through the surgical end effector). As can be seen from reference to FIGS. 25-32, in the illustrated examples, $M_{A2}>M_{A3}>M_{A1}>M_{A4}$. FIGS. 25, 27, 29 and 31 also illustrate the resistive forces established by the tissue during the closure process. $T_F$ represents the force generated by the tissue when the tissue is clamped between the anvil and the staple cartridge. These forces establish a "counter" moment $C_T$ that is applied to the anvil about the point/area where the distal closure tube segment is in camming contact with the anvil cam surface on the anvil mounting portion. In these illustrated examples, the tissue moment arm for each surgical instrument (tool assembly) is generally larger than the closure moment arm for that instrument. It may be appreciated from the difference between a typical tissue moment arm encountered when clamping tissue between the anvil and the surgical staple/fastener cartridge and the closure moment arm of the instrument results in the need for sufficient closure forces to be applied by the distal closure tube segment to the anvil in order to sufficiently close the anvil onto the tissue. Thus, the distal closure tube segment must be sufficiently strong and robust to handle the considerable stresses formed therein during the closure process. To establish a stress state in the distal closure tube segment that more closely resembles a "hoop stress" state instead of a "ring stress" state, the sidewalls of the distal closure tube segment may be thickened so as to contact the side walls and anvil mounting portions of the corresponding elongate channel. Such arrangement may also add strength to the overall hoop-like structure of the tube. Maximizing the thickness on the anvil side of the distal closure tube segment may also improve the strength of the tube segment (hoop) while allowing room for a large bearing or cam surface to cam the anvil downward towards the cartridge. U.S. patent application Ser. No. 15/385,911, entitled SURGICAL STAPLE/

FASTENERS WITH INDEPENDENTLY ACTUATABLE CLOSING AND FIRING SYSTEMS discloses several distal closure tube segment configurations which may be employed in the various interchangeable surgical tool assemblies disclosed herein.

The forgoing discussion and comparisons may illustrate that closure system designs that have large closure moment arms may lead to improved efficiencies of the closure system components and can reduce the amount of closure forces that are required to achieve full anvil closure onto the tissue. However, as noted above, there may be tradeoffs with other design variables when attempting to maximize the closure moment arm. For example, another desirable attribute relates to "jaw aperture". "Jaw aperture" may refer to a distance $J_A$ which is measured from the middle of a distalmost staple or fastener center along a line that is perpendicular to the corresponding distalmost staple forming pocket on the underside or tissue contact surface of the anvil body portion. FIG. 33 illustrates the jaw aperture $J_{A1}$ for the surgical end effector 1500. In the illustrated example, the distalmost staple/fastener pockets 1730 contain the distalmost staples or fasteners (not shown) therein. Each distalmost staple or fastener corresponds to a distalmost staple/fastener forming pocket 1815 (shown in phantom in FIG. 33) that is formed in the underside or tissue contacting surface 1813 of the anvil body 1812. The distance $J_{A1}$ between the distalmost staple/fastener pocket 1730 and the corresponding distalmost staple/fastener forming pocket 1815 is the "jaw aperture" for the surgical end effector 1500. In at least one embodiment, for example, $J_{A1}$ is approximately 1.207 inches. FIG. 34 illustrates the jaw aperture $J_{A2}$ for the surgical end effector 3500. In the illustrated example, the distalmost staple/fastener pockets 3730 contain the distalmost staples or fasteners (not shown) therein. Each distalmost staple or fastener corresponds to a distalmost staple/fastener forming pocket 3815 that is formed in the underside or tissue contact surface 3813 of the anvil body 3812. The distance $J_{A2}$ between the distalmost staple/fastener pocket 3730 and the corresponding distalmost staple/fastener forming pocket 3815 is the "jaw aperture" for the surgical end effector 3500. In at least one embodiment, for example, $J_{A2}$ is approximately 0.781 inches. FIG. 35 illustrates the jaw aperture $J_{A3}$ for the surgical end effector 5500. In the illustrated example, the distalmost staple/fastener pockets 5730 contain the distalmost staples/fasteners (not shown therein). Each distalmost staple/fastener corresponds to a distalmost staple/fastener forming pocket 5815 that is formed in the underside or tissue contact surface 5813 of the anvil body 5812. The distance $J_{A3}$ between the distalmost staple/fastener pocket 5730 and the corresponding distalmost staple/fastener forming pocket 5815 is the "jaw aperture" for the surgical end effector 5500. In at least one embodiment, for example, $J_{A3}$ is approximately 0.793 inches. FIG. 36 illustrates the jaw aperture $J_{A4}$ for the surgical end effector 7500. In the illustrated example, the distalmost staple/fastener pockets 7730 contain the distalmost staples or fasteners (not shown) therein. Each distalmost staple or fastener corresponds to a distalmost staple/fastener forming pocket 7815 that is formed in the underside or tissue contact surface 7813 of the anvil body 7812. The distance $J_{A4}$ between the distalmost staple/fastener pocket 7730 and the corresponding distalmost staple/fastener forming pocket 7815 is the "jaw aperture" for the surgical end effector 7500. In at least one embodiment, for example, $J_{A4}$ is approximately 0.717 inches. Thus, for these examples, $J_{A1} > J_{A3} > J_{A2} > J_{A4}$. As such, comparatively, surgical end effector 1500 has the greatest jaw aperture.

Figure 37:
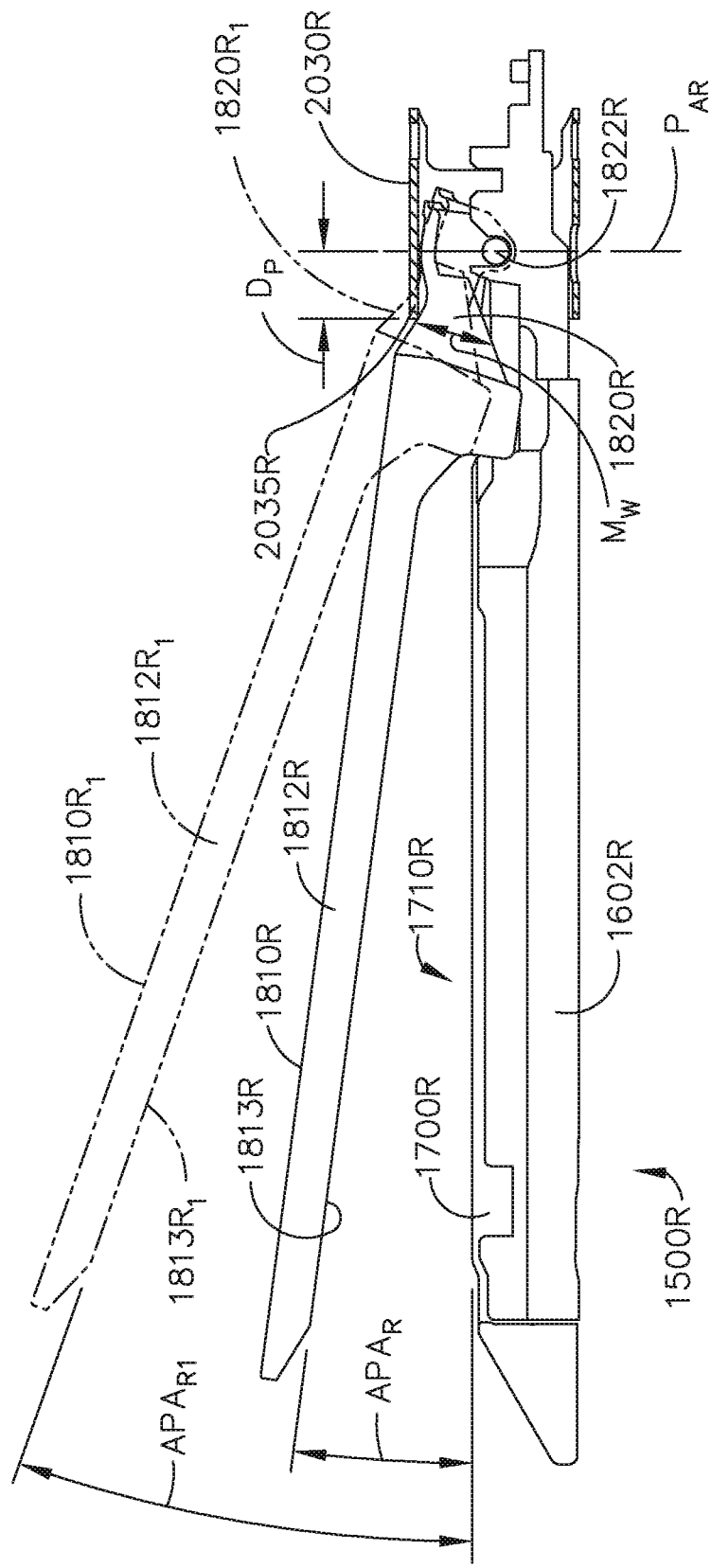
FIG. 37 is a side elevational view of a distal portion of another interchangeable surgical tool assembly with the anvil thereof shown in one open position in solid lines and another open position in phantom lines.

In those surgical end effector designs that employ separate and distinct closure and firing systems that utilize an axially movable closure ring or distal closure tube segment such as the examples described above, the interrelationships between the anvil or jaw pivot axis $P_A$ and the distal end of the distal closure tube segment as well as the robustness of the anvil mounting portion may determine the magnitude of the jaw aperture that is attainable for each specific end effector design. These interrelationships may be better appreciated from reference to FIG. 37, for example. FIG. 37 depicts a surgical end effector 1500R that employs an anvil 1810R that has an anvil mounting portion 1820R that is shown in solid lines. The anvil mounting portion 1820R includes anvil trunnions 1822R that define a reference pivot axis $P_{AR}$ about which the anvil mounting portion 1820R may pivot relative to an elongate channel 1602R. The surgical end effector 1500R also employs a distal closure tube segment 2030R that has a distal end 2035R that is configured to cammingly contact the anvil mounting portion 1820R in the various manners discussed above. A surgical staple/fastener cartridge 1700R is supported in the elongate channel 1602R and has a cartridge deck surface or tissue contact surface 1710R. FIG. 37 depicts a distance $D_P$ between the reference pivot axis $P_{AR}$ and the distal end 2035R of the distal closure tube segment 2030R. FIG. 37 illustrates the anvil 1810R in solid lines. The anvil body 1812R is in its maximum open position when the distal closure tube segment 2030R is in its proximal most starting position relative to the anvil mounting portion 1820R. The maximum aperture angle $APA_R$ for that configuration is approximately ten degrees, for example. This aperture angle $APA_R$ is typical for many end effector arrangements. In another end effector arrangement, the aperture angle is 12.25 degrees. In one arrangement, for example, $D_P$ may be approximately 0.200 inches. To attain a larger aperture angle $APA_{R1}$ of, for example, twenty-two degrees, if the relationship between the distal end 2035R of the distal closure tube segment 2030R and the reference pivot axis $P_{AR}$ remains unchanged, then a cross-sectional width $M_w$ of an anvil mounting portion 1820R$_1$ must undesirably be decreased. The anvil 1810R$_1$ is illustrated in phantom lines. As can be seen in that Figure, an abrupt ledge must be formed between the anvil body 1812R$_1$ and the anvil mounting portion 1820R$_1$ such that the cross-sectional width thereof is reduced. The aperture angle $APA_{R1}$ is measured from the underside 1813R$_1$ of the anvil body 1812R$_1$ and the deck surface 1710R of the surgical staple/fastener cartridge 1700R. Such reduction in robustness of the anvil mounting portion of the anvil may lead to reduced anvil reliability and is less desirable than anvils that have anvil mounting portions with larger cross-sectional profiles.

Referring now to FIGS. 38 and 39, increases in jaw aperture (or aperture angle) may be more easily achieved as the pivot or pivot axis PA moves closer to the distal end of the starting or proximal position of the distal closure tube segment. FIG. 38 illustrates a surgical end effector 1500' that is substantially similar to surgical end effector 1500, except for the location of the pivot axis PA' relative to the distal end 2035 of the distal closure tube segment 2030. As can be seen in that Figure, the distance between the pivot axis PA' and the distal end 2035 of the distal closure tube segment 2030 when the distal closure tube segment 2030 is in its proximalmost starting position is represented by DP' and the aperture angle is APA. Stated another way, when the distal closure tube segment 2030 is in its starting position that corresponds with the fully open position of the anvil 1810, the distal end 2035 thereof is on a reference plane RF that is perpendicular to said shaft axis SA. The distance between the pivot axis PA' and the reference plane RF' measured along a line that is perpendicular to the reference plane RF' and extends through the pivot axis PA' is DP'. In at least one arrangement, DP' is approximately 0.200 inches and the aperture angle APA may be approximately 10°.

FIG. 38 illustrates the aperture angle APA of a surgical end effector 1500' with a distance DP' between the reference pivot axis PA' and the distal end 2035 of the distal closure tube segment 2030. Turning next to FIG. 39, as can be seen in that Figure, the distance DP between the pivot axis PA and the reference plane RF upon which the distal end 2035 of the distal closure tube segment 2030 is located when the distal closure tube segment 2030 is in its proximal most starting position is less than distance DP' and the aperture angle $APA_1$ is greater than APA. For example, in at least one embodiment, the distance DP is approximately 0.090 inches and the aperture angle $APA_1$ is approximately twenty two degrees. Thus, by moving the pivot axis PA closer to the distal end of the distal closure tube segment when the distal closure tube segment is in its proximal most starting position, the jaw aperture may be significantly increased without the need to reduce the cross-sectional width of the anvil mounting position. This may represent a significant improvement over other surgical end effector arrangements. In various circumstances, the center of the anvil trunnions 1822 may ideally be located between 0.010-0.060 inches from the distal end 2035 of the distal closure tube segment 2030 when the distal closure tube segment is in the starting (proximal most) position. A maximum distance for large jaw aperture applications may be, for example, 0.090 inches. As can also be seen in FIG. 39, when the anvil 1810 is in its fully open position as shown, the downwardly extending portion 1832 of the tissue stop 1830 generally stops at the staple cartridge deck surface 1710 to prevent any proximal movement of the target tissue during clamping.

Figure 40:
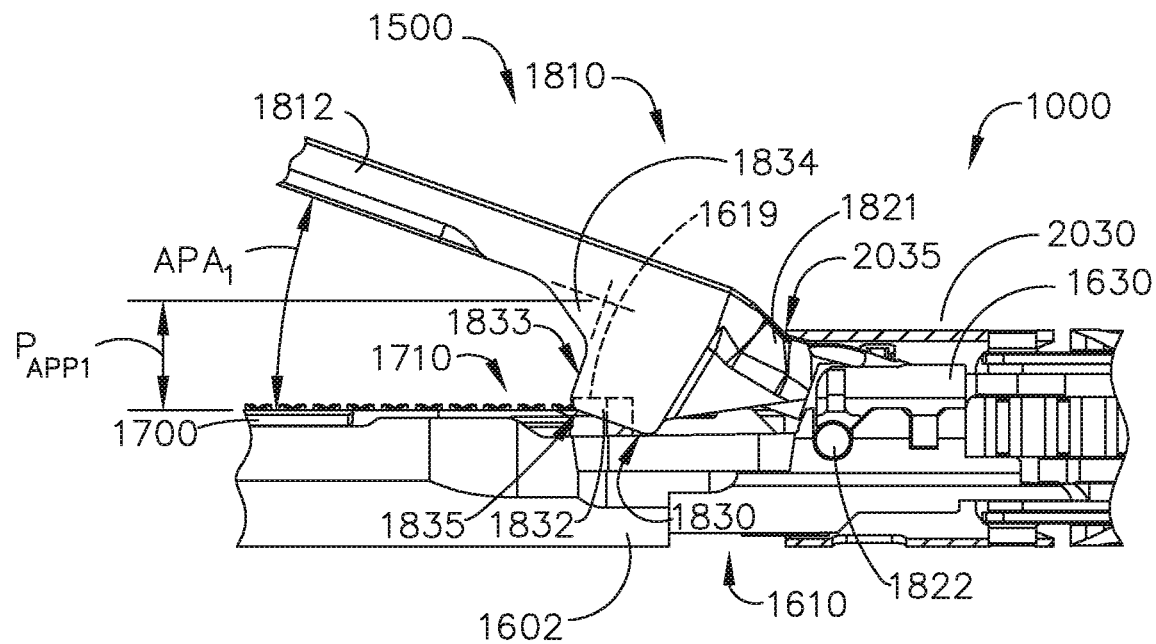
FIG. 40 is an enlarged side elevational view of the anvil mounting portion and elongate channel of the interchangeable surgical tool assembly of FIG. 39.
Figure 41:
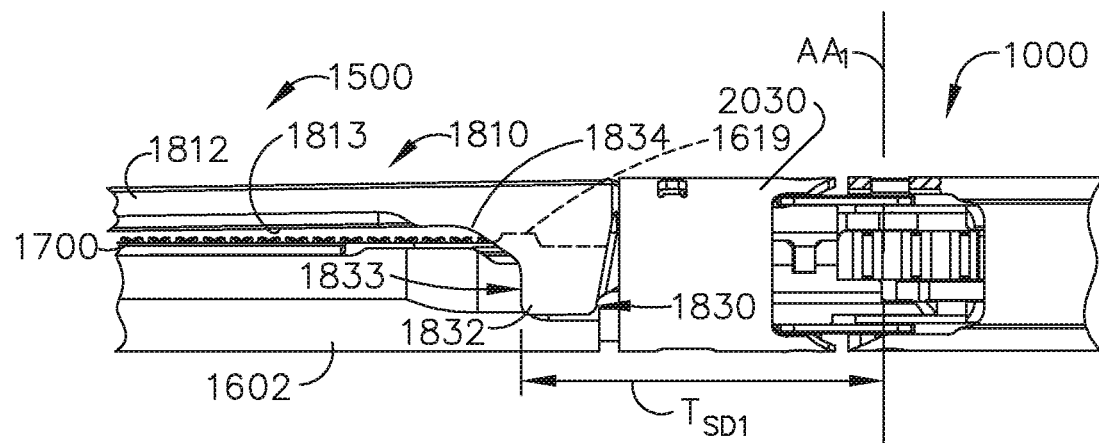
FIG. 41 is a side elevational view of a distal portion of the interchangeable surgical tool assembly of FIGS. 39 and 40 with the anvil thereof in a fully closed position.

FIGS. 40 and 41 illustrate tissue stop or tissue locator arrangements 1830 employed on one form of the surgical end effector 1500. As indicated above, the tissue stops 1830 comprise a downwardly extending portion 1832 and a chamfered portion 1834. The downwardly extending portion 1832 comprises a distal edge 1833 that terminates in a distal corner portion 1835. FIG. 40 illustrates the anvil 1810 in its fully open position. The underside 1813 of the anvil body 1812 is positioned at an aperture angle $APA_1$. In at least one arrangement, the aperture angle $APA_1$ is greater than 12.25 degrees (12.25°) and may be as large as eighteen degrees (18°). When in that fully open position, the surgical end effector 1500 may further have a proximal aperture $P_{APP1}$ that in at least one arrangement may be approximately 0.254 inches, for example. The proximal aperture defines how much tissue can be positioned between the proximal portions of the jaws (anvil and cartridge). A large proximal aperture may be most advantageous, for example, when cutting and fastening lung tissue which may be partially inflated when being introduced between the anvil and cartridge. The proximal aperture may be measured from the center of the proximal most fastener pocket or pocket pair directly vertical to the underside or tissue contact surface on the anvil body.

When the anvil 1810 is in the fully opened position as shown in FIG. 40, the distal corner 1835 does not extend above the cartridge deck surface 1710 so as to prevent tissue from moving proximal to the proximal most staples in the proximal most staple pockets 1720. In at least one embodiment, an upstanding channel stop portion 1619 may extend upwardly from the side walls of the elongate channel 1602 so as to coincide with each corresponding tissue stop 1830 to further prevent any proximal infiltration of tissue between the tissue stop 1830 and the channel stop portion 1619. FIG. 41 illustrates the anvil 1810 in a fully closed position. When in that position, the distal edges 1833 of the tissue stops 1830 are approximately aligned or coincident with the locations of the proximal most staples/fasteners in the staple/fastener cartridge 1700. The distance from the articulation axis $AA_1$ to the proximal most staples/fasteners is identified as $T_{SD1}$. In one arrangement, $T_{SD1}$ is approximately 1.044 inches, for example. When the anvil 1810 is fully closed, the tissue stops 1830 may be sized and shaped relative to the proximal end portion 1610 of the elongate channel 1602 so as to facilitate easy insertion through a correspondingly sized standard trocar. In at least one example, the tissue stops 1830 of the anvil 1810 are sized and shaped relative to the elongate channel 1602 so as to permit the surgical end effector 1500 to be inserted through a conventional 12 mm trocar.

Figure 42:
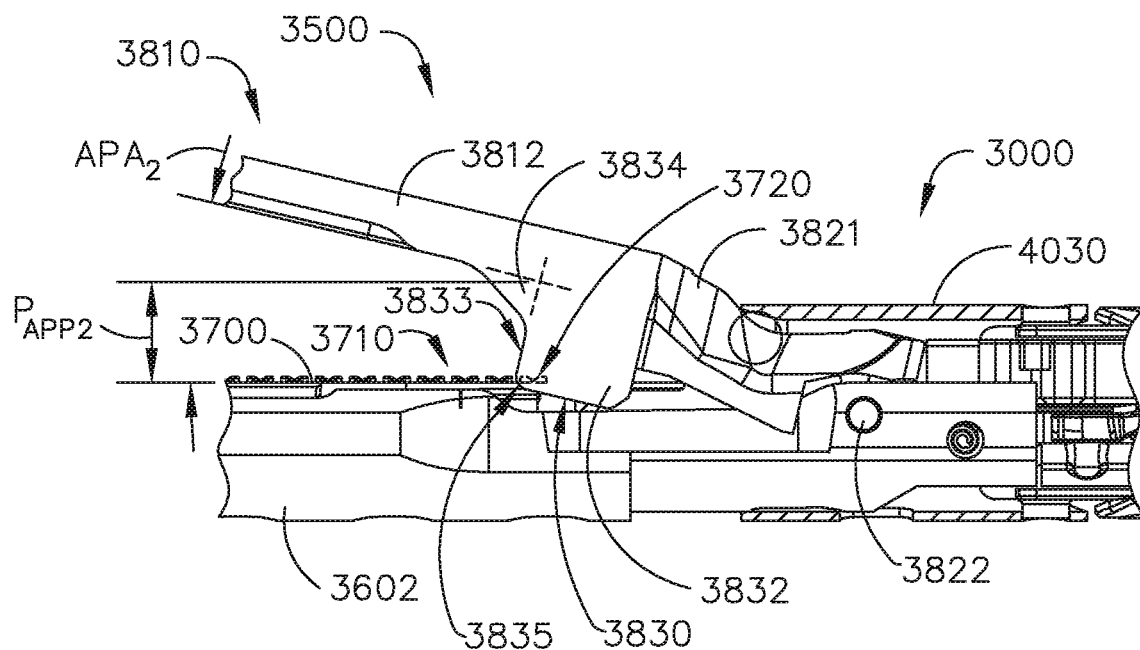
FIG. 42 is an enlarged side elevational view of the anvil mounting portion and elongate channel of the interchangeable surgical tool assembly of FIG. 16 with the anvil thereof in a fully open position.
Figure 43:
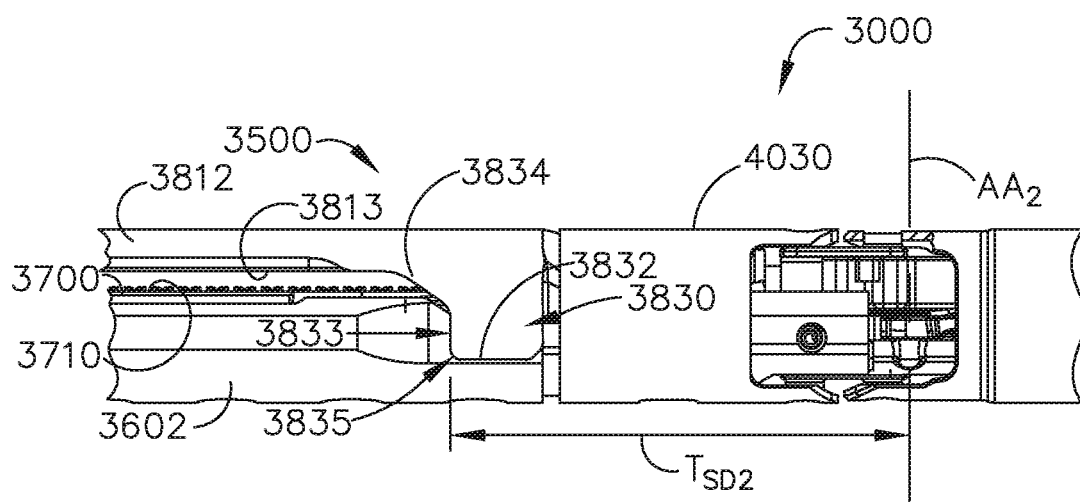
FIG. 43 is a side elevational view of a distal portion of the interchangeable surgical tool assembly of FIG. 42 with the anvil thereof in a fully closed position.

FIGS. 42 and 43 illustrate tissue stop arrangements 3830 employed on one form of the surgical end effector 3500. As indicated above, the tissue stops 3830 comprise a downwardly extending portion 3832 and a chamfered portion 3834. The downwardly extending portion 3832 comprises a distal edge 3833 that terminates in a distal corner portion 3835. FIG. 42 illustrates the anvil 3810 in its fully open position. The underside 3813 of the anvil body 3812 is positioned at an aperture angle $APA_2$. In at least one arrangement, the aperture angle $APA_2$ is approximately thirteen and one half degrees (13.5°). When in that fully open position, the surgical end effector 3500 may further have a proximal aperture $P_{APP2}$ that in at least one arrangement may be approximately 0.242 inches, for example. When the anvil 3810 is in the fully opened position as shown in FIG. 42, the distal corner 3835 does not extend above the cartridge deck surface 3710 so as to prevent tissue from moving proximal to the proximal most staples/fasteners in the proximal most staple/fastener pockets 3720. FIG. 43 illustrates the anvil 3810 in a fully closed position. When in that position, the distal edges 3833 of the tissue stops 3830 are approximately aligned or coincident with the locations of the proximal most staples/fasteners in the staple/fastener cartridge 3700. The distance from the articulation axis $AA_2$ to the proximal most staples/fasteners is identified as $T_{SD2}$. In one arrangement, $T_{SD2}$ is approximately 1.318 inches, for example.

Figure 44:
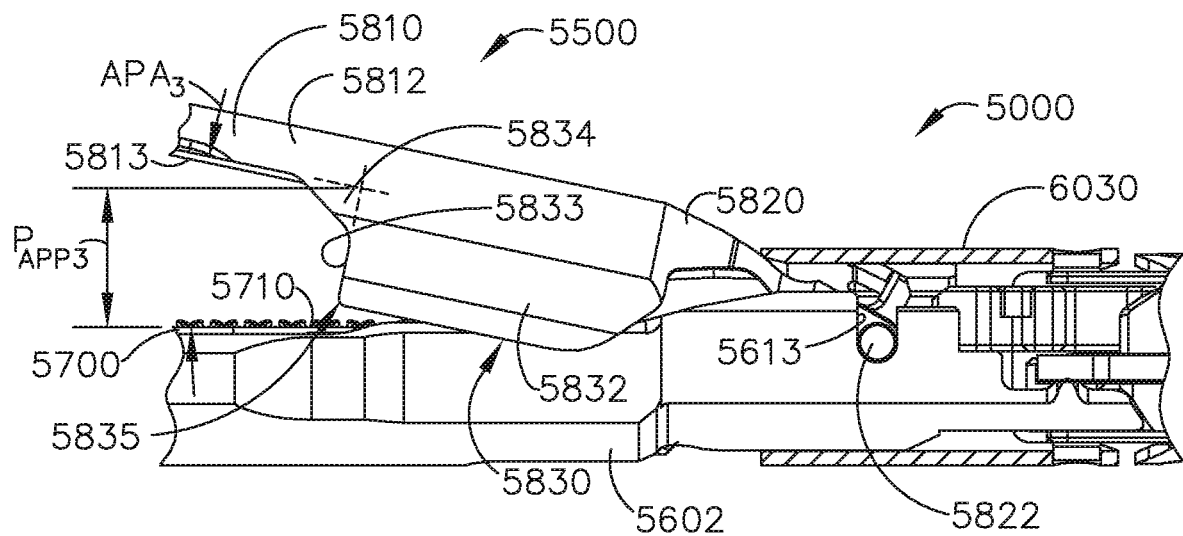
FIG. 44 is an enlarged side elevational view of the anvil mounting portion and elongate channel of the interchangeable surgical tool assembly of FIG. 19 with the anvil thereof in a fully open position.
Figure 45:
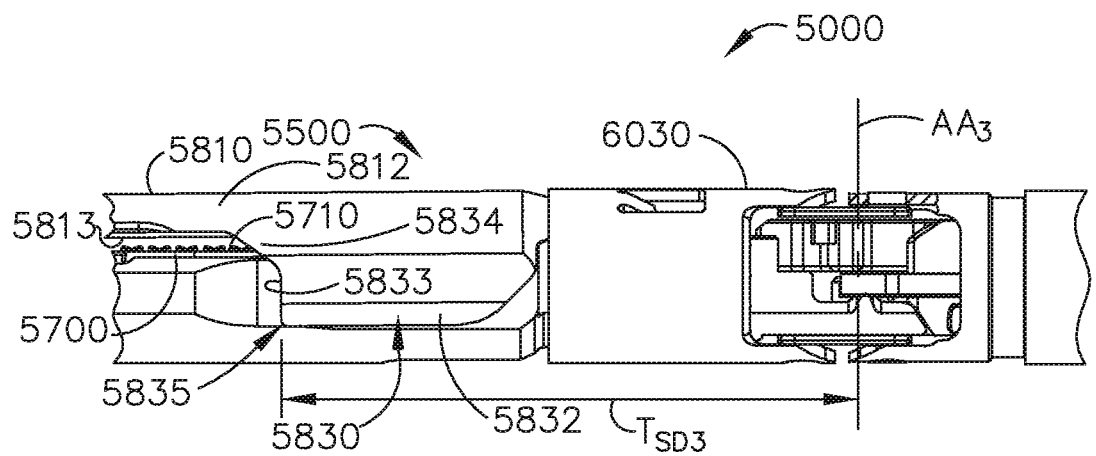
FIG. 45 is a side elevational view of a distal portion of the interchangeable surgical tool assembly of FIG. 44 with the anvil thereof in a fully closed position.

FIGS. 44 and 45 illustrate tissue stop arrangements 5830 employed on one form of the surgical end effector 5500. As indicated above, the tissue stops 5830 comprise a downwardly extending portion 5832 and a chamfered portion 5834. The downwardly extending portion 5832 comprises a distal edge 5833 that terminates in a distal corner portion 5835. FIG. 44 illustrates the anvil 5810 in its fully open position. The underside 5813 of the anvil body 5812 is positioned at an aperture angle $APA_3$. In at least one arrangement, the aperture angle $APA_3$ is approximately eight degrees (8°). When in that fully open position, the surgical end effector 5500 may further have a proximal aperture $P_{APP3}$ that in at least one arrangement may be approximately 0.226 inches, for example. When the anvil 5810 is in the fully opened position as shown in FIG. 44, the distal corner 3835 extends slightly above the cartridge deck surface 5710. FIG. 45 illustrates the anvil 5810 in a fully closed position. When in that position, the distal edges 5833 of the tissue stops 5830 are approximately aligned or coincident with the locations of the proximal most staples/fasteners in the staple/fastener cartridge 5700. The distance from the articulation axis $AA_3$ to the proximal most staples/fasteners is identified as $T_{SD3}$. In one arrangement, $T_{SD3}$ is approximately 1.664 inches, for example.

Figure 46:
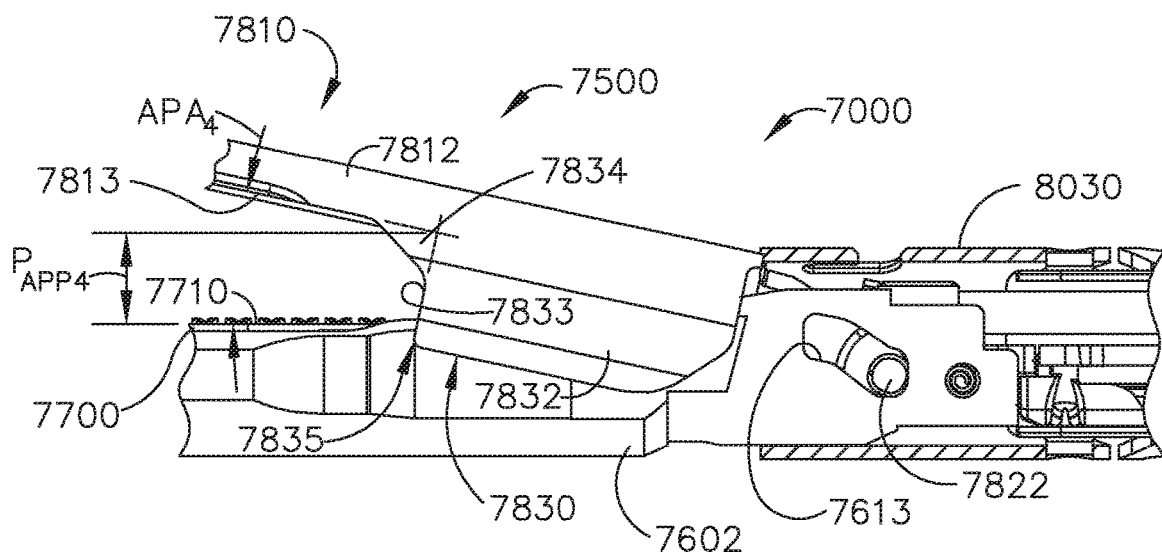
FIG. 46 is an enlarged side elevational view of the anvil mounting portion and elongate channel of the interchangeable surgical tool assembly of FIG. 22 with the anvil thereof in a fully open position.
Figure 47:
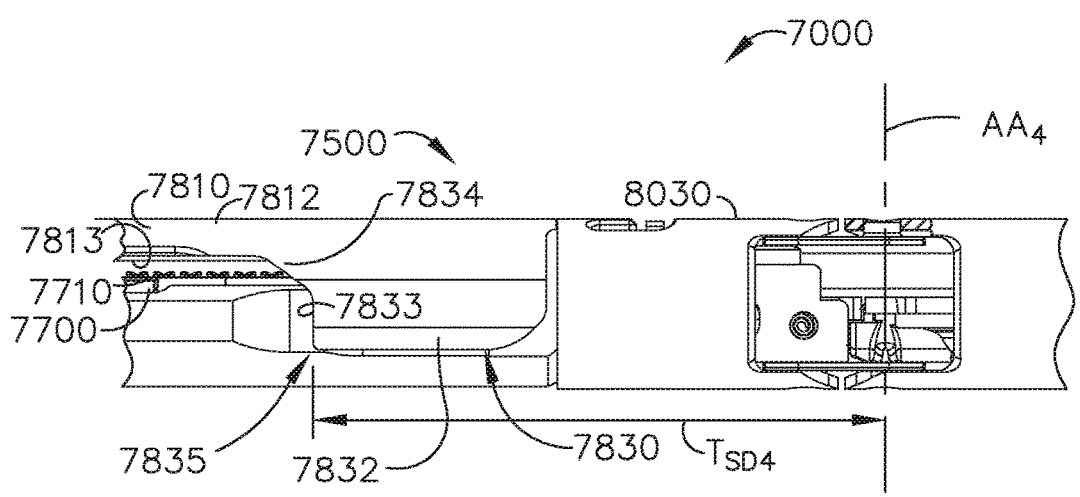
FIG. 47 is a side elevational view of a distal portion of the interchangeable surgical tool assembly of FIG. 46 with the anvil thereof in a fully closed position.

FIGS. 46 and 47 illustrate tissue stop arrangements 7830 employed on one form of the surgical end effector 7500. As indicated above, the tissue stops 7830 comprise a downwardly extending portion 7832 and a chamfered portion 7834. The downwardly extending portion 7832 comprises a distal edge 7833 that terminates in a distal corner portion 7835. FIG. 46 illustrates the anvil 7810 in its fully open position. The underside 7813 of the anvil body portion 7812 is positioned at an aperture angle $APA_4$. In at least one arrangement, the aperture angle $APA_4$ is approximately ten degrees (10°). When in that fully open position, the surgical end effector 7500 may further have a proximal aperture $P_{APP4}$ that in at least one arrangement may be approximately 0.188 inches, for example. When the anvil 7810 is in the fully opened position as shown in FIG. 46, the distal corner portion 7835 extends slightly below the cartridge deck surface 7710 so as to prevent tissue from getting proximal to the proximal most staples/fasteners in the proximal most staple pockets 7720. FIG. 47 illustrates the anvil 7810 in a fully closed position. When in that position, the distal edges 7833 of the tissue stops 7830 is approximately aligned or coincident with the locations of the proximal most staples/fasteners in the staple/fastener cartridge 7700. The distance from the articulation axis $AA_4$ to the proximal most staples/fasteners is identified as $T_{SD4}$. In one arrangement, $T_{SD4}$ is approximately 1.686 inches, for example.

Figure 51:
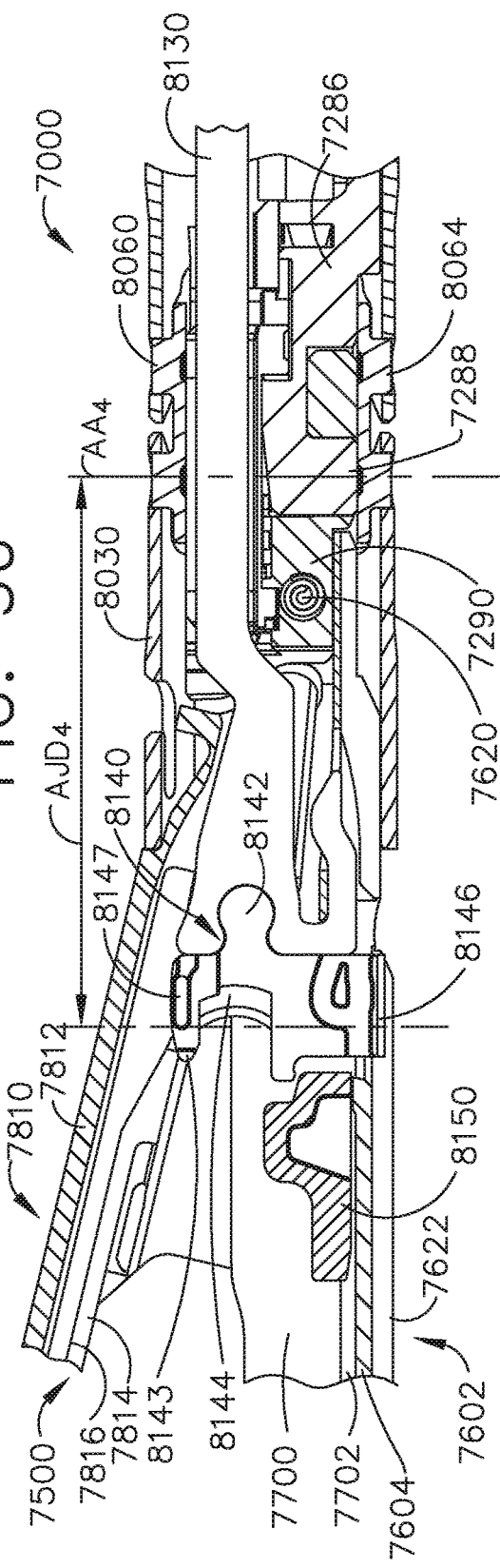
FIG. 51 is a partial cross-sectional view of the anvil mounting portion and elongate channel of the interchangeable surgical tool assembly of FIG. 22 with the anvil in a fully open position.

In various circumstances, the relationships of the firing member to the articulation axis AA as well as to the jaw pivot axis PA about which the anvil pivots may bear upon the length of the articulation joint arrangement. Of course, longer articulation joint arrangements may detrimentally affect the end effector's maneuverability within tight spaces and also limit the magnitude of the jaw aperture that may ultimately be obtained by the end effector. FIG. 48 illustrates the surgical end effector 1500 in a fully open position. That is, the anvil 1810 has been pivoted to its fully open position and the firing member 2140 is in its home or starting position. The distance between the distal end of each of the anvil engagement features 2147 and the articulation axis $AA_1$ is represented by $AJD_1$. In at least one example, $AJD_1$ is approximately 0.517 inches. By way of comparison and turning to FIG. 49, the distance $AJD_2$ from the distal end of each of the anvil engagement features 4147 and the articulation axis $AA_2$ is, in at least one example, is approximately 0.744 inches. Referring to FIG. 50, the distance $AJD_3$ from the distal end of each of the anvil engagement features 6147 and the articulation axis $AA_3$ is, in at least one example, is approximately 1.045 inches. Turning to FIG. 51, the distance $AJD_4$ from the distal end of each of the anvil engagement features 8147 and the articulation axis $AA_4$ is, in at least one example, is approximately 1.096 inches. Thus, as can be seen from this comparison, the articulation joint arrangement (as measured by distances $AJD_1$, $AJD_2$, $AJD_3$, $AJD_4$) of the surgical end effector 1500 is more compact and thus may be more maneuverable than the surgical end effectors 3500, 5500 and 7500 in at least some surgical applications.

Another factor that may affect the length of the joint arrangement relates to the location of the firing member relative to the anvil pivot axis PA about which the anvil pivots. For example, FIG. 52 illustrates the anvil 1810 of surgical end effector 1500 in its fully open position. When in that position, the firing member 2140 is in its parked or "starting position". As can be seen in that Figure, one useful metric for comparing the "compactness" of the articulation joint arrangement is the proximal tab distance $TD_1$ between the proximal end 2149 of each of the top anvil engagement features 2147 and the anvil pivot axis $PA_1$. In at least one preferred arrangement, the proximal tab distance $TD_1$ is approximately greater than thirty-five percent (35%) of the overall length $TL_1$ of each of the anvil engagement features 2147 when the anvil 1810 is in a fully open position and the firing member 2140 is in its proximal most or starting position. Stated another way, when the anvil 1810 and the firing member 2140 are in the above described positions, at least 35% of each of the anvil engagement features 2147 extends proximally past the anvil pivot axis $PA_1$. FIG. 53 illustrates the end effector 1500 with the anvil 1810 in the closed position and the firing member 2140 in its proximal most or starting position. As can be seen in that Figure, at least 35% of each of the anvil engagement features 2147 extends proximally past the anvil pivot axis $PA_1$.

Figure 54:
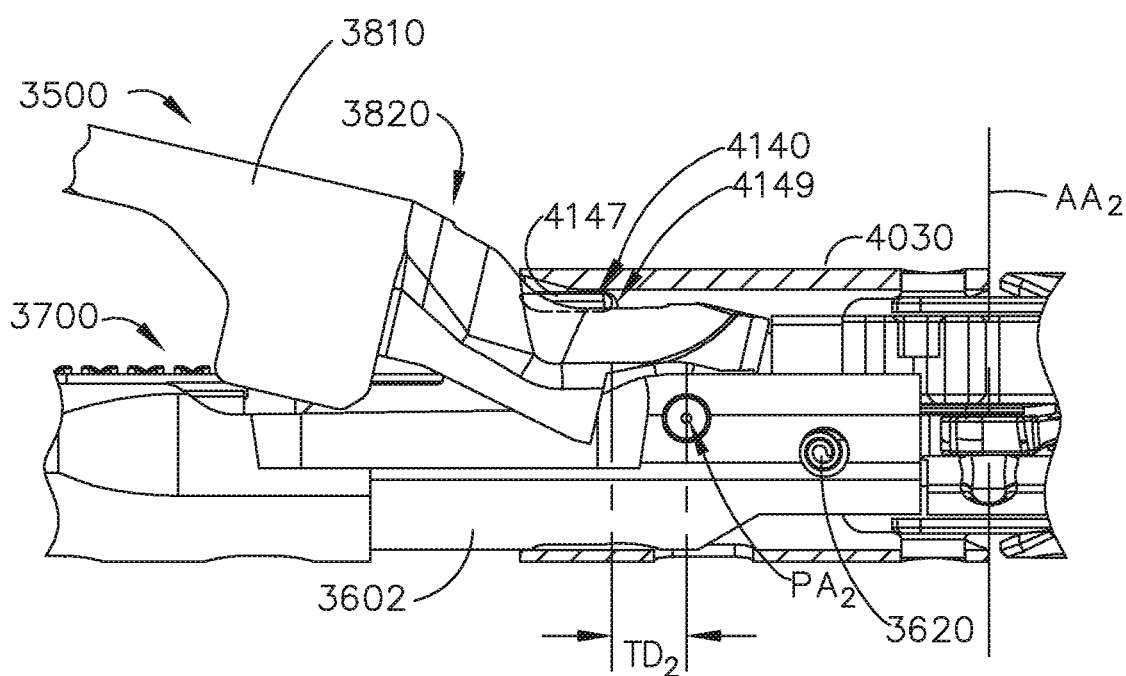
FIG. 54 is another partial cross-sectional view of a portion of the interchangeable surgical tool assembly of FIG. 16 wherein the anvil is in a fully open position.
Figure 55:
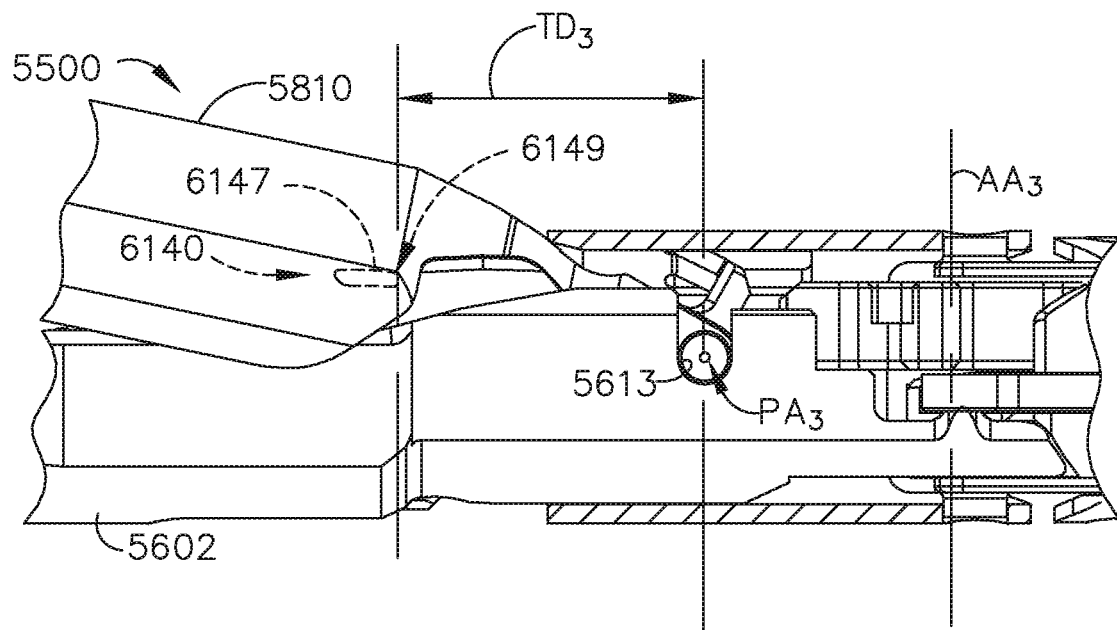
FIG. 55 is another partial cross-sectional view of a portion of the interchangeable surgical tool assembly of FIG. 19 wherein the anvil is in a fully open position.
Figure 56:
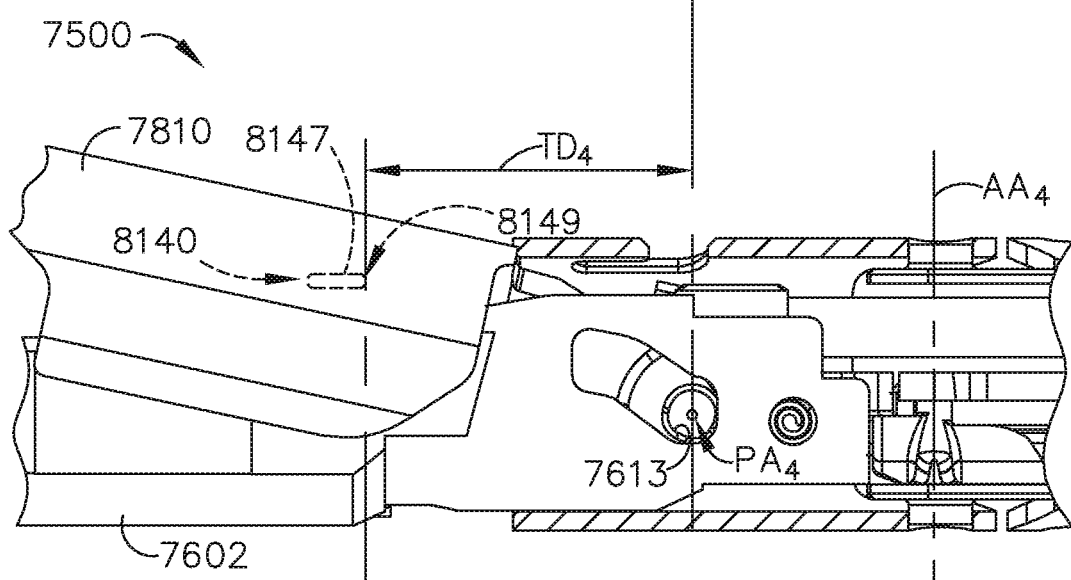
FIG. 56 is another partial cross-sectional view of a portion of the interchangeable surgical tool assembly of FIG. 22 wherein the anvil is in a fully open position.

FIG. 54 illustrates the position of the firing member 4140 of the surgical end effector 3500 when the anvil 3810 is in its fully open position and the firing member 4140 is in its proximal most or starting position. As can be seen in that Figure, each of the anvil engagement features 4147 are completely distal to the anvil pivot axis $PA_2$ thereby resulting in a longer articulation joint arrangement. Thus, the distance $TD_2$, is the distal distance between the proximal ends 4149 of the anvil engagement features 4147 and the anvil pivot axis $PA_2$. FIG. 55 illustrates the position of the firing member 6140 of the surgical end effector 5500 when the anvil 5810 is in its fully open position and the firing member 6140 is in its proximal most or starting position. As can be seen in that Figure, each of the anvil engagement features 6147 are completely distal to the anvil pivot axis $PA_3$ thereby resulting in a longer articulation joint arrangement. Thus, the distance $TD_3$, is the distal distance between the proximal ends 6149 of the anvil engagement features 6147 and the anvil pivot axis $PA_3$. FIG. 56 illustrates the position of the firing member 8140 of the surgical end effector 7500 when the anvil 7810 is in its fully open position and the firing member 8140 is in its proximal-most or starting position. As can be seen in that Figure, each of the anvil engagement features 8147 are completely distal to the anvil pivot axis $PA_4$ thereby resulting in a longer articulation joint arrangement. Thus, the distance $TD_4$, is the distal distance between the proximal ends 8149 of the anvil engagement features 8147 and the anvil pivot axis $PA_4$. For comparison purposes, the surgical end effector 1500 is the only surgical end effector wherein a portion of the anvil engagement features on the firing member extend proximally past the anvil pivot axis when the firing member is in its proximal most or starting position. The anvil engagement features of each of the firing members of the surgical end effectors 3500, 5500 and 7500 are completely distal to their respective anvil pivot axes when the firing members are in their proximal most or starting position. Taking this comparison further, for example, the surgical end effector 1500 is the only surgical end effector wherein at least thirty-five percent (35%) of the anvil engagement features reside between the anvil pivot axis and the articulation axis when the firing member is in its starting position and the anvil is fully opened. Similar comparisons may be drawn from comparing the same distances between the location of the lower channel engagement features on the firing member to the jaw pivot axis when the firing member is in its proximal most starting position.

Another metric that may be used to assess the compactness of the articulation joint arrangement may comprise comparing the ratio between the distance from the articulation axis to the distal end of the anvil engagement features on the firing member (distances $AJD_1$, $AJD_2$, $AJD_3$, $AJD_4$-FIGS. 48-51) relative to the distance from the articulation axis to the distal edge of the tissue stops or the proximal most staple/fastener (distances $TSD_1$, $TSD_2$, $TSD_3$, $TSD_4$-FIGS. 41, 43, 45, 47) for each end effector. For example, in a preferred arrangement, AJD/TSD<0.500. The ratio of AJD/TSD may be referred to herein as the "compactness ratio" of that particular surgical end effector. In one arrangement, for example, for end effector 1500, $AJD_1/TSD_1$=0.517 inches/1.044 inches=0.495. In one illustrated example for end effector 3500, $AJD_2/TSD_2$=0.744 inches/1.318 inches=0.564. In one illustrated example for end effector 5500, $AJD_3/TSD_3$=1.045 inches/1.664 inches=0.628. In one illustrated arrangement, $AJD_4/TSD_4$=1.096 inches/1.686 inches=0.650. Thus, in at least one preferred arrangement wherein the articulation joint arrangement is the most compact, has the largest jaw aperture and is the most maneuverable, the ratio between the distance from the articulation axis to the proximal end of the anvil engagement features on the firing member and the distance from the articulation axis to the distal edge of the tissue stops or the proximal most staple/fastener is approximately less than 0.500.

Figure 57:
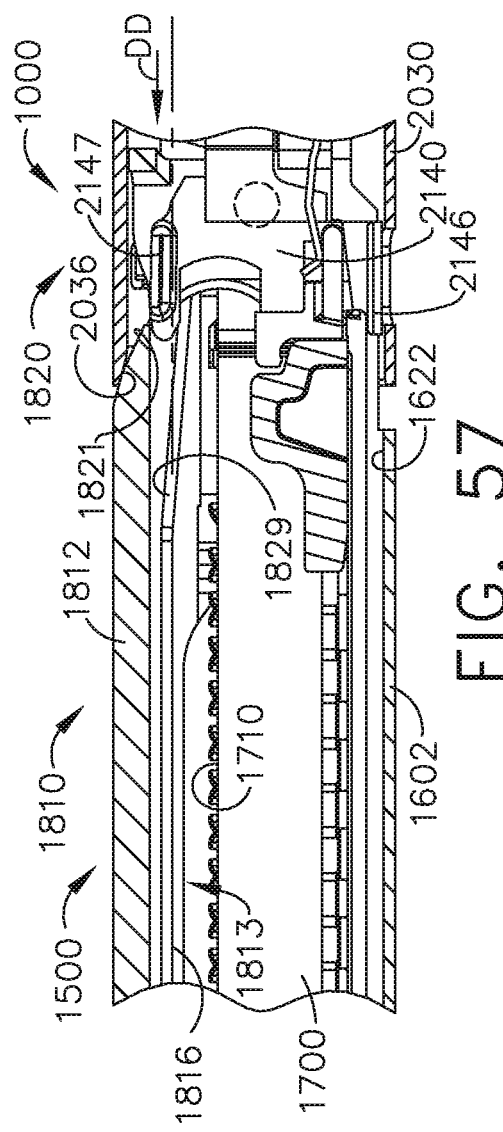
FIG. 57 is another partial cross-sectional view of a portion of the interchangeable surgical tool assembly of FIG. 3 wherein the firing member thereof is in a starting position.
Figure 58:
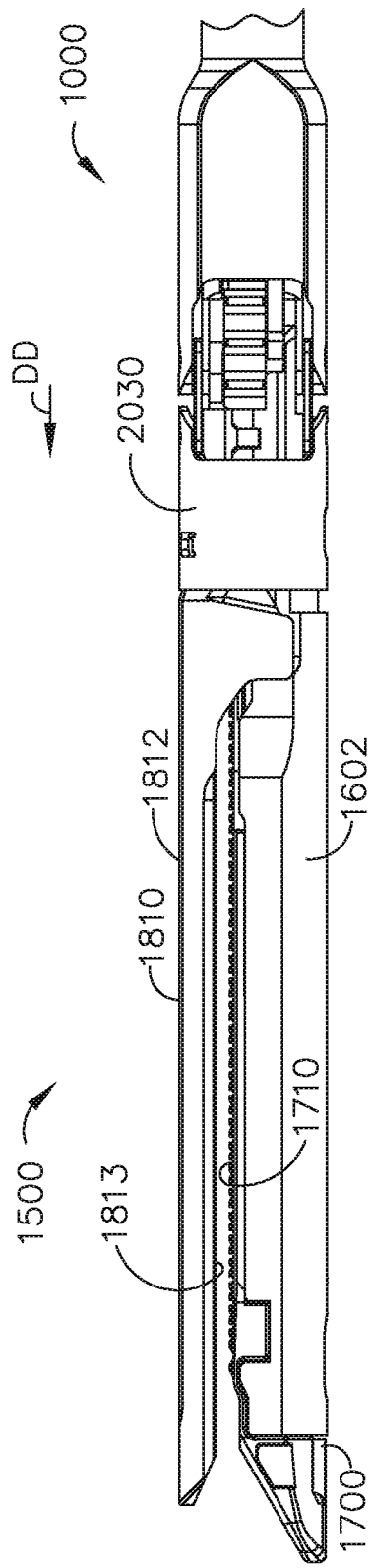
FIG. 58 is a side elevational view of the surgical end effector of FIG. 57 with the anvil in a fully closed position.
Figure 59:
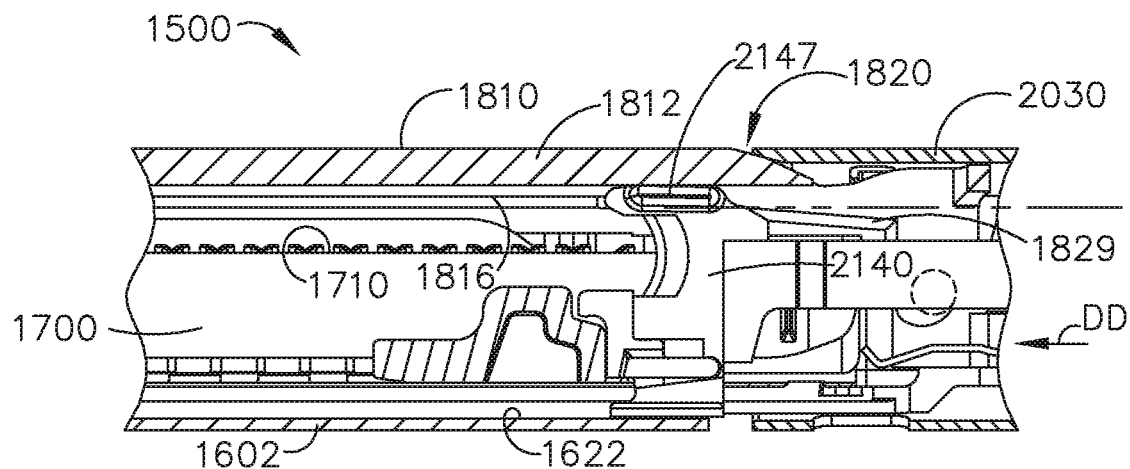
FIG. 59 is another partial cross-sectional view of the portion of the surgical end effector of FIGS. 57 and 58 wherein the firing member is in initial engagement with the anvil thereof.
Figure 61:
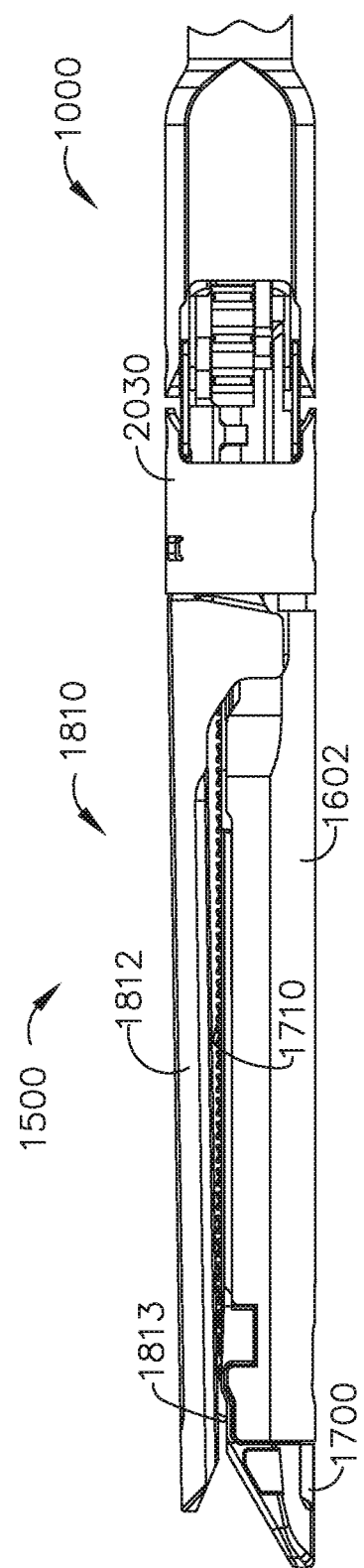
FIG. 61 is another side elevational view of the surgical end effector of FIGS. 57-60 with the anvil in an over closed position.

FIGS. 57-61 illustrate a progressive closure arrangement for moving the anvil 1810 of the surgical end effector 1500 from a fully open position to a closed position and then to an over closed position. FIGS. 57 and 58 illustrate the anvil 1810 in a closed position. In both of those Figures, the distal closure tube segment 2030 has been advanced in the distal direction DD to its fully closed position. As was discussed above, the interaction between an internal cam surface 2036 on the distal closure tube segment 2030 and an anvil cam surface 1821 on the anvil mounting portion 1820 causes the anvil 1810 to pivot to the closed position. As can be seen in FIG. 58, the staple forming underside or tissue contacting surface 1813 of the anvil body 1812 may be relatively parallel and spaced relative to the cartridge deck surface 1710 of the surgical staple/fastener cartridge. When in that initial closed position, the firing member 2140 is in its starting position as can be seen in FIG. 57. When in that position, the anvil engagement features 2147 of the firing member 2140 have not engaged the anvil 1810 but are in substantial horizontal alignment with the ledges 1816 formed in the anvil 1810. In at least one arrangement, a ramp segment 1829 is formed proximal to each of the horizontal anvil ledges 1816. FIG. 59 illustrates the position of the firing member 2140 after it has been distally advanced to a point wherein the anvil engagement features 2147 have initially engaged the horizontal anvil ledges 1816 on the anvil 1810 and FIG. 61 illustrates the position of the firing member 2140 and the anvil 1810 such that the anvil engagement features are in full engagement with the anvil ledges 1816 to apply an "overclosure" force to the anvil 1810 as the firing member 2140 continues to be distally advanced. In at least one arrangement as illustrated in FIG. 61, for example, when the anvil 1810 is in the over closed position (with no tissue being clamped between the anvil and the cartridge), the distal portion of the anvil 1810 will contact with the cartridge deck surface 1710. As a result of such configuration, the force required to distally advance the firing member from its starting position to its ending position within the end effector may generally be less than other surgical end effector arrangements that do not employ such progressive closure arrangements.

Figure 62:
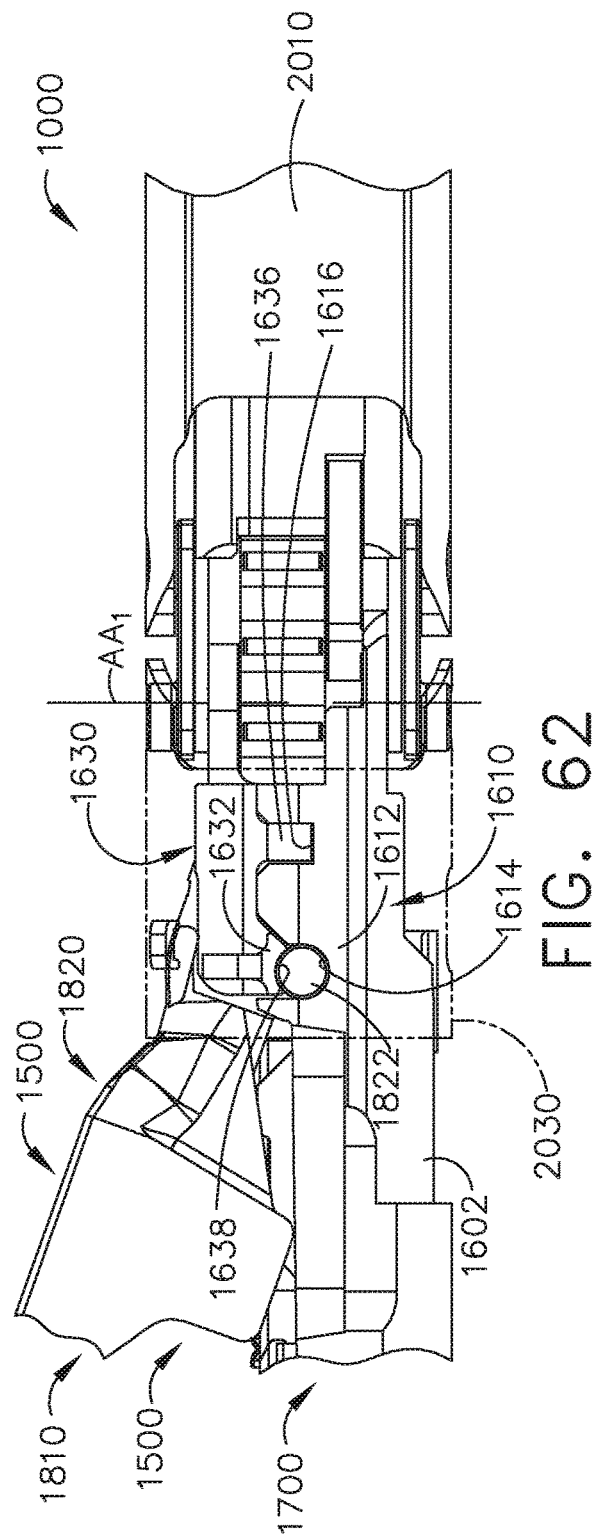
FIG. 62 is a partial side elevational view of the surgical end effector of the interchangeable surgical tool assembly of FIG. 3 in a fully open position with the distal closure tube segment shown in phantom to illustrate the anvil retaining member.
Figure 63:
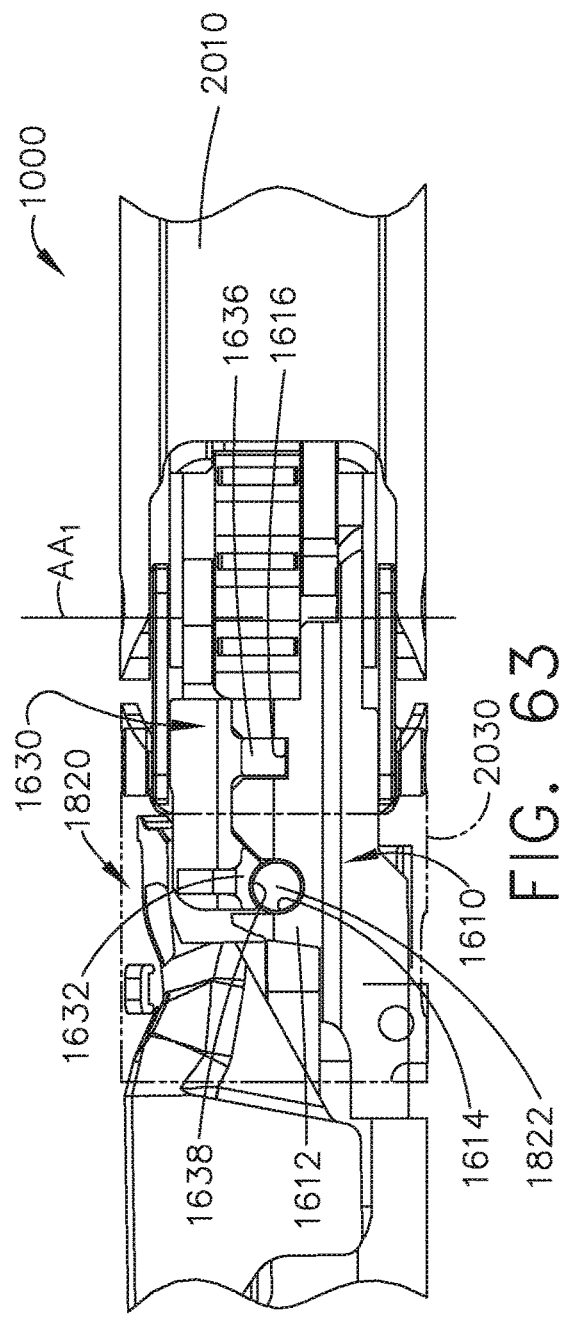
FIG. 63 is another partial side elevational view of the surgical end effector of FIG. 62 with the anvil in a fully closed position.

FIG. 62 illustrates the anvil 1810 of the surgical end effector 1500 in a fully opened position. As was discussed above, each of the anvil trunnions 1822 are received in a corresponding trunnion cradle 1614 that is formed in the upstanding walls 1612 of the proximal end portion 1610 of the elongate channel 1602. The anvil trunnions 1822 are pivotally retained in their corresponding trunnion cradle 1614 by the channel cap or anvil retainer 1630. The channel cap 1630 includes a pair of attachment lugs 1636 that are configured to be retainingly received within corresponding lug grooves or notches 1616 formed in the upstanding walls 1612 of the proximal end portion 1610 of the elongate channel 1602. During a portion of the closure stroke for the anvil 1810 on thick tissue, counterforces established during the tissue clamping process seek to push the anvil trunnions 1822 out of their respective trunnion cradles 1614. The channel cap 1630 includes a pair of slot cap portions 1632 that correspond to each trunnion cradle 1614. When the channel cap 1630 is installed onto the proximal end portion 1610 of the elongate channel 1602, each slot cap portion 1632 serves to retain the anvil trunnions 1822 within their respective trunnion cradles 1614 during the closure process. As can be seen in FIGS. 62 and 63, each slot cap portion 1632 may have an arcuate bottom portion 1638 that is configured to pivotally receive the corresponding anvil trunnion 1822. Each slot cap 1632 may have a wedge shape to completely block the open end of the trunnion cradles 1614. Such channel cap arrangement 1630 may facilitate ease of assembly of the anvil 1810 to the elongate channel 1602. Once the anvil trunnions 1822 have been placed into their respective trunnion cradles 1614, the channel cap 1630 may then be installed as shown. In at least one arrangement, the distal closure tube segment 2030 serves to retain the channel cap 1630 in position which serves to prevent the anvil trunnions 1822 from moving vertically in their respective trunnion cradles 1614 during closure as shown in FIG. 63. In another arrangement, the attachment lugs 1636 may be frictionally retained within their respective notches 1616 or otherwise be retained therein by adhesive or other fastening means.

The four interchangeable tool assemblies 1000, 3000, 5000 and 7000 employ different jaw opening configurations to facilitate moving the anvil from a closed position to a fully open position. For example, the distal closure tube segment 4030 of the interchangeable tool assembly 3000 includes positive jaw or anvil opening features 4040 that correspond to each of the sidewalls of the distal closure tube segment 4030 and protrude inwardly therefrom. The positive anvil opening features 4040 extend inwardly through corresponding openings in the transitional sidewalls and may be welded to the distal closure tube segment 4030. In this arrangement, the positive anvil opening features are axially aligned with each other and are configured to operably interface with corresponding opening ramps formed on the undersides of the anvil mounting portion 3820. When the anvil 3810 and the distal closure tube segment 4030 are in their fully closed positions, each of the positive anvil opening features 4040 is located in a cavity that is established between the anvil opening ramps and the bottom portion of the elongate channel 3602. When in that position, the positive anvil opening features 4040 do not contact the anvil mounting portion 3820 or at least may not apply any significant opening motions or forces thereto. When the distal closure tube segment 4030 is moved in the proximal direction, the anvil opening features 4040 are brought into contact with the anvil opening ramps to cause the anvil 3810 to pivot to an open position. Further details regarding the positive anvil opening features 4040 may be found in U.S. patent application Ser. No. 15/385,911, entitled SURGICAL

STAPLE/FASTENERS WITH INDEPENDENTLY ACTUATABLE CLOSING AND FIRING SYSTEMS.

With regard to the surgical end effector 5500 of tool assembly 5000, the distal closure tube segment 6030 includes two inwardly extending positive anvil opening tabs 6038 that may be punched into the wall of the distal closure tube segment 6030. See FIG. 21. In the illustrated arrangement, the tabs 6038 are axially aligned with each other and are configured to contact corresponding upstanding anvil tails 5827 formed on the anvil mounting portion 5820. When the distal closure tube segment 6030 is moved in the proximal direction, the anvil opening features 6038 are brought into contact with the anvil tails 5827 to cause the anvil 5810 to pivot to an open position.

With regard to the surgical end effector 7500 of the tool assembly 7000, a positive anvil opening motion is applied to the anvil 7810 by the distal closure tube segment 8030 when the distal closure tube segment 8030 is moved proximally. As was discussed above, an upstanding anvil tab 7824 is formed on the anvil mounting portion 7820 and extends into the horseshoe-shaped opening 8038 in the distal closure tube segment 8030. See FIG. 24. Opening 8038 defines an opening tab 8039 that is configured to operably interface with the anvil tab 7824 as the distal closure tube segment 8030 is retracted in the distal direction. Such interaction between the opening tab 8039 and the anvil tab 7824 applies an opening motion to the anvil 7810 to thereby cause the anvil 7810 to move to an open position.

Figure 64:
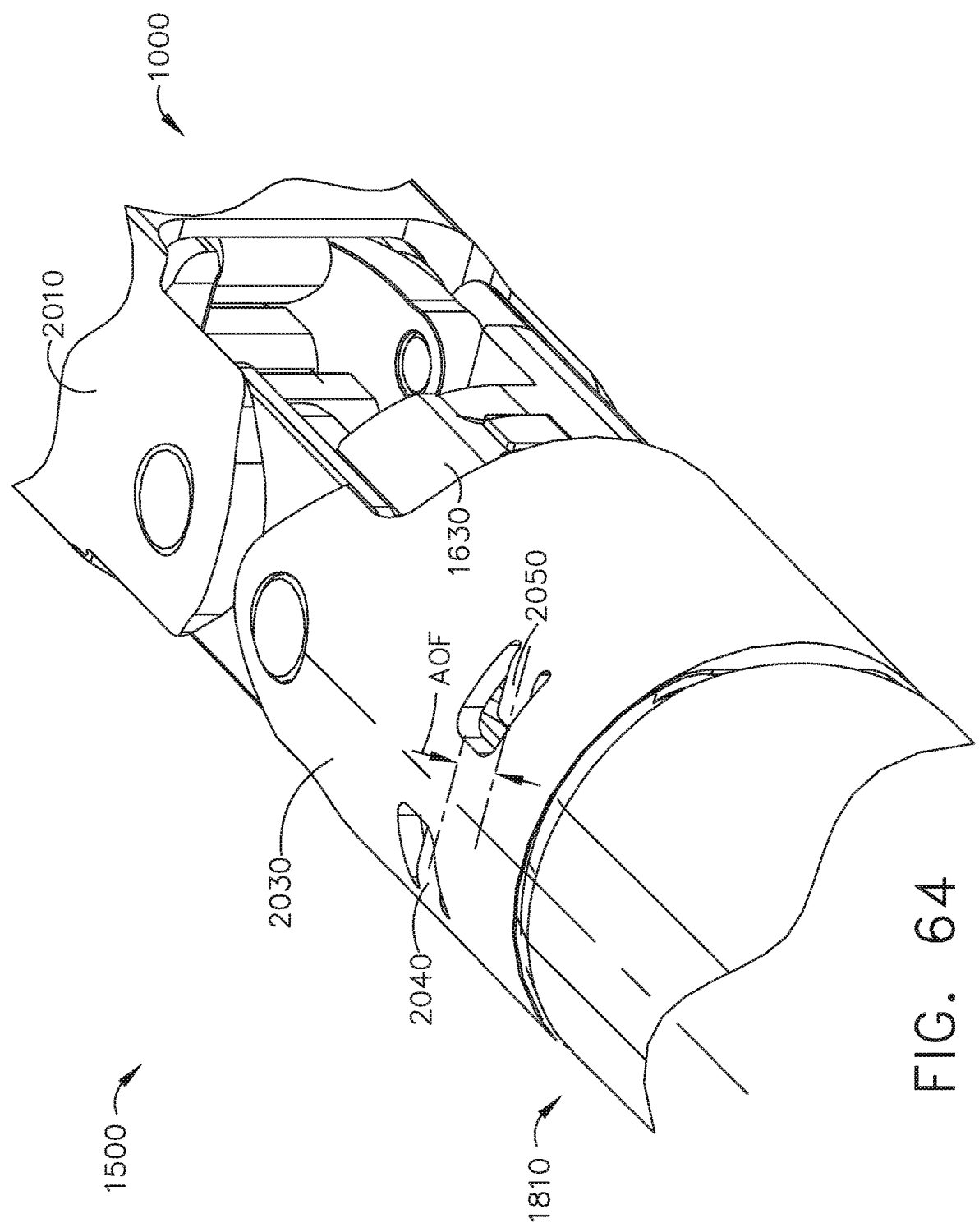
FIG. 64 is a partial perspective view of a distal closure tube segment of the interchangeable surgical tool assembly of FIG. 3 with the anvil in a fully closed position.
Figure 65:
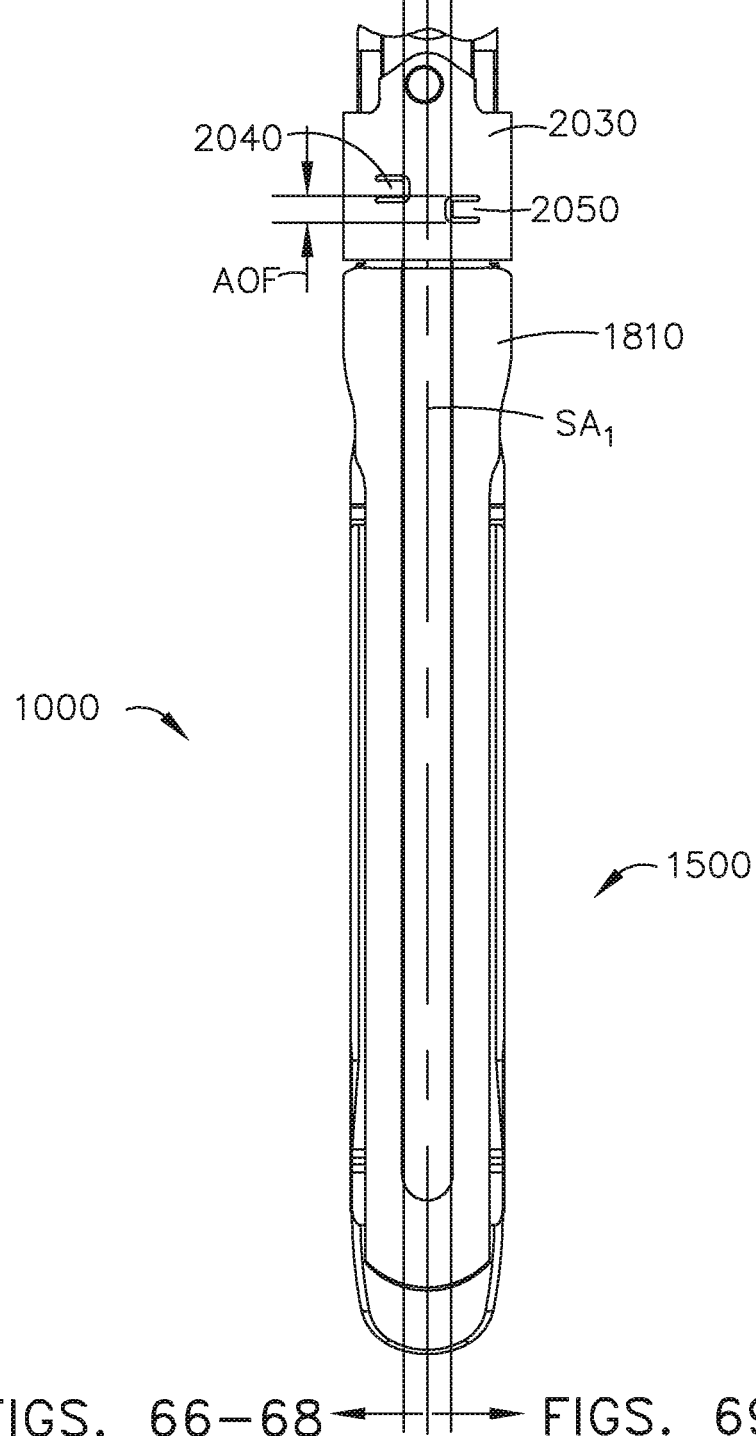
FIG. 65 is a top plan view of the distal closure tube segment and anvil of FIG. 64.
Figure 66:
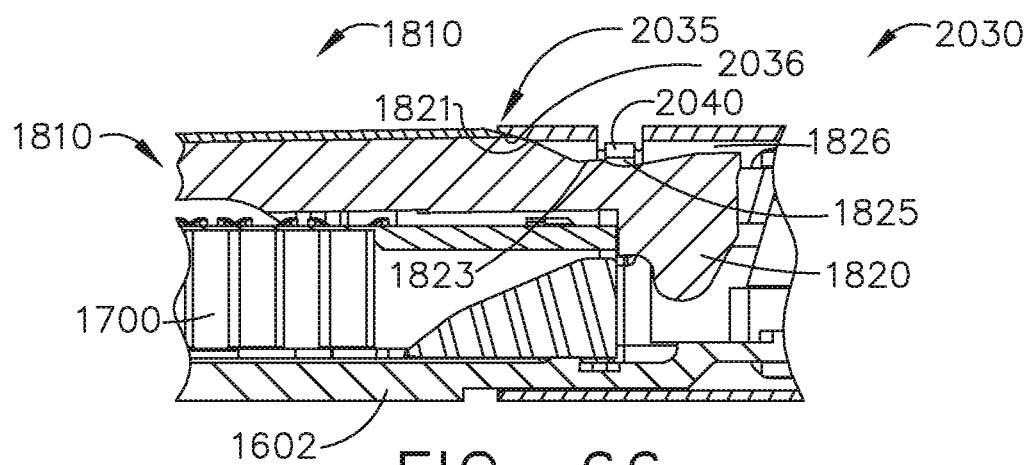
FIG. 66 is a partial cross-sectional view of the anvil and distal closure tube segment of FIGS. 64 and 65 illustrating the position of a proximal jaw opening feature when the anvil is in a fully closed position.
Figure 67:
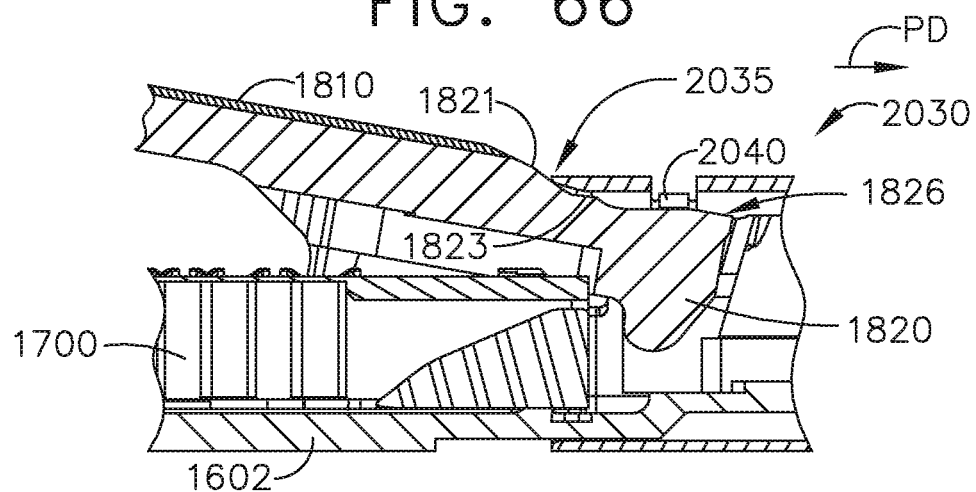
FIG. 67 is another partial cross-sectional view of a portion of the anvil and distal closure tube segment of FIGS. 64-66 illustrating the position of the proximal jaw opening feature when the anvil is between the fully open and fully closed positions.
Figure 72:
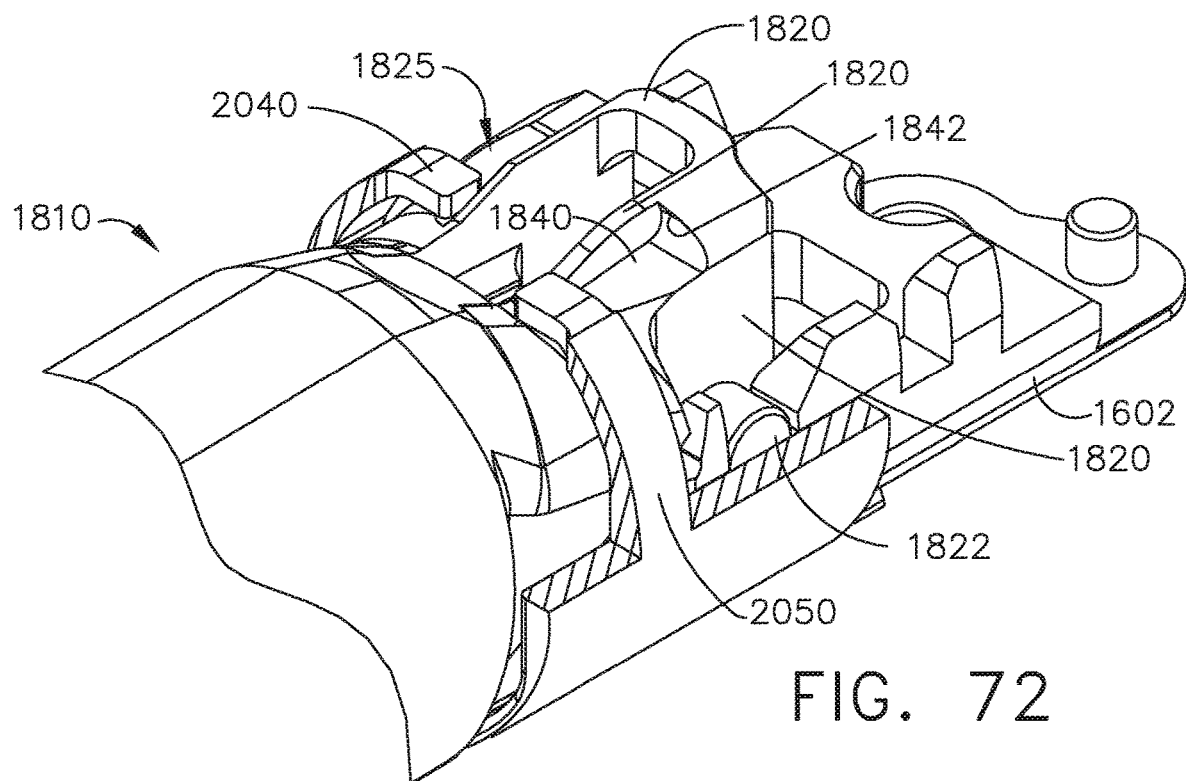
FIG. 72 is a partial left side perspective view of the anvil and distal closure tube segment of FIGS. 64-71 with the anvil in a fully closed position.
Figure 73:
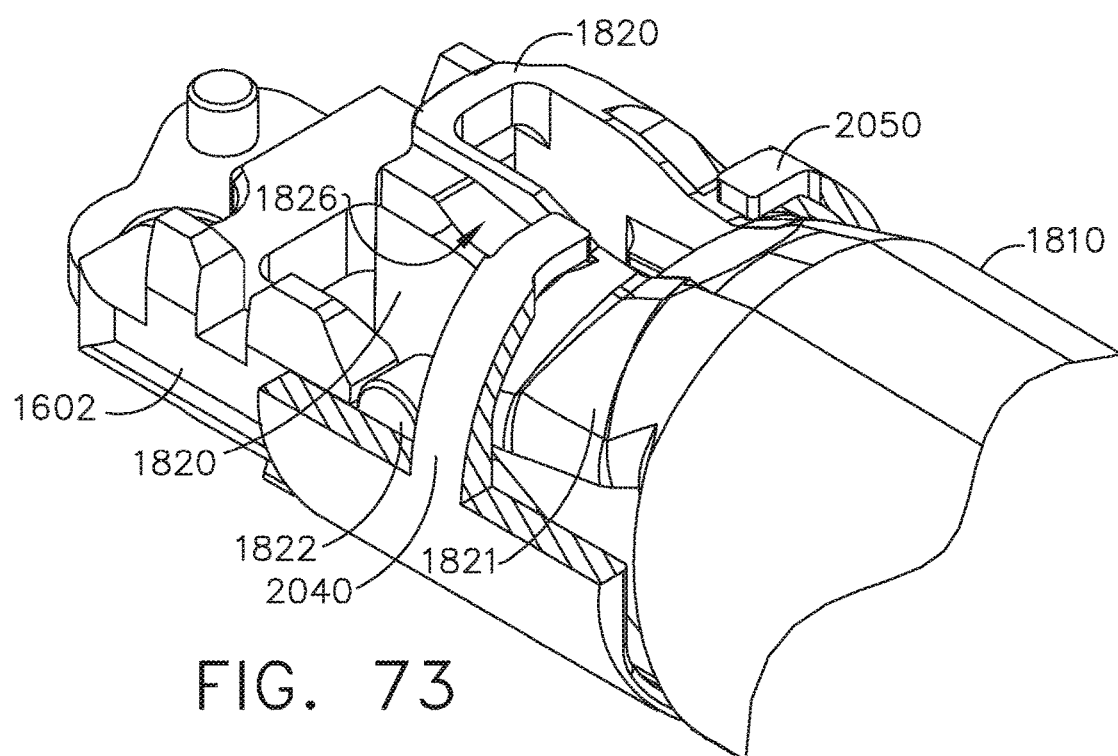
FIG. 73 is a partial right side perspective view of the anvil and distal closure tube segment of FIGS. 64-72 with the anvil in a fully closed position.

With regard to surgical end effector 1500 of the interchangeable tool assembly 1000, in the illustrated example, the distal closure tube segment 2030 employs two axially offset, proximal and distal positive jaw opening features 2040 and 2050 as illustrated in FIGS. 64-77. As can be seen in FIGS. 64 and 65, the proximal positive jaw opening feature 2040 is axially proximal to the distal positive jaw opening feature 2050 by an axial offset distance AOF. In FIG. 65, the proximal positive jaw opening feature 2040 is located on the right side (as viewed by a user of the tool assembly) of the shaft axis $SA_1$. FIGS. 66, 72 and 73 illustrate the position of the proximal positive jaw opening feature 2040 when the anvil 1810 is in the closed position. As can be most particularly seen in FIG. 66, when in that position, the proximal positive jaw opening feature 2040 is in a right side or first relieved area 1825 formed in the anvil mounting portion 1820. FIGS. 69, 72 and 73 illustrate the position of the distal positive jaw opening feature 2050 when the anvil 1810 is in the closed position. As can be most particularly seen in FIG. 69, when in that position, the distal positive jaw opening feature is in contact with a stepped portion 1823 of the anvil cam surface 1821.

Figure 70:
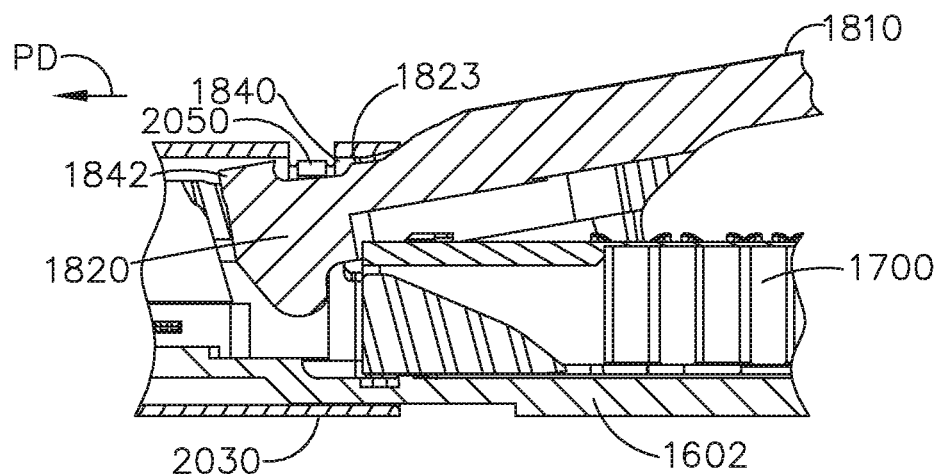
FIG. 70 is a partial cross-sectional view of the anvil and distal closure tube segment of FIGS. 64-69 illustrating the position of the distal jaw opening feature when the anvil is between the fully open and fully closed positions.
Figure 74:
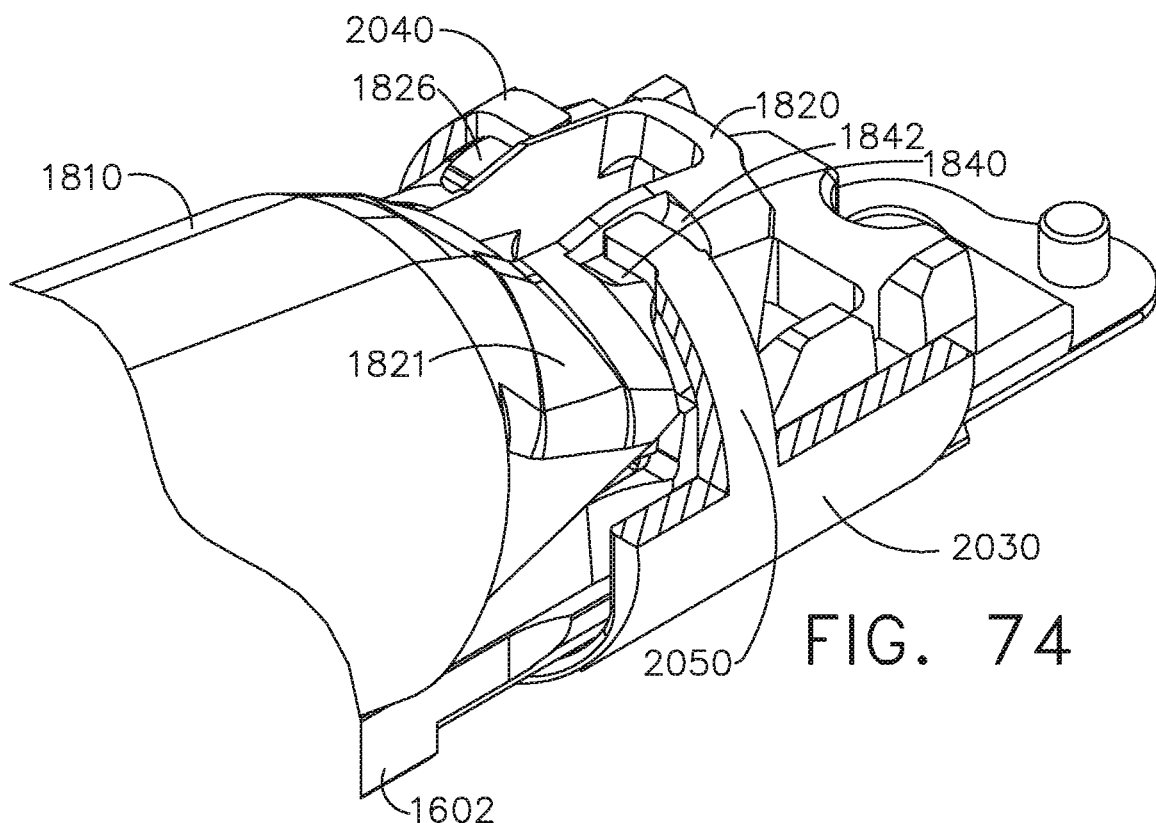
FIG. 74 is a partial left side perspective view of the anvil and distal closure tube segment of FIGS. 64-73 with the anvil in a partially open position.
Figure 75:
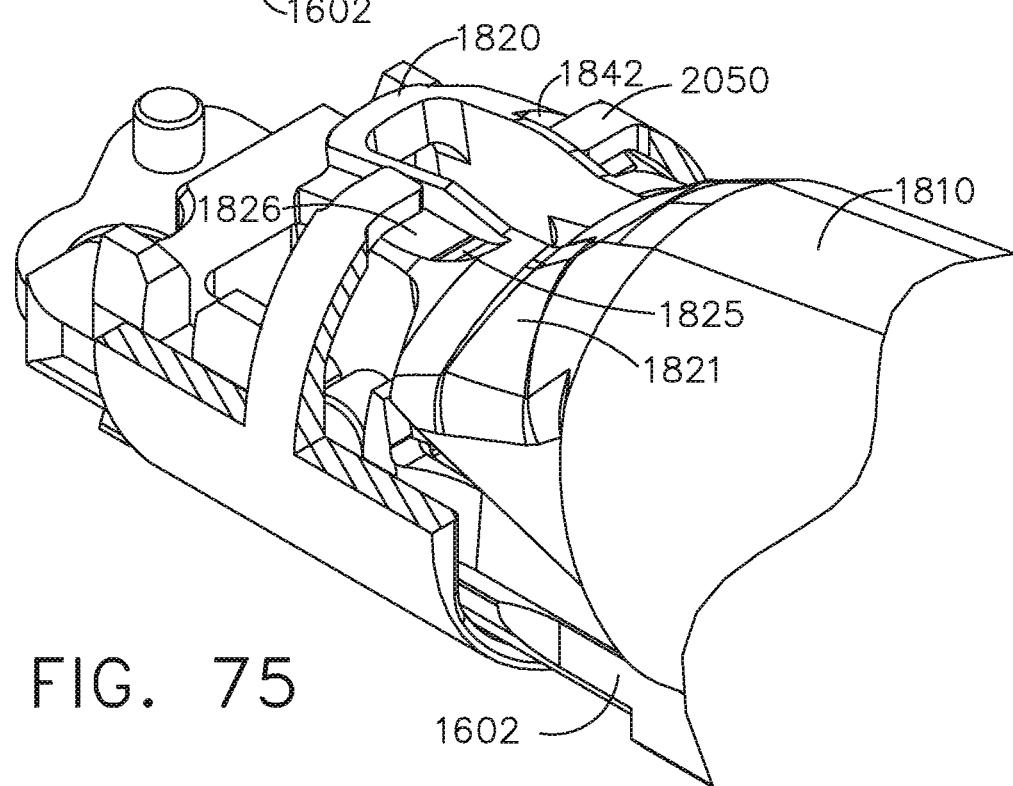
FIG. 75 is a partial right side perspective view of the anvil and distal closure tube segment of FIGS. 64-74 with the anvil in a partially open position.
Figure 76:
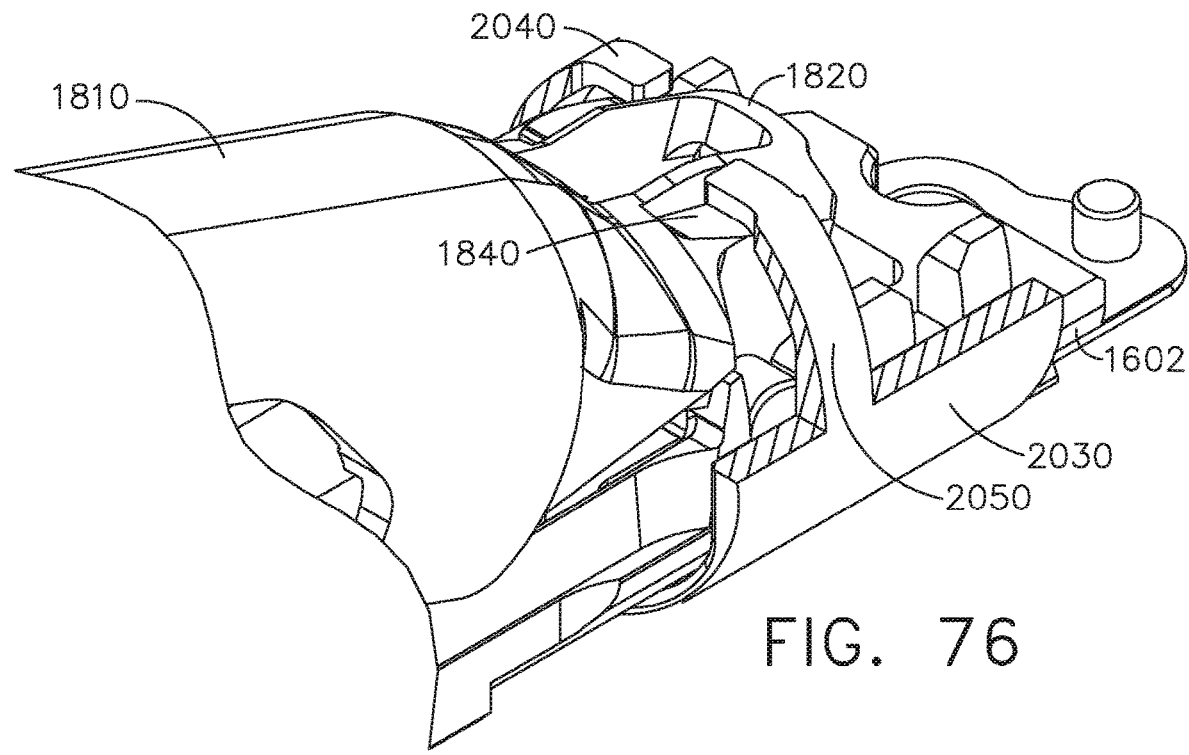
FIG. 76 is a partial left side perspective view of the anvil and distal closure tube segment of FIGS. 64-75 with the anvil in a fully open position.
Figure 77:
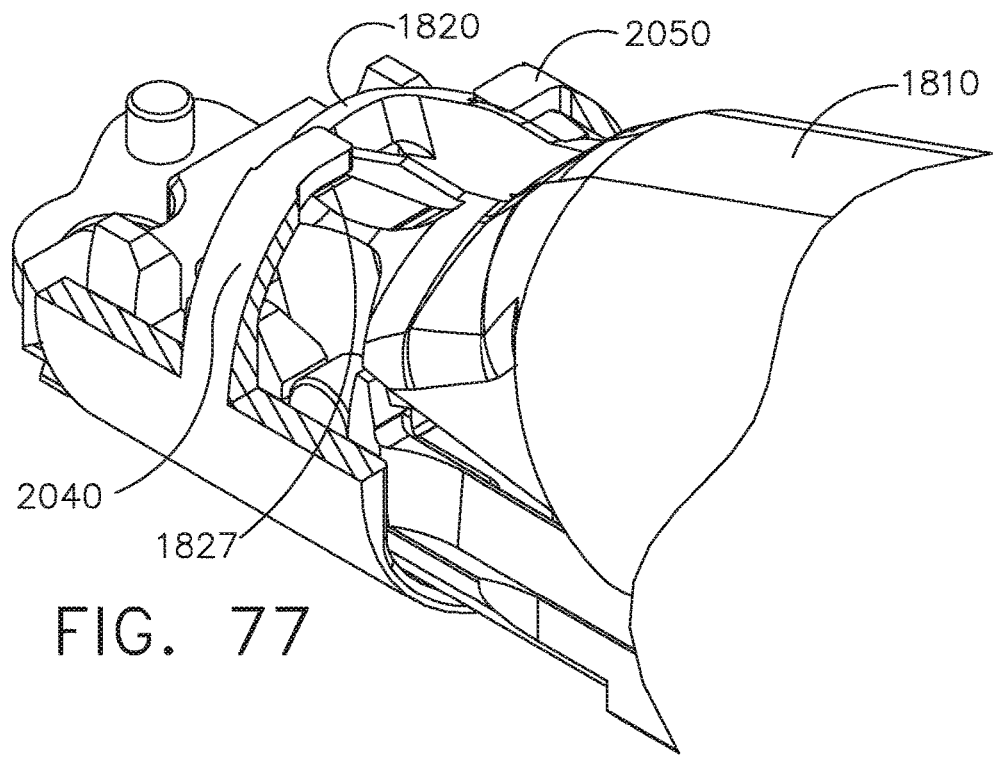
FIG. 77 is a partial right side perspective view of the anvil and distal closure tube segment of FIGS. 64-76 with the anvil in a fully open position.

To commence the opening process, the jaw closure system is actuated to move the distal closure tube segment 2030 in the proximal direction PD. As the distal closure tube segment 2030 is moved in the proximal direction PD, the proximal positive jaw opening feature 2040 contacts a first or right side jaw opening cam surface 1826 and begins to apply a jaw opening motion to the anvil 1810. See FIGS. 67, 74 and 75. As can be seen in FIGS. 70, 74 and 75, during this proximal movement of the distal closure tube segment 2030, the distal positive jaw opening feature 2050 is axially movable within a second or left relief area 1840 formed in the anvil mounting portion 1820. Thus, while the proximal positive jaw opening feature 2040 is applying a first or initial opening motion to the anvil mounting portion 1820, the distal positive jaw opening feature 2050 is not applying any significant opening motion to the anvil 1810. Further proximal motion of the distal closure tube segment 2030 will result in the distal positive jaw opening feature 2050 contacting a left anvil open tab 1842 and the proximal positive jaw opening feature 2040 disengaging the jaw opening cam surface 1826. Thus, the proximal positive jaw opening feature 2040 has disengaged the anvil mounting portion 1820 and is not applying any further opening motion thereto while the distal positive jaw opening feature 2050 is applying a second jaw opening motion to the anvil mounting portion 1820 to pivot the anvil 1810 to a fully open position illustrated in FIGS. 68, 71, 76 and 77.

Figure 78:
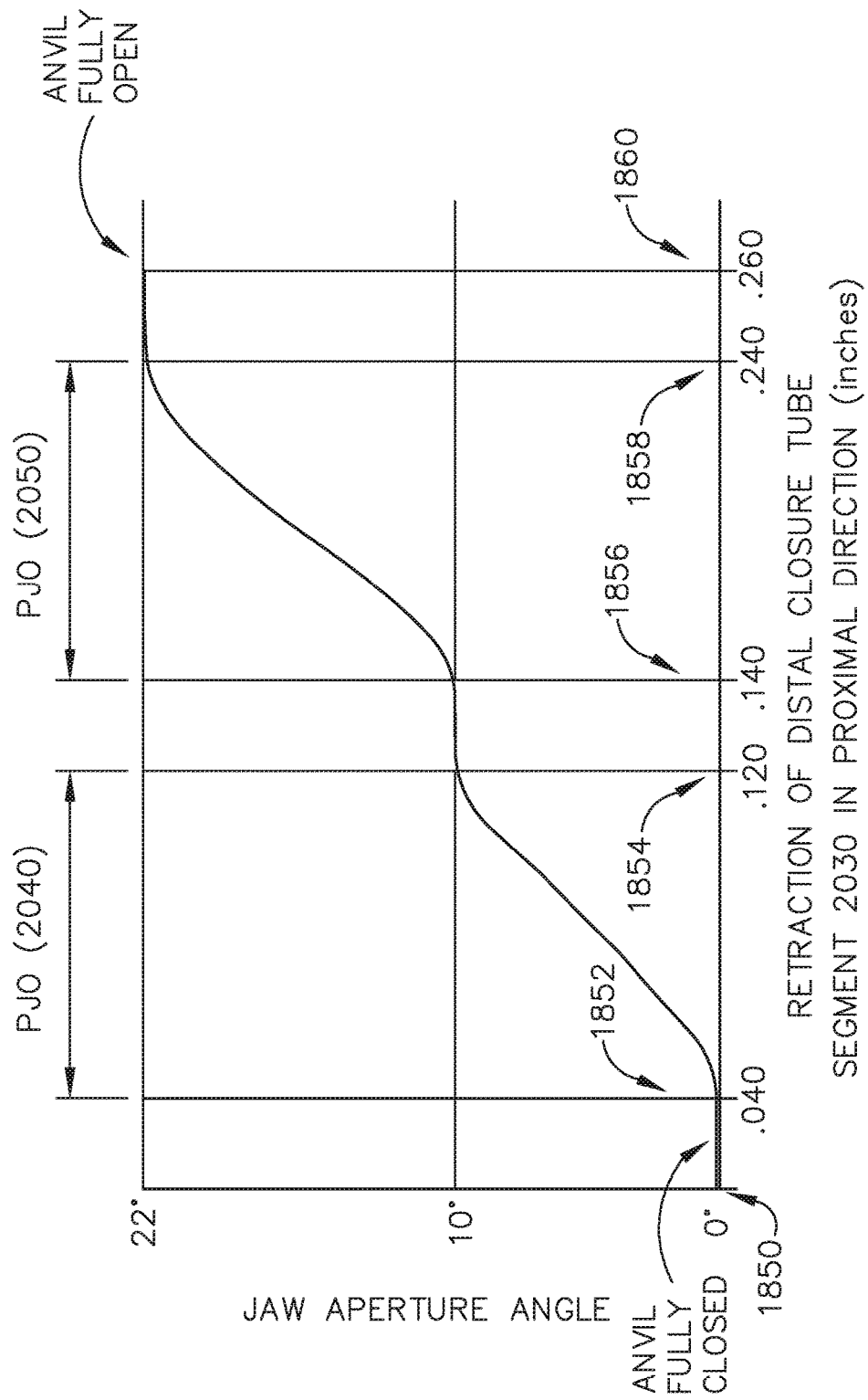
FIG. 78 is a graphical comparison between the jaw aperture angle and retraction of the distal closure tube segment of FIGS. 64-77.

FIG. 78 depicts the anvil or jaw opening process employed by the interchangeable tool assembly 1000 in graphical form. As can be seen in that Figure, the left or vertical axis of the graph represents the amount of jaw aperture from about 0° to about 22° ("anvil aperture angle") and the bottom or horizontal axis represents the approximate proximal axial travel of the distal closure tube segment 2030 from a position wherein the anvil is fully closed to a position wherein the anvil is fully open. As indicated above, the "anvil aperture angle" or "jaw aperture angle" may represent the angle between the cartridge deck surface or tissue contacting surface on the surgical fastener cartridge or "first jaw" and the fastener forming surface or tissue contacting surface on the anvil or "second jaw". When the anvil is fully closed, the anvil aperture angle may be approximately 0°, for example. In the illustrated arrangement, the distal closure tube segment 2030 can move proximally from a first position (1850 on the graph) that corresponds to the fully closed position a proximal distance of, for example, about 0.040 inches to a first intermediate position (1852 on the graph) before the proximal positive jaw opening feature 2040 begins to apply a first jaw opening motion to the anvil 1810. As the distal closure tube segment 2030 continues to move proximally from the first intermediate position 1852 to a second intermediate position (1854 on the graph) a further proximal distance of, for example, about 0.040 inches to about 0.120 inches, the proximal positive jaw opening feature 2040 moves the anvil 1810 through an anvil aperture angle from 0° to about 10°. While the distal closure tube segment 2030 continues to travel proximally from the second intermediate position 1854 to a third intermediate position (1856 on the graph) a further proximal distance (from about 0.120 inches to about 0.140 inches), the anvil remains at about a 10° anvil aperture angle. Further proximal movement of the distal closure tube segment 2030 from the third intermediate position 1856 to a fourth intermediate position (1858 on the graph) a proximal distance (from about 0.140 inches to about 0.240 inches), the distal positive jaw opening feature 2050 begins to apply a second jaw opening motion to the anvil 1810. As the distal closure tube segment 2030 continues to move proximally from the third intermediate position 1856 to a fourth intermediate position (1858 on the graph) a further proximal distance (from, for example, about 0.140 inches to about 0.240 inches), the distal positive jaw opening feature 2050 moves the anvil 1810 relative to the elongate channel 1602 such that the anvil aperture angle increases from about 10° to about 22°, for example. While the distal closure tube segment 2030 continues to travel proximally from the fourth intermediate position 1858 to a final proximal position (1860 on the graph) a further proximal distance (from about 0.240 inches to about 0.260 inches, for example), the anvil 1810 remains at a fully open position with an anvil aperture angle of approximately 22°.

The closure process of the illustrated example of the interchangeable tool assembly 1000 may be understood from reference to FIGS. 67-69 and 70-72, as well as FIG. 78.

Figure 68:
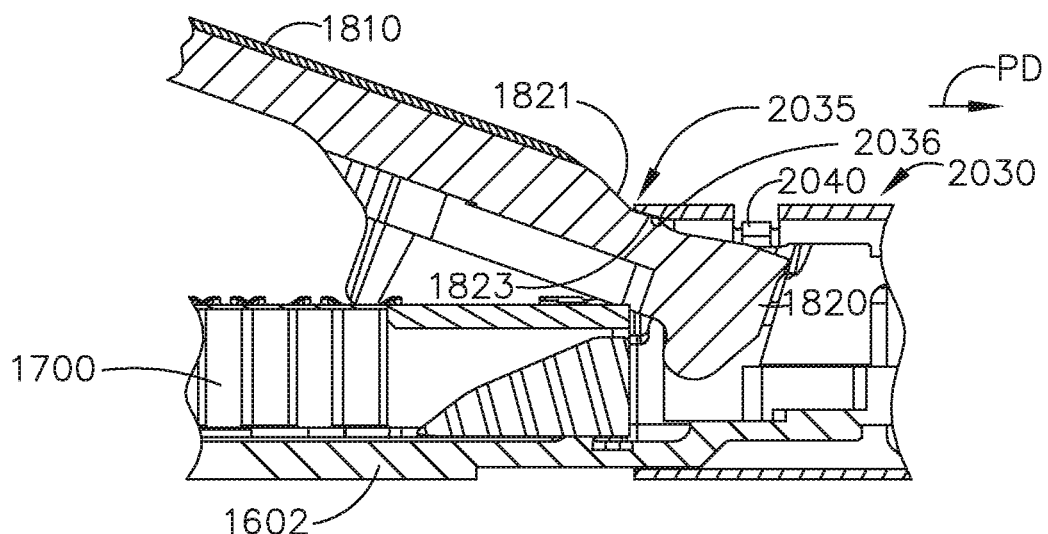
FIG. 68 is another partial cross-sectional view of a portion of the anvil and distal closure tube segment of FIGS. 64-67 illustrating the position of the proximal jaw opening feature when the anvil is in the fully open position.
Figure 69:
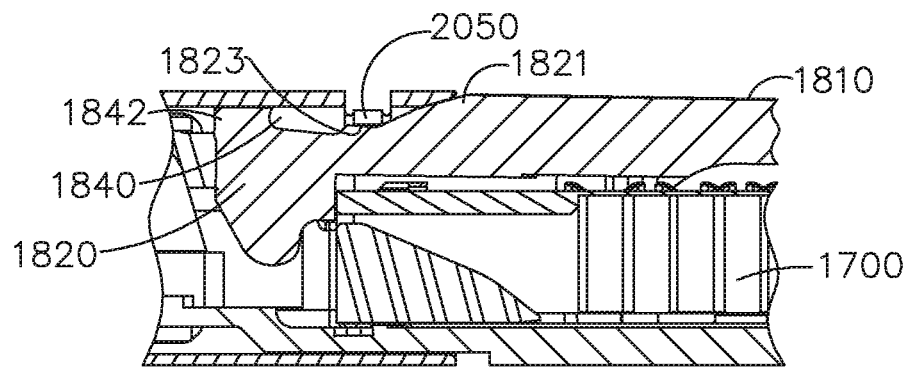
FIG. 69 is a partial cross-sectional view of the anvil and distal closure tube segment of FIGS. 64-68 illustrating the position of a distal jaw opening feature when the anvil is in a fully closed position.
Figure 71:
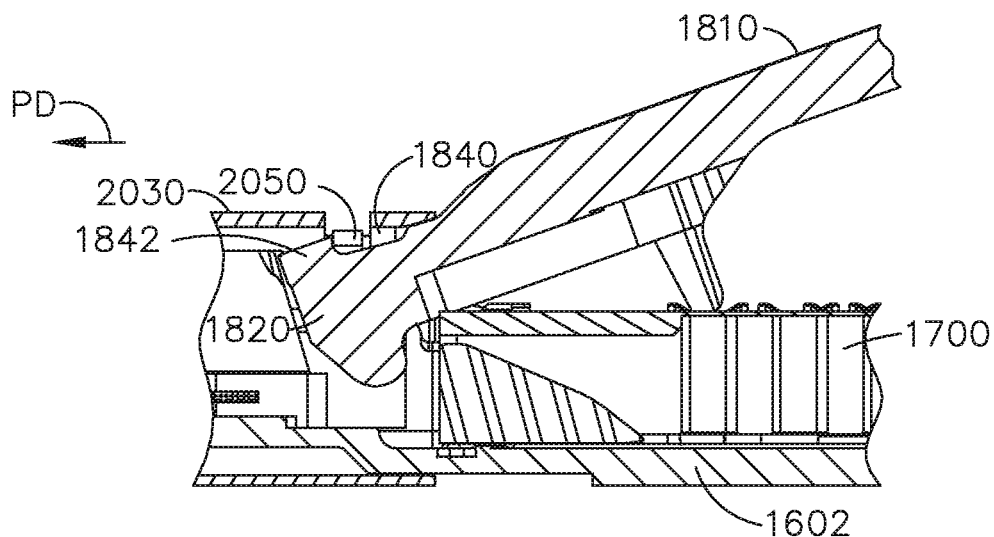
FIG. 71 is another partial cross-sectional view of a portion of the anvil and distal closure tube segment of FIGS. 64-70 illustrating the position of the distal jaw opening feature when the anvil is in the fully open position.

FIGS. 68 and 71 illustrate the anvil 1810 in its fully open position. As can be seen in those Figures, the proximal positive jaw opening feature 2040 is out of contact with the anvil mounting portion 1820 and the distal positive jaw opening feature 2050 is in contact with the left anvil open tab 1842. When the anvil closure process is commenced, the closure drive system is actuated to move the distal closure tube segment 2030 in the distal direction DD. As the distal closure tube segment moves from the final proximal position 1860 to the fourth intermediate position 1858 (FIG. 78), the anvil 1810 remains in its fully open position. Thus, once the closure process is commenced, in at least one example, the distal closure tube segment 2030 may move distally a first or initial predetermined axial closure distance before the anvil 1810 begins to move. Stated another way, the distal closure tube segment may move the first predetermined axial closure distance before any closure motion is applied to the anvil 1810. In at least one example, the first or initial predetermined closure distance may be approximately 0.020 inches. As the distal closure tube segment 2030 continues to move distally through an intermediate axial closure distance, the distal end 2035 of the distal closure tube segment 2030 begins to contact the anvil cam surface 1821 on the anvil mounting portion 1820 (FIGS. 67 and 70) until the internal cam surface 2036 on the distal closure tube segment 2030 begins to cammingly contact the anvil cam surface 1821. As the internal cam surface 2036 travels up the anvil cam surface 1821, the anvil 1810 is pivoted to the fully closed position. The anvil cam surface 1821 and the internal cam surface 2036 may be configured to permit further distal travel of the distal closure tube segment 2030 from, for example, first intermediate point or position 1852 to the first position 1850 (FIG. 78). Thus, in at least one example, the distal closure tube segment 2030 may move distally a final predetermined axial closure distance during the closing process after the anvil 1810 has attained its fully closed position. In at least one example, the final predetermined axial closure distance may be approximately 0.040 inches.

In those surgical stapling devices that employ a firing member assembly that comprises a firing member that has a tissue cutting surface, it may be desirable for the firing system and portions of the end effector to be configured in such a way so as to prevent the inadvertent advancement of the firing member unless an unspent staple cartridge is properly supported in the end effector. If, for example, no staple cartridge is present at all and the firing member is distally advanced through the end effector, the tissue would be severed, but not stapled. Similarly, if a spent staple cartridge (i.e., a staple cartridge wherein at least some of the staples have already been fired therefrom) is present in the end effector and the firing member is advanced, the tissue would be severed, but may not be completely stapled, if at all. It will be appreciated that such occurrences could lead to undesirable catastrophic results during the surgical procedure. U.S. Pat. No. 6,988,649 entitled SURGICAL STAPLING INSTRUMENT HAVING A SPENT CARTRIDGE LOCKOUT, U.S. Pat. No. 7,044,352 entitled SURGICAL STAPLING INSTRUMENT HAVING A SINGLE LOCKOUT MECHANISM FOR PREVENTION OF FIRING, U.S. Pat. No. 7,380,695 entitled SURGICAL STAPLING INSTRUMENT HAVING A SINGLE LOCKOUT MECHANISM FOR PREVENTION OF FIRING, U.S. Patent Application Publication No. 2016-0367247-A1, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING and U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT each disclose various firing member lockout arrangements. Each of those references is hereby incorporated by reference in its entirety herein.

Referring to FIGS. 60A-60I, there is shown a surgical end effector 9010 that comprises a portion of a surgical tool assembly 9000 that comprises a first jaw 9020 and a second jaw 9120. In the illustrated arrangement, for example, the first jaw 9020 comprises an elongate channel 9022 that is configured to removably and operably support a surgical staple cartridge 9600 therein. The elongate channel 9022 is attached to an elongate shaft assembly 9300 of the surgical tool assembly. In the arrangement depicted in FIGS. 60C and 60D, for example, the elongate channel 9022 is pivotally coupled to a spine assembly 9310 of the elongate shaft assembly 9300 for selective articulation relative thereto. See FIGS. 60D, 60E, 60H and 60I. The elongate shaft assembly 9300 may define a shaft axis SA. The second jaw 9120 comprises an anvil 9122 that is movably supported on the elongate channel 9022 and which is movable between open and closed positions by the closure system 9400. The anvil 9122 includes an anvil body 9124 and an anvil mounting portion 9126 that is pivotally supported for pivotal travel relative to the proximal end 9024 of the elongate channel 9022. The closure system 9400 may include, for example, an axially movable distal closure tube segment 9410 that is configured to cammingly engage a cam surface 9128 on the anvil mounting portion 9126 when the distal closure tube segment 9410 is axially advanced in the distal direction DD. The distal closure tube segment 9410 may also be configured to apply opening motions to the anvil mounting portion 9126 when the distal closure tube segment 9410 is moved in the proximal direction PD. See FIGS. 60C and 60D.

The surgical tool assembly 9000 further includes a firing system 9500 that, in the illustrated arrangement, comprises a firing member assembly 9510 that is configured to receive firing motions from a firing control system supported in a housing of a handheld control system or a robotic control system, for example. In the illustrated embodiment, one form of firing member assembly 9510 comprises a first firing member element 9520 that consists of a firing member body 9522 that supports a tissue cutting surface or blade 9524 thereon. The firing member body 9522 is coupled to a firing bar or knife bar 9530 that operably interfaces with corresponding portions of the firing system 9500 to receive the firing motions from the firing control system. The firing member body 9522 may include second jaw or anvil engagement features 9526 that may comprise laterally extending tab features configured to be received within corresponding second jaw passages or slots 9125 in the anvil body 9124. In addition, the firing member body 9522 may further include first jaw or channel engagement features or a foot 9528 that is configured to be received in corresponding first jaw passages or slots or openings 9023 in the elongate channel 9022.

The staple cartridge 9600 comprises a cartridge body 9602. See FIGS. 60H and 60I. The cartridge body 9602 includes a proximal end 9604, a distal end (not shown), and a deck 9606 extending between the proximal end and the distal end. In use, the staple cartridge 9600 is positioned on a first side of the tissue to be stapled and the anvil 9122 is positioned on a second side of the tissue. The anvil 9122 is moved toward the staple cartridge 9600 to compress and clamp the tissue against the deck 9606. Thereafter, staples or fasteners removably stored in the cartridge body 9602 can be deployed into the tissue. The cartridge body 9602 includes staple or fastener cavities (not shown) defined therein wherein staples or fasteners (not shown) are removably stored in the staple cavities. The staple cavities may be arranged in longitudinal rows. In one arrangement, for example, three rows of staple cavities are positioned on a first side of a longitudinal slot and three rows of staple cavities are positioned on a second side of the longitudinal slot. The longitudinal slot is configured to axially receive the first firing member element 9520 therethrough. Other arrangements of staple/fastener cavities and staples or fasteners may be possible.

Figure 60:
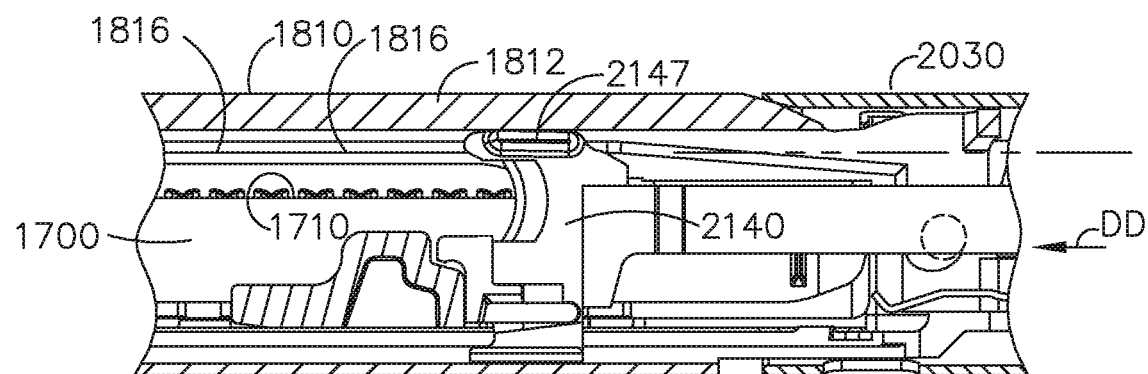
FIG. 60 is another partial cross-sectional view of the surgical end effector of FIGS. 57 and 58 after the firing member thereof has been distally advanced during the firing process.
Figure 60B:
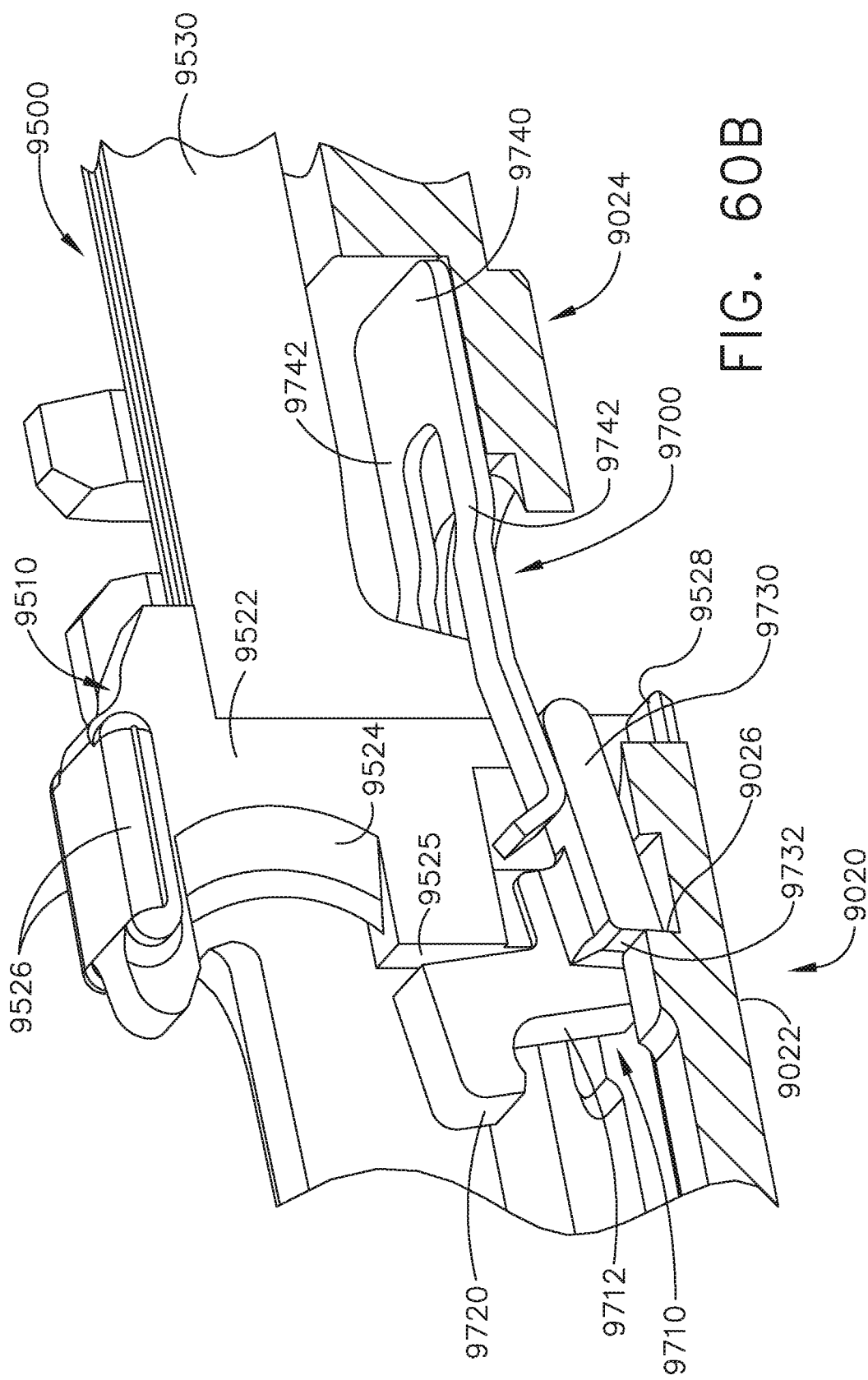
FIG. 60B is another perspective view of the firing member assembly of FIG. 60A with the second firing member element in the locked position.
Figure 60C:
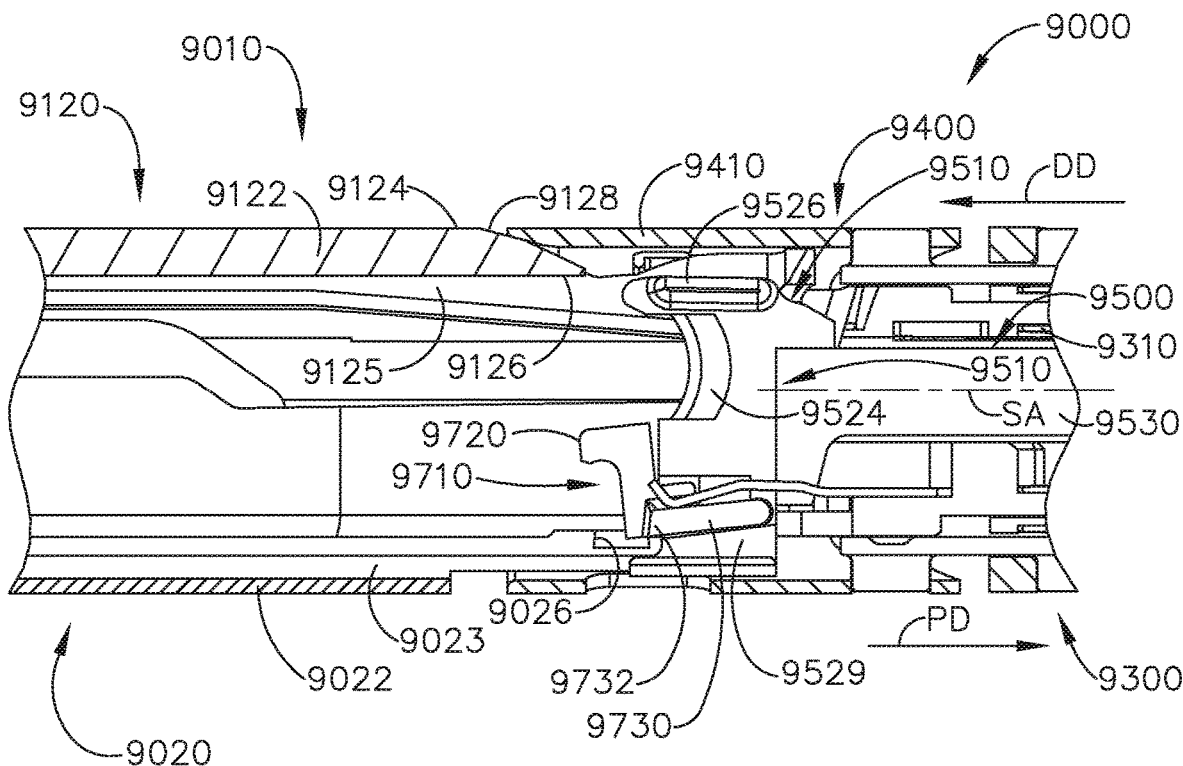
FIG. 60C is a cross-sectional elevational view of the surgical stapling instrument of FIG. 60A with the firing member assembly in a starting position.
Figure 60D:
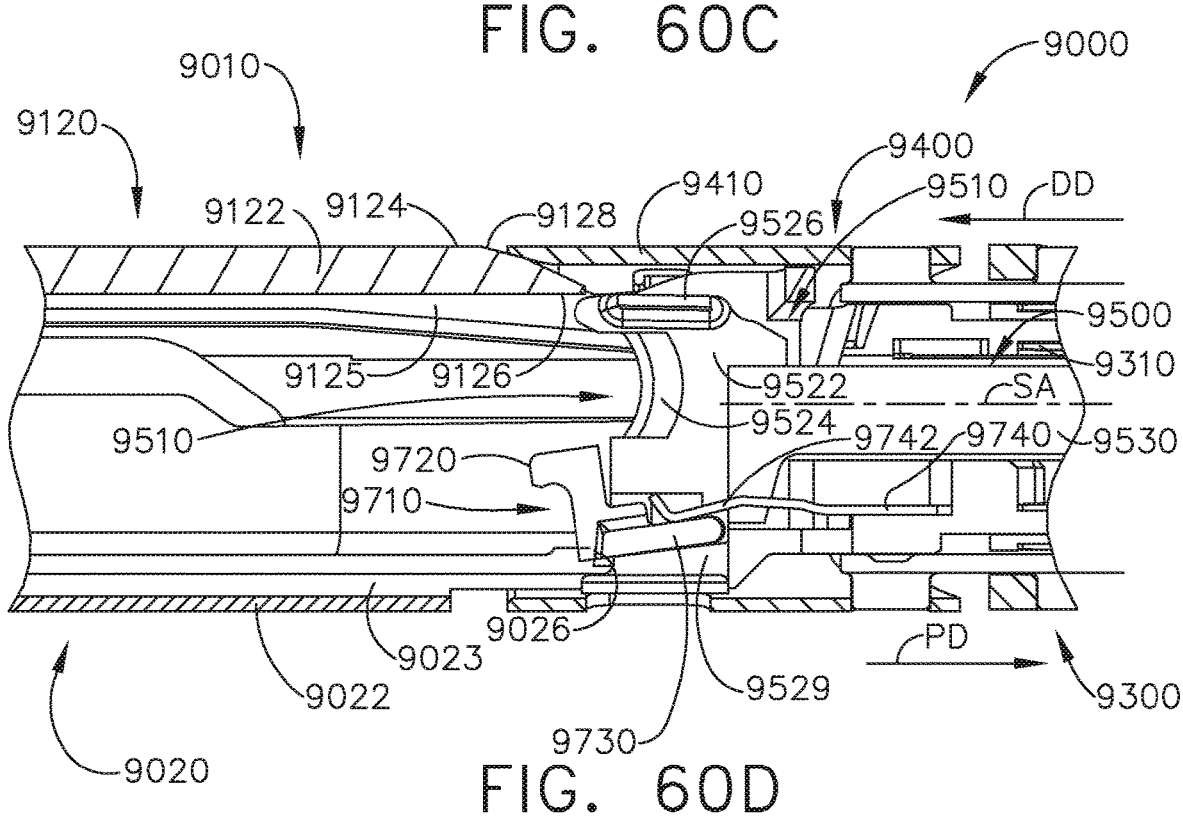
FIG. 60D is another cross-sectional view of the surgical stapling instrument of FIG. 60C illustrated in a locked out configuration.

The staples or fasteners are supported by staple drivers (not shown) that are movably supported in the cartridge body 9602. The drivers are movable between a first, or unfired position, and a second, or fired, position to eject the staples or fasteners from the cavities. The drivers are retained in the cartridge body 9602 by a retainer (not shown) which extends around the bottom of the cartridge body 9602 and includes resilient members configured to grip the cartridge body and hold the retainer to the cartridge body. The drivers are movable between their unfired positions and their fired positions by a sled 9610. The sled 9610 is movable between a proximal, or "unfired" position adjacent the proximal end 9604 and a distal or "fired" position adjacent the distal end (after firing). As can be seen in FIG. 60G, the sled 9610 comprises a plurality of ramped or cam surfaces 9620 that are configured to slide under the drivers and lift the drivers, and the staples or fasteners supported thereon, toward the anvil. An "unfired", "unspent", "fresh" or "new" staple cartridge 9600 means herein that the staple cartridge 9600 has all of its staples or fasteners in their "ready-to-be-fired positions". When in that position, the sled assembly 9610 is located in its starting or "unfired" position. The new staple cartridge 9600 is seated within the elongate channel 9022 and may be retained therein by snap features on the cartridge body 9602 that are configured to retainingly engage corresponding portions of the elongate channel 9022. FIGS. 60G and 60H illustrate a portion of the surgical end effector 9010 with a new or unfired surgical staple cartridge 9600 seated therein. As can be seen in FIGS. 60G and 60H, the sled 9610 is in the unfired position. To prevent the firing system 9500 from being activated and, more precisely, to prevent the first firing member element 9520 from being distally driven through the surgical end effector 9010 unless an unfired or new surgical staple cartridge 9600 has been properly seated within the elongate channel 9022, the illustrated surgical tool assembly 9000 employs a firing member lockout system generally designated as 9700.

Figure 60E:
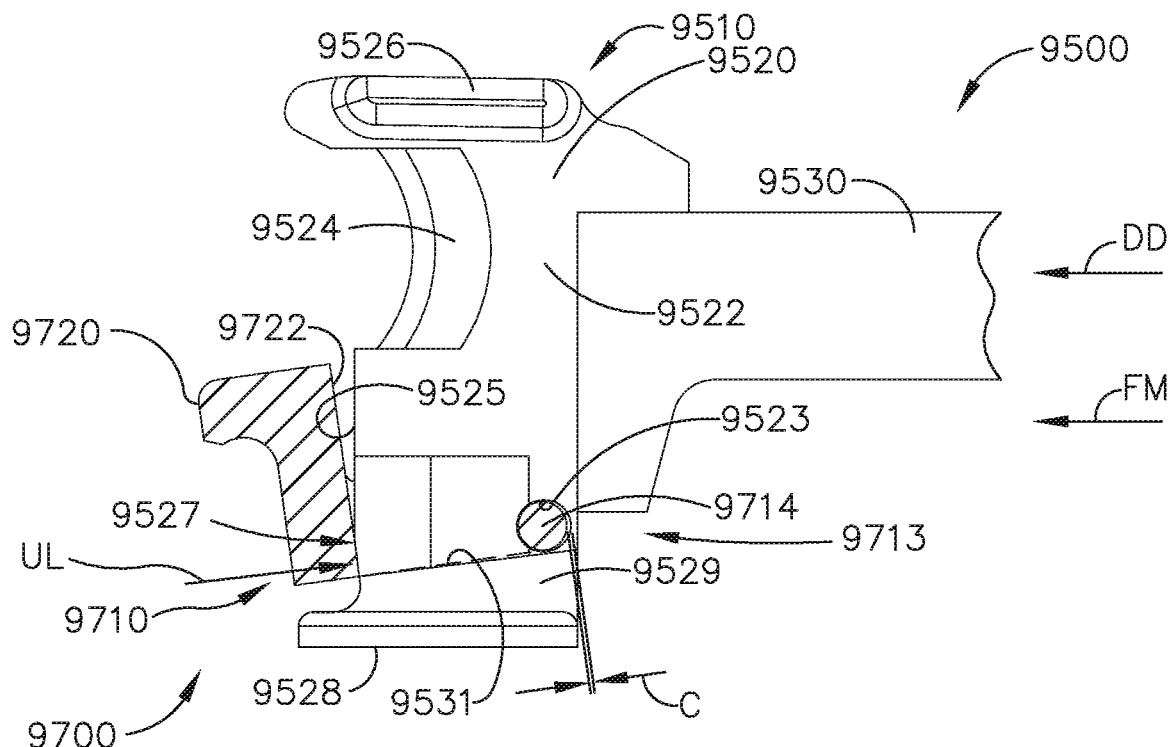
FIG. 60E is a side view of a firing member assembly with the second firing member element in a lockout orientation.
Figure 60F:
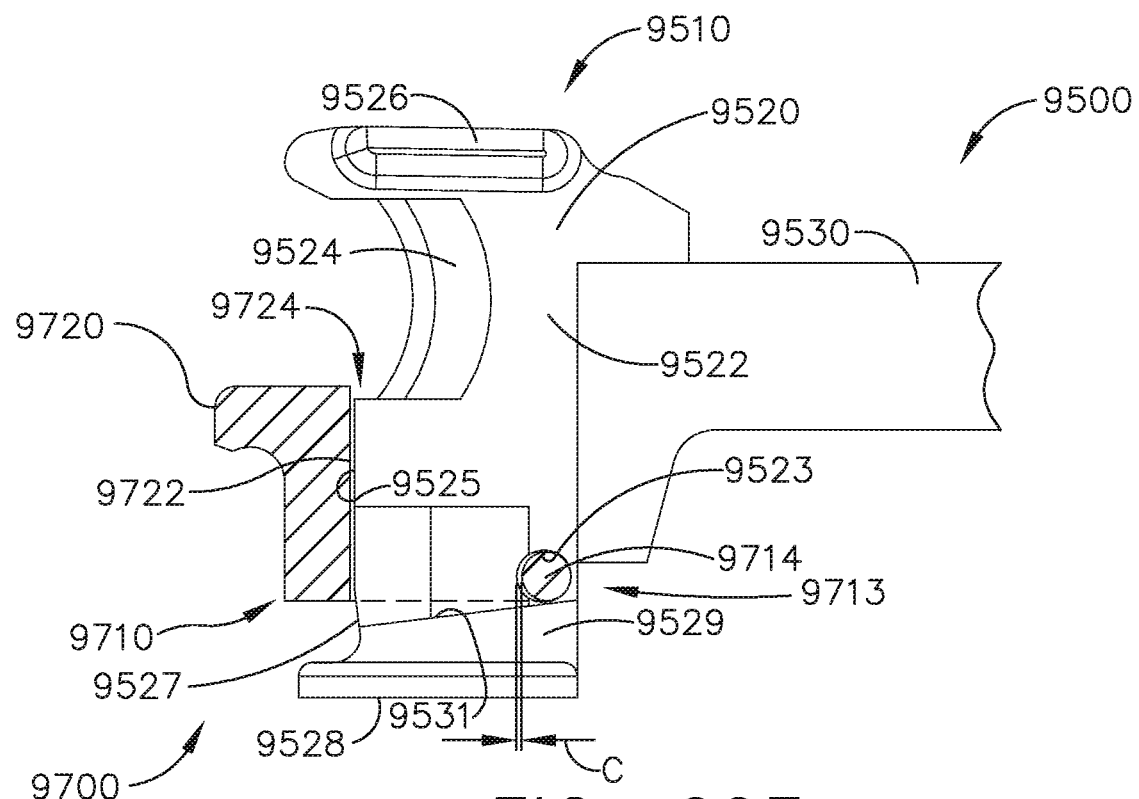
FIG. 60F is another side view of the firing member assembly of FIG. 60E with the second firing member element illustrated in an unlocked or firing orientation.
Figure 60G:
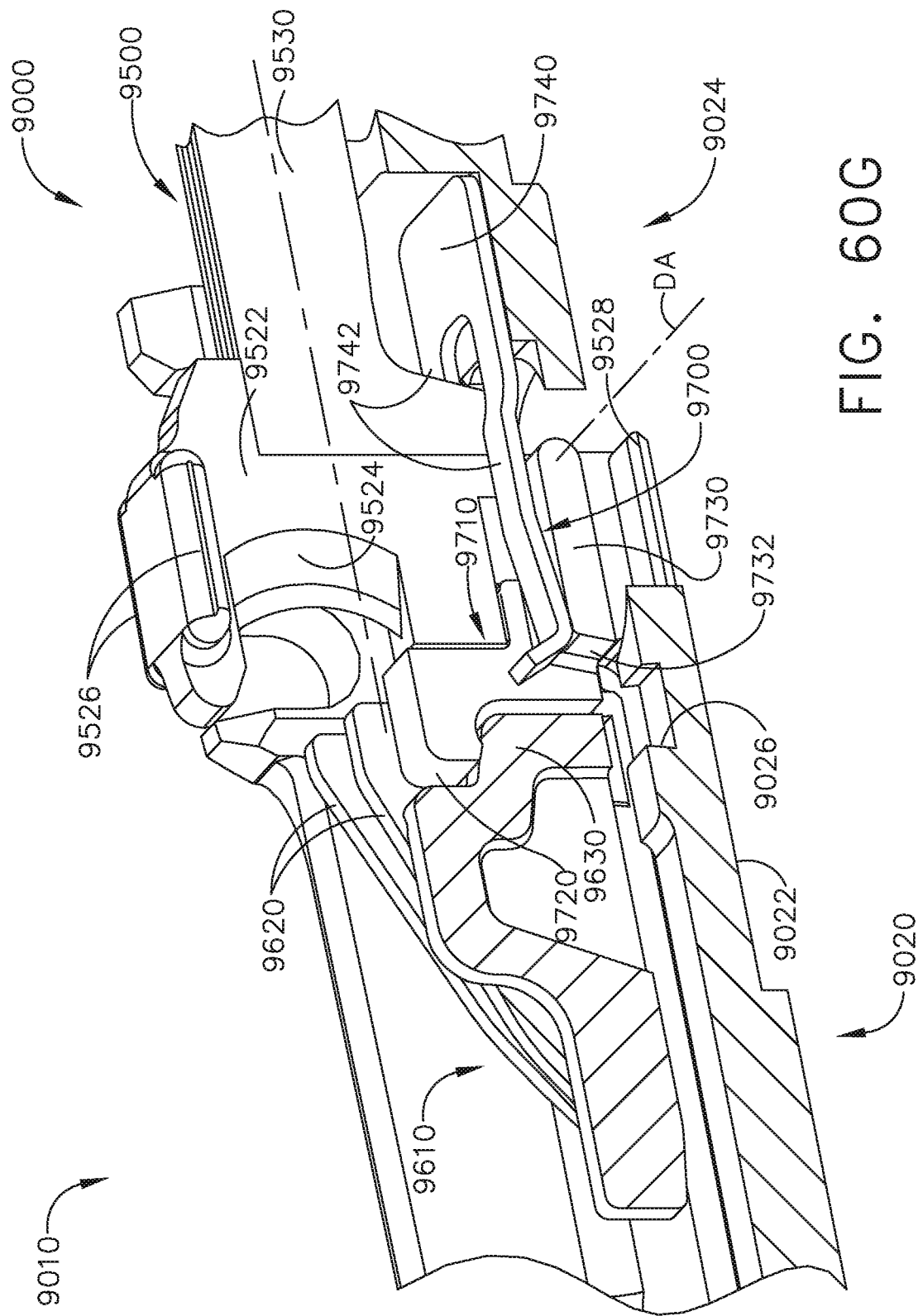
FIG. 60G is another partial perspective view of the surgical stapling instrument of FIG. 60A illustrated in an unlocked configuration.
Figure 60H:
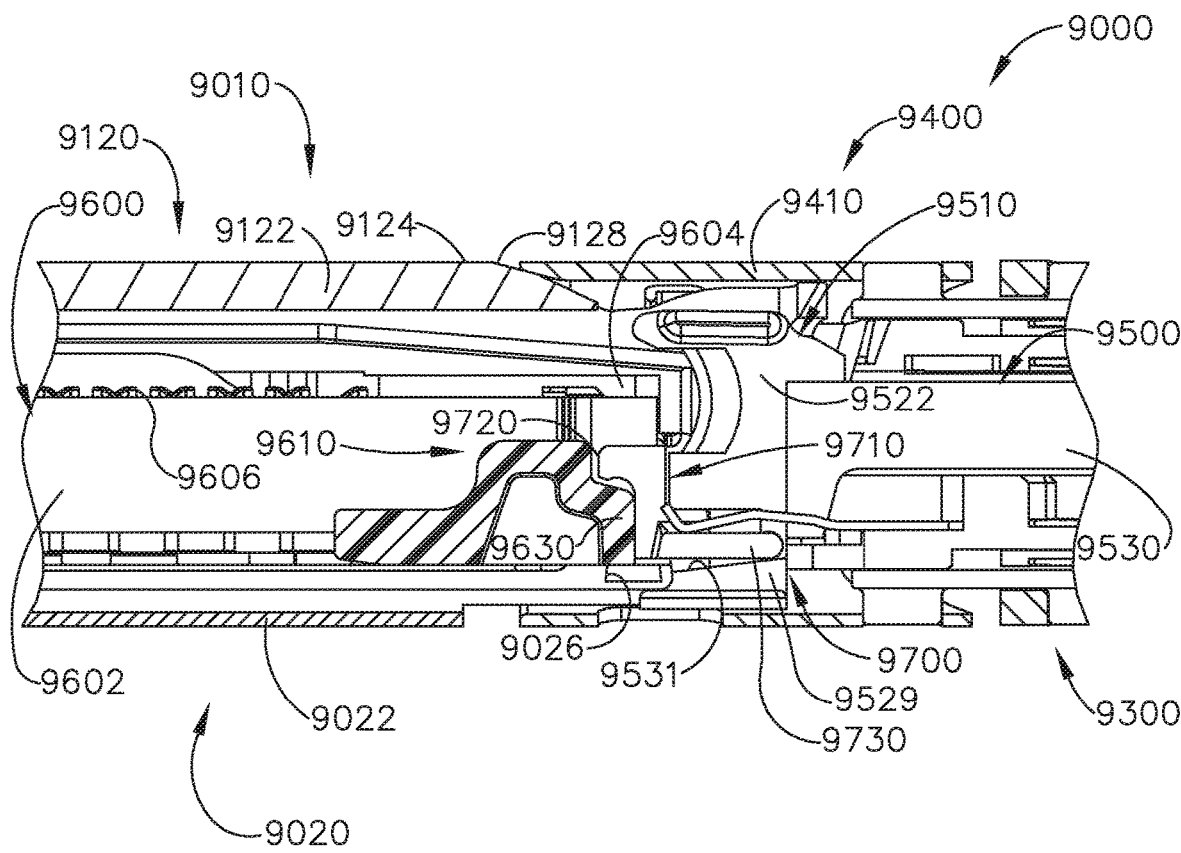
FIG. 60H is a cross-sectional view of the surgical stapling instrument of FIG. 60A with an unfired surgical fastener cartridge operably supported in an elongate channel thereof and with the firing member assembly illustrated in a starting position.

Referring now to FIGS. 60E and 60F, in one form, the firing member lockout system 9700 comprises a second firing member element or tippable element 9710 that comprises a sled engaging portion 9720. In the illustrated arrangement, the second firing member element 9710 is pivotally coupled to the firing member body 9522 by an attachment joint 9713 in the form of, for example, a pivot member or members 9714 that are pivotally received in corresponding pivot holes 9523 provided in the firing member body 9522 for pivotal travel relative thereto about a pivot axis PA that is transverse to the shaft axis SA. Such arrangement facilitates pivotal travel of the second firing member element 9710 relative to the firing member body 9522 between a locked position (FIG. 60E) and an unlocked position (FIG. 60F). In the illustrated example, the firing member body 9522 comprises a distal surface 9525 that is approximately perpendicular to the channel engagement features 9528 and a lockout surface 9527 that is angled relative to the distal surface 9525. In addition, one or more support ramps 9529 are formed on the firing member body 9522 that serve to define corresponding landing surfaces 9531 for receiving the second firing member element 9710 when in the locked configuration. See FIG. 60E.

As can be seen in FIG. 60F, when the second firing member element 9710 is in the unlocked position, a space, generally indicated as 9724, is provided between a proximal surface 9722 of the second firing member element 9710 and the distal surface 9525 of the firing member body 9522. Thus, when in the unlocked position, the proximal surface 9722 of the second firing member element 9710 is not in contact with the distal surface 9525 of the firing member body 9522. Referring now to FIGS. 60A-60D, the second firing member element 9710 further comprises at least one lockout-engaging portion 9730 that includes an angled lock end 9732 that is configured to engage a corresponding lock-out notch 9026 that is formed in the elongate channel 9022 when the second firing member element 9710 is in the locked position. In one embodiment, for example, the second firing member element 9710 includes two lockout-engaging portions 9730. As can also be seen in FIGS. 60A-60D, a lockout spring or biasing member 9740 is mounted in the proximal end 9024 of the elongate channel 9022 and includes two spring arms 9742 that each correspond to a lockout-engaging portion 9730. The spring arms 9742 serve to bias the second firing member element 9710 into the locked position as shown in FIGS. 60B-60D.

Figure 60I:
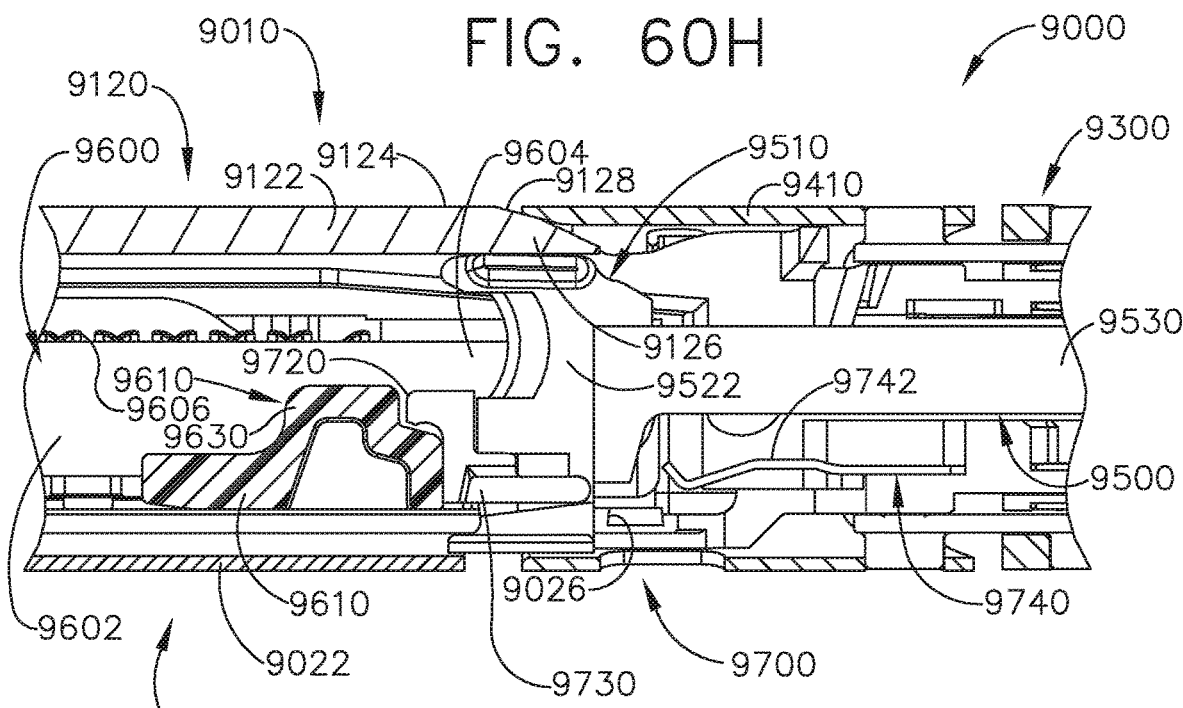
FIG. 60I is another cross-sectional view of the surgical stapling instrument of FIG. 60H with the firing member assembly illustrated in a partially-fired configuration.

Turning now to FIGS. 60G-60I, the sled 9610 comprises an unlocking portion 9630 that is configured to engage the sled engaging portion 9720 on the second firing member element 9710 when the sled 9610 is in the unfired position. Such arrangement serves to pivot the second firing member element 9710 into the unlocked position. When in the unlocked position, the angled lock end 9732 of each lockout-engaging portion 9730 is pivoted out of the corresponding lock-out notch 9026 in the elongate channel 9022 so that the firing member assembly 9510 may be fired or distally advanced through the staple cartridge. If the staple cartridge that has been loaded into the elongate channel 9022 was previously fired or even partially fired, the sled 9610 will not be in the unfired position so as to pivot the second firing member element 9710 into the unlocked position. In such instance therefor, the clinician will be unable to distally advance or fire the firing member assembly 9510. When in the unlocked position, actuation of the firing system 9500 will result in the distal travel of the firing member assembly 9510. As indicated above, when the firing member assembly 9510 is driven distally, the second firing member element 9710 is in contact with the firing member body 9522 through the pivot members 9714. However, when the second firing member element 9710 is pivoted into the locked position (FIG. 60E), a portion of the proximal surface 9722 is in abutting contact with the angled lockout surface 9527 on the firing member body 9522. In addition, as can be most particularly seen in FIGS. 60E and 60F, the pivot hole 9523 in the firing member body 9522 is sized relative to the corresponding pivot member 9714 to provide clearance C therebetween so that the load is transferred through the second firing member element directly to the firing member body 9522 and not through the pivot members 9714. As can be seen in FIG. 60E, the angled lockout surface 9527 facilitates pivotal travel of the sled engaging portion 9720 into the locked position. When the second firing member element 9720 is in the locked position, should the clinician inadvertently apply a firing motion FM to the firing member assembly 9510 in the distal direction DD, the engagement between the second firing member element 9720 and the lock-out notch 9026 in the elongate channel 9022 will prevent the distal advancement of the firing member assembly 9510 and cause a resultant unlocking load force UL to be applied to the second firing member element 9720. This unlocking load force UL will be applied to the angled lockout surface 9527 on the firing member body 9522 and will not be applied to the pivot members 9714. Such arrangement avoids loading or stressing the pivot members 9714 should the clinician inadvertently attempt to advance the firing member assembly 9510 when in the locked position. Thus, this configuration may prevent the pivot members 9714 from shearing off during such attempted advancement of the firing member assembly 9510.

Thus, the foregoing firing member assembly 9510 and firing member lockout assembly 9700 may provide several advantages. For example, as was discussed above, the distal surface 9525 on the firing member body 9522 carries the load during firing and avoids transferring such load to the pivot members that attach the second firing member element 9710 to the first firing member element 9520. When in the lockout state or locked position, the load is carried by the angled lock ends 9732 on the lockout engaging portions 9730. Such arrangement also avoids the need for the firing member assembly 9510 or more precisely the first firing member element 9520 from moving vertically which may inadvertently lead to misalignment with the anvil and elongate channel when moved into an unlocked state for firing. Moreover, because the first firing member element 9520 does not move vertically, the anvil engagement features as well as the channel engagement features may be advantageously shaped and designed to obtain desirable engagement with the anvil and channel during firing. The design and shape of the firing member body may also afford a large surface area for attachment to the knife bar by, for example, welding. For example, the distal end of the knife bar may be attached to the firing member body by a butt weld and a laser weld from both sides to interconnect the laminates forming the knife bar at the distal end. Such weld configuration may be more longitudinally compact than prior weld configurations and can lead to superior joint length. Other advantages may also be enjoyed from the foregoing firing member and lockout system arrangements.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

EXAMPLES

Example 1

A surgical instrument that comprises an elongate shaft assembly that defines a shaft axis. A surgical end effector is operably coupled to the elongate shaft assembly for selective articulation relative thereto about an articulation axis that is transverse to the shaft axis. The surgical end effector comprises a first end effector jaw that is coupled to an articulation joint that is coupled to the elongate shaft assembly. A second end effector jaw is coupled to the first end effector jaw for selective pivotal travel relative thereto about a jaw pivot axis that is transverse to the shaft axis. One of the first and second end effector jaws is configured to operably support therein a surgical fastener cartridge that comprises a proximal most fastener location. One of the first and second end effector jaws is movable between an open position and a fully closed position by an axially movable closure member that comprises a closure member cam surface that is configured for camming contact with a jaw cam surface on one of the first and second effector jaws. A first distance between the articulation axis and an area of camming contact between the closure member cam surface and the jaw cam surface divided by a second distance from the articulation axis to the proximal most fastener location is less than 0.5.

Example 2

The surgical instrument of Example 1, wherein the first distance between the jaw pivot axis and the area of camming contact between the closure cam member surface and the jaw cam surface divided by the second distance from the articulation axis to the proximal fastener location is greater than 0.2 and less than 0.5.

Example 3

The surgical instrument of Examples 1 or 2, wherein the surgical fastener cartridge is supported in the first end effector jaw and wherein the second end effector jaw comprises an anvil comprising the jaw cam surface.

Example 4

The surgical instrument of Examples 1, 2 or 3, wherein the jaw pivot axis is fixed.

Example 5

The surgical instrument of Example 3, wherein the anvil comprises at least one tissue stop member comprising a distal tissue contact surface that corresponds to the proximal most fastener location when the anvil is in the fully closed position.

Example 6

The surgical instrument of Examples 3 or 5, wherein the anvil comprises an anvil body and an anvil mounting portion that comprises the jaw cam surface and a pair of laterally extending anvil trunnions that are configured to be pivotally supported in corresponding openings in the first end effector jaw.

Example 7

The surgical instrument of Examples 1, 2, 3, 4, 5 or 6, wherein the closure member comprises an axially movable distal closure tube segment comprising the closure member cam surface.

Example 8

The surgical instrument of Example 7, wherein the elongate shaft assembly comprises a spine assembly that is operably coupled to the first end effector jaw and a proximal closure tube assembly that is movably supported for axial travel relative to the spine assembly and is pivotally coupled to the axially movable distal closure tube segment.

Example 9

The surgical instrument of Example 8, wherein the proximal closure tube assembly operably interfaces with a closure system that is configured to selectively apply axial closure and opening motions to the proximal closure tube assembly.

Example 10

The surgical instrument of Example 9, wherein the closure system is supported by a handheld housing.

Example 11

The surgical instrument of Example 10, wherein the closure system is supported by a housing that operably interfaces with a robotic controlled actuator.

Example 12

A surgical instrument that comprises an elongate shaft assembly that defines a shaft axis and further comprises a surgical end effector that is operably coupled to the elongate shaft assembly for selective articulation relative thereto about an articulation axis that is transverse to the shaft axis. The surgical end effector comprises an elongate channel that is coupled to an articulation joint that is coupled to the elongate shaft assembly. The elongate channel is configured to operably support a surgical fastener cartridge. The surgical fastener cartridge comprises a proximal most fastener location. The surgical end effector further comprises an anvil that is pivotally coupled to the elongate channel for selective pivotal travel relative thereto about a fixed anvil pivot axis that is transverse to the shaft axis. The anvil is movable between an open position and a fully closed position by an axially movable closure member that comprises a closure member cam surface that is configured for camming contact with an anvil cam surface on the anvil. A first distance between the articulation axis and an area of camming contact between the closure member cam surface and the cam surface divided by a second distance from the articulation axis to the proximal most fastener location is less than 0.5.

Example 13

The surgical instrument of Example 12, wherein the first distance between the anvil pivot axis and the area of camming contact between the closure member cam surface and the anvil cam surface divided by the second distance from the articulation axis to the proximal most fastener location is greater than 0.2 and less than 0.5.

Example 14

The surgical instrument of Examples 12 or 13, wherein the anvil comprises at least one tissue stop member that comprises a distal tissue contact surface that corresponds to the proximal most fastener location when the anvil is in the fully closed position.

Example 15

The surgical instrument of Examples 12, 13 or 14, wherein the anvil comprises an anvil body and an anvil mounting portion that comprises the anvil cam surface and a pair of laterally extending anvil trunnions that are configured to be pivotally supported in corresponding openings in the elongate channel.

Example 16

The surgical instrument of Examples 12, 13, 14 or 15, wherein the closure member comprises an axially movable distal closure tube segment that comprises the closure member cam surface.

Example 17

The surgical instrument of Example 16, wherein the elongate shaft assembly comprises a spine assembly that is operably coupled to the elongate channel. A proximal closure tube assembly is movably supported for axial travel relative to the spine assembly and is pivotally coupled to the axially movable distal closure tube segment.

Example 18

The surgical instrument of Example 17, wherein the proximal closure tube assembly operably interfaces with a closure system that is configured to selectively apply axial closure and opening motions to the proximal closure tube assembly.

Example 19

The surgical instrument of Example 18, further comprising a firing member that is operably supported for axial travel through the surgical fastener cartridge upon application of axial firing motions thereto.

Example 20

A surgical system that comprises a housing that operably supports a closure system therein. The surgical system further comprises an interchangeable surgical tool assembly that comprises an elongate shaft assembly that is operably and removably couplable to the housing such that a proximal closure portion thereof is configured to receive axial closure motions from the closure system. The elongate shaft assembly defines a shaft axis. A surgical end effector is operably coupled to the elongate shaft assembly for selective articulation relative thereto about an articulation axis that is transverse to the shaft axis. The surgical end effector comprises a first end effector jaw that is coupled to an articulation joint that is coupled to the elongate shaft assembly. A second end effector jaw is coupled to the first end effector jaw for selective pivotal travel relative thereto about a jaw pivot axis that is transverse to the shaft axis. One of the first and second end effector jaws is configured to operably support a surgical fastener cartridge that includes a proximal most fastener location. One of the first and second end effector jaws is movable between an open position and a fully closed position by an axially movable distal closure member that is operably coupled to the proximal closure portion of the elongate shaft assembly. The distal closure member comprises a closure member cam surface that is configured for camming contact with a jaw cam surface on one of the first and second end effector jaws. A first distance between the articulation axis and an area of camming contact between the closure member cam surface and the jaw cam surface divided by a second distance from the articulation axis to the proximal most fastener location is less than 0.5.

Example 21

A surgical instrument comprising an elongate shaft assembly that defines a shaft axis. A surgical end effector is operably coupled to the elongate shaft assembly for selective articulation relative thereto about an articulation axis that is transverse to the shaft axis. The surgical end effector also comprises a first end effector jaw that is coupled to an articulation joint that is coupled to the elongate shaft assembly. A second end effector jaw is coupled to the first end effector jaw for selective pivotal travel relative thereto about a jaw pivot axis that is transverse to the shaft axis. The surgical instrument further comprises an axially movable firing member that comprises at least one jaw engagement feature that is configured to apply a closure motion to the second end effector jaw as the axially movable firing member is moved from a starting position to an end position within the first end effector jaw. At least one jaw engagement feature is configured such that a portion thereof is positioned between the jaw pivot axis and the articulation axis when the axially movable firing member is in the starting position.

Example 22

The surgical instrument of Example 21, wherein the portion of at least one jaw engagement feature is positioned between the jaw pivot axis and the articulation axis when the axially movable firing member is in the starting position and the second end effector jaw is in a fully opened position.

Example 23

The surgical instrument of Examples 21 or 22, wherein at least thirty five percent of each jaw engagement feature is located between the jaw pivot axis and the articulation axis when the axially movable firing member is in the starting position.

Example 24

The surgical instrument of Example 22, wherein at least thirty-five percent of each jaw engagement feature is between the jaw pivot axis and the articulation axis when the axially movable firing member is in the starting position and the end effector second jaw is in a fully opened position.

Example 25

The surgical instrument of Examples 21, 22, 23 or 24, further comprising an axially movable closure member that is independently movable relative to the axially movable firing member and is configured to selectively apply additional closure motions to the second end effector jaw.

Example 26

The surgical instrument of Example 25, wherein the axially movable closure member comprises a closure member cam surface that is configured for camming contact with a jaw cam surface on the second end effector jaw.

Example 27

The surgical instrument of Examples 21, 22, 23, 24, 25 or 26, wherein the axially movable firing member comprises a tissue cutting surface.

Example 28

The surgical instrument of Examples 21, 22, 23, 24, 25, 26 or 27, wherein the first end effector jaw comprises an elongate channel that is configured to operably support a surgical fastener cartridge therein and wherein the second end effector jaw comprises an anvil.

Example 29

The surgical instrument of Examples 21, 22, 23, 24, 25, 26, 27 or 28, wherein the jaw pivot axis is fixed.

Example 30

A surgical instrument comprising an elongate shaft assembly that defines a shaft axis. A surgical end effector is operably coupled to the elongate shaft assembly for selective articulation relative thereto about an articulation axis that is transverse to the shaft axis. The surgical end effector comprises an elongate channel that is coupled to the elongate shaft assembly and is configured to operably support a surgical fastener cartridge therein. An anvil is coupled to the elongate channel for selective pivotal travel relative thereto about a fixed jaw pivot axis that is transverse to the shaft axis. The surgical instrument further comprises an axially movable firing member that comprises at least one anvil engagement feature that is configured to apply a closure motion to the anvil as the axially movable firing member is moved from a starting position to an end position within the elongate channel. At least one anvil engagement feature is configured such that a portion thereof is positioned between the fixed jaw pivot axis and the articulation axis when the axially movable firing member is in the starting position.

Example 31

The surgical instrument of Example 30, wherein the portion of the at least one anvil engagement feature is positioned between the fixed jaw pivot axis and the articulation axis when the axially movable firing member is in the starting position and the anvil is in a fully opened position.

Example 32

The surgical instrument of Examples 30 or 31, wherein at least thirty-five percent of each anvil engagement feature is located between the fixed jaw pivot axis and the articulation axis when the axially movable firing member is in the starting position.

Example 33

The surgical instrument of Examples 30, 31 or 32, wherein at least thirty-five percent of each anvil engagement feature is located between the fixed jaw pivot axis and the articulation axis when the axially movable firing member is in the starting position.

Example 34

The surgical instrument of Example 30, wherein at least thirty-five percent of each anvil engagement feature is located between the jaw pivot axis and the articulation axis when the axially movable firing member is in the starting position and the anvil is in a fully opened position.

Example 35

The surgical instrument of Examples 30, 31, 32, 33 or 34, further comprising an axially movable closure member that is independently movable relative to the axially movable firing member and is configured to selectively apply additional closure motions to the anvil.

Example 36

The surgical instrument of Example 35, wherein the axially movable closure member comprises a closure member cam surface that is configured for camming contact with an anvil cam surface on the anvil.

Example 37

The surgical instrument of Examples 30, 31, 32, 33, 34, 35 or 36, wherein the firing member comprises a tissue cutting surface.

Example 38

The surgical instrument of Examples 30, 31, 32, 33, 34, 35 or 36, wherein the firing member comprises a firing member body comprising a tissue cutting surface thereon and wherein at least one anvil engagement feature comprises a first anvil engagement tab that protrudes from a first lateral side of a top portion of the firing member body and a second anvil engagement tab that protrudes from a second lateral side of the top portion of the firing member body.

Example 39

The surgical instrument of Example 38, wherein the firing member body extends through a slot in an anvil mounting portion of the anvil when the firing member is in the starting position.

Example 40

A surgical system comprising a housing that operably supports a closure system and a firing system. The closure system and the firing system are independently actuatable relative to each other. The surgical system further comprises an interchangeable surgical tool assembly that comprises an elongate shaft assembly that is operably and removably couplable to the housing such that a proximal closure portion thereof is configured to receive axial closure motions from the closure system and a proximal firing member thereof is configured to receive firing motions from the firing system. The elongate shaft assembly defines a shaft axis. A surgical end effector is operably coupled to the elongate shaft assembly for selective articulation relative thereto about an articulation axis that is transverse to the shaft axis. The surgical end effector comprises an elongate channel that is coupled to the elongate shaft assembly and is configured to operably support a surgical fastener cartridge therein. An anvil is coupled to the elongate channel for selective pivotal travel relative thereto about a jaw pivot axis that is transverse to the shaft axis. An axially movable firing member is operably coupled to the proximal firing member and comprises at least one anvil engagement feature that is configured to apply a closure motion to the anvil as the axially movable firing member is moved from a starting position to an end position within the elongate channel. At least one anvil engagement feature is configured such that a portion thereof is positioned between the jaw pivot axis and the articulation axis when the axially movable firing member is in the starting position.

Example 41

The surgical system of Example 40, wherein the housing comprises a portion of a robotic system.

Example 42

A surgical instrument comprising an elongate shaft assembly that defines a shaft axis. A first end effector jaw is coupled to the elongate shaft assembly and a second end effector jaw is coupled to the first end effector jaw for selective pivotal travel relative thereto between a fully open position and a fully closed position about a fixed jaw pivot axis that is transverse to the shaft axis and extends therethrough. The elongate shaft assembly comprises a closure member that is axially movable between a starting position that corresponds to the fully open position of the second end effector jaw and an ending position that corresponds to a fully closed position of the second end effector jaw relative to the first end effector jaw. When the closure member is in the starting position, a distal end thereof is located on a plane that is spaced distally from the jaw pivot axis a distance that is measured along the shaft axis that is no more than 0.090 inches.

Example 43

The surgical instrument of Example 42, wherein when the closure member is in the starting position, the distal end of the closure member is located on the plane and the plane intersects the jaw pivot axis.

Example 44

The surgical instrument of Examples 42 or 43, wherein the distance is within 0.010-0.060 inches.

Example 45

The surgical instrument of Examples 42, 43 or 44, wherein the closure member comprises an axially movable distal closure tube segment that comprises a closure cam surface that is configured to cammingly engage a jaw cam surface on the second end effector jaw as the axially movable distal closure tube segment is moved from the starting position to the ending position.

Example 46

The surgical instrument of Examples 42, 43, 44 or 45, wherein the first end effector jaw comprises an elongate channel that is configured to operably support a surgical fastener cartridge therein and wherein the second end effector jaw comprises an anvil.

Example 47

The surgical instrument of Example 46, wherein the anvil comprises an anvil body and an anvil mounting portion that comprises an anvil cam surface and a pair of laterally extending anvil trunnions that are configured to be pivotally supported in corresponding openings in the elongate channel.

Example 48

The surgical instrument of Examples 46 or 47, wherein the closure member comprises an axially movable distal closure tube segment that comprises a closure cam surface that is configured to cammingly engage the anvil cam surface on the anvil as the axially movable distal closure tube segment is moved from the starting position to the ending position.

Example 49

The surgical instrument of Example 48, wherein the elongate shaft assembly comprises a spine assembly that is operably coupled to the elongate channel and a proximal closure tube assembly that is movably supported for axial travel relative to the spine assembly and is pivotally coupled to the axially movable distal closure tube segment.

Example 50

The surgical instrument of Example 49, wherein proximal closure tube assembly operably interfaces with a closure system that is configured to selectively apply axial closure and opening motions to the proximal closure tube assembly.

Example 51

The surgical instrument of Example 50, wherein closure system is supported by a handheld housing.

Example 52

The surgical instrument of Example 50, wherein the closure system is supported by a housing that operably interfaces with a robotic controlled actuator.

Example 53

A surgical instrument comprising an elongate shaft assembly that defines a shaft axis. An elongate channel is configured to operably support a surgical fastener cartridge therein and is operably coupled to the elongate shaft assembly for selective articulation relative thereto about an articulation axis that is transverse to the shaft axis. An anvil is pivotally coupled to the elongate channel for selective pivotal travel relative thereto between a fully open position and a fully closed position about a fixed jaw pivot axis that transversely intersects the shaft axis. The elongate shaft assembly comprises a closure member that is axially movable between a starting position that corresponds to the fully open position of the anvil and an ending position that corresponds to a fully closed position of the anvil. When the closure member is in the starting position, a distal end thereof is located on a plane that is spaced distally from the jaw pivot axis a distance that is measured along the shaft axis that is no more than 0.090 inches.

Example 54

The surgical instrument of Example 53, wherein when the closure member is in the starting position, the distal end of the closure member is located on the plane and the plane intersects the jaw pivot axis.

Example 55

The surgical instrument of Examples 53 or 54, wherein the distance is within 0.010-0.060 inches.

Example 56

The surgical instrument of Examples 53, 54 or 55, wherein the anvil comprises an anvil body and an anvil mounting portion that comprises an anvil cam surface and a pair of laterally extending anvil trunnions that are configured to be pivotally supported in corresponding openings in the elongate channel.

Example 57

The surgical instrument of Examples 53, 54, 55 or 56, wherein the closure member comprises an axially movable distal closure tube segment that comprises a closure cam surface that is configured to cammingly engage the anvil cam surface on the anvil as the axially movable distal closure tube segment is moved from the starting position and to the ending position.

Example 58

The surgical instrument of Example 57, wherein the elongate shaft assembly comprises a spine assembly that is operably coupled to the elongate channel and a proximal closure tube assembly that is movably supported for axial travel relative to the spine assembly and is pivotally coupled to the axially movable distal closure tube segment.

Example 59

The surgical instrument of Example 58, wherein the proximal closure tube assembly operably interfaces with a closure system that is supported by a handheld housing and is configured to selectively apply axial closure and opening motions to the proximal closure tube assembly.

Example 60

The surgical instrument of Example 58, wherein the proximal closure tube assembly operably interfaces with a closure system that is supported by a housing that is configured to interface with a robotic system. The closure system is configured to selectively apply axial closure and opening motions to the proximal closure tube assembly.

Example 61

A surgical system that comprises a housing that operably supports a closure system. The surgical system further comprises an interchangeable surgical tool assembly that comprises an elongate shaft assembly that is operably and removably couplable to the housing such that a proximal closure portion thereof is configured to receive axial closure motions from the closure system. The elongate shaft assembly defines a shaft axis. A surgical end effector is operably coupled to the elongate shaft assembly for selective articulation relative thereto about an articulation axis that is transverse to the shaft axis. The surgical end effector comprises an elongate channel that is coupled to the elongate shaft assembly and is configured to operably support a surgical fastener cartridge therein. An anvil is coupled to the elongate channel for selective pivotal travel relative thereto about a jaw pivot axis that transversely intersects the shaft axis. The elongate shaft assembly comprises a closure member that is axially movable between a starting position that corresponds to a fully open position of the anvil and an ending position that corresponds to a fully closed position of the anvil. When the closure member is in the starting position, a distal end thereof is located on a plane that is spaced distally from the jaw pivot axis a distance that is measured along the shaft axis that is no more than 0.090 inches.

Example 62

A surgical stapling device that comprises an elongate shaft assembly that defines a shaft axis. A surgical end effector is operably coupled to the elongate shaft assembly by an articulation joint that is configured to facilitate selective articulation of the surgical end effector about an articulation axis that is transverse to the shaft axis. The surgical end effector comprises a surgical staple cartridge that operably supports a plurality of surgical staples therein. An anvil is supported for selective pivotal travel relative to the surgical staple cartridge between a fully open position and a closed position. The anvil comprises a plurality of staple forming pockets that correspond to the surgical staples in the surgical staple cartridge. The surgical stapling device further comprises an axially movable firing member that comprises at least one anvil engagement feature thereon that is configured to engage the anvil when the anvil is in the closed position as the axially movable firing member is moved from a proximal most position to a distalmost position. The surgical stapling device also comprises means for increasing a jaw aperture distance between a distalmost staple in the surgical staple cartridge and a corresponding one of the staple forming pockets in the anvil while minimizing a joint distance between the articulation axis and a distal end of the anvil engagement feature on the axially movable firing member when the axially movable firing member is in the proximal most position.

Example 63

The surgical stapling device of Example 62, wherein the means for increasing comprises a closure member that is configured to apply closure motions to the anvil, wherein the closure member is axially movable between a starting position corresponding to the fully open position of the second end effector jaw and an ending position corresponding to a fully closed position of the anvil. When the closure member is in the starting position and the axially movable firing member is in the proximal most position, the distal end of the closure member is distally spaced from the distal end of the anvil engagement feature a horizontal distance that is within a range of 0.4-0.9 inches.

Example 64

The surgical stapling device of Example 63, wherein the horizontal distance is measured along a horizontal line that is parallel to or coincident with the shaft axis.

Example 65

The surgical stapling device of Examples 62, 63 or 64, wherein the closure member comprises an axially movable distal closure tube segment that comprises a closure cam surface that is configured to cammingly engage a cam surface on the anvil as the axially movable distal closure tube segment is moved from the starting position to the ending position.

Example 66

The surgical stapling device of Examples 62, 63, 64 or 65, wherein the surgical fastener cartridge is removably supported in an elongate channel that is operably coupled to the elongate shaft assembly by the articulation joint.

Example 67

The surgical stapling device of Example 66, wherein the anvil comprises an anvil body and an anvil mounting portion that comprises an anvil cam surface and a pair of laterally extending anvil trunnions that are configured to be pivotally supported in corresponding openings in the elongate channel.

Example 68

The surgical stapling device of Examples 63, 64, 65, 66 or 67, wherein the elongate shaft assembly comprises an axially movable proximal closure tube assembly and wherein the closure member comprises an axially movable distal closure tube segment that is operably coupled to the axially movable proximal closure tube assembly.

Example 69

The surgical stapling device of Example 68, wherein the axially movable distal closure tube segment comprises a closure cam surface that is configured to cammingly engage the anvil cam surface on the anvil as the axially movable distal closure tube segment is moved from the starting position to the ending position.

Example 70

The surgical stapling device of Examples 68 or 69, wherein the elongate shaft assembly comprises a spine assembly that is operably coupled to the elongate channel and movably supports at least a portion of the proximal closure tube assembly thereon and wherein the proximal closure tube assembly operably interfaces with a closure system that is configured to selectively apply axial closure and opening motions to the proximal closure tube assembly.

Example 71

The surgical stapling device of Example 70, wherein the closure system is supported by a handheld housing.

Example 72

The surgical stapling device of Example 70, wherein the closure system is supported by a housing that operably interfaces with a robotic controlled actuator.

Example 73

A surgical instrument that comprises an elongate shaft assembly that has an elongate channel coupled thereto that is configured to operably support a surgical fastener cartridge therein. An anvil is pivotally coupled to the elongate channel for selective pivotal travel relative thereto between a fully open position and a fully closed position about a fixed jaw pivot axis. A closure member is configured to apply closure motions to the anvil to move the anvil between the fully open position and the fully closed position as the closure member is moved from a starting position to an ending position. The surgical instrument further comprises an axially movably firing member that has at least one anvil engagement feature thereon that is configured to apply additional closure motions to the anvil as the axially movable firing member is moved from a proximal most position to a distalmost position within the elongate channel. When the closure member is in the starting position and the axially movable firing member is in the proximal most position, a distal end of the closure member is distal to a distal end of the anvil engagement feature.

Example 74

The surgical instrument of Example 73, wherein when the closure member is in the starting position and the axially movable firing member is in the proximal most position, the distal end of the closure member is distally spaced from the distal end of the anvil engagement feature a horizontal distance within a range of 0.4-0.9 inches.

Example 75

The surgical instrument of Example 74, wherein the elongate shaft assembly defines a shaft axis and wherein the horizontal distance is measured along a horizontal line that is parallel to or coincident with the shaft axis.

Example 76

The surgical instrument of Examples 73, 74 or 75, wherein the closure member comprises an axially movable distal closure tube segment that comprises a closure cam surface that is configured to cammingly engage an anvil cam surface on the anvil as the axially movable distal closure tube segment is moved from the starting position to the ending position.

Example 77

The surgical instrument of Example 76, wherein the elongate shaft assembly comprises a spine assembly that is operably coupled to the elongate channel. A proximal closure tube assembly is movably supported for axial travel relative to the spine assembly and is pivotally coupled to the axially movable distal closure tube segment.

Example 78

The surgical instrument of Example 77, wherein the proximal closure tube assembly operably interfaces with a closure system that is configured to selectively apply axial closure and opening motions to the proximal closure tube assembly.

Example 79

The surgical instrument of Example 78, wherein the closure system is supported by a handheld housing.

Example 80

The surgical instrument of Example 78, wherein the closure system is supported by a housing that operably interfaces with a robotic controlled actuator.

Example 81

A surgical system comprising a housing that operably supports a closure system. The surgical system further comprises an interchangeable surgical tool assembly that comprises an elongate shaft assembly that is operably and removably couplable to the housing such that a proximal closure portion thereof is configured to receive axial closure motions from the closure system. The elongate shaft assembly defines a shaft axis. The surgical tool assembly further comprises a surgical end effector that is operably coupled to the elongate shaft assembly for selective articulation relative thereto about an articulation axis that is transverse to the shaft axis. The surgical end effector comprises an elongate channel that is coupled to the elongate shaft assembly and is configured to operably support a surgical fastener cartridge therein. An anvil is coupled to the elongate channel for selective pivotal travel relative thereto between a fully open position and a fully closed position about a jaw pivot axis that is transverse to the shaft axis. The elongate shaft assembly comprises a distal closure member that is operably coupled to the proximal closure portion and is configured to apply closure motions to the anvil to move the anvil between the fully open position and the fully closed position as the distal closure member is moved from a starting position to an ending position. An axially movable firing member comprises at least one anvil engagement feature that is configured to apply additional closure motions to the anvil as the axially movable firing member is moved from a proximal most position to a distalmost position within the elongate channel. When the distal closure member is in the starting position and the axially movable firing member is in the proximal most position, a distal end of the distal closure member is distal to a distal end of the anvil engagement feature.

Example 82

A surgical instrument comprising a surgical end effector that comprises a first jaw that defines a first tissue contacting surface and a second jaw that is pivotally coupled to the first jaw. The second jaw is selectively movable between a fully open position and a fully closed position about a fixed jaw pivot axis. The second jaw comprises a second tissue contacting surface that faces the first tissue contacting surface. At least one tissue locating feature is on the second jaw and extends downward beyond the second tissue contacting surface and is configured to prevent tissue received between the first and second tissue contacting surfaces from extending proximally beyond a distal end portion of the at least one tissue locating feature when the second jaw is in the fully closed position. When the second jaw is in the fully open position, the distal end portion of each tissue locating feature is positioned relative to a corresponding portion of the first tissue contacting surface to prevent a gap therebetween. A jaw aperture angle between the first and second tissue contacting surfaces when the second jaw is in the fully open position is greater than 12.25 degrees.

Example 83

The surgical instrument of Example 82, wherein the distal end portion of each tissue locating feature is located a distance that is less than 0.750 inches from the fixed jaw pivot axis when the second jaw is in the fully closed position.

Example 84

The surgical instrument of Examples 82 or 83, wherein the first jaw comprises an elongate channel that is configured to operably support a surgical fastener cartridge therein and wherein the first tissue contacting surface comprises a deck surface of the surgical fastener cartridge.

Example 85

The surgical instrument of Examples 82, 83 or 84, wherein the second jaw comprises an anvil and wherein the second tissue contacting surface comprises a fastener forming undersurface of a portion of the anvil.

Example 86

The surgical instrument of Example 85, wherein the anvil comprises an anvil body portion and wherein the at least one tissue locating feature is formed on a proximal portion of the anvil body portion.

Example 87

The surgical instrument of Examples 82, 83, 84, 85 or 86, wherein the surgical end effector is sized to pass through a trocar cannula when the second jaw is in the fully closed position.

Example 88

The surgical instrument of Examples 82, 83, 84, 85, 86 or 87, further comprising means for applying closing and opening motions to the second jaw.

Example 89

The surgical instrument of Example 88, wherein the means for applying closing and opening motions comprises an axially movable closure tube. The closure tube comprises a closure cam surface on a distal end thereof that is configured to cammingly engage a jaw cam surface on the second jaw to apply closure motions thereto and at least one jaw opening feature that is configured to apply jaw opening motions to the second jaw when the axially movable closure tube is moved in a proximal direction.

Example 90

A surgical instrument comprising a surgical end effector that comprises a surgical fastener cartridge that comprises a cartridge body that operably supports a plurality of surgical fasteners therein. The cartridge body defines a tissue contacting surface through which the surgical fasteners are ejected. An anvil is pivotally supported relative to the surgical fastener cartridge for selective pivotal travel relative thereto between a fully open position and a fully closed position about a fixed jaw pivot axis. The anvil comprises an anvil body that defines a fastener forming surface that comprises a plurality of fastener forming formations, wherein each fastener forming formation corresponds to one of the surgical fasteners in the surgical fastener cartridge. The fastener forming surface faces the tissue contacting surface on the surgical fastener cartridge. At least one tissue stop protrudes from the anvil body and extends downward beyond the fastener forming surface and is configured to prevent tissue received between the tissue contacting surface and the fastener forming surface from extending proximally beyond a distal end portion of the tissue stop when the anvil is in the fully closed position. When the anvil is in the fully closed position, the distal end portion of each tissue stop is spaced from the fixed jaw pivot axis an axial distance that is less than 0.750 inches and wherein a vertical distance between a distalmost one of the fasteners in the surgical cartridge and a corresponding one of the fastener forming formations on the fastener forming surface when the anvil is in the fully open position is at least 0.900 inches.

Example 91

The surgical instrument of Example 90, wherein when the anvil is in the fully open position, a jaw aperture angle between the fastener forming surface and the tissue contacting surface is greater than 12.25 degrees.

Example 92

The surgical instrument of Examples 90 or 91, wherein the surgical end effector is sized to pass through a trocar cannula when the anvil is in the fully closed position.

Example 93

The surgical instrument of Examples 90, 91 or 92, further comprising means for applying closing and opening motions to the anvil.

Example 94

The surgical instrument of Example 93, wherein the means for applying closing and opening motions comprises an axially movable closure tube. The axially movable closure tube comprises a closure cam surface on a distal end thereof that is configured to cammingly engage an anvil cam surface on the anvil to apply closure motions thereto. At least one jaw opening feature is configured to apply jaw opening motions to the anvil when the axially movable closure tube is moved in a proximal direction.

Example 95

The surgical instrument of Examples 90, 91, 92, 93 or 94, wherein the surgical end effector is operably coupled to an elongate shaft assembly that defines a shaft axis.

Example 96

The surgical instrument of Example 95, wherein the tissue contacting surface of the cartridge body is parallel to the shaft axis and wherein the vertical distance is measured along a line extending from a distal most fastener and the corresponding fastener forming formation and perpendicular to the shaft axis.

Example 97

The surgical instrument of Example 90, 91, 92, 93, 94, 95 or 96, wherein the when the anvil is in the fully open position, the distal end portion of each tissue stop is positioned relative to a corresponding portion of the tissue contacting surface to prevent a gap therebetween.

Example 98

The surgical instrument of Example 97, wherein when the anvil is in the fully open position, a portion of each tissue stop is even with or extends below the tissue contacting surface to prevent tissue on the tissue contacting surface from extending proximally past the tissue stops.

Example 99

The surgical instrument of Examples 90, 91, 92, 93, 94, 95, 96, 97 or 98, wherein when the anvil is in the fully open position, a portion of each tissue stop is even with or extends below the tissue contacting surface to prevent tissue on the tissue contacting surface from extending proximally past the tissue stops.

Example 100

A surgical system comprising a housing that operably supports a closure system. An interchangeable surgical tool assembly comprises an elongate shaft assembly that is operably and removably couplable to the housing such that a proximal closure portion thereof is configured to receive axial closure motions from the closure system and defines a shaft axis. A surgical end effector is operably coupled to the elongate shaft assembly for selective articulation relative thereto about an articulation axis that is transverse to the shaft axis. The surgical end effector comprises a surgical fastener cartridge that comprises a cartridge body that operably supports a plurality of surgical fasteners therein and defines a tissue contacting surface through which the surgical fasteners are ejected. An anvil is pivotally supported relative to the surgical fastener cartridge for selective pivotal travel relative thereto between a fully open position and a fully closed position about a fixed jaw pivot axis. The anvil comprises an anvil body that defines a fastener forming surface that comprises a plurality of fastener forming formations, wherein each fastener forming formation corresponds to one of the surgical fasteners in the surgical fastener cartridge. The fastener forming surface faces the tissue contacting surface on the surgical fastener cartridge. At least one tissue stop protrudes from the anvil body and extends downward beyond the fastener forming surface and is configured to prevent tissue that is received between the tissue contacting surface and the fastener forming surface from extending proximally beyond a distal end portion of at least one tissue stop when the anvil is in the fully closed position. When the anvil is in the fully closed position, the distal end portion of each tissue stop is spaced from the fixed jaw pivot axis an axial distance that is less than 0.750 inches and wherein a vertical distance between a distalmost one of the fasteners in the surgical cartridge and a corresponding one of the fastener forming formations on the fastener forming surface when the anvil is in the fully open position is at least 0.900 inches.

Example 101

The surgical instrument of Example 100, wherein, when the anvil is in the fully open position, a jaw aperture angle between the fastener forming surface the tissue contacting surface is greater than 12.25 degrees.

Example 102

The surgical instrument of Examples 100 or 101, wherein the surgical end effector is sized to pass through a trocar cannula when the anvil is in the fully closed position.

Example 103

A surgical instrument that comprises a first jaw that includes a pair of laterally aligned vertical slots that are formed in a proximal end portion of the first jaw. Each vertical slot has an open upper end. A second jaw is movably supported for selective pivotal travel relative to the first jaw between a fully open and a fully closed position. The second jaw comprises a second jaw body and a pair of pivot members that protrude laterally from a proximal end of the second jaw body. Each pivot member is pivotally received in a corresponding one of the vertical slots in the first jaw such that the pivot members may pivot therein to facilitate pivotal travel of the second jaw relative to the first jaw. The surgical instrument further comprises a retainer member that is configured to operably engage the proximal end portion of the first jaw and retain the pivot members in the corresponding vertical slots as the second jaw moves between the fully open and the fully closed positions. An axially movable closure member is configured to apply closing and opening motions to the second jaw and retain the retainer member in retaining engagement with the proximal end portion of the first jaw.

Example 104

The surgical instrument of Example 103, wherein each pivot member has a circular cross-sectional shape and wherein the retainer member comprises a slot cap that corresponds to each vertical slot and is sized to extend therein through the open end. Each slot cap has an arcuate bottom portion that is configured to pivotally receive the corresponding pivot pin therein.

Example 105

The surgical instrument of Example 103, wherein each vertical slot is formed in a corresponding upstanding vertical wall portion of the first jaw and wherein the retainer member comprises a retainer body that is sized to span between the vertical wall portions. The retainer member further comprises a slot cap that corresponds to each vertical slot and is sized to extend therein through the open end. A mounting formation is on the retainer body and corresponds to each upstanding vertical wall portion and is configured to be seated in a correspondingly shaped mounting opening therein.

Example 106

The surgical instrument of Example 105, wherein the mounting formations are located proximal to the slot caps.

Example 107

The surgical instrument of Examples 103, 104, 105 or 106, wherein the axially movable closure member comprises an axially movable distal closure tube segment that is sized to slidably move over the retainer member to provide opening and closing motions to the second jaw and retain the retainer member in retaining engagement with the proximal end portion of the first jaw.

Example 108

The surgical instrument of Example 107, wherein the first jaw is operably coupled to an elongate shaft assembly.

Example 109

The surgical instrument of Example 108, wherein the elongate shaft assembly comprises a spine assembly that is operably coupled to the first jaw. A proximal closure tube assembly is movably supported for axial travel relative to the spine assembly and is pivotally coupled to the axially movable distal closure tube segment.

Example 110

The surgical instrument of Example 109, wherein the proximal closure tube assembly operably interfaces with a closure system that is configured to selectively apply axial closure and opening motions to the proximal closure tube assembly.

Example 111

The surgical instrument of Example 110, wherein the closure system is supported by a handheld housing.

Example 112

The surgical instrument of Example 110, wherein the closure system is supported by a housing that operably interfaces with a robotic controlled actuator.

Example 113

A surgical instrument comprising an elongate channel that is configured to operably support a surgical fastener cartridge therein. The elongate channel includes a pair of laterally aligned vertical slots that are formed in a proximal end portion of the elongate channel wherein each vertical slot includes an open upper end. An anvil is movably supported for selective pivotal travel relative to the elongate channel between a fully open and a fully closed position. The anvil comprises an anvil body and a pair of anvil trunnions that protrude laterally from an anvil mounting portion of the anvil body. Each anvil trunnion is pivotally received in a corresponding vertical slot in the elongate channel such that the anvil trunnions may pivot therein to facilitate pivotal travel of the anvil relative to the elongate channel. The surgical instrument further comprises a retainer member that is configured to be supported on the proximal end portion of the elongate channel and pivotally retain each anvil trunnion in the corresponding vertical slots as the anvil moves between the fully open and fully closed positions. An axially movable closure member is configured to apply closing and opening motions to the anvil and retain the retainer member in retaining engagement with the proximal end portion of the elongate channel.

Example 114

The surgical instrument of Example 113, wherein each anvil trunnion comprises a circular cross-sectional shape and wherein the retainer member comprises a slot cap that corresponds to each vertical slot and is sized to extend therein through the open end. Each slot cap has an arcuate bottom portion that is configured to pivotally receive the corresponding anvil trunnion therein.

Example 115

The surgical instrument of Example 113, wherein each vertical slot is formed in a corresponding upstanding vertical wall portion of the elongate channel and wherein the retainer member comprises a retainer body that is sized to span between the vertical wall portions. The retainer member further comprises a slot cap that corresponds to each vertical slot and is sized to extend therein through the open end. The retainer member also comprises mounting formations on the retainer body that correspond to each upstanding vertical wall portion and are configured to be seated in a correspondingly shaped mounting opening therein.

Example 116

The surgical instrument of Example 115, wherein the slot cap has a wedge shape that is configured to be inserted into the open end of the corresponding vertical slot.

Example 117

The surgical instrument of Examples 113, 114, 115 or 116, wherein the retainer member is affixed to the elongate channel by at least one of frictional engagement with the elongate channel, adhesive and welding.

Example 118

The surgical instrument of Examples 113, 114, 115, 116 or 117, wherein the axially movable closure member comprises an axially movable distal closure tube segment that is sized to slidably move over the retainer member to provide opening and closing motions to the anvil and retain the retainer member in retaining engagement with the proximal end portion of the elongate channel.

Example 119

The surgical instrument of Examples 113, 114, 115, 116, 117 or 118, wherein the elongate channel is operably coupled to an elongate shaft assembly.

Example 120

The surgical instrument of Example 119, wherein the elongate shaft assembly comprises a spine assembly that is operably coupled to the elongate channel and a proximal closure tube assembly that is movably supported for axial travel relative to the spine assembly and is pivotally coupled to the axially movable closure member.

Example 121

A surgical system comprising a housing that operably supports a closure system. The surgical system further comprises an interchangeable surgical tool assembly that includes an elongate shaft assembly that is operably and removably couplable to the housing such that a proximal closure portion thereof is configured to receive axial closure motions from the closure system. The interchangeable surgical tool assembly further comprises a surgical end effector that comprises an elongate channel that is configured to operably support a surgical fastener cartridge therein and includes a pair of laterally aligned vertical slots that are formed in a proximal end portion of the elongate channel. Each vertical slot includes an open upper end. An anvil is movably supported for selective pivotal travel relative to the elongate channel between a fully open and a fully closed position. The anvil comprises an anvil body and a pair of anvil trunnions that protrude laterally from an anvil mounting portion of the anvil body. Each anvil trunnion is pivotally received in a corresponding vertical slot in the elongate channel such that the anvil trunnions may pivot therein to facilitate pivotal travel of the anvil relative to elongate channel. The surgical system further comprises a retainer member that is configured to be supported on the proximal end portion of the elongate channel and pivotally retain each anvil trunnion in the corresponding vertical slots as the anvil moves between the fully open and the fully closed positions. An axially movable closure member is configured to apply closing and opening motions to the anvil and retain the retainer member in retaining engagement with the proximal end portion of the elongate channel.

Example 122

The surgical system of Example 121, wherein the axially movable closure member comprises an axially movable distal closure tube segment that is sized to slidably move over the retainer member to provide opening and closing motions to the anvil and retain the retainer member in retaining engagement with the proximal end portion of the elongate channel. The elongate shaft assembly further comprises a spine assembly that is operably coupled to the elongate channel; and a proximal closure tube assembly that is movably supported for axial travel relative to the spine assembly and is pivotally coupled to the axially movable distal closure tube segment.

Example 123

A surgical instrument comprising a first jaw and a second jaw that is coupled to the first jaw for selective pivotal travel relative thereto between a fully open position and a fully closed position. An axially movable closure member is selectively axially movable in a closure direction to move the second jaw from the fully open position to the fully closed position and in an axial opening direction to move the second jaw from the fully closed position to the fully open position. The axially movable closure member comprises a first jaw opening feature that is configured to apply a first jaw opening motion to the second jaw. A second jaw opening feature is axially spaced from the first jaw opening feature such that, when the closure member is moved in the axial opening direction, the first jaw opening feature applies the first jaw opening motion to the second jaw and when the closure member has axially moved a predetermined axial distance in the axial opening direction, the first jaw opening feature discontinues application of the first jaw opening motion and the second jaw opening feature applies a second jaw opening motion to the second jaw to move the second jaw to the fully open position.

Example 124

The surgical instrument of Example 123, wherein the first jaw opening feature is axially proximal to the second jaw opening feature.

Example 125

The surgical instrument of Examples 123 or 124, wherein the first jaw defines a central jaw axis wherein the first jaw opening feature is axially spaced from the central jaw axis on a first lateral side thereof on the closure member and wherein the second jaw opening feature is spaced from the central jaw axis on a second lateral side thereof that is opposite to the first lateral side on the closure member.

Example 126

The surgical instrument of Examples 123, 124 or 125, wherein the second jaw comprises a second jaw mounting portion that is pivotally supported on the first jaw. The second jaw mounting portion comprises a second jaw cam surface on the second jaw mounting portion and is configured to be axially cammingly contacted by the first jaw opening feature as the closure member is axially moved in the axial opening direction through the predetermined axial distance. The second jaw cam surface is configured to disengage the first jaw opening feature as the closure member continues to move in the axial opening direction beyond the predetermined axial distance. The second jaw mounting portion further comprises a second jaw cam surface that is configured to be axially camming contacted by the second jaw opening feature as the closure member continues to move in the axial opening direction beyond the predetermined axial distance.

Example 127

The surgical instrument of Example 126, wherein the closure member is axially movable in the axial opening direction from a first position corresponding to the fully closed position of the second jaw to a first intermediate axial position without applying the first jaw opening motion thereto.

Example 128

The surgical instrument of Example 127, wherein when the closure member is axially moved in the axial opening direction from the first intermediate axial position to a second intermediate axial position, the first jaw opening feature applies the first jaw opening motion to the second jaw to cause the second jaw to move relative to the first jaw through a second jaw aperture angle.

Example 129

The surgical instrument of Example 128, wherein the second jaw aperture angle is 10°.

Example 130

The surgical instrument of Examples 128 or 129, wherein when the closure member is axially moved in the axial opening direction between the second intermediate axial position and a third intermediate axial position, the first jaw opening feature does not move the second jaw relative to the first jaw beyond the second jaw aperture angle.

Example 131

The surgical instrument of Example 130, wherein axial movement of the closure member in the axial opening direction from the third intermediate axial position to a fourth intermediate axial position, causes the second jaw opening feature to apply the second jaw opening motion to the second jaw.

Example 132

The surgical instrument of Example 131, wherein axial movement of the closure member in the axial opening direction between the third intermediate axial position and the fourth intermediate axial position causes the second jaw to move relative to the first jaw to a second jaw aperture angle.

Example 133

The surgical instrument of Example 132, wherein the second jaw aperture angle is 22°.

Example 134

The surgical instrument of Examples 131, 132 or 133, wherein axial movement of the closure member in the axial opening direction from the third intermediate axial position to the fourth intermediate axial position causes the first jaw opening feature to discontinue application of the first jaw opening motion to the second jaw.

Example 135

The surgical instrument of Example 134, wherein axial movement of the closure member in the axial opening direction from the fourth intermediate axial position to a final axial position causes the second jaw opening feature to discontinue application of the second jaw opening motion to the second jaw.

Example 136

The surgical instrument of Examples 123, 124, 125, 126, 127, 128, 129, 130, 131, 132, 133, 134 or 135, wherein the first jaw comprises a surgical fastener cartridge and wherein the second jaw comprises an anvil.

Example 137

A surgical instrument comprising an elongate channel that is configured to operably support a surgical fastener cartridge therein. An anvil is pivotally supported on the elongate channel for selective pivotal travel relative thereto between a fully open position and a fully closed position. An axially movable closure member is selectively axially movable in a closure direction to move the anvil from the fully open position to the fully closed position and in an axial opening direction to move the anvil from the fully closed to the fully open position. The axially movable closure member comprises a proximal jaw opening feature that is configured to apply a first jaw opening motion to the anvil. A distal jaw opening feature is axially spaced from the proximal jaw opening feature such that, when the closure member is moved in the axial opening direction, the proximal jaw opening feature applies the first jaw opening motion to the anvil and when the closure member has axially moved a predetermined axial distance in the axial opening direction, the proximal jaw opening feature discontinues application of the first jaw opening motion and the distal jaw opening feature applies a second jaw opening motion to the anvil to move the anvil to the fully open position.

Example 138

The surgical instrument of Example 137, wherein when the closure member is axially moved in the axial opening direction from a first intermediate axial position to a second intermediate axial position, the first jaw opening feature causes the anvil to move through a first jaw aperture angle that is measured between a deck surface of the surgical fastener cartridge that is supported in the elongate channel and a fastener forming underside of the anvil.

Example 139

The surgical instrument of Example 138, wherein the first jaw aperture angle is 10°.

Example 140

The surgical instrument of Examples 138 or 139, wherein when the closure member is axially moved in the axial opening direction between the second intermediate axial position and a third intermediate axial position, the first jaw opening feature does not move the anvil relative to the elongate channel beyond the first jaw aperture angle.

Example 141

The surgical instrument of Example 140, wherein axial movement of the closure member in the axial opening direction from the third intermediate axial position to a fourth intermediate axial position, causes the second jaw opening feature to move the anvil through a second jaw aperture angle that is greater than the first jaw aperture angle.

Example 142

A surgical instrument comprising an elongate channel that is configured to operably support a surgical fastener cartridge therein. An anvil is pivotally supported on the elongate channel for selective pivotal travel relative thereto between a fully open position and a fully closed position. An axially movable distal closure tube segment is selectively axially movable in a closure direction to move the anvil from the fully open position to the fully closed position and in an axial opening direction to move the anvil from the fully closed position to the fully open position. The axially movable distal closure tube segment comprises a proximal jaw opening feature that is formed on the distal closure tube segment and is configured to apply a first jaw opening motion to the anvil. A distal jaw opening feature is formed on the distal closure tube segment and is axially spaced from the proximal jaw opening feature such that, when the distal closure tube segment is moved in the axial opening direction, the proximal jaw opening feature applies the first jaw opening motion to the anvil and when the distal closure tube segment has axially moved a predetermined axial distance in the opening direction, the proximal jaw opening feature discontinues application of the first jaw opening motion and the distal jaw opening feature applies a second jaw opening motion to the anvil to move the anvil to the fully open position.

Example 143

A surgical instrument comprising a first jaw and a second jaw that is coupled to the first jaw for selective pivotal travel relative thereto between a fully open position and a fully closed position. A closure member is configured to apply closure motions to the second jaw as the closure member is axially movable in a distal direction from a starting position corresponding to the fully open position of the second jaw to an ending position corresponding to the fully closed position of the second jaw. The closure member is further configured to move distally from the starting position an initial predetermined axial closure distance before applying the closure motion to the second jaw.

Example 144

The surgical instrument of Example 143, wherein the initial predetermined axial closure distance is 0.020 inches.

Example 145

The surgical instrument of Examples 143 or 144, wherein closure member is configured to distally move through a final predetermined axial closure distance after the second jaw has been moved to the fully closed position.

Example 146

The surgical instrument of Example 145, wherein the final predetermined axial closure distance is 0.040 inches.

Example 147

The surgical instrument of Examples 143, 144, 145 or 146, wherein the closure member comprises a closure camming surface that is configured to cammingly engage a jaw camming surface on the second jaw to apply the closure motions thereto.

Example 148

The surgical instrument of Examples 143, 144, 145, 146 or 147, wherein the closure member further comprises means for applying opening motions to the second jaw when the closure member axially moves in a proximal direction from the ending position to the starting position.

Example 149

The surgical instrument of Example 148, wherein the means for applying opening motions comprises a first jaw opening feature on the closure member that is configured to apply a first amount of jaw opening motion to the second jaw as the closure member is axially moved from the ending position to an intermediate axial position between the ending and starting position. The means further comprises a second jaw opening feature on the closure member that is axially spaced from the first jaw opening feature and is configured to apply a second amount of jaw opening motion to the second jaw as the closure member is axially moved from the intermediate position to the starting position.

Example 150

A surgical instrument comprising an elongate channel that is configured to operably support a surgical staple/fastener cartridge therein. An anvil is pivotally supported on the elongated channel for selective pivotal travel relative thereto between a fully open position and a fully closed position. A closure member is configured to apply closure motions to the anvil as the closure member is axially movable in a distal direction from a starting position corresponding to the fully open position of the anvil to an ending position corresponding to the fully closed position of the anvil. The closure member is configured to move distally from the starting position an initial predetermined axial closure distance before applying the closure motion to the anvil.

Example 151

The surgical instrument of Example 150, wherein the initial predetermined axial closure distance is 0.020 inches.

Example 152

The surgical instrument of Examples 150 or 151, wherein the closure member is configured to distally move through a final predetermined axial closure distance after the anvil has been moved to the fully closed position.

Example 153

The surgical instrument of Example 152, wherein the final predetermined axial closure distance is 0.040 inches.

Example 154

The surgical instrument of Examples 152 or 153, wherein the closure member is configured to apply the closure motion to the anvil as the closure member moves distally through an intermediate predetermined axial closure distance after the closure member traveled the initial predetermined axial closure distance and prior to traveling the final predetermined axial closure distance.

Example 155

The surgical instrument of Example 154, wherein the intermediate predetermined axial closure distance is 0.200 inches.

Example 156

The surgical instrument of Examples 150, 151, 152, 153, 154 or 155, wherein the closure member comprises a closure camming surface configured to cammingly engage an anvil camming surface on an anvil mounting portion of the anvil to apply the closure motion thereto.

Example 157

The surgical instrument of Examples 150, 151, 152, 153, 154, 155, 156 or 157, wherein the closure member further comprises means for applying opening motions to the anvil when the closure member axially moves in a proximal direction from the ending position to the starting position.

Example 158

The surgical instrument of Example 157, wherein the means for applying opening motions comprises a first jaw opening feature on the closure member that is configured to apply a first amount of jaw opening motion to the anvil as the closure member is axially moved from the ending position to an intermediate axial position between the ending position and starting position. The means further comprises a second jaw opening feature on the closure member that is axially spaced from the first jaw opening feature and is configured to apply a second amount of jaw opening motion to the anvil as the closure member is axially moved from the intermediate axial position to the starting position.

Example 159

A surgical system comprising a housing that operably supports a closure system. The surgical system further comprises an interchangeable surgical tool assembly that comprises an elongate shaft assembly that is operably and removably couplable to the housing such that a proximal closure portion of the elongate shaft assembly is configured to receive axial closure motions from the closure system. The interchangeable surgical tool assembly further comprises a surgical end effector that is operably coupled to the elongate shaft assembly. The surgical end effector comprises an elongate channel that is coupled to the elongate shaft assembly and is configured to operably support a surgical fastener cartridge therein. An anvil is coupled to the elongate channel for selective pivotal travel relative thereto between a fully open position and a fully closed position. The elongate shaft assembly comprises an axially movable proximal closure member that is configured to receive the axial closure motions. A distal closure member is operably coupled to the proximal closure member and is configured to apply the axial closure motions to the anvil as the distal closure member is axially movable in a distal direction from a starting position corresponding to the fully open position of the anvil to an ending position corresponding to the fully closed position of the anvil. The distal closure member is configured to move distally from the starting position an initial predetermined axial closure distance before applying the closure motions to the anvil.

Example 160

The surgical instrument of Example 159, wherein the distal closure member is configured to distally move through a final predetermined axial closure distance after the anvil has been moved to the fully closed position.

Example 161

A surgical tool assembly that comprises a first jaw and a second jaw that is movable relative to the first jaw. The surgical tool assembly further comprises a firing system that comprises a firing member assembly that is configured to move distally from a starting position upon application of a firing motion thereto. The firing member assembly comprises a first firing member element and a second firing member element that is pivotally coupled to the first firing member element at an attachment joint. The second firing member element is configured to move between a locked position wherein the second firing member element is in locking engagement with a lockout portion of the first jaw to prevent the firing member assembly from moving distally from the starting position upon application of the firing motion thereto and an unlocked position wherein the firing member assembly is distally advanceable from the starting position upon the application of the firing motion to the firing member assembly. The surgical tool assembly further comprises means for preventing an unlocking load from being applied to the attachment joint when the second firing member is in the locked position and the firing motion is applied to the first firing member element.

Example 162

The surgical tool assembly of Example 161, wherein the lockout portion comprises at least one lockout notch in the first jaw that is configured to retainingly engage the second firing member element when the second firing member element is in the locked position.

Example 163

The surgical tool assembly of Examples 161 or 162, further comprising a biasing member in the first jaw that is configured to bias the second firing member element into the locked position.

Example 164

The surgical tool assembly of Examples 161, 162 or 163, wherein the first firing member element comprises at least one first jaw engaging feature that is configured to be movably received within a corresponding first jaw passage and at least one second jaw engaging feature that is configured to be movably received within a corresponding second jaw passage.

Example 165

The surgical tool assembly of Example 164, wherein when the firing member assembly is in the starting position, each first jaw engaging feature is in axial alignment with the corresponding first jaw passage and each second jaw engaging feature is in axial alignment with the corresponding second jaw passage regardless of a position of the second firing member element.

Example 166

The surgical tool assembly of Example 165, wherein when the firing member assembly is in the starting position and the second firing member element is in the locked position, each first jaw engaging feature is in axial alignment with the corresponding first jaw passage and each said second jaw engaging feature is in axial alignment with the corresponding second jaw passage.

Example 167

The surgical tool assembly of Examples 161, 162, 163, 164, 165 or 166, wherein the first jaw is configured to operably support a removable surgical component therein that operably supports a movable component element therein. The movable component element is movable between an unfired and fired positions. The second firing member element is configured to be moved from the locked position by the movable component element when the removable surgical component is supported in the first jaw and the movable component element is in the unfired position.

Example 168

The surgical tool assembly of Examples 161, 162, 163, 164, 165, 166 or 167, wherein the first jaw is operably coupled to an elongate shaft that defines a shaft axis and wherein the second firing member element is pivotable relative to the first firing member element about a pivot axis that is transverse to the shaft axis.

Example 169

The surgical tool assembly of Claim Examples 161, 162, 163, 164, 165, 166, 167 or 168, wherein the first firing member element comprises a tissue cutting surface.

Example 170

The surgical tool assembly of Examples 161, 162, 163, 164, 165, 166, 168 or 169, wherein the first jaw is configured to operably support a surgical staple cartridge that operably supports a sled therein. The sled is movable between an unfired position and fired positions. The second firing member element is configured to be moved from the locked position by the sled when the surgical staple cartridge is supported in the first jaw and the sled is in the unfired position.

Example 171

The surgical tool assembly of Examples 161, 162, 163, 164, 165, 166, 167, 168, 169 or 170, wherein the means for preventing comprises a distal surface and a lockout surface on the first firing member element. The distal surface is configured relative to a proximal surface on the second firing member element such that a space is provided therebetween when the second firing member is in the unlocked position. The proximal surface abuts the lockout surface when the second firing member element is in the locked position.

Example 172

The surgical tool assembly of Examples 161, 162, 163, 164, 165, 166, 167, 168, 169, 170 or 171, wherein the attachment joint comprises at least one pivot member on the second firing member element and pivotally received within a corresponding pivot hole in the first firing member element.

Example 173

The surgical tool assembly of Example 172, further comprising a clearance between each pivot member and its corresponding pivot hole such that the unlocking load is not transferred to the at least one pivot member when the second firing member is in the locked position and the firing motion is applied to the first firing member element.

Example 174

A stapling assembly comprising an anvil jaw and a staple cartridge jaw comprising a lockout surface. A firing member includes a distal end that comprises anvil-camming portions and channel-camming portions. The firing member further comprises a distal edge that comprises a cutting member and a lockout force-receiving surface. A lockout member is pivotally coupled to the distal end of the firing member by at least one pivot member. The lockout member is configured to engage the lockout surface of the staple cartridge jaw to block the advancement of the firing member when a staple cartridge is not installed within the staple cartridge jaw or when a partially-spent staple cartridge is installed within the staple cartridge jaw and a firing motion is applied to the firing member. The firing member and the lockout member are configured to prevent an unlocking load from being applied to the pivot members when the lockout member is in engagement with the lockout surface and the firing motion is applied to the firing member.

Example 175

The stapling assembly of Example 174, wherein the staple cartridge jaw comprises a staple cartridge that includes a sled that is movable between an unfired position and a fired position. The sled is configured to engage the lockout member to prevent the lockout member from moving relative to the firing member to engage the lockout surface when the sled is in the unfired position.

Example 176

The stapling assembly of Examples 174 or 175, further comprising a spring that is configured to bias the lockout member relative to the firing member into a locked configuration when a partially-spent staple cartridge is present and when a staple cartridge is not present.

Example 177

The stapling assembly of Examples 174, 175 or 176, wherein the firing member is configured to not move substantially vertically.

Example 178

A surgical fastening instrument that comprises a first jaw that is configured to operably support an unfired surgical fastener cartridge therein. An anvil is movably supported relative to the first jaw. The surgical fastening instrument further includes a firing system that comprises a firing member assembly that is configured to axially move between a starting position and an ending position. The firing member assembly comprises a firing member that comprises a cutting surface and a tippable element that is pivotally coupled to the firing member by an attachment joint. The tippable element is configured to move relative to the firing member between a locked position wherein the tippable element is in locking engagement with a lockout portion of the first jaw to prevent the firing member assembly from moving distally from the starting position upon application of a firing motion thereto and an unlocked position wherein the firing member assembly is distally advanceable from the starting position upon the application of the firing motion to the firing member assembly. The firing member and tippable element are configured to prevent an unlocking load from being applied to the attachment joint when the tippable element is the locked position and the firing motion is applied to the firing member assembly. The surgical fastening instrument further comprises means for biasing the tippable element into the locking engagement unless an unfired surgical fastener cartridge is operably supported in the first jaw.

Example 179

The surgical fastening instrument of Example 178, wherein the attachment joint comprises at least one pivot member that is on the tippable element and is pivotally received within a corresponding pivot hole in the firing member.

Example 180

The surgical fastening instrument of Example 179, further comprising a clearance between each pivot member and its corresponding pivot hole such that the unlocking load is not transferred to each pivot member when the tippable element is in the locked position and the firing motion is applied to the firing member assembly.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments.

Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical system, comprising:
    a housing operably supporting a closure system;
    an interchangeable surgical tool assembly comprising:
        an elongate shaft assembly operably and removably couplable to said housing such that a proximal closure portion thereof is configured to receive axial closure motions from said closure system; and
        a surgical end effector operably coupled to said elongate shaft assembly, said surgical end effector comprising:
            an elongate channel coupled to said elongate shaft assembly and configured to operably support a surgical fastener cartridge therein;
            an anvil coupled to said elongate channel for selective pivotal travel relative thereto between a fully open position and a fully closed position wherein said elongate shaft assembly comprises:
                an axially movable proximal closure member configured to receive said axial closure motions; and
                a distal closure member operably coupled to said axially movable proximal closure member and configured to apply said axial closure motions to said anvil as said distal closure member is axially moved in a distal direction from a starting position corresponding to said fully open position of said anvil to an ending position corresponding to said fully closed position of said anvil, said distal closure member configured to move distally from said starting position an initial predetermined axial closure distance before applying said axial closure motions to said anvil, and wherein said distal closure member further comprises:
                    a first jaw opening feature on said distal closure member on one side of a shaft axis, wherein said first jaw opening feature is configured to apply a first amount of jaw opening motion to said anvil as said distal closure member is axially moved from said ending position to an intermediate axial position between said ending position and said starting position; and
                    a second jaw opening feature on said distal closure member on another side of said shaft axis, wherein said second jaw opening feature is axially spaced from said first jaw opening feature, and wherein said second jaw opening feature is configured to apply a second amount of jaw opening motion to said anvil as said distal closure member is axially moved from said intermediate axial position to said starting position.

2. The surgical system of claim 1, wherein said distal closure member is configured to distally move through a final predetermined axial closure distance after said anvil has been moved to said fully closed position.

3. The surgical system of claim 1, wherein said initial predetermined axial closure distance is 0.020 inches.

4. The surgical system of claim 2, wherein said final predetermined axial closure distance is 0.040 inches.

5. The surgical system of claim 2, wherein said distal closure member is configured to apply said axial closure motions to said anvil as said distal closure member moves distally through an intermediate predetermined axial closure distance after said distal closure member traveled said initial predetermined axial closure distance and prior to traveling said final predetermined axial closure distance.

6. The surgical system of claim 5, wherein said intermediate predetermined axial closure distance is 0.200 inches.

7. The surgical system of claim 1, wherein said distal closure member comprises a closure camming surface configured to cammingly engage an anvil camming surface on said anvil to apply said axial closure motions thereto.

8. A surgical instrument, comprising:
a first jaw;
a second jaw coupled to said first jaw for selective pivotal travel relative thereto between a fully open position and a fully closed position; and
a closure member configured to apply closure motions to said second jaw as said closure member is axially movable in a distal direction from a starting position corresponding to said fully open position of said second jaw to an ending position corresponding to said fully closed position of said second jaw, wherein said closure member is configured to move distally from said starting position an initial predetermined axial closure distance before applying said closure motion to said second jaw, wherein said closure member comprises at least one jaw opening feature on said closure member for applying opening motions to said second jaw as said closure member axially moves in a proximal direction from said ending position to said starting position, and wherein said at least one jaw opening feature comprises:
   a first jaw opening feature on said closure member and configured to apply a first amount of jaw opening motion to said second jaw as said closure member is axially moved from said ending position to an intermediate axial position between said ending position and said starting position; and
   a second jaw opening feature on said closure member axially spaced from said first jaw opening feature and configured to apply a second amount of jaw opening motion to said second jaw as said closure member is axially moved from said intermediate position to said starting position.

9. The surgical instrument of claim 8, wherein said initial predetermined axial closure distance is 0.020 inches.

10. The surgical instrument of claim 8, wherein said closure member is configured to distally move through a final predetermined axial closure distance after said second jaw has been moved to said fully closed position.

11. The surgical instrument of claim 10, wherein said final predetermined axial closure distance is 0.040 inches.

12. The surgical instrument of claim 10, wherein said closure member is configured to apply said closure motions to said second jaw as said closure member moves distally through an intermediate predetermined axial closure distance after said closure member traveled said initial predetermined axial closure distance and prior to traveling said final predetermined axial closure distance.

13. The surgical instrument of claim 12, wherein said intermediate predetermined axial closure distance is 0.200 inches.

14. The surgical instrument of claim 8, wherein said closure member comprises a closure camming surface configured to cammingly engage a jaw camming surface on said second jaw to apply said closure motions thereto.

15. A surgical instrument, comprising:
an elongate channel configured to operably support a surgical staple/fastener cartridge therein;
an anvil pivotally supported on said elongated channel for selective pivotal travel relative thereto between a fully open position and a fully closed position; and
a closure member configured to apply closure motions to said anvil as said closure member is axially movable in a distal direction from a starting position corresponding to said fully open position of said anvil to an ending position corresponding to said fully closed position of said anvil, said closure member configured to move distally from said starting position an initial predetermined axial closure distance before applying said closure motion to said anvil, wherein said closure member comprises means on said closure member for applying opening motions to said anvil as said closure member axially moves in a proximal direction from said ending position to said starting position, and wherein said means for applying opening motions comprises:
   a first jaw opening feature on said closure member and configured to apply a first amount of jaw opening motion to said anvil as said closure member is axially moved from said ending position to an intermediate axial position between said ending position and said starting position; and
   a second jaw opening feature on said closure member axially spaced from said first jaw opening feature and configured to apply a second amount of j aw opening motion to said anvil as said closure member is axially moved from said intermediate axial position to said starting position.

16. The surgical instrument of claim 15, wherein said initial predetermined axial closure distance is 0.020 inches.

17. The surgical instrument of claim 15, wherein said closure member is configured to distally move through a final predetermined axial closure distance after said anvil has been moved to said fully closed position.

18. The surgical instrument of claim 17, wherein said final predetermined axial closure distance is 0.040 inches.

19. The surgical instrument of claim 17, wherein said closure member is configured to apply said closure motions to said anvil as said closure member moves distally through an intermediate predetermined axial closure distance after said closure member traveled said initial predetermined axial closure distance and prior to traveling said final predetermined axial closure distance.

20. The surgical instrument of claim 19, wherein said intermediate predetermined axial closure distance is 0.200 inches.

21. The surgical instrument of claim 17, wherein said closure member comprises a closure camming surface configured to cammingly engage an anvil camming surface on an anvil mounting portion of said anvil to apply said closure motions thereto.

* * * * *